US005853733A

United States Patent [19]
Cochran et al.

[11] Patent Number: 5,853,733
[45] Date of Patent: Dec. 29, 1998

[54] RECOMBINANT HERPESVIRUS OF TURKEYS AND USES THEREOF

[75] Inventors: Mark D. Cochran, Carlsbad; Richard D. Macdonald, San Diego, both of Calif.

[73] Assignee: Syntro Corporation, Lenexa, Kans.

[21] Appl. No.: 663,566

[22] Filed: Jun. 13, 1996

Related U.S. Application Data

[63] Continuation of Ser. No. 288,065, Aug. 9, 1994, which is a continuation-in-part of PCT/US93/05681 Jun. 14, 1993, which is a continuation-in-part of Ser. No. 23,610, Feb. 26, 1993.

[51] Int. Cl.⁶ .......... A61K 39/12; A61K 39/245; C12N 7/01
[52] U.S. Cl. .......... 424/199.1; 424/229.1; 424/816; 435/235.1; 435/69.1; 435/69.3; 435/320.1
[58] Field of Search .......... 435/235.1, 69.1, 435/69.3, 320.1; 424/229.1, 199.1, 816

[56] References Cited

U.S. PATENT DOCUMENTS

| | | | |
|---|---|---|---|
| 4,877,737 | 10/1989 | Shih et al. | 424/205.1 |
| 5,047,237 | 9/1991 | Cochran | 424/205.1 |
| 5,171,677 | 12/1992 | Sakaguchi et al. | 435/172.3 |
| 5,187,087 | 2/1993 | Sondermeijer et al. | 435/172.1 |
| 5,223,424 | 6/1993 | Cochran et al. | 435/236 |
| 5,225,336 | 7/1993 | Paoletti | 435/69.1 |
| 5,240,703 | 8/1993 | Cochran | 424/205.1 |
| 5,252,717 | 10/1993 | Velicer et al. | 530/395 |
| 5,266,489 | 11/1993 | Rey-Senelonge et al. | 435/320.1 |
| 5,283,191 | 2/1994 | Morgan et al. | 435/252.3 |
| 5,470,734 | 11/1995 | Sondermeijer et al. | 424/229.1 |

FOREIGN PATENT DOCUMENTS

| | | |
|---|---|---|
| 431668 | 6/1991 | European Pat. Off. . |
| 447303 | 9/1991 | European Pat. Off. . |
| 473210 | 3/1992 | European Pat. Off. . |
| 477056 | 3/1992 | European Pat. Off. . |
| 486106 | 5/1992 | European Pat. Off. . |
| WO8807088 | 9/1988 | WIPO . |
| WO8901040 | 2/1989 | WIPO . |
| WO9002802 | 3/1990 | WIPO . |
| WO9002803 | 3/1990 | WIPO . |
| WO9203554 | 3/1992 | WIPO . |
| WO9215672 | 9/1992 | WIPO . |
| WO9410321 | 5/1994 | WIPO . |

OTHER PUBLICATIONS

Cantello, J., et al. (1991) "Isolation of a Marek's Disease Virus (MDV) Recombinant Containing the lacZ Gene of *Escherichia coli*", J. Virology 65:1584–1588.

Chen, X., et al. (1992) "Identification of a Unique Marek's Disease Virus Gene Which Encodes a 38–Kilodalton Phosphoprotein and Is Expressed in both Lytically Infected Cells and Latently Infected Lymphoblastoid Tumor Cells", J. Virology 66:85–94.

Gibbs, C., et al. (1984) "Extensive Homology Exists between Marek Disease Herpesvirus and its Vaccine Virus, Herpesvirus of Turkeys", Proc. Natl. Acad. Sci. USA 81:3365–3369.

(List continued on next page.)

*Primary Examiner*—Mary E. Mosher
*Assistant Examiner*—Ali R. Salimi
*Attorney, Agent, or Firm*—John P. White; Cooper & Dunham LLP

[57] ABSTRACT

The present invention provides a recombinant herpesvirus of turkeys designated S-HVT-050 (ATCC Accession No. VR 2400). A vaccine is provided which comprises an effective immunizing amount of S-HVT-050 and a suitable carrier. A method of immunizing a fowl against disease caused by Marek's disease virus and Newcastle disease virus is also provided which comprises administering to the fowl an effective immunizing dose of the vaccine of the present invention.

27 Claims, 23 Drawing Sheets

OTHER PUBLICATIONS

Igarashi, T., et al. (1987) "Restriction Enzyme Map of Herpesvirus of Turkey DNA and Its Collinear Relationship with Marke's Disease Virus DNA", Virology 157:351–358.

Kaschka–Dierich, C., et al. (1979) "No Homology Detectable between Marek's Disease Virus (MDV) DNA and Herpesvirus of the Turkey (HVT) DNA", Med. Microbiol. Immunol. 165:223–239.

Kato, A., et al. (1989) "Homologies between Herpesvirus of Turkey and Marek's Disease Virus Type–1 DNAs within Two Co–linearly Arranged Open Reading Frames, One Encoding Glycoprotein A", Gene 84:399–405.

Lee, Y–S., et al. (1979) "Minor DNA Homology between Herpesvirus of Turkey and Marek's Disease Virus?", Virology 93:277–280.

Morgan, R., et al. (1992) "Protection of Chickens from Newcastle and Marek's Diseases with a Recombinant Herpesvirus of Turkeys Vaccine Expressing the Newcastle Disease Virus Fusion Protein", Avian Diseases 36:858–870.

Ross, L., et al. (1991) "DNA Sequence and Organization of Genes in a 5.5 kbp EcoRI Fragment Mapping in the Short Unique Segment of Marek's Disease Virus (Strain RB1B)", J. General Virology 72:949–954.

Ross, L., et al. (1991) "Properties and Evolutionary Relationships of the Marek's Disease Virus Homologues of Protein Kinase, Glycoprotein D and Glycoprotein I of Herpes Simplex Virus", J. General Virology 72:939–947.

Weber, P., et al. (1987) "Rapid Identification of Nonessential Genes of Herpes Simplex Virus Type 1 by Tn5 Mutagenesis", Science 236:576–579.

Reilly, David J. and Silva, Robert F. (1993) "Cosmid library of the turkey herpesvirus genome constructed from nanogram quantities of viral DNA associate wiyj an excess of cellular DNA", J. Virological 41:323–332.

Sondermeijer, Paul J.A. et al. (1993) "Avian herpesvirus as a live viral vector for the expression of heterologous antigens", Vaccine, vol. 11, Issue 3.

Ross, L.J.N., et al. (1993) "Construction and properties of a turkey herpesvirus recombinant expressing the Marek's disease virus homologue of glycoprotein B of herpes simplex virus", 7 J. Virology 74, 371–377.

Scott, Simon D., et al. (1993) "Identification and sequence analysis of the homologues of the herpes simplex virus type 1 glycoprotein H in Marek's disease virus and the herpesvirus of turkeys", J. Virology 74, 1185–1190.

Marshall, D.R., et al. (1993) "Selection of Marek's Disease Virus Recombinants Expressing the *Escherichia coli* gpt Gene", Virology 195, 638–648.

Zelnik, V., et al. (1993) "The complete sequence and gene organization of the short unique region of herpesvirus of turkeys", J. Virology 74, 2151–2162.

Morgan, Robin W., et al. (1993) "Efficacy in chickens of a herpesvirus of Turkeys Recombinant Vaccine Containing the Fusion Gene of Newcastle Disease Virus: Onset of Protection and Effect of Maternal Antibodies", Avian Diseases 37:1032–1040.

Lindenmaier, W. and Bauer, H.J. (1994) "Cosmid cloning and restriction endonuclease mapping of the herpesvirus of turkeys (HVT) genome", Arch Virol 135:171–177.

Meignier, Bernard, (1991) "Genetically Engineered Attenuated Herpes Simplex Viruses", reviews of Infectious Diseases 13 (Suppl II): S895–S897.

Zuckermann, F.A. et al., (1989) "Role of Pseudorabies Virus Glycoproteins In Immune Response", Vaccinatio and Control of Aujeszky's Disease pp. 107–117.

Petrovskis, Erik A., et al. (1986) "Deletions in Vaccine Strains of Pseudorabies Virus and Their Effect on Synthesis of Glycoprotein gp63", J. Virology pp. 1166–1169 vol. 60 No. 3.

Ben–Porat, T., et al. (1986) "Role of Glycoproteins of Pseudorabies Virus in Eliciting Neutralizing Antobodies", Virology 154, 325–334.

Price, Richard W., and Khan, Atia; (1981) "Resistance of Peripheral Autonomic Neurons to In Vivo Productive Infection by Herpes Simplex Virus Mutants Deficient in Thymidine Kinase Activity", Infection and Immunity, pp. 571–580, vol.34 No.2.

Tenser, Richard B., et al. (1983) "The Role of Pseudorabies Virus Thymidine Kinase Expression in Trigeminal Ganglion Infection", J.Gen. Virol. 64, 1369–1373.

Lomniczi, Bela, et al. (1984) "Deletions in the Genomes of Pseudorabies Virus Vaccine Strains and Existence of Flour Isomers of the Genomes", J. Virology pp. 970–979; vol.49 No.3.

Thomsen, Darrell R., et al. (1987) "Pseudorabies virus as a live virus vector for expression of foreign genes", Gene 57, 261–265.

Honess, R.W., (1984) "Herpes Simplex and 'The Herpes Complex': Diverse Observations and A Unifying Hypothesis", J._Gen. Virol. 65, 2077–2107.

Cook, Margery L. and Stevens, J.G., (1976) "Latent Herpetic Infections Following Experimental Viraemia", J.Gen. Virol. 31, 75–80.

Thompson, R.L., et al. (1983) "Physical Location of a Herpes Simplex Virus Type–1 Gene Function(s) Specifically Associated with a 10 Million–Fold Increase in HSV Neurovirulence", Virology 131, 180–192.

Fukuchi, K., et al. (1985) "The Structure of Marek disease virus DNA: The presence of unique expansion in nonpathogenic viral DNA", Proc.Natl.Acad.Sci.USA vol.82, pp. 751–754.

Koomey, Michael J., et al. (1984) "Deletion of DNA Sequences in a Nononcogenic Variant of *Herpesvirus saimiri*", J. Virol. pp. 662–665, vol.50 No. 2.

Spaete, Richard R. and Mocarski, Edward S., (1987) "Insertion and deletion mutagenesis of the human cytomegalovirus genome", Proc.Natl.Acad.Sci.USA vol. 84, pp. 7213–7217.

Shih, Meng–Fu et al. (1984) "Expression of hepatitis B virus S gene by herpes simplex virus type 1 vectors carrying α–and β–regulated gene chimeras", Proc. Natl. Acad. Sci. USA vol. 81, pp. 5867–5870.

Edwards, Stirling J., (1988) "Plasmodium Falciparum Antigens In Recombinant HSV–1", Technological advances in Vaccine Development, pp. 223–234.

Roizman, Bernard, et al. (1983) "Bioengineering of Herpes Simplex Virus Variants for potential Use as Live Vaccines", Cold Spring Harbor Ocnference on New Approaches to Virla Vaccines, pp. 275–281.

Moss, Bernard, (1991) "Vaccinia Virus: A Tool for Research and Vaccine Development" Science 252:1662–1667.

Weir, Jerry P., and Narayanan, P.R., (1988) "The use of β–galactosidase as a marker gene to define the regulatory sequences of the herpes simplex virus type 1 glycoprotein C gene in recombinant herpesviruses", Nucleic Acids Research 16:10267–10282.

BamHI fragments

BamHI #16

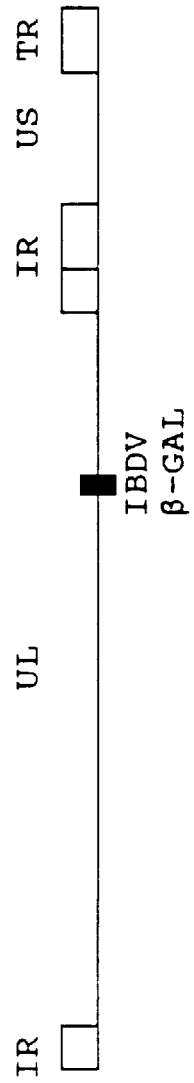
FIG. 3A
FIG. 3B

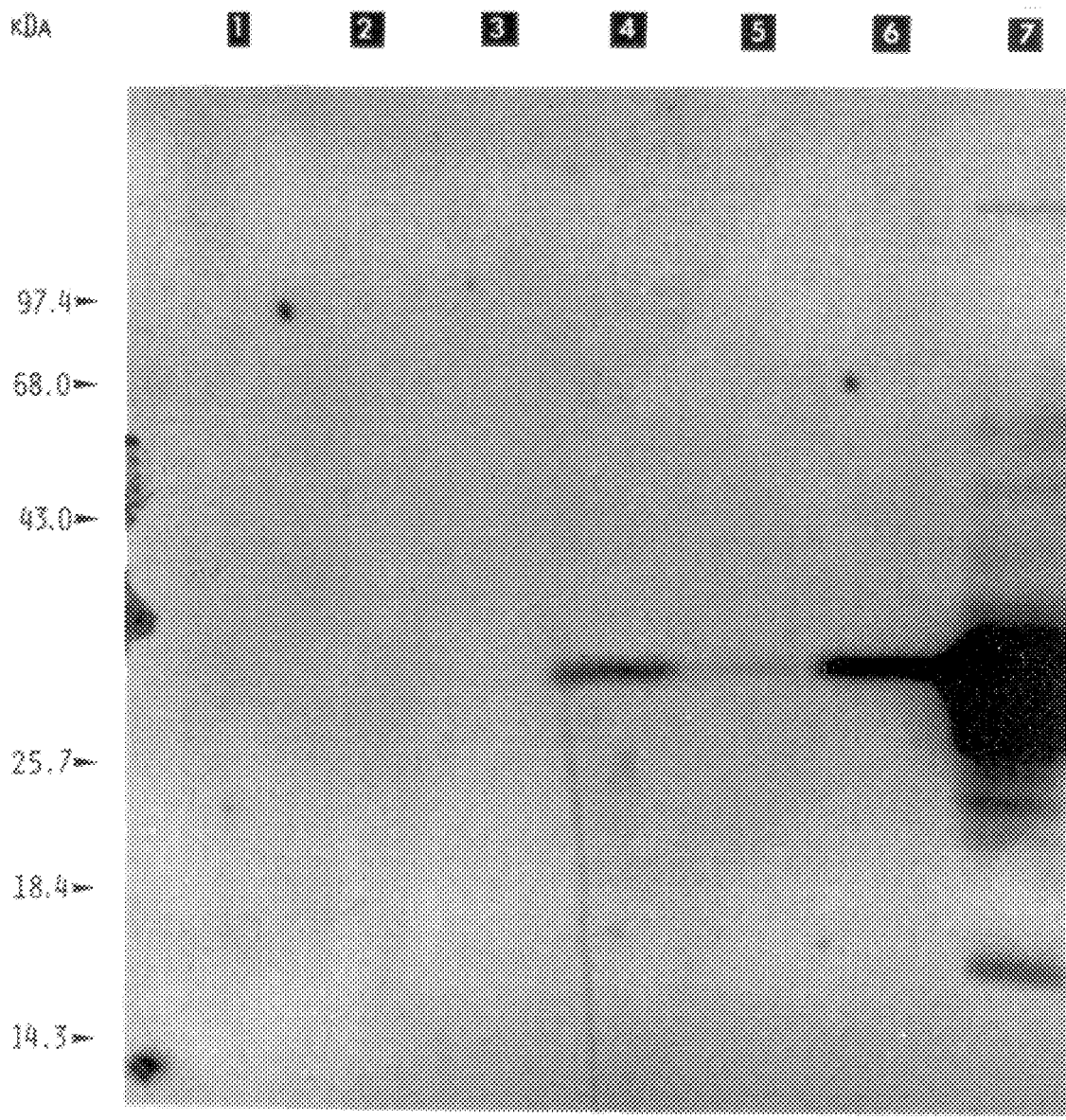

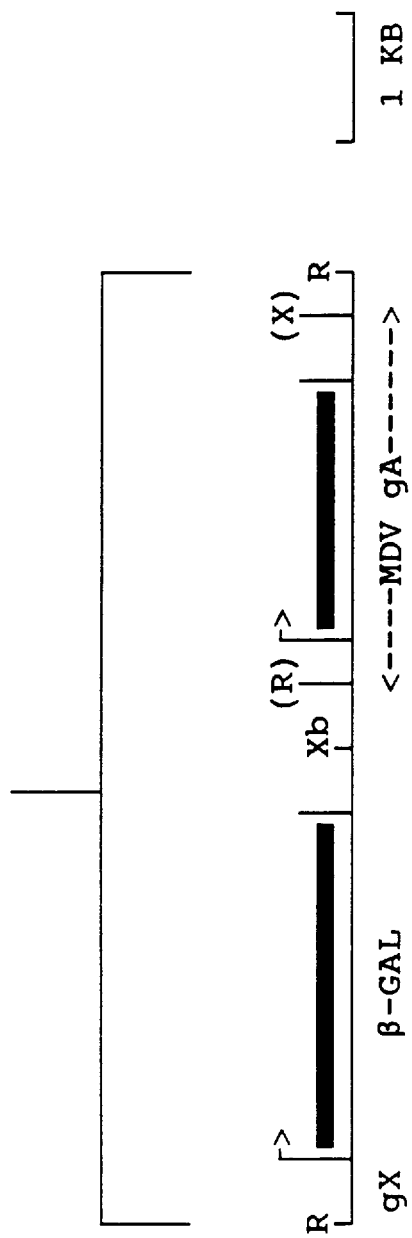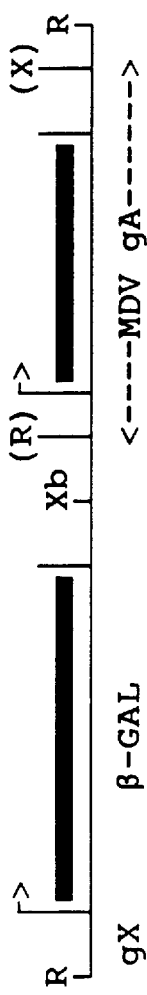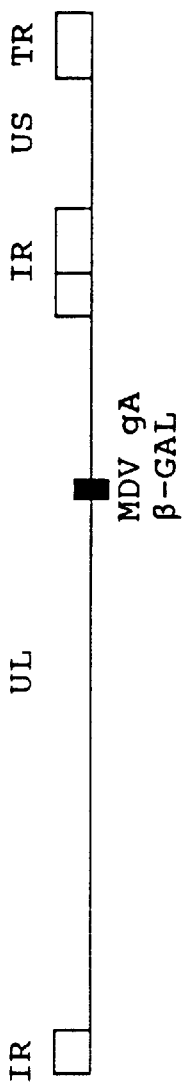
FIG. 6A
FIG. 6B
FIG. 6C

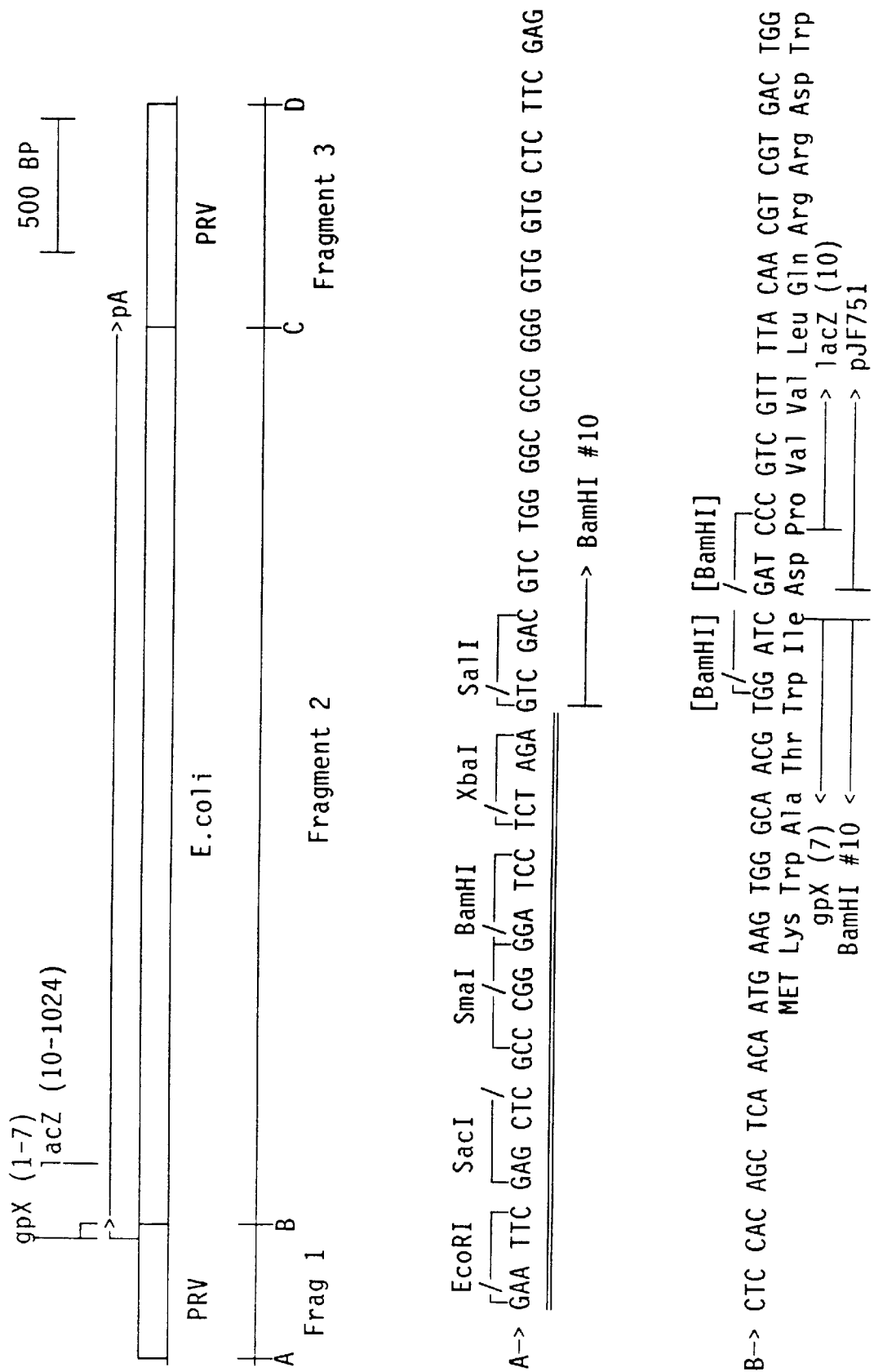

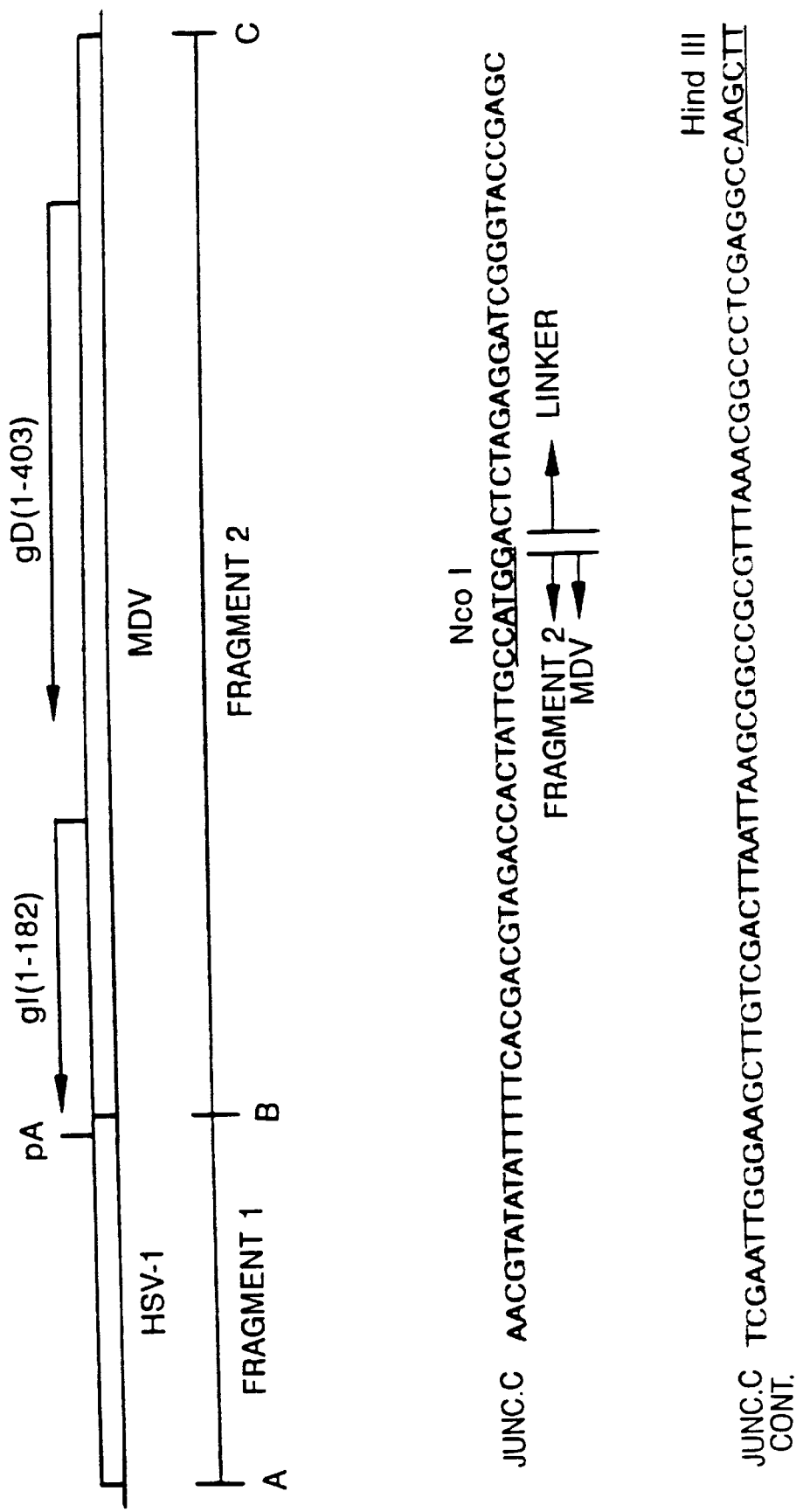

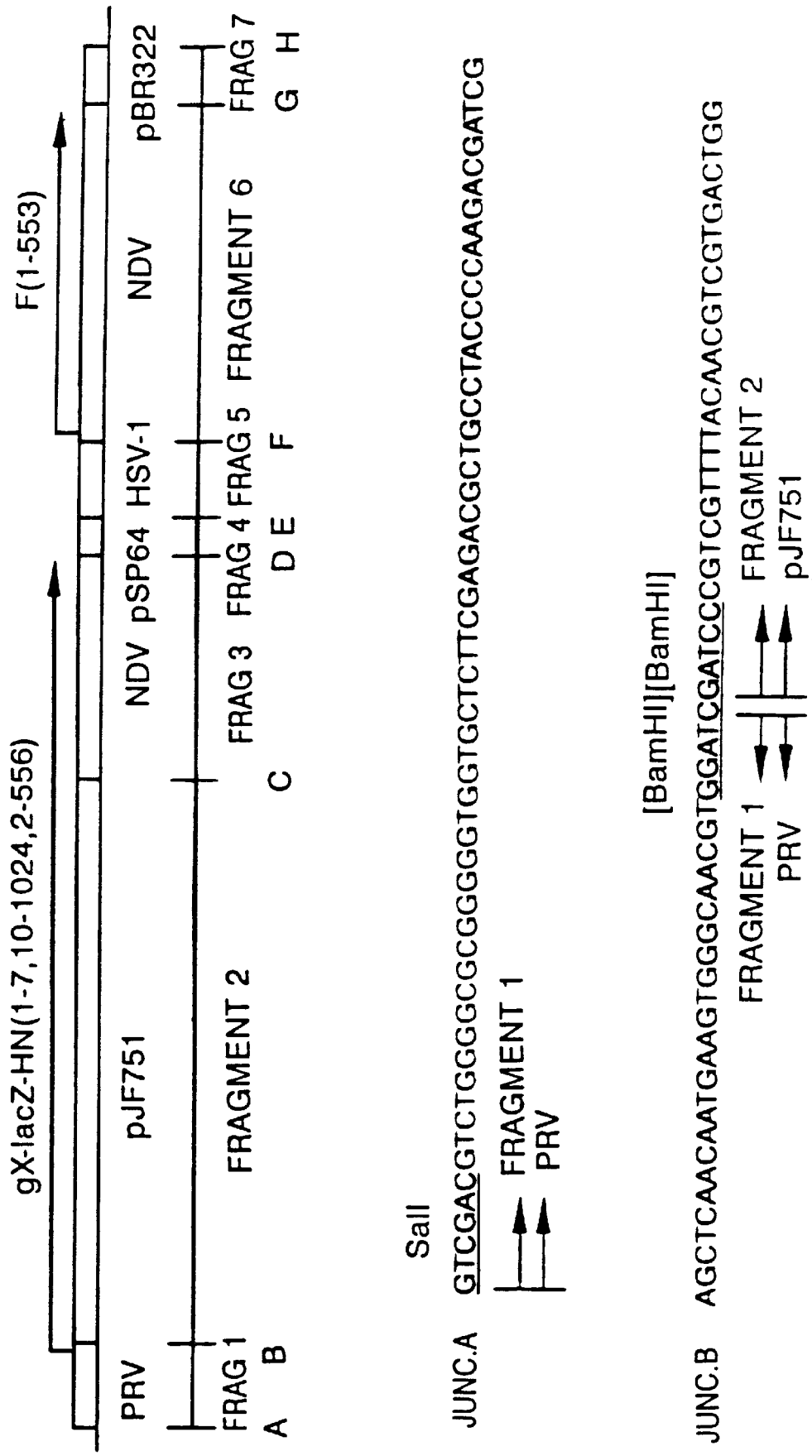

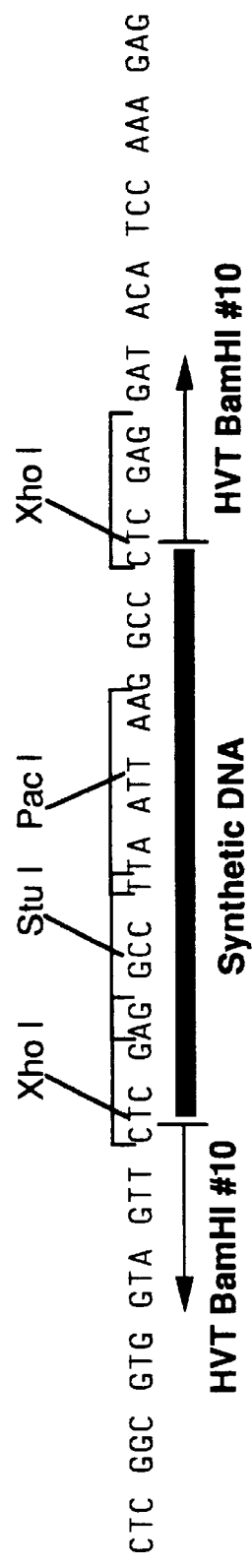
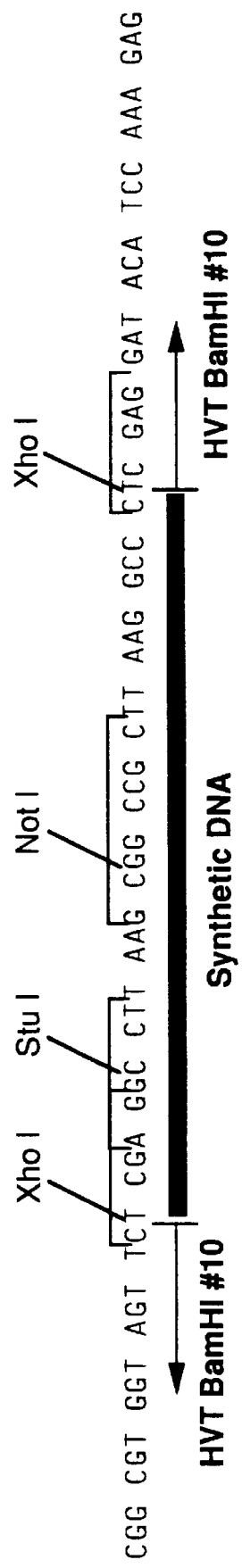
FIG. 13A
FIG. 13B

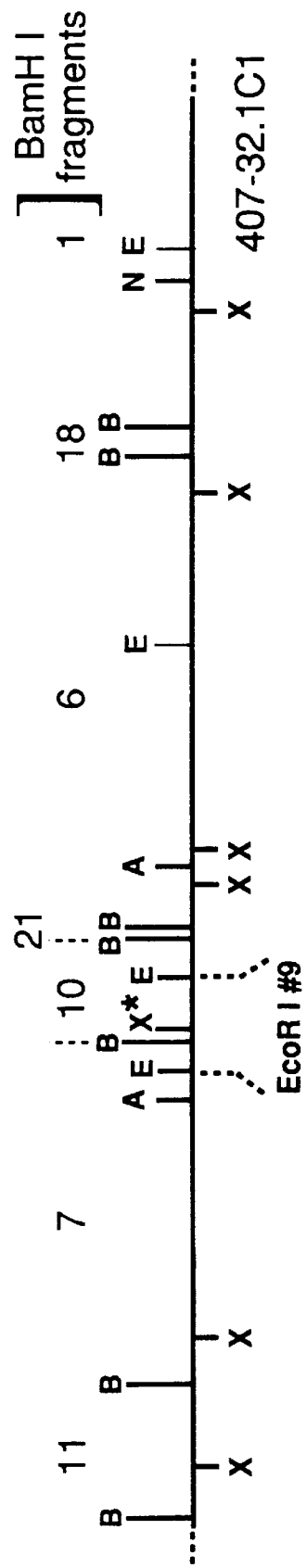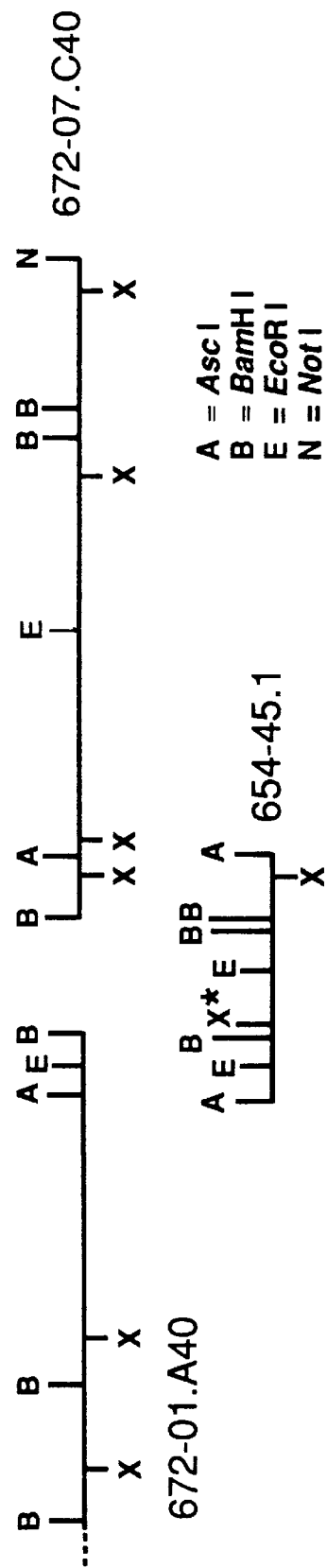
FIG. 15

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 3350 base pairs
        ( B ) TYPE: nucleic acid
        ( C ) STRANDEDNESS: double ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
            ( A ) NAME/KEY: CDS
            ( B ) LOCATION: 129..2522

( x i ) SEQUENCE DESCRIPTION: SEQ ID NO:1:

```
GGATACGATC  GGTCTGACCC  GGGGGAGTCA  CCCGGGGACA  GCCGTCAAGG  CCTTGTTCCA         60

GGATAGAACT  CCTCCTTCTA  CAACGCTATC  ATTGATGGTC  AGTAGAGATC  AGACAAACGA        120

TCGCAGCG ATG ACA AAC CTG CAA GAT CAA ACC CAA CAG ATT GTT CCG TTC              170
         Met Thr Asn Leu Gln Asp Gln Thr Gln Gln Ile Val Pro Phe
          1               5                       10

ATA CGG AGC CTT CTG ATG CCA ACA ACC GGA CCG GCG TCC ATT CCG GAG               218
Ile Arg Ser Leu Leu Met Pro Thr Thr Gly Pro Ala Ser Ile Pro Glu
 15              20                  25                      30

ACA CCC TGG AGA AGC ACA CTC TCA GGT CAG AGA CTG ACC TAC AAT TTG               266
Thr Pro Trp Arg Ser Thr Leu Ser Gly Gln Arg Leu Thr Tyr Asn Leu
                 35                  40                      45

ACT GTG GGG GAC ACA GGG TCA GGG CTA ATT GTC TTT TTC CCT GGA TTC               314
Thr Val Gly Asp Thr Gly Ser Gly Leu Ile Val Phe Phe Pro Gly Phe
                 50                  55                      60

CCT GGC TCA ATT GTG GGT GCT CAC TAC ACA CTG CAG AGC AAT GGG AAC               362
Pro Gly Ser Ile Val Gly Ala His Tyr Thr Leu Gln Ser Asn Gly Asn
             65                  70                  75

TAC AAG TTC GAT CGG ATG CTC CTG ACT GCC CAG AAC CTA CCG GCC AGT               410
Tyr Lys Phe Asp Arg Met Leu Leu Thr Ala Gln Asn Leu Pro Ala Ser
         80                  85                  90

TAC AAC TAC TGC AGG CTA GTG AGT CGG AGT CTC ACA GTG AGG TCA AGC               458
Tyr Asn Tyr Cys Arg Leu Val Ser Arg Ser Leu Thr Val Arg Ser Ser
 95                 100                 105                 110

ACA CTT CCT GGT GGC GTT TAT GCA CTA AAC GGC ACC ATA AAC GCC GTG               506
Thr Leu Pro Gly Gly Val Tyr Ala Leu Asn Gly Thr Ile Asn Ala Val
                 115                 120                 125

ACC TTC CAA GGA AGC CTG AGT GAA CTG ACA GAT GTT AGC TAC AAT GGG               554
Thr Phe Gln Gly Ser Leu Ser Glu Leu Thr Asp Val Ser Tyr Asn Gly
                 130                 135                 140

TTG ATG TCT GCA ACA GCC AAC ATC AAC GAC AAA ATT GGG AAC GTC CTA               602
Leu Met Ser Ala Thr Ala Asn Ile Asn Asp Lys Ile Gly Asn Val Leu
                 145                 150                 155

GTA GGG GAA GGG GTC ACC GTC CTC AGC TTA CCC ACA TCA TAT GAT CTT               650
Val Gly Glu Gly Val Thr Val Leu Ser Leu Pro Thr Ser Tyr Asp Leu
         160                 165                 170

GGG TAT GTG AGG CTT GGT GAC CCC ATT CCC GCA ATA GGG CTT GAC CCA               698
Gly Tyr Val Arg Leu Gly Asp Pro Ile Pro Ala Ile Gly Leu Asp Pro
175                 180                 185                 190

AAA ATG GTA GCC ACA TGT GAC AGC AGT GAC AGG CCC AGA GTC TAC ACC               746
Lys Met Val Ala Thr Cys Asp Ser Ser Asp Arg Pro Arg Val Tyr Thr
                 195                 200                 205

ATA ACT GCA GCC GAT GAT TAC CAA TTC TCA TCA CAG TAC CAA CCA GGT               794
Ile Thr Ala Ala Asp Asp Tyr Gln Phe Ser Ser Gln Tyr Gln Pro Gly
                 210                 215                 220

GGG GTA ACA ATC ACA CTG TTC TCA GCC AAC ATT GAT GCC ATC ACA AGC               842
Gly Val Thr Ile Thr Leu Phe Ser Ala Asn Ile Asp Ala Ile Thr Ser
                 225                 230                 235

CTC AGC GTT GGG GGA GAG CTC GTG TTT CGA ACA AGC GTC CAC GGC CTT               890
Leu Ser Val Gly Gly Glu Leu Val Phe Arg Thr Ser Val His Gly Leu
```

|     |     |     |     |     | 240 |     |     |     |     | 245 |     |     |     |     | 250 |      |
|-----|-----|-----|-----|-----|-----|-----|-----|-----|-----|-----|-----|-----|-----|-----|-----|------|
| GTA | CTG | GGC | GCC | ACC | ATC | TAC | CTC | ATA | GGC | TTT | GAT | GGG | ACA | ACG | GTA | 938  |
| Val | Leu | Gly | Ala | Thr | Ile | Tyr | Leu | Ile | Gly | Phe | Asp | Gly | Thr | Thr | Val |      |
| 255 |     |     |     |     | 260 |     |     |     |     | 265 |     |     |     |     | 270 |      |
| ATC | ACC | AGG | GCT | GTG | GCC | GCA | AAC | ACT | GGG | CTG | ACG | ACC | GGC | ACC | GAC | 986  |
| Ile | Thr | Arg | Ala | Val | Ala | Ala | Asn | Thr | Gly | Leu | Thr | Thr | Gly | Thr | Asp |      |
|     |     |     |     | 275 |     |     |     |     | 280 |     |     |     |     | 285 |     |      |
| AAC | CTT | ATG | CCA | TTC | AAT | CTT | GTG | ATT | CCA | ACA | AAC | GAG | ATA | ACC | CAG | 1034 |
| Asn | Leu | Met | Pro | Phe | Asn | Leu | Val | Ile | Pro | Thr | Asn | Glu | Ile | Thr | Gln |      |
|     |     |     | 290 |     |     |     |     | 295 |     |     |     |     | 300 |     |     |      |
| CCA | ATC | ACA | TCC | ATC | AAA | CTG | GAG | ATA | GTG | ACC | TCC | AAA | AGT | GGT | GGT | 1082 |
| Pro | Ile | Thr | Ser | Ile | Lys | Leu | Glu | Ile | Val | Thr | Ser | Lys | Ser | Gly | Gly |      |
|     |     | 305 |     |     |     |     | 310 |     |     |     |     | 315 |     |     |     |      |
| CAG | GCA | GGG | GAT | CAG | ATG | TTA | TGG | TCG | GCA | AGA | GGG | AGC | CTA | GCA | GTG | 1130 |
| Gln | Ala | Gly | Asp | Gln | Met | Leu | Trp | Ser | Ala | Arg | Gly | Ser | Leu | Ala | Val |      |
|     | 320 |     |     |     |     | 325 |     |     |     |     | 330 |     |     |     |     |      |
| ACG | ATC | CAT | GGT | GGC | AAC | TAT | CCA | GGG | GCC | CTC | CGT | CCC | GTC | ACG | CTA | 1178 |
| Thr | Ile | His | Gly | Gly | Asn | Tyr | Pro | Gly | Ala | Leu | Arg | Pro | Val | Thr | Leu |      |
| 335 |     |     |     |     | 340 |     |     |     |     | 345 |     |     |     |     | 350 |      |
| GTG | GCC | TAC | GAA | AGA | GTG | GCA | ACA | GGA | TCC | GTC | GTT | ACG | GTC | GCT | GGG | 1226 |
| Val | Ala | Tyr | Glu | Arg | Val | Ala | Thr | Gly | Ser | Val | Val | Thr | Val | Ala | Gly |      |
|     |     |     |     | 355 |     |     |     |     | 360 |     |     |     |     | 365 |     |      |
| GTG | AGC | AAC | TTC | GAG | CTG | ATC | CCA | AAT | CCT | GAA | CTA | GCA | AAG | AAC | CTG | 1274 |
| Val | Ser | Asn | Phe | Glu | Leu | Ile | Pro | Asn | Pro | Glu | Leu | Ala | Lys | Asn | Leu |      |
|     |     |     | 370 |     |     |     |     | 375 |     |     |     |     | 380 |     |     |      |
| GTT | ACA | GAA | TAC | GGC | CGA | TTT | GAC | CCA | GGA | GCC | ATG | AAC | TAC | ACA | AAA | 1322 |
| Val | Thr | Glu | Tyr | Gly | Arg | Phe | Asp | Pro | Gly | Ala | Met | Asn | Tyr | Thr | Lys |      |
|     |     | 385 |     |     |     |     | 390 |     |     |     |     | 395 |     |     |     |      |
| TTG | ATA | CTG | AGT | GAG | AGG | GAC | CGT | CTT | GGC | ATC | AAG | ACC | GTC | TGG | CCA | 1370 |
| Leu | Ile | Leu | Ser | Glu | Arg | Asp | Arg | Leu | Gly | Ile | Lys | Thr | Val | Trp | Pro |      |
| 400 |     |     |     |     | 405 |     |     |     |     | 410 |     |     |     |     |     |      |
| ACA | AGG | GAG | TAC | ACT | GAC | TTT | CGT | GAA | TAC | TTC | ATG | GAG | GTG | GCC | GAC | 1418 |
| Thr | Arg | Glu | Tyr | Thr | Asp | Phe | Arg | Glu | Tyr | Phe | Met | Glu | Val | Ala | Asp |      |
| 415 |     |     |     |     | 420 |     |     |     |     | 425 |     |     |     |     | 430 |      |
| CTC | AAC | TCT | CCC | CTG | AAG | ATT | GCA | GGA | GCA | TTC | GGC | TTC | AAA | GAC | ATA | 1466 |
| Leu | Asn | Ser | Pro | Leu | Lys | Ile | Ala | Gly | Ala | Phe | Gly | Phe | Lys | Asp | Ile |      |
|     |     |     |     | 435 |     |     |     |     | 440 |     |     |     |     | 445 |     |      |
| ATC | CGG | GCC | ATA | AGG | AGG | ATA | GCT | GTG | CCG | GTG | GTC | TCC | ACA | TTG | TTC | 1514 |
| Ile | Arg | Ala | Ile | Arg | Arg | Ile | Ala | Val | Pro | Val | Val | Ser | Thr | Leu | Phe |      |
|     |     |     | 450 |     |     |     |     | 455 |     |     |     |     | 460 |     |     |      |
| CCA | CCT | GCC | GCT | CCC | CTA | GCC | CAT | GCA | ATT | GGG | GAA | GGT | GTA | GAC | TAC | 1562 |
| Pro | Pro | Ala | Ala | Pro | Leu | Ala | His | Ala | Ile | Gly | Glu | Gly | Val | Asp | Tyr |      |
|     |     | 465 |     |     |     |     | 470 |     |     |     |     | 475 |     |     |     |      |
| CTG | CTG | GGC | GAT | GAG | GCA | CAG | GCT | GCT | TCA | GGA | ACT | GCT | CGA | GCC | GCG | 1610 |
| Leu | Leu | Gly | Asp | Glu | Ala | Gln | Ala | Ala | Ser | Gly | Thr | Ala | Arg | Ala | Ala |      |
|     | 480 |     |     |     |     | 485 |     |     |     |     | 490 |     |     |     |     |      |
| TCA | GGA | AAA | GCA | AGA | GCT | GCC | TCA | GGC | CGC | ATA | AGG | CAG | CTG | ACT | CTC | 1658 |
| Ser | Gly | Lys | Ala | Arg | Ala | Ala | Ser | Gly | Arg | Ile | Arg | Gln | Leu | Thr | Leu |      |
| 495 |     |     |     |     | 500 |     |     |     |     | 505 |     |     |     |     | 510 |      |
| GCC | GCC | GAC | AAG | GGG | TAC | GAG | GTA | GTC | GCG | AAT | CTA | TTC | CAG | GTG | CCC | 1706 |
| Ala | Ala | Asp | Lys | Gly | Tyr | Glu | Val | Val | Ala | Asn | Leu | Phe | Gln | Val | Pro |      |
|     |     |     |     | 515 |     |     |     |     | 520 |     |     |     |     | 525 |     |      |
| CAG | AAT | CCC | GTA | GTC | GAC | GGG | ATT | CTT | GCT | TCA | CCT | GGG | GTA | CTC | CGC | 1754 |
| Gln | Asn | Pro | Val | Val | Asp | Gly | Ile | Leu | Ala | Ser | Pro | Gly | Val | Leu | Arg |      |
|     |     |     | 530 |     |     |     |     | 535 |     |     |     |     | 540 |     |     |      |
| GGT | GCA | CAC | AAC | CTC | GAC | TGC | GTG | TTA | AGA | GAG | GGT | GCC | ACG | CTA | TTC | 1802 |
| Gly | Ala | His | Asn | Leu | Asp | Cys | Val | Leu | Arg | Glu | Gly | Ala | Thr | Leu | Phe |      |
|     |     | 545 |     |     |     |     | 550 |     |     |     |     | 555 |     |     |     |      |
| CCT | GTG | GTT | ATT | ACG | ACA | GTG | GAA | GAC | GCC | ATG | ACA | CCC | AAA | GCA | TTG | 1850 |
| Pro | Val | Val | Ile | Thr | Thr | Val | Glu | Asp | Ala | Met | Thr | Pro | Lys | Ala | Leu |      |

```
                560                              565                              570
AAC  AGC  AAA  ATG  TTT  GCT  GTC  ATT  GAA  GGC  GTG  CGA  GAA  GAC  CTC  CAA      1898
Asn  Ser  Lys  Met  Phe  Ala  Val  Ile  Glu  Gly  Val  Arg  Glu  Asp  Leu  Gln
575                      580                     585                          590

CCT  CCA  TCT  CAA  AGA  GGA  TCC  TTC  ATA  CGA  ACT  CTC  TCT  GGA  CAC  AGA      1946
Pro  Pro  Ser  Gln  Arg  Gly  Ser  Phe  Ile  Arg  Thr  Leu  Ser  Gly  His  Arg
                    595                          600                          605

GTC  TAT  GGA  TAT  GCT  CCA  GAT  GGG  GTA  CTT  CCA  CTG  GAG  ACT  GGG  AGA      1994
Val  Tyr  Gly  Tyr  Ala  Pro  Asp  Gly  Val  Leu  Pro  Leu  Glu  Thr  Gly  Arg
               610                     615                          620

GAC  TAC  ACC  GTT  GTC  CCA  ATA  GAT  GAT  GTC  TGG  GAC  GAC  AGC  ATT  ATG      2042
Asp  Tyr  Thr  Val  Val  Pro  Ile  Asp  Asp  Val  Trp  Asp  Asp  Ser  Ile  Met
          625                         630                          635

CTG  TCC  AAA  GAT  CCC  ATA  CCT  CCT  ATT  GTG  GGA  AAC  AGT  GGA  AAT  CTA      2090
Leu  Ser  Lys  Asp  Pro  Ile  Pro  Pro  Ile  Val  Gly  Asn  Ser  Gly  Asn  Leu
640                      645                                        650

GCC  ATA  GCT  TAC  ATG  GAT  GTG  TTT  CGA  CCC  AAA  GTC  CCA  ATC  CAT  GTG      2138
Ala  Ile  Ala  Tyr  Met  Asp  Val  Phe  Arg  Pro  Lys  Val  Pro  Ile  His  Val
655                           660                     665                     670

GCT  ATG  ACG  GGA  GCC  CTC  AAT  GCT  TGT  GGC  GAG  ATT  GAG  AAA  GTA  AGC      2186
Ala  Met  Thr  Gly  Ala  Leu  Asn  Ala  Cys  Gly  Glu  Ile  Glu  Lys  Val  Ser
                    675                     680                          685

TTT  AGA  AGC  ACC  AAG  CTC  GCC  ACT  GCA  CAC  CGA  CTT  GGC  CTT  AAG  TTG      2234
Phe  Arg  Ser  Thr  Lys  Leu  Ala  Thr  Ala  His  Arg  Leu  Gly  Leu  Lys  Leu
               690                          695                     700

GCT  GGT  CCC  GGA  GCA  TTC  GAT  GTA  AAC  ACC  GGG  CCC  AAC  TGG  GCA  ACG      2282
Ala  Gly  Pro  Gly  Ala  Phe  Asp  Val  Asn  Thr  Gly  Pro  Asn  Trp  Ala  Thr
               705                     710                          715

TTC  ATC  AAA  CGT  TTC  CCT  CAC  AAT  CCA  CGC  GAC  TGG  GAC  AGG  CTC  CCC      2330
Phe  Ile  Lys  Arg  Phe  Pro  His  Asn  Pro  Arg  Asp  Trp  Asp  Arg  Leu  Pro
     720                          725                     730

TAC  CTC  AAC  CTA  CCA  TAC  CTT  CCA  CCC  AAT  GCA  GGA  CGC  CAG  TAC  CAC      2378
Tyr  Leu  Asn  Leu  Pro  Tyr  Leu  Pro  Pro  Asn  Ala  Gly  Arg  Gln  Tyr  His
735                     740                          745                     750

CTT  GCC  ATG  GCT  GCA  TCA  GAG  TTC  AAG  AGA  CCC  CGA  ACT  CGA  GAG  TGC      2426
Leu  Ala  Met  Ala  Ala  Ser  Glu  Phe  Lys  Arg  Pro  Arg  Thr  Arg  Glu  Cys
                    755                          760                          765

CGT  CAG  AGC  AAT  GGA  AGC  AGC  AGC  CAA  CGT  GGA  CCC  ACT  ATT  CCA  ATC      2474
Arg  Gln  Ser  Asn  Gly  Ser  Ser  Ser  Gln  Arg  Gly  Pro  Thr  Ile  Pro  Ile
               770                          775                          780

TGC  ACT  CAG  TGT  GTT  CAT  GTG  GCT  GGA  AGA  GAA  TGG  GAT  TGT  GAC  TGA      2522
Cys  Thr  Gln  Cys  Val  His  Val  Ala  Gly  Arg  Glu  Trp  Asp  Cys  Asp
                    785                          790                     795

CATGGCCAAC  TTCGCACTCA  GCGACCCGAA  CGCCCATCGG  ATGCGAAATT  TTTTTGCAAA            2582

CGACCACAAG  CAGGCAGCAA  GTCGCAAAGG  GCCAAGTACG  GGACAGCAGG  CTACGGAGTG            2642

GAGGCTCGGG  GCCCCCACAC  CAGAGGAAGC  ACAGAGGGAA  AAAGACACAC  GGATCTCAAA            2702

GAAGATGGAG  ACCATGGGCA  TCTACTTTGC  AACACCAGAA  TGGGTAGCAC  TCAATGGGCA            2762

CCGAGGGCCA  AGCCCCGGCC  AGCTAAAGTA  CGGGCAGAAC  ACACGAGAAA  TACGGACCCA            2822

AACGAGGACT  ATCTAGACTA  CGTGCATGCA  GAGAAGAGCC  GGTTGGCATC  AGAAGAACAA            2882

ATCCTAAGGG  CAGCTACGTC  AGATCTACGG  GGCTCCAGGA  CAGGCAGAGC  ACCCCAAGCT            2942

TTCATAGACG  AAGTTGCCAA  AGTCTATGAA  ATCAACCATG  ACGTGGCCC   AAACCAAGAA            3002

CAGATGAAAG  ATCTGCTCTT  GACTGCGATG  GAGATGAAGC  ATCGCAATCC  CAGGCGGGCT            3062

CTACCAAAGC  CCAAGCAAAA  ACCCAATGCT  CCAACACAGA  GACCCCTGG   TCGGCTGGGG            3122

CTGGATCAGG  ACCGTCTCTG  ATGAGGACCT  TGAGTGAGGC  TCCTGGGAGT  CTCCCGACAA            3182
```

| | | | | | | | |
|---|---|---|---|---|---|---|---|
| CACCCGCGCA | GGTGTGGACA | CAATTCGGCC | TTACAACATC | CCAAATTGGA | TCCGTTCGCG | | 3242 |
| GGTCCCCAAA | AAAAAAAAA | AAAAAAAAA | AAAAAAAAA | AAAAAAAAA | AAAAAAAAA | | 3302 |
| AAGTACCTTC | TGAGGCGGAA | AGAACCAGCC | GGATCCCTCG | AGGGATCC | | | 3350 |

(2) INFORMATION FOR SEQ ID NO:2:

(i) SEQUENCE CHARACTERISTICS:
        (A) LENGTH: 797 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Asn Leu Gln Asp Gln Thr Gln Gln Ile Val Pro Phe Ile Arg
  1               5                  10                  15
Ser Leu Leu Met Pro Thr Thr Gly Pro Ala Ser Ile Pro Glu Thr Pro
                 20                  25                  30
Trp Arg Ser Thr Leu Ser Gly Gln Arg Leu Thr Tyr Asn Leu Thr Val
             35                  40                  45
Gly Asp Thr Gly Ser Gly Leu Ile Val Phe Phe Pro Gly Phe Pro Gly
         50                  55                  60
Ser Ile Val Gly Ala His Tyr Thr Leu Gln Ser Asn Gly Asn Tyr Lys
 65                  70                  75                  80
Phe Asp Arg Met Leu Leu Thr Ala Gln Asn Leu Pro Ala Ser Tyr Asn
                 85                  90                  95
Tyr Cys Arg Leu Val Ser Arg Ser Leu Thr Val Arg Ser Ser Thr Leu
                100                 105                 110
Pro Gly Gly Val Tyr Ala Leu Asn Gly Thr Ile Asn Ala Val Thr Phe
            115                 120                 125
Gln Gly Ser Leu Ser Glu Leu Thr Asp Val Ser Tyr Asn Gly Leu Met
130                 135                 140
Ser Ala Thr Ala Asn Ile Asn Asp Lys Ile Gly Asn Val Leu Val Gly
145                 150                 155                 160
Glu Gly Val Thr Val Leu Ser Leu Pro Thr Ser Tyr Asp Leu Gly Tyr
                165                 170                 175
Val Arg Leu Gly Asp Pro Ile Pro Ala Ile Gly Leu Asp Pro Lys Met
                180                 185                 190
Val Ala Thr Cys Asp Ser Ser Asp Arg Pro Arg Val Tyr Thr Ile Thr
            195                 200                 205
Ala Ala Asp Asp Tyr Gln Phe Ser Ser Gln Tyr Gln Pro Gly Gly Val
210                 215                 220
Thr Ile Thr Leu Phe Ser Ala Asn Ile Asp Ala Ile Thr Ser Leu Ser
225                 230                 235                 240
Val Gly Gly Glu Leu Val Phe Arg Thr Ser Val His Gly Leu Val Leu
                245                 250                 255
Gly Ala Thr Ile Tyr Leu Ile Gly Phe Asp Gly Thr Thr Val Ile Thr
            260                 265                 270
Arg Ala Val Ala Ala Asn Thr Gly Leu Thr Thr Gly Thr Asp Asn Leu
            275                 280                 285
Met Pro Phe Asn Leu Val Ile Pro Thr Asn Glu Ile Thr Gln Pro Ile
290                 295                 300
Thr Ser Ile Lys Leu Glu Ile Val Thr Ser Lys Ser Gly Gly Gln Ala
305                 310                 315                 320
Gly Asp Gln Met Leu Trp Ser Ala Arg Gly Ser Leu Ala Val Thr Ile
                325                 330                 335
```

| | | | | | | | | | | | | | | |
|---|---|---|---|---|---|---|---|---|---|---|---|---|---|---|
| His | Gly | Gly | Asn<br>340 | Tyr | Pro | Gly<br>345 | Ala | Leu | Arg | Pro | Val<br>350 | Leu | Val | Ala |
| Tyr | Glu | Arg<br>355 | Val | Ala | Thr | Gly<br>360 | Ser | Val | Val | Thr<br>365 | Val | Ala | Gly | Val | Ser |
| Asn | Phe<br>370 | Glu | Leu | Ile | Pro<br>375 | Asn | Pro | Glu | Leu | Ala<br>380 | Lys | Asn | Leu | Val | Thr |
| Glu<br>385 | Tyr | Gly | Arg | Phe | Asp<br>390 | Pro | Gly | Ala | Met | Asn<br>395 | Tyr | Thr | Lys | Leu | Ile<br>400 |
| Leu | Ser | Glu | Arg | Asp<br>405 | Arg | Leu | Gly | Ile | Lys<br>410 | Thr | Val | Trp | Pro | Thr<br>415 | Arg |
| Glu | Tyr | Thr | Asp<br>420 | Phe | Arg | Glu | Tyr | Phe<br>425 | Met | Glu | Val | Ala | Asp<br>430 | Leu | Asn |
| Ser | Pro | Leu<br>435 | Lys | Ile | Ala | Gly | Ala<br>440 | Phe | Gly | Phe | Lys | Asp<br>445 | Ile | Ile | Arg |
| Ala | Ile<br>450 | Arg | Arg | Ile | Ala | Val<br>455 | Pro | Val | Val | Ser | Thr<br>460 | Leu | Phe | Pro | Pro |
| Ala<br>465 | Ala | Pro | Leu | Ala | His<br>470 | Ala | Ile | Gly | Glu | Gly<br>475 | Val | Asp | Tyr | Leu | Leu<br>480 |
| Gly | Asp | Glu | Ala | Gln<br>485 | Ala | Ala | Ser | Gly | Thr<br>490 | Ala | Arg | Ala | Ala | Ser<br>495 | Gly |
| Lys | Ala | Arg | Ala<br>500 | Ala | Ser | Gly | Arg | Ile<br>505 | Arg | Gln | Leu | Thr | Leu<br>510 | Ala | Ala |
| Asp | Lys | Gly<br>515 | Tyr | Glu | Val | Val | Ala<br>520 | Asn | Leu | Phe | Gln | Val<br>525 | Pro | Gln | Asn |
| Pro | Val<br>530 | Val | Asp | Gly | Ile | Leu<br>535 | Ala | Ser | Pro | Gly | Val<br>540 | Leu | Arg | Gly | Ala |
| His<br>545 | Asn | Leu | Asp | Cys | Val<br>550 | Leu | Arg | Glu | Gly | Ala<br>555 | Thr | Leu | Phe | Pro | Val<br>560 |
| Val | Ile | Thr | Thr | Val<br>565 | Glu | Asp | Ala | Met | Thr<br>570 | Pro | Lys | Ala | Leu | Asn<br>575 | Ser |
| Lys | Met | Phe | Ala<br>580 | Val | Ile | Glu | Gly | Val<br>585 | Arg | Glu | Asp | Leu | Gln<br>590 | Pro | Pro |
| Ser | Gln | Arg<br>595 | Gly | Ser | Phe | Ile | Arg<br>600 | Thr | Leu | Ser | Gly | His<br>605 | Arg | Val | Tyr |
| Gly | Tyr<br>610 | Ala | Pro | Asp | Gly | Val<br>615 | Leu | Pro | Leu | Glu | Thr<br>620 | Gly | Arg | Asp | Tyr |
| Thr<br>625 | Val | Val | Pro | Ile | Asp<br>630 | Asp | Val | Trp | Asp | Ser<br>635 | Ile | Met | Leu | Ser<br>640 | |
| Lys | Asp | Pro | Ile | Pro<br>645 | Pro | Ile | Val | Gly | Asn<br>650 | Ser | Gly | Asn | Leu | Ala<br>655 | Ile |
| Ala | Tyr | Met | Asp<br>660 | Val | Phe | Arg | Pro | Lys<br>665 | Val | Pro | Ile | His | Val<br>670 | Ala | Met |
| Thr | Gly | Ala<br>675 | Leu | Asn | Ala | Cys | Gly<br>680 | Glu | Ile | Glu | Lys | Val<br>685 | Ser | Phe | Arg |
| Ser | Thr | Lys<br>690 | Leu | Ala | Thr | Ala | His<br>695 | Arg | Leu | Gly | Leu<br>700 | Lys | Leu | Ala | Gly |
| Pro<br>705 | Gly | Ala | Phe | Asp | Val<br>710 | Asn | Thr | Gly | Pro | Asn<br>715 | Trp | Ala | Thr | Phe | Ile<br>720 |
| Lys | Arg | Phe | Pro | His<br>725 | Asn | Pro | Arg | Asp | Trp<br>730 | Asp | Arg | Leu | Pro | Tyr<br>735 | Leu |
| Asn | Leu | Pro | Tyr<br>740 | Leu | Pro | Pro | Asn | Ala<br>745 | Gly | Arg | Gln | Tyr | His<br>750 | Leu | Ala |
| Met | Ala | Ala | Ser | Glu | Phe | Lys | Arg | Pro | Arg | Thr | Arg | Glu | Cys | Arg | Gln |

|   |   |   |   |   |   | 755 |   |   |   | 760 |   |   |   | 765 |   |
|---|---|---|---|---|---|---|---|---|---|---|---|---|---|---|---|
| Ser | Asn | Gly | Ser | Ser | Ser | Gln | Arg | Gly | Pro | Thr | Ile | Pro | Ile | Cys | Thr |
|   | 770 |   |   |   |   | 775 |   |   |   | 780 |   |   |   |   |   |
| Gln | Cys | Val | His | Val | Ala | Gly | Arg | Glu | Trp | Asp | Cys | Asp |   |   |   |
| 785 |   |   |   |   | 790 |   |   |   |   | 795 |   |   |   |   |   |

( 2 ) INFORMATION FOR SEQ ID NO:3:

( i ) SEQUENCE CHARACTERISTICS:
    ( A ) LENGTH: 5426 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: CDS
    ( B ) LOCATION: 73..1182
    ( D ) OTHER INFORMATION: /product="HVT UL42"

( i x ) FEATURE:
    ( A ) NAME/KEY: CDS
    ( B ) LOCATION: 1306..2574
    ( D ) OTHER INFORMATION: /product="HVT UL43"

( i x ) FEATURE:
    ( A ) NAME/KEY: CDS
    ( B ) LOCATION: 2790..4259
    ( D ) OTHER INFORMATION: /product="HVT gA"

( i x ) FEATURE:
    ( A ) NAME/KEY: CDS
    ( B ) LOCATION: 4701..5339
    ( D ) OTHER INFORMATION: /product="HVT UL45"

( x i ) SEQUENCE DESCRIPTION: SEQ ID NO:3:

```
GGATCCGAGC TTCTACTATA CAACGCGGAC GATAATTTTG TCCACCCCAT CGGTGTTCGA           60

GAAAGGGTTT TT ATG ATG GCA GGA ATA ACT GTC GCA TGT GAC CAC ACT              108
              Met Met Ala Gly Ile Thr Val Ala Cys Asp His Thr
                1               5                   10

GCA GGA GAG GCT CAT ACA CCC GAG GAT ATG CAA AAG AAA TGG AGG ATT            156
Ala Gly Glu Ala His Thr Pro Glu Asp Met Gln Lys Lys Trp Arg Ile
            15                  20                  25

ATA TTG GCA GGG GAA AAA TTC ATG ACT ATA TCG GCA TCG TTG AAA TCG            204
Ile Leu Ala Gly Glu Lys Phe Met Thr Ile Ser Ala Ser Leu Lys Ser
         30                  35                  40

ATC GTC AGT TGT GTG AAA AAC CCC CTT CTC ACG TTT GGC GCA GAT GGG            252
Ile Val Ser Cys Val Lys Asn Pro Leu Leu Thr Phe Gly Ala Asp Gly
 45                  50                  55                  60

CTC ATT GTA CAA GGT ACT GTC TGC GGA CAG CGC ATT TTT GTT CCA ATC            300
Leu Ile Val Gln Gly Thr Val Cys Gly Gln Arg Ile Phe Val Pro Ile
                 65                  70                  75

GAC CGT GAT TCC TTC AGC GAA TAT GAA TGG CAT GGG CCA ACT GCG ATG            348
Asp Arg Asp Ser Phe Ser Glu Tyr Glu Trp His Gly Pro Thr Ala Met
             80                  85                  90

TTT CTA GCA TTA ACT GAT TCC AGA CGC ACT CTT TTA GAT GCA TTC AAA            396
Phe Leu Ala Leu Thr Asp Ser Arg Arg Thr Leu Leu Asp Ala Phe Lys
         95                 100                 105

TGT GAA AAG AGA AGG GCA ATT GAC GTC TCC TTT ACC TTC GCG GGA GAG            444
Cys Glu Lys Arg Arg Ala Ile Asp Val Ser Phe Thr Phe Ala Gly Glu
110                 115                 120

CCT CCA TGT AGG CAT TTA ATC CAA GCC GTC ACA TAC ATG ACC GAC GGT            492
```

```
Pro  Pro  Cys  Arg  His  Leu  Ile  Gln  Ala  Val  Thr  Tyr  Met  Thr  Asp  Gly
125            130                      135                      140

GGT  TCA  GTA  TCG  AAT  ACA  ATC  ATT  AAA  TAT  GAG  CTC  TGG  AAT  GCG  TCT      540
Gly  Ser  Val  Ser  Asn  Thr  Ile  Ile  Lys  Tyr  Glu  Leu  Trp  Asn  Ala  Ser
                    145                      150                      155

ACA  ATT  TTC  CCC  CAA  AAA  ACT  CCC  GAT  GTT  ACC  TTT  TCT  CTA  AAC  AAA      588
Thr  Ile  Phe  Pro  Gln  Lys  Thr  Pro  Asp  Val  Thr  Phe  Ser  Leu  Asn  Lys
               160                      165                      170

CAA  CAA  TTG  AAC  AAA  ATA  TTG  GCC  GTC  GCT  TCA  AAA  CTG  CAA  CAC  GAA      636
Gln  Gln  Leu  Asn  Lys  Ile  Leu  Ala  Val  Ala  Ser  Lys  Leu  Gln  His  Glu
          175                      180                      185

GAA  CTT  GTA  TTC  TCT  TTA  AAA  CCT  GAA  GGA  GGG  TTC  TAC  GTA  GGA  ACG      684
Glu  Leu  Val  Phe  Ser  Leu  Lys  Pro  Glu  Gly  Gly  Phe  Tyr  Val  Gly  Thr
     190                      195                      200

GTT  TGT  ACT  GTT  ATA  AGT  TTC  GAA  GTA  GAT  GGG  ACT  GCC  ATG  ACT  CAG      732
Val  Cys  Thr  Val  Ile  Ser  Phe  Glu  Val  Asp  Gly  Thr  Ala  Met  Thr  Gln
205                 210                      215                      220

TAT  CCT  TAC  AAC  CCT  CCA  ACC  TCG  GCT  ACC  CTA  GCT  CTC  GTA  GTA  GCA      780
Tyr  Pro  Tyr  Asn  Pro  Pro  Thr  Ser  Ala  Thr  Leu  Ala  Leu  Val  Val  Ala
                    225                      230                      235

TGC  AGA  AAG  AAG  AAG  GCG  AAT  AAA  AAC  ACT  ATT  TTA  ACG  GCC  TAT  GGA      828
Cys  Arg  Lys  Lys  Lys  Ala  Asn  Lys  Asn  Thr  Ile  Leu  Thr  Ala  Tyr  Gly
               240                      245                      250

AGT  GGT  AAA  CCC  TTT  TGT  GTT  GCA  TTG  GAA  GAT  ACT  AGT  GCA  TTT  AGA      876
Ser  Gly  Lys  Pro  Phe  Cys  Val  Ala  Leu  Glu  Asp  Thr  Ser  Ala  Phe  Arg
          255                      260                      265

AAT  ATC  GTC  AAT  AAA  ATC  AAG  GCG  GGT  ACG  TCG  GGA  GTT  GAT  CTG  GGG      924
Asn  Ile  Val  Asn  Lys  Ile  Lys  Ala  Gly  Thr  Ser  Gly  Val  Asp  Leu  Gly
     270                      275                      280

TTT  TAT  ACA  ACT  TGC  GAT  CCG  CCG  ATG  CTA  TGT  ATT  CGC  CCA  CAC  GCA      972
Phe  Tyr  Thr  Thr  Cys  Asp  Pro  Pro  Met  Leu  Cys  Ile  Arg  Pro  His  Ala
285                 290                      295                      300

TTT  GGA  AGT  CCT  ACC  GCA  TTC  CTG  TTT  TGT  AAC  ACA  GAC  TGT  ATG  ACA     1020
Phe  Gly  Ser  Pro  Thr  Ala  Phe  Leu  Phe  Cys  Asn  Thr  Asp  Cys  Met  Thr
                    305                      310                      315

ATA  TAT  GAA  CTG  GAA  GAA  GTA  AGC  GCC  GTT  GAT  GGT  GCA  ATC  CGA  GCA     1068
Ile  Tyr  Glu  Leu  Glu  Glu  Val  Ser  Ala  Val  Asp  Gly  Ala  Ile  Arg  Ala
               320                      325                      330

AAA  CGC  ATC  AAC  GAA  TAT  TTC  CCA  ACA  GTA  TCG  CAG  GCT  ACT  TCC  AAG     1116
Lys  Arg  Ile  Asn  Glu  Tyr  Phe  Pro  Thr  Val  Ser  Gln  Ala  Thr  Ser  Lys
          335                      340                      345

AAG  AGA  AAA  CAG  TCG  CCG  CCC  CCT  ATC  GAA  AGA  GAA  AGG  AAA  ACC  ACC     1164
Lys  Arg  Lys  Gln  Ser  Pro  Pro  Pro  Ile  Glu  Arg  Glu  Arg  Lys  Thr  Thr
     350                      355                      360

AGA  GCG  GAT  ACC  CAA  TAAAATGCCA  GACAAACCCG  GCATCCTGGT  TAGAGGGCAG            1219
Arg  Ala  Asp  Thr  Gln
365                 370

GTGGGCTGGG  CCAACCTTCA  CGGGCGTCCG  ACAGATCGGT  GACACTCATA  CGTTAACTAA            1279

ACGCCGGCAG  CTTTGCAGAA  GAAAAT  ATG  CCT  TCC  GGA  GCC  AGC  TCG  AGT  CCT       1332
                               Met  Pro  Ser  Gly  Ala  Ser  Ser  Ser  Pro
                                1                      5

CCA  CCA  GCT  TAT  ACA  TCT  GCA  GCT  CCG  CTT  GAG  ACT  TAT  AAC  AGC  TGG     1380
Pro  Pro  Ala  Tyr  Thr  Ser  Ala  Ala  Pro  Leu  Glu  Thr  Tyr  Asn  Ser  Trp
     10                       15                      20                      25

CTA  AGT  GCC  TTT  TCA  TGC  GCA  TAT  CCC  CAA  TGC  ACT  GCG  GGA  AGA  GGA     1428
Leu  Ser  Ala  Phe  Ser  Cys  Ala  Tyr  Pro  Gln  Cys  Thr  Ala  Gly  Arg  Gly
               30                       35                      40

CAT  CGA  CAA  AAT  GGC  AAG  AAG  TGT  ATA  CGG  TGT  ATA  GTG  ATC  AGT  GTA     1476
His  Arg  Gln  Asn  Gly  Lys  Lys  Cys  Ile  Arg  Cys  Ile  Val  Ile  Ser  Val
          45                       50                      55
```

| | | | | | | | | | | | | | | | | |
|---|---|---|---|---|---|---|---|---|---|---|---|---|---|---|---|---|
| TGT | TCC | TTA | GTG | TGC | ATC | GCT | GCA | CAT | TTA | GCT | GTT | ACC | GTG | TCG | GGA | 1524 |
| Cys | Ser | Leu | Val | Cys | Ile | Ala | Ala | His | Leu | Ala | Val | Thr | Val | Ser | Gly | |
| | 60 | | | | 65 | | | | | | 70 | | | | | |
| GTG | GCA | TTA | ATT | CCG | CTT | ATC | GAT | CAA | AAC | AGA | GCT | TAC | GGA | AAC | TGT | 1572 |
| Val | Ala | Leu | Ile | Pro | Leu | Ile | Asp | Gln | Asn | Arg | Ala | Tyr | Gly | Asn | Cys | |
| | 75 | | | | | 80 | | | | | 85 | | | | | |
| ACG | GTA | TGT | GTA | ATT | GCC | GGA | TTC | ATC | GCT | ACG | TTT | GCT | GCA | CGA | CTT | 1620 |
| Thr | Val | Cys | Val | Ile | Ala | Gly | Phe | Ile | Ala | Thr | Phe | Ala | Ala | Arg | Leu | |
| 90 | | | | | 95 | | | | | 100 | | | | | 105 | |
| ACG | ATA | AGA | CTT | TCG | GAA | ACG | CTT | ATG | CTA | GTG | GGC | AAG | CCG | GCG | CAG | 1668 |
| Thr | Ile | Arg | Leu | Ser | Glu | Thr | Leu | Met | Leu | Val | Gly | Lys | Pro | Ala | Gln | |
| | | | | 110 | | | | | 115 | | | | | 120 | | |
| TTT | ATA | TTT | GCT | ATA | ATC | GCT | TCC | GTT | GCG | GAA | ACA | CTG | ATC | AAT | AAC | 1716 |
| Phe | Ile | Phe | Ala | Ile | Ile | Ala | Ser | Val | Ala | Glu | Thr | Leu | Ile | Asn | Asn | |
| | | | 125 | | | | | 130 | | | | | 135 | | | |
| GAG | GCG | CTT | GCC | ATC | AGT | AAT | ACT | ACT | TAC | AAA | ACT | GCA | TTG | CGA | ATA | 1764 |
| Glu | Ala | Leu | Ala | Ile | Ser | Asn | Thr | Thr | Tyr | Lys | Thr | Ala | Leu | Arg | Ile | |
| | | 140 | | | | | 145 | | | | | 150 | | | | |
| ATC | GAA | GTA | ACA | TCT | TTG | GCG | TGT | TTT | GTT | ATG | CTC | GGG | GCA | ATA | ATT | 1812 |
| Ile | Glu | Val | Thr | Ser | Leu | Ala | Cys | Phe | Val | Met | Leu | Gly | Ala | Ile | Ile | |
| 155 | | | | | 160 | | | | | 165 | | | | | | |
| ACA | TCC | CAC | AAC | TAT | GTC | TGC | ATT | TCA | ACG | GCA | GGG | GAC | TTG | ACT | TGG | 1860 |
| Thr | Ser | His | Asn | Tyr | Val | Cys | Ile | Ser | Thr | Ala | Gly | Asp | Leu | Thr | Trp | |
| 170 | | | | | 175 | | | | | 180 | | | | | 185 | |
| AAG | GGC | GGG | ATT | TTT | CAT | GCT | TAC | CAC | GGA | ACA | TTA | CTC | GGT | ATA | ACA | 1908 |
| Lys | Gly | Gly | Ile | Phe | His | Ala | Tyr | His | Gly | Thr | Leu | Leu | Gly | Ile | Thr | |
| | | | | 190 | | | | | 195 | | | | | 200 | | |
| ATA | CCA | AAC | ATA | CAC | CCA | ATC | CCT | CTC | GCG | GGG | TTT | CTT | GCA | GTC | TAT | 1956 |
| Ile | Pro | Asn | Ile | His | Pro | Ile | Pro | Leu | Ala | Gly | Phe | Leu | Ala | Val | Tyr | |
| | | | 205 | | | | | 210 | | | | | 215 | | | |
| ACA | ATA | TTG | GCT | ATA | AAT | ATC | GCT | AGA | GAT | GCA | AGC | GCT | ACA | TTA | TTA | 2004 |
| Thr | Ile | Leu | Ala | Ile | Asn | Ile | Ala | Arg | Asp | Ala | Ser | Ala | Thr | Leu | Leu | |
| | | 220 | | | | | 225 | | | | | 230 | | | | |
| TCC | ACT | TGC | TAT | TAT | CGC | AAT | TGC | CGC | GAG | AGG | ACT | ATA | CTT | CGC | CCT | 2052 |
| Ser | Thr | Cys | Tyr | Tyr | Arg | Asn | Cys | Arg | Glu | Arg | Thr | Ile | Leu | Arg | Pro | |
| | 235 | | | | | 240 | | | | | 245 | | | | | |
| TCT | CGT | CTC | GGA | CAT | GGT | TAC | ACA | ATC | CCT | TCT | CCC | GGT | GCC | GAT | ATG | 2100 |
| Ser | Arg | Leu | Gly | His | Gly | Tyr | Thr | Ile | Pro | Ser | Pro | Gly | Ala | Asp | Met | |
| 250 | | | | | 255 | | | | | 260 | | | | | 265 | |
| CTT | TAT | GAA | GAA | GAC | GTA | TAT | AGT | TTT | GAC | GCA | GCT | AAA | GGC | CAT | TAT | 2148 |
| Leu | Tyr | Glu | Glu | Asp | Val | Tyr | Ser | Phe | Asp | Ala | Ala | Lys | Gly | His | Tyr | |
| | | | | 270 | | | | | 275 | | | | | 280 | | |
| TCG | TCA | ATA | TTT | CTA | TGT | TAT | GCC | ATG | GGG | CTT | ACA | ACA | CCG | CTG | ATT | 2196 |
| Ser | Ser | Ile | Phe | Leu | Cys | Tyr | Ala | Met | Gly | Leu | Thr | Thr | Pro | Leu | Ile | |
| | | | 285 | | | | | 290 | | | | | 295 | | | |
| ATT | GCG | CTC | CAT | AAA | TAT | ATG | GCG | GGC | ATT | AAA | AAT | TCG | TCA | GAT | TGG | 2244 |
| Ile | Ala | Leu | His | Lys | Tyr | Met | Ala | Gly | Ile | Lys | Asn | Ser | Ser | Asp | Trp | |
| | | 300 | | | | | 305 | | | | | 310 | | | | |
| ACT | GCT | ACA | TTA | CAA | GGC | ATG | TAC | GGG | CTT | GTC | TTG | GGA | TCG | CTA | TCG | 2292 |
| Thr | Ala | Thr | Leu | Gln | Gly | Met | Tyr | Gly | Leu | Val | Leu | Gly | Ser | Leu | Ser | |
| | 315 | | | | | 320 | | | | | 325 | | | | | |
| TCA | CTA | TGT | ATT | CCA | TCC | AGC | AAC | AAC | GAT | GCC | CTA | ATT | CGT | CCC | ATT | 2340 |
| Ser | Leu | Cys | Ile | Pro | Ser | Ser | Asn | Asn | Asp | Ala | Leu | Ile | Arg | Pro | Ile | |
| 330 | | | | | 335 | | | | | 340 | | | | | 345 | |
| CAA | ATT | TTG | ATA | TTG | ATA | ATC | GGT | GCA | CTG | GCC | ATT | GCA | TTG | GCT | GGA | 2388 |
| Gln | Ile | Leu | Ile | Leu | Ile | Ile | Gly | Ala | Leu | Ala | Ile | Ala | Leu | Ala | Gly | |
| | | | | 350 | | | | | 355 | | | | | 360 | | |
| TGT | GGT | CAA | ATT | ATA | GGG | CCT | ACA | TTA | TTT | GCC | GCG | AGT | TCG | GCT | GCG | 2436 |
| Cys | Gly | Gln | Ile | Ile | Gly | Pro | Thr | Leu | Phe | Ala | Ala | Ser | Ser | Ala | Ala | |
| | | | 365 | | | | | 370 | | | | | 375 | | | |

```
ATG TCA TGT TTT ACA TGT ATC AAT ATT CGC GCT ACT AAT AAG GGT GTC           2484
Met Ser Cys Phe Thr Cys Ile Asn Ile Arg Ala Thr Asn Lys Gly Val
        380                 385                 390

AAC AAA TTG GCA GCA GCC AGT GTC GTG AAA TCT GTA CTG GGC TTC ATT           2532
Asn Lys Leu Ala Ala Ala Ser Val Val Lys Ser Val Leu Gly Phe Ile
        395                 400                 405

ATT TCC GGG ATG CTT ACT TGC GTG CTA TTA CCA CTA TCG TGATAGATCG            2581
Ile Ser Gly Met Leu Thr Cys Val Leu Leu Pro Leu Ser
410                 415                 420

TCGGTCTGCG CATCGCCCAT GCTGGCGGAA CGCTCTTTCG AACCGTGAAT AAAACTTTGT         2641

ATCTACTAAA CAATAACTTT GTGTTTTATT GAGCGGTCGA AAACAATGAG GAGCTGCAAT         2701

TTAAAGCTAA CCGCATACGC CGGGCGGGTA AGACCATTT TATACCATAT TACGCATCTA          2761

TCGAAACTTG TTCGAGAACC GCAAGTAT ATG GTT TCC AAC ATG CGC GTT CTA            2813
                                Met Val Ser Asn Met Arg Val Leu
                                  1                 5

CGC GTA CTG CGC CTG ACG GGA TGG GTG GGC ATA TTT CTA GTT CTG TCT           2861
Arg Val Leu Arg Leu Thr Gly Trp Val Gly Ile Phe Leu Val Leu Ser
         10                  15                 20

TTA CAG CAA ACC TCT TGT GCC GGA TTG CCC CAT AAC GTC GAT ACC CAT           2909
Leu Gln Gln Thr Ser Cys Ala Gly Leu Pro His Asn Val Asp Thr His
 25                  30                 35                  40

CAT ATC CTA ACT TTC AAC CCT TCT CCC ATT TCG GCC GAT GGC GTT CCT           2957
His Ile Leu Thr Phe Asn Pro Ser Pro Ile Ser Ala Asp Gly Val Pro
             45                  50                 55

TTG TCA GAG GTG CCC AAT TCG CCT ACC GAA TTA TCT ACA ACT GTC               3005
Leu Ser Glu Val Pro Asn Ser Pro Thr Thr Glu Leu Ser Thr Thr Val
             60                  65                 70

GCC ACC AAG ACA GCT GTA CCG ACG ACT GAA AGC ACT AGT TCC TCC GAA           3053
Ala Thr Lys Thr Ala Val Pro Thr Thr Glu Ser Thr Ser Ser Ser Glu
         75                  80                 85

GCG CAC CGC AAC TCT TCT CAC AAA ATA CCT GAT ATA ATC TGC GAC CGA           3101
Ala His Arg Asn Ser Ser His Lys Ile Pro Asp Ile Ile Cys Asp Arg
         90                  95                 100

GAA GAA GTA TTC GTA TTC CTT AAC AAT ACA GGA AGA ATT TTG TGT GAC           3149
Glu Glu Val Phe Val Phe Leu Asn Asn Thr Gly Arg Ile Leu Cys Asp
105                 110                 115                 120

CTT ATA GTC GAC CCC CCT TCA GAC GAT GAA TGG TCC AAC TTC GCT CTT           3197
Leu Ile Val Asp Pro Pro Ser Asp Asp Glu Trp Ser Asn Phe Ala Leu
                125                 130                 135

GAC GTC ACG TTC AAT CCA ATC GAA TAC CAC GCC AAC GAA AAG AAT GTA           3245
Asp Val Thr Phe Asn Pro Ile Glu Tyr His Ala Asn Glu Lys Asn Val
             140                 145                 150

GAG GTT GCC CGA GTG GCC GGT CTA TAC GGA GTA CCG GGG TCG GAT TAT           3293
Glu Val Ala Arg Val Ala Gly Leu Tyr Gly Val Pro Gly Ser Asp Tyr
         155                 160                 165

GCA TAC CCT AGG AAA TCG GAA TTA ATA TCC TCC ATT CGA CGG GAT CCC           3341
Ala Tyr Pro Arg Lys Ser Glu Leu Ile Ser Ser Ile Arg Arg Asp Pro
         170                 175                 180

CAG GGT TCT TTC TGG ACT AGT CCT ACA CCC CGT GGA AAT AAA TAT TTC           3389
Gln Gly Ser Phe Trp Thr Ser Pro Thr Pro Arg Gly Asn Lys Tyr Phe
185                 190                 195                 200

ATA TGG ATT AAT AAA ACA ATG CAC ACC ATG GGC GTG GAA GTT AGA AAT           3437
Ile Trp Ile Asn Lys Thr Met His Thr Met Gly Val Glu Val Arg Asn
                205                 210                 215

GTC GAC TAC AAA GAC AAC GGC TAC TTT CAA GTG ATA CTG CGT GAT AGA           3485
Val Asp Tyr Lys Asp Asn Gly Tyr Phe Gln Val Ile Leu Arg Asp Arg
             220                 225                 230

TTT AAT CGC CCA TTG GTA GAA AAA CAT ATT TAC ATG CGT GTG TGC CAA           3533
```

```
            Phe Asn Arg Pro Leu Val Glu Lys His Ile Tyr Met Arg Val Cys Gln
                    235                 240                 245

CGA CCC GCA TCC GTG GAT GTA TTG GCC CCT CCA GTT CTC AGC GGA GAA          3581
Arg Pro Ala Ser Val Asp Val Leu Ala Pro Pro Val Leu Ser Gly Glu
    250                 255                 260

AAC TAC AAA GCA TCT TGC ATC GTT AGA CAT TTT TAT CCC CCG GGA TCT          3629
Asn Tyr Lys Ala Ser Cys Ile Val Arg His Phe Tyr Pro Pro Gly Ser
265                 270                 275                 280

GTC TAC GTA TCT TGG AGA CGT AAC GGA AAC ATT GCC ACA CCC CGC AAG          3677
Val Tyr Val Ser Trp Arg Arg Asn Gly Asn Ile Ala Thr Pro Arg Lys
                285                 290                 295

GAC CGT GAC GGG AGT TTT TGG TGG TTC GAA TCT GGC CGC GGG GCC ACA          3725
Asp Arg Asp Gly Ser Phe Trp Trp Phe Glu Ser Gly Arg Gly Ala Thr
            300                 305                 310

CTA GTA TCC ACA ATA ACC CTC GGA AAC TCT GGA CTC GAA TCT CCT CCA          3773
Leu Val Ser Thr Ile Thr Leu Gly Asn Ser Gly Leu Glu Ser Pro Pro
        315                 320                 325

AAG GTT TCC TGC TTG GTA GCG TGG AGG CAA GGC GAT ATG ATA AGC ACA          3821
Lys Val Ser Cys Leu Val Ala Trp Arg Gln Gly Asp Met Ile Ser Thr
    330                 335                 340

TCG AAT GCT ACA GCT GTA CCG ACG GTA TAT TAT CAC CCC CGT ATC TCT          3869
Ser Asn Ala Thr Ala Val Pro Thr Val Tyr Tyr His Pro Arg Ile Ser
345                 350                 355                 360

CTG GCA TTT AAA GAT GGG TAT GCA ATA TGT ACT ATA GAA TGT GTT CCC          3917
Leu Ala Phe Lys Asp Gly Tyr Ala Ile Cys Thr Ile Glu Cys Val Pro
                365                 370                 375

TCT GGG ATT ACT GTG AGG TGG TTA GTT CAT GAT GAA CCC CAG CCT AAC          3965
Ser Gly Ile Thr Val Arg Trp Leu Val His Asp Glu Pro Gln Pro Asn
            380                 385                 390

ACA ACT TAT GAT ACT GTG GTT ACA GGT CTC TGC AGG ACC ATC GAT CGT          4013
Thr Thr Tyr Asp Thr Val Val Thr Gly Leu Cys Arg Thr Ile Asp Arg
        395                 400                 405

TAT AGA AAT CTC GCC AGT CGG ATT CCA GTC CAG GAC AAC TGG GCG AAA          4061
Tyr Arg Asn Leu Ala Ser Arg Ile Pro Val Gln Asp Asn Trp Ala Lys
    410                 415                 420

ACG AAG TAT ACG TGC AGA CTA ATT GGA TAT CCG TTC GAC GTG GAT AGA          4109
Thr Lys Tyr Thr Cys Arg Leu Ile Gly Tyr Pro Phe Asp Val Asp Arg
425                 430                 435                 440

TTT CAA AAT TCC GAA TAT TAT GAT GCA ACG CCG TCG GCA AGA GGA ATG          4157
Phe Gln Asn Ser Glu Tyr Tyr Asp Ala Thr Pro Ser Ala Arg Gly Met
                445                 450                 455

CCG ATG ATT GTA ACA ATT ACG GCC GTT CTA GGA CTG GCC TTG TTT TTA          4205
Pro Met Ile Val Thr Ile Thr Ala Val Leu Gly Leu Ala Leu Phe Leu
            460                 465                 470

GGT ATT GGT ATC ATT ATC ACA GCC CTA TGC TTT TAC CTA CCG GGG CGG          4253
Gly Ile Gly Ile Ile Ile Thr Ala Leu Cys Phe Tyr Leu Pro Gly Arg
        475                 480                 485

AAT TAAGATTAAC CATCGTATGT GATATAAAAA TTATTAAGTG TTATAACCGA               4306
Asn
    490

TCGCATTCTT CTGTTTCGAT TCACAATAAA TAAAATGGTA TTGTAATCAG CACCATCGCA        4366

TTGTTTCGTA GATGACTCAT GTTCAGTCCG CGTGATGTCA AAAATACGTA TTTTTGGTAT        4426

CACGCAGCGG CCAAAATGCC CATTATGTTA TTTTTACTCC AAACGCGGTA TTTAAAACAT        4486

CGGGACGTAC ATCATGTGGC GCACGTTAAT CGTATACGGT GCCGCTACAT TAAAAATCGC        4546

AAGTCTCCGA ATATCAAGCT CACGGCCAAA ACGTCGGTAA TAATCTTACG CATCGAATGT        4606

GATACGGATA CCGTACAATC GCTGAGTAGA TTTCCTATAT AGTTACTCAG TAGTGATACA        4666

CAATCACAAA ATCGCTGGGG TATATCATAT AAGA ATG ATG TCG CCC ACC CCT           4718
```

```
                                    Met Met Ser Pro Thr Pro
                                     1               5
GAA GAT GAT CGC GAT CTC GTT GTG GTT CGT GGA CGT CTC CGA ATG ATG        4766
Glu Asp Asp Arg Asp Leu Val Val Val Arg Gly Arg Leu Arg Met Met
             10              15                  20

GAT AGC GGC ACG GAA ACA GAT AGA GAG CAA CGA CAT CCA CGT ACG ACT        4814
Asp Ser Gly Thr Glu Thr Asp Arg Glu Gln Arg His Pro Arg Thr Thr
         25              30                  35

TGG CGA TCG ATC TGT TGT GGG TGT ACG ATA GGA ATG GTA TTT ACC ATA        4862
Trp Arg Ser Ile Cys Cys Gly Cys Thr Ile Gly Met Val Phe Thr Ile
         40              45                  50

TTC GTT CTC GTA GCG GCA GTA TTG TTG GGA TCA CTA TTC ACT GTT TCA        4910
Phe Val Leu Val Ala Ala Val Leu Leu Gly Ser Leu Phe Thr Val Ser
 55              60                  65                      70

TAC ATG GCC ATG GAA TCG GGA ACA TGT CCC GAT GAA TGG ATT GGT TTG        4958
Tyr Met Ala Met Glu Ser Gly Thr Cys Pro Asp Glu Trp Ile Gly Leu
             75              80                      85

GGT TAT AGT TGC ATG CGC GTG GCC GGG AAA AAT GCA ACT GAT CTT GAG        5006
Gly Tyr Ser Cys Met Arg Val Ala Gly Lys Asn Ala Thr Asp Leu Glu
         90              95                  100

GCG TTG GAT ACA TGT GCT CGG CAT AAC AGC AAA CTT ATT GAC TTC GCA        5054
Ala Leu Asp Thr Cys Ala Arg His Asn Ser Lys Leu Ile Asp Phe Ala
         105             110                 115

AAC GCC AAA GTT CTG GTT GAA GCT ATC GCC CCA TTC GGT GTG CCA AAT        5102
Asn Ala Lys Val Leu Val Glu Ala Ile Ala Pro Phe Gly Val Pro Asn
 120             125                 130

GCA GCA TAT GGG GAA GTC TTC CGG TTA AGG GAC AGC AAA ACC ACG TGT        5150
Ala Ala Tyr Gly Glu Val Phe Arg Leu Arg Asp Ser Lys Thr Thr Cys
 135             140                 145                     150

ATA CGA CCT ACC ATG GGA GGA CCC GTG TCG GCA GAC TGT CCT GTA ACA        5198
Ile Arg Pro Thr Met Gly Gly Pro Val Ser Ala Asp Cys Pro Val Thr
                 155                 160                 165

TGT ACC GTT ATA TGT CAG CGA CCC AGG CCT CTA AGT ACC ATG TCT TCC        5246
Cys Thr Val Ile Cys Gln Arg Pro Arg Pro Leu Ser Thr Met Ser Ser
             170             175                 180

ATC ATT AGA GAT GCC CGC GTG TAT CTT CAT TTA GAA CGA CGC GAT TAT        5294
Ile Ile Arg Asp Ala Arg Val Tyr Leu His Leu Glu Arg Arg Asp Tyr
         185             190                 195

TAT GAA GTC TAC GCC TCT GTC CTC TCT AAT GCG ATG AGT AAATAAAAACGCA      5346
Tyr Glu Val Tyr Ala Ser Val Leu Ser Asn Ala Met Ser Lys
     200             205                 210

CCTCTAACGG TTACTGTGTT TATTATCCAA TCACACCATA GACATTATTA CAATAATATG      5406

GATCTTTATT TCATATAATG                                                  5426
```

( 2 ) INFORMATION FOR SEQ ID NO:4:

( i ) SEQUENCE CHARACTERISTICS:
        ( A ) LENGTH: 369 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Met Ala Gly Ile Thr Val Ala Cys Asp His Thr Ala Gly Glu Ala
 1               5                  10                      15

His Thr Pro Glu Asp Met Gln Lys Lys Trp Arg Ile Ile Leu Ala Gly
             20              25                  30

Glu Lys Phe Met Thr Ile Ser Ala Ser Leu Lys Ser Ile Val Ser Cys
         35              40                  45
```

-continued

| Val | Lys | Asn | Pro | Leu | Leu | Thr | Phe | Gly | Ala | Asp | Gly | Leu | Ile | Val | Gln |
| | 50 | | | | 55 | | | | | 60 | | | | | |

| Gly | Thr | Val | Cys | Gly | Gln | Arg | Ile | Phe | Val | Pro | Ile | Asp | Arg | Asp | Ser |
| 65 | | | | | 70 | | | | | 75 | | | | | 80 |

| Phe | Ser | Glu | Tyr | Glu | Trp | His | Gly | Pro | Thr | Ala | Met | Phe | Leu | Ala | Leu |
| | | | | 85 | | | | | 90 | | | | | 95 | |

| Thr | Asp | Ser | Arg | Arg | Thr | Leu | Leu | Asp | Ala | Phe | Lys | Cys | Glu | Lys | Arg |
| | | | 100 | | | | | 105 | | | | | 110 | | |

| Arg | Ala | Ile | Asp | Val | Ser | Phe | Thr | Phe | Ala | Gly | Glu | Pro | Pro | Cys | Arg |
| | | 115 | | | | | 120 | | | | | 125 | | | |

| His | Leu | Ile | Gln | Ala | Val | Thr | Tyr | Met | Thr | Asp | Gly | Gly | Ser | Val | Ser |
| | | 130 | | | | 135 | | | | | 140 | | | | |

| Asn | Thr | Ile | Ile | Lys | Tyr | Glu | Leu | Trp | Asn | Ala | Ser | Thr | Ile | Phe | Pro |
| 145 | | | | | 150 | | | | | 155 | | | | | 160 |

| Gln | Lys | Thr | Pro | Asp | Val | Thr | Phe | Ser | Leu | Asn | Lys | Gln | Gln | Leu | Asn |
| | | | | 165 | | | | | 170 | | | | | 175 | |

| Lys | Ile | Leu | Ala | Val | Ala | Ser | Lys | Leu | Gln | His | Glu | Glu | Leu | Val | Phe |
| | | | 180 | | | | | 185 | | | | | 190 | | |

| Ser | Leu | Lys | Pro | Glu | Gly | Gly | Phe | Tyr | Val | Gly | Thr | Val | Cys | Thr | Val |
| | | 195 | | | | | 200 | | | | | 205 | | | |

| Ile | Ser | Phe | Glu | Val | Asp | Gly | Thr | Ala | Met | Thr | Gln | Tyr | Pro | Tyr | Asn |
| | 210 | | | | | 215 | | | | | 220 | | | | |

| Pro | Pro | Thr | Ser | Ala | Thr | Leu | Ala | Leu | Val | Val | Ala | Cys | Arg | Lys | Lys |
| 225 | | | | | 230 | | | | | 235 | | | | | 240 |

| Lys | Ala | Asn | Lys | Asn | Thr | Ile | Leu | Thr | Ala | Tyr | Gly | Ser | Gly | Lys | Pro |
| | | | | 245 | | | | | 250 | | | | | 255 | |

| Phe | Cys | Val | Ala | Leu | Glu | Asp | Thr | Ser | Ala | Phe | Arg | Asn | Ile | Val | Asn |
| | | | 260 | | | | | 265 | | | | | 270 | | |

| Lys | Ile | Lys | Ala | Gly | Thr | Ser | Gly | Val | Asp | Leu | Gly | Phe | Tyr | Thr | Thr |
| | | 275 | | | | | 280 | | | | | 285 | | | |

| Cys | Asp | Pro | Pro | Met | Leu | Cys | Ile | Arg | Pro | His | Ala | Phe | Gly | Ser | Pro |
| | 290 | | | | | 295 | | | | | 300 | | | | |

| Thr | Ala | Phe | Leu | Phe | Cys | Asn | Thr | Asp | Cys | Met | Thr | Ile | Tyr | Glu | Leu |
| 305 | | | | | 310 | | | | | 315 | | | | | 320 |

| Glu | Glu | Val | Ser | Ala | Val | Asp | Gly | Ala | Ile | Arg | Ala | Lys | Arg | Ile | Asn |
| | | | | 325 | | | | | 330 | | | | | 335 | |

| Glu | Tyr | Phe | Pro | Thr | Val | Ser | Gln | Ala | Thr | Ser | Lys | Lys | Arg | Lys | Gln |
| | | | 340 | | | | | 345 | | | | | 350 | | |

| Ser | Pro | Pro | Pro | Ile | Glu | Arg | Glu | Arg | Lys | Thr | Thr | Arg | Ala | Asp | Thr |
| | | 355 | | | | | 360 | | | | | 365 | | | |

| Gln |

( 2 ) INFORMATION FOR SEQ ID NO:5:

( i ) SEQUENCE CHARACTERISTICS:
        ( A ) LENGTH: 422 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Pro | Ser | Gly | Ala | Ser | Ser | Ser | Pro | Pro | Ala | Tyr | Thr | Ser | Ala |
| 1 | | | | 5 | | | | | 10 | | | | | 15 |

| Ala | Pro | Leu | Glu | Thr | Tyr | Asn | Ser | Trp | Leu | Ser | Ala | Phe | Ser | Cys | Ala |
| | | | 20 | | | | | 25 | | | | | 30 | | |

```
Tyr  Pro  Gln  Cys  Thr  Ala  Gly  Arg  Gly  His  Arg  Gln  Asn  Gly  Lys  Lys
          35                       40                       45
Cys  Ile  Arg  Cys  Ile  Val  Ile  Ser  Val  Cys  Ser  Leu  Val  Cys  Ile  Ala
     50                       55                       60
Ala  His  Leu  Ala  Val  Thr  Val  Ser  Gly  Val  Ala  Leu  Ile  Pro  Leu  Ile
65                        70                       75                            80
Asp  Gln  Asn  Arg  Ala  Tyr  Gly  Asn  Cys  Thr  Val  Cys  Val  Ile  Ala  Gly
                    85                       90                       95
Phe  Ile  Ala  Thr  Phe  Ala  Ala  Arg  Leu  Thr  Ile  Arg  Leu  Ser  Glu  Thr
               100                      105                      110
Leu  Met  Leu  Val  Gly  Lys  Pro  Ala  Gln  Phe  Ile  Phe  Ala  Ile  Ile  Ala
          115                      120                      125
Ser  Val  Ala  Glu  Thr  Leu  Ile  Asn  Asn  Glu  Ala  Leu  Ala  Ile  Ser  Asn
          130                      135                      140
Thr  Thr  Tyr  Lys  Thr  Ala  Leu  Arg  Ile  Ile  Glu  Val  Thr  Ser  Leu  Ala
145                      150                      155                           160
Cys  Phe  Val  Met  Leu  Gly  Ala  Ile  Ile  Thr  Ser  His  Asn  Tyr  Val  Cys
               165                      170                      175
Ile  Ser  Thr  Ala  Gly  Asp  Leu  Thr  Trp  Lys  Gly  Gly  Ile  Phe  His  Ala
               180                      185                      190
Tyr  His  Gly  Thr  Leu  Leu  Gly  Ile  Thr  Ile  Pro  Asn  Ile  His  Pro  Ile
          195                      200                      205
Pro  Leu  Ala  Gly  Phe  Leu  Ala  Val  Tyr  Thr  Ile  Leu  Ala  Ile  Asn  Ile
     210                      215                      220
Ala  Arg  Asp  Ala  Ser  Ala  Thr  Leu  Leu  Ser  Thr  Cys  Tyr  Tyr  Arg  Asn
225                      230                      235                           240
Cys  Arg  Glu  Arg  Thr  Ile  Leu  Arg  Pro  Ser  Arg  Leu  Gly  His  Gly  Tyr
               245                      250                      255
Thr  Ile  Pro  Ser  Pro  Gly  Ala  Asp  Met  Leu  Tyr  Glu  Glu  Asp  Val  Tyr
               260                      265                      270
Ser  Phe  Asp  Ala  Ala  Lys  Gly  His  Tyr  Ser  Ser  Ile  Phe  Leu  Cys  Tyr
          275                      280                      285
Ala  Met  Gly  Leu  Thr  Thr  Pro  Leu  Ile  Ile  Ala  Leu  His  Lys  Tyr  Met
290                      295                      300
Ala  Gly  Ile  Lys  Asn  Ser  Ser  Asp  Trp  Thr  Ala  Thr  Leu  Gln  Gly  Met
305                      310                      315                           320
Tyr  Gly  Leu  Val  Leu  Gly  Ser  Leu  Ser  Ser  Leu  Cys  Ile  Pro  Ser  Ser
                    325                      330                      335
Asn  Asn  Asp  Ala  Leu  Ile  Arg  Pro  Ile  Gln  Ile  Leu  Ile  Leu  Ile  Ile
               340                      345                      350
Gly  Ala  Leu  Ala  Ile  Ala  Leu  Ala  Gly  Cys  Gly  Gln  Ile  Ile  Gly  Pro
          355                      360                      365
Thr  Leu  Phe  Ala  Ala  Ser  Ser  Ala  Ala  Met  Ser  Cys  Phe  Thr  Cys  Ile
     370                      375                      380
Asn  Ile  Arg  Ala  Thr  Asn  Lys  Gly  Val  Asn  Lys  Leu  Ala  Ala  Ala  Ser
385                      390                      395                           400
Val  Val  Lys  Ser  Val  Leu  Gly  Phe  Ile  Ile  Ser  Gly  Met  Leu  Thr  Cys
                    405                      410                      415
Val  Leu  Leu  Pro  Leu  Ser
               420
```

( 2 ) INFORMATION FOR SEQ ID NO:6:

( i ) SEQUENCE CHARACTERISTICS:
        ( A ) LENGTH: 489 amino acids (B) TYPE: amino acid
(D) TOPOLOGY: linear (ii) MOLECULE TYPE: protein (xi) SEQUENCE DESCRIPTION: SEQ ID NO:6:

```
Met Val Ser Asn Met Arg Val Leu Arg Val Leu Arg Leu Thr Gly Trp
 1               5                  10                  15

Val Gly Ile Phe Leu Val Leu Ser Leu Gln Gln Thr Ser Cys Ala Gly
                20                  25                  30

Leu Pro His Asn Val Asp Thr His His Ile Leu Thr Phe Asn Pro Ser
             35                  40                  45

Pro Ile Ser Ala Asp Gly Val Pro Leu Ser Glu Val Pro Asn Ser Pro
         50                  55                  60

Thr Thr Glu Leu Ser Thr Thr Val Ala Thr Lys Thr Ala Val Pro Thr
 65                  70                  75                  80

Thr Glu Ser Thr Ser Ser Ser Glu Ala His Arg Asn Ser Ser His Lys
                 85                  90                  95

Ile Pro Asp Ile Ile Cys Asp Arg Glu Glu Val Phe Val Phe Leu Asn
            100                 105                 110

Asn Thr Gly Arg Ile Leu Cys Asp Leu Ile Val Asp Pro Pro Ser Asp
        115                 120                 125

Asp Glu Trp Ser Asn Phe Ala Leu Asp Val Thr Phe Asn Pro Ile Glu
    130                 135                 140

Tyr His Ala Asn Glu Lys Asn Val Glu Val Ala Arg Val Ala Gly Leu
145                 150                 155                 160

Tyr Gly Val Pro Gly Ser Asp Tyr Ala Tyr Pro Arg Lys Ser Glu Leu
                165                 170                 175

Ile Ser Ser Ile Arg Arg Asp Pro Gln Gly Ser Phe Trp Thr Ser Pro
            180                 185                 190

Thr Pro Arg Gly Asn Lys Tyr Phe Ile Trp Ile Asn Lys Thr Met His
        195                 200                 205

Thr Met Gly Val Glu Val Arg Asn Val Asp Tyr Lys Asp Asn Gly Tyr
    210                 215                 220

Phe Gln Val Ile Leu Arg Asp Arg Phe Asn Arg Pro Leu Val Glu Lys
225                 230                 235                 240

His Ile Tyr Met Arg Val Cys Gln Arg Pro Ala Ser Val Asp Val Leu
                245                 250                 255

Ala Pro Pro Val Leu Ser Gly Glu Asn Tyr Lys Ala Ser Cys Ile Val
            260                 265                 270

Arg His Phe Tyr Pro Pro Gly Ser Val Tyr Val Ser Trp Arg Arg Asn
        275                 280                 285

Gly Asn Ile Ala Thr Pro Arg Lys Asp Arg Asp Gly Ser Phe Trp Trp
    290                 295                 300

Phe Glu Ser Gly Arg Gly Ala Thr Leu Val Ser Thr Ile Thr Leu Gly
305                 310                 315                 320

Asn Ser Gly Leu Glu Ser Pro Pro Lys Val Ser Cys Leu Val Ala Trp
                325                 330                 335

Arg Gln Gly Asp Met Ile Ser Thr Ser Asn Ala Thr Ala Val Pro Thr
            340                 345                 350

Val Tyr Tyr His Pro Arg Ile Ser Leu Ala Phe Lys Asp Gly Tyr Ala
        355                 360                 365

Ile Cys Thr Ile Glu Cys Val Pro Ser Gly Ile Thr Val Arg Trp Leu
370                 375                 380

Val His Asp Glu Pro Gln Pro Asn Thr Thr Tyr Asp Thr Val Val Thr
```

-continued

```
385                 390                 395                 400
Gly Leu Cys Arg Thr Ile Asp Arg Tyr Arg Asn Leu Ala Ser Arg Ile
                405                 410                 415
Pro Val Gln Asp Asn Trp Ala Lys Thr Lys Tyr Thr Cys Arg Leu Ile
                420                 425                 430
Gly Tyr Pro Phe Asp Val Asp Arg Phe Gln Asn Ser Glu Tyr Tyr Asp
                435                 440                 445
Ala Thr Pro Ser Ala Arg Gly Met Pro Met Ile Val Thr Ile Thr Ala
            450             455                 460
Val Leu Gly Leu Ala Leu Phe Leu Gly Ile Gly Ile Ile Ile Thr Ala
465                 470                 475                 480
Leu Cys Phe Tyr Leu Pro Gly Arg Asn
                485
```

(2) INFORMATION FOR SEQ ID NO:7:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO:7:

```
Met Met Ser Pro Thr Pro Glu Asp Asp Arg Asp Leu Val Val Val Arg
 1               5                  10                  15
Gly Arg Leu Arg Met Met Asp Ser Gly Thr Glu Thr Asp Arg Glu Gln
                20                  25                  30
Arg His Pro Arg Thr Thr Trp Arg Ser Ile Cys Cys Gly Cys Thr Ile
                35                  40                  45
Gly Met Val Phe Thr Ile Phe Val Leu Val Ala Ala Val Leu Leu Gly
            50                  55                  60
Ser Leu Phe Thr Val Ser Tyr Met Ala Met Glu Ser Gly Thr Cys Pro
65                  70                  75                  80
Asp Glu Trp Ile Gly Leu Gly Tyr Ser Cys Met Arg Val Ala Gly Lys
                85                  90                  95
Asn Ala Thr Asp Leu Glu Ala Leu Asp Thr Cys Ala Arg His Asn Ser
                100                 105                 110
Lys Leu Ile Asp Phe Ala Asn Ala Lys Val Leu Val Glu Ala Ile Ala
                115                 120                 125
Pro Phe Gly Val Pro Asn Ala Ala Tyr Gly Glu Val Phe Arg Leu Arg
            130                 135                 140
Asp Ser Lys Thr Thr Cys Ile Arg Pro Thr Met Gly Gly Pro Val Ser
145                 150                 155                 160
Ala Asp Cys Pro Val Thr Cys Thr Val Ile Cys Gln Arg Pro Arg Pro
                165                 170                 175
Leu Ser Thr Met Ser Ser Ile Ile Arg Asp Ala Arg Val Tyr Leu His
                180                 185                 190
Leu Glu Arg Arg Asp Tyr Tyr Glu Val Tyr Ala Ser Val Leu Ser Asn
                195                 200                 205
Ala Met Ser Lys
        210
```

(2) INFORMATION FOR SEQ ID NO:8:

(i) SEQUENCE CHARACTERISTICS:
        (A) LENGTH: 1506 base pairs
        (B) TYPE: nucleic acid (C) STRANDEDNESS: double
(D) TOPOLOGY: linear (ii) MOLECULE TYPE: DNA (genomic)

(iii) HYPOTHETICAL: NO (iv) ANTI-SENSE: NO (ix) FEATURE:
 (A) NAME/KEY: CDS
 (B) LOCATION: 1..1506

(xi) SEQUENCE DESCRIPTION: SEQ ID NO:8:

| ATG | CTC | ACG | CCG | CGT | GTG | TTA | CGA | GCT | TTG | GGG | TGG | ACT | GGA | CTC | TTT | 48 |
|---|---|---|---|---|---|---|---|---|---|---|---|---|---|---|---|---|
| Met | Leu | Thr | Pro | Arg | Val | Leu | Arg | Ala | Leu | Gly | Trp | Thr | Gly | Leu | Phe | |
| 1 | | | | 5 | | | | | 10 | | | | | 15 | | |

| TTT | TTG | CTT | TTA | TCT | CCG | AGC | AAC | GTC | CTA | GGA | GCC | AGC | CTT | AGC | CGG | 96 |
|---|---|---|---|---|---|---|---|---|---|---|---|---|---|---|---|---|
| Phe | Leu | Leu | Leu | Ser | Pro | Ser | Asn | Val | Leu | Gly | Ala | Ser | Leu | Ser | Arg | |
| | | | 20 | | | | | 25 | | | | | 30 | | | |

| GAT | CTC | GAA | ACA | CCC | CCA | TTT | CTA | TCC | TTT | GAT | CCA | TCC | AAC | ATT | TCA | 144 |
|---|---|---|---|---|---|---|---|---|---|---|---|---|---|---|---|---|
| Asp | Leu | Glu | Thr | Pro | Pro | Phe | Leu | Ser | Phe | Asp | Pro | Ser | Asn | Ile | Ser | |
| | | | 35 | | | | 40 | | | | | 45 | | | | |

| ATT | AAC | GGC | GCG | CCT | TTA | ACT | GAG | GTA | CCT | CAT | GCA | CCT | TCC | ACA | GAA | 192 |
|---|---|---|---|---|---|---|---|---|---|---|---|---|---|---|---|---|
| Ile | Asn | Gly | Ala | Pro | Leu | Thr | Glu | Val | Pro | His | Ala | Pro | Ser | Thr | Glu | |
| | 50 | | | | | 55 | | | | | 60 | | | | | |

| AGT | GTG | TCA | ACA | AAT | TCG | GAA | AGT | ACC | AAT | GAA | CAT | ACC | ATA | ACA | GAA | 240 |
|---|---|---|---|---|---|---|---|---|---|---|---|---|---|---|---|---|
| Ser | Val | Ser | Thr | Asn | Ser | Glu | Ser | Thr | Asn | Glu | His | Thr | Ile | Thr | Glu | |
| 65 | | | | | 70 | | | | | 75 | | | | | 80 | |

| ACG | ACG | GGC | AAG | AAC | GCA | TAC | ATC | CAC | AAC | AAT | GCG | TCT | ACG | GAC | AAG | 288 |
|---|---|---|---|---|---|---|---|---|---|---|---|---|---|---|---|---|
| Thr | Thr | Gly | Lys | Asn | Ala | Tyr | Ile | His | Asn | Asn | Ala | Ser | Thr | Asp | Lys | |
| | | | | 85 | | | | | 90 | | | | | 95 | | |

| CAA | AAT | GCG | AAC | GAC | ACT | CAT | AAA | ACG | CCC | AAT | ATA | CTC | TGC | GAT | ACG | 336 |
|---|---|---|---|---|---|---|---|---|---|---|---|---|---|---|---|---|
| Gln | Asn | Ala | Asn | Asp | Thr | His | Lys | Thr | Pro | Asn | Ile | Leu | Cys | Asp | Thr | |
| | | | 100 | | | | | 105 | | | | | 110 | | | |

| GAA | GAA | GTT | TTT | GTT | TTC | CTT | AAC | GAA | ACG | GGA | AGA | TTT | GTT | TGT | ACT | 384 |
|---|---|---|---|---|---|---|---|---|---|---|---|---|---|---|---|---|
| Glu | Glu | Val | Phe | Val | Phe | Leu | Asn | Glu | Thr | Gly | Arg | Phe | Val | Cys | Thr | |
| | | 115 | | | | | 120 | | | | | 125 | | | | |

| CTC | AAA | GTC | GAC | CCC | CCC | TCG | GAT | AGT | GAA | TGG | TCC | AAC | TTT | GTT | CTA | 432 |
|---|---|---|---|---|---|---|---|---|---|---|---|---|---|---|---|---|
| Leu | Lys | Val | Asp | Pro | Pro | Ser | Asp | Ser | Glu | Trp | Ser | Asn | Phe | Val | Leu | |
| | 130 | | | | | 135 | | | | | 140 | | | | | |

| GAT | CTG | ATC | TTT | AAC | CCA | ATT | GAA | TAC | CAC | GCC | AAC | GAA | AAG | AAT | GTG | 480 |
|---|---|---|---|---|---|---|---|---|---|---|---|---|---|---|---|---|
| Asp | Leu | Ile | Phe | Asn | Pro | Ile | Glu | Tyr | His | Ala | Asn | Glu | Lys | Asn | Val | |
| 145 | | | | | 150 | | | | | 155 | | | | | 160 | |

| GAA | GCG | GCG | CGT | ATC | GCT | GGT | CTC | TAT | GGA | GTC | CCC | GGA | TCA | GAC | TAT | 528 |
|---|---|---|---|---|---|---|---|---|---|---|---|---|---|---|---|---|
| Glu | Ala | Ala | Arg | Ile | Ala | Gly | Leu | Tyr | Gly | Val | Pro | Gly | Ser | Asp | Tyr | |
| | | | | 165 | | | | | 170 | | | | | 175 | | |

| GCA | TAC | CCA | CGT | CAA | TCT | GAA | TTA | ATT | TCT | TCG | ATT | CGA | CGA | GAT | CCC | 576 |
|---|---|---|---|---|---|---|---|---|---|---|---|---|---|---|---|---|
| Ala | Tyr | Pro | Arg | Gln | Ser | Glu | Leu | Ile | Ser | Ser | Ile | Arg | Arg | Asp | Pro | |
| | | | 180 | | | | | 185 | | | | | 190 | | | |

| CAG | GGC | ACA | TTT | TGG | ACG | AGC | CCA | TCA | CCT | CAT | GGA | AAC | AAG | TAC | TTC | 624 |
|---|---|---|---|---|---|---|---|---|---|---|---|---|---|---|---|---|
| Gln | Gly | Thr | Phe | Trp | Thr | Ser | Pro | Ser | Pro | His | Gly | Asn | Lys | Tyr | Phe | |
| | | 195 | | | | | 200 | | | | | 205 | | | | |

| ATA | TGG | ATA | AAC | AAA | ACA | ACC | AAT | ACG | ATG | GGC | GTG | GAA | ATT | AGA | AAT | 672 |
|---|---|---|---|---|---|---|---|---|---|---|---|---|---|---|---|---|
| Ile | Trp | Ile | Asn | Lys | Thr | Thr | Asn | Thr | Met | Gly | Val | Glu | Ile | Arg | Asn | |
| | 210 | | | | | 215 | | | | | 220 | | | | | |

| GTA | GAT | TAT | GCT | GAT | AAT | GGC | TAC | ATG | CAA | GTC | ATT | ATG | CGT | GAC | CAT | 720 |
|---|---|---|---|---|---|---|---|---|---|---|---|---|---|---|---|---|
| Val | Asp | Tyr | Ala | Asp | Asn | Gly | Tyr | Met | Gln | Val | Ile | Met | Arg | Asp | His | |
| 225 | | | | | 230 | | | | | 235 | | | | | 240 | |

| TTT | AAT | CGG | CCT | TTA | ATA | GAT | AAA | CAT | ATT | TAC | ATA | CGT | GTG | TGT | CAA | 768 |
|---|---|---|---|---|---|---|---|---|---|---|---|---|---|---|---|---|
| Phe | Asn | Arg | Pro | Leu | Ile | Asp | Lys | His | Ile | Tyr | Ile | Arg | Val | Cys | Gln | |
| | | | | 245 | | | | | 250 | | | | | 255 | | |

| CGA | CCT | GCA | TCA | GTG | GAT | GTA | CTG | GCC | CCT | CCA | GTC | CTC | AGC | GGA | GAA | 816 |

```
Arg Pro Ala Ser Val Asp Val Leu Ala Pro Pro Val Leu Ser Gly Glu
            260                 265                 270

AAT TAC AAG GCA TCT TGT ATC GTT AGA CAC TTT TAT CCC CCT GGA TCT         864
Asn Tyr Lys Ala Ser Cys Ile Val Arg His Phe Tyr Pro Pro Gly Ser
        275                 280                 285

GTC TAT GTA TCT TGG AGA CAG AAT GGA AAC ATT GCA ACT CCT CGG AAA         912
Val Tyr Val Ser Trp Arg Gln Asn Gly Asn Ile Ala Thr Pro Arg Lys
    290                 295                 300

GAT CGC GAT GGA AGT TTT TGG TGG TTC GAA TCT GGT AGA GGA GCT ACG         960
Asp Arg Asp Gly Ser Phe Trp Trp Phe Glu Ser Gly Arg Gly Ala Thr
305                 310                 315                 320

TTG GTT TCT ACA ATA ACA TTG GGA AAT TCA GGA ATT GAT TTC CCC CCC        1008
Leu Val Ser Thr Ile Thr Leu Gly Asn Ser Gly Ile Asp Phe Pro Pro
                325                 330                 335

AAA ATA TCT TGT CTG GTT GCC TGG AAG CAG GGT GAT ATG ATC AGC ACG        1056
Lys Ile Ser Cys Leu Val Ala Trp Lys Gln Gly Asp Met Ile Ser Thr
            340                 345                 350

ACG AAT GCC ACA GCT ATC CCG ACG GTA TAT CAT CAT CCC CGT TTA TCC        1104
Thr Asn Ala Thr Ala Ile Pro Thr Val Tyr His His Pro Arg Leu Ser
        355                 360                 365

CTG GCT TTT AAA GAT GGG TAT GCA ATA TGT ACT ATA GAA TGT GTC CCC        1152
Leu Ala Phe Lys Asp Gly Tyr Ala Ile Cys Thr Ile Glu Cys Val Pro
    370                 375                 380

TCT GAG ATT ACT GTA CGG TGG TTA GTA CAT GAT GAA GCG CAG CCT AAC        1200
Ser Glu Ile Thr Val Arg Trp Leu Val His Asp Glu Ala Gln Pro Asn
385                 390                 395                 400

ACA ACT TAT AAT ACT GTG GTT ACA GGT CTC TGC CGG ACC ATC GAT CGC        1248
Thr Thr Tyr Asn Thr Val Val Thr Gly Leu Cys Arg Thr Ile Asp Arg
                405                 410                 415

CAT AGA AAT CTC CTC AGC CGC ATT CCA GTA TGG GAC AAT TGG ACG AAA        1296
His Arg Asn Leu Leu Ser Arg Ile Pro Val Trp Asp Asn Trp Thr Lys
            420                 425                 430

ACA AAA TAT ACG TGC AGA CTC ATA GGC TAC CCC TTC GAT GAA GAT AAA        1344
Thr Lys Tyr Thr Cys Arg Leu Ile Gly Tyr Pro Phe Asp Glu Asp Lys
        435                 440                 445

TTT CAA GAT TCG GAA TAT TAC GAT GCA ACT CCA TCT GCA AGA GGA ACA        1392
Phe Gln Asp Ser Glu Tyr Tyr Asp Ala Thr Pro Ser Ala Arg Gly Thr
    450                 455                 460

CCC ATG GTT ATT ACG GTT ACG GCA GTT TTG GGA TTG GCT GTA ATT TTA        1440
Pro Met Val Ile Thr Val Thr Ala Val Leu Gly Leu Ala Val Ile Leu
465                 470                 475                 480

GGG ATG GGG ATA ATC ATG ACT GCC CTA TGT TTA TAC AAC TCC ACA CGA        1488
Gly Met Gly Ile Ile Met Thr Ala Leu Cys Leu Tyr Asn Ser Thr Arg
                485                 490                 495

AAA AAT ATT CGA TTA TAA                                                 1506
Lys Asn Ile Arg Leu
            500
```

( 2 ) INFORMATION FOR SEQ ID NO:9:

( i ) SEQUENCE CHARACTERISTICS:
        ( A ) LENGTH: 501 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Leu Thr Pro Arg Val Leu Arg Ala Leu Gly Trp Thr Gly Leu Phe
 1               5                  10                  15

Phe Leu Leu Leu Ser Pro Ser Asn Val Leu Gly Ala Ser Leu Ser Arg
                20                  25                  30
```

Asp Leu Glu Thr Pro Pro Phe Leu Ser Phe Asp Pro Ser Asn Ile Ser
            35                    40                    45

Ile Asn Gly Ala Pro Leu Thr Glu Val Pro His Ala Pro Ser Thr Glu
        50                    55                    60

Ser Val Ser Thr Asn Ser Glu Ser Thr Asn Glu His Thr Ile Thr Glu
65                      70                    75                    80

Thr Thr Gly Lys Asn Ala Tyr Ile His Asn Asn Ala Ser Thr Asp Lys
                85                    90                        95

Gln Asn Ala Asn Asp Thr His Lys Thr Pro Asn Ile Leu Cys Asp Thr
            100                   105                  110

Glu Glu Val Phe Val Phe Leu Asn Glu Thr Gly Arg Phe Val Cys Thr
            115                   120                  125

Leu Lys Val Asp Pro Pro Ser Asp Ser Glu Trp Ser Asn Phe Val Leu
    130                   135                  140

Asp Leu Ile Phe Asn Pro Ile Glu Tyr His Ala Asn Glu Lys Asn Val
145                   150                  155                       160

Glu Ala Ala Arg Ile Ala Gly Leu Tyr Gly Val Pro Gly Ser Asp Tyr
                165                   170                  175

Ala Tyr Pro Arg Gln Ser Glu Leu Ile Ser Ser Ile Arg Arg Asp Pro
            180                   185                  190

Gln Gly Thr Phe Trp Thr Ser Pro Ser Pro His Gly Asn Lys Tyr Phe
            195                   200                  205

Ile Trp Ile Asn Lys Thr Thr Asn Thr Met Gly Val Glu Ile Arg Asn
    210                   215                  220

Val Asp Tyr Ala Asp Asn Gly Tyr Met Gln Val Ile Met Arg Asp His
225                   230                  235                       240

Phe Asn Arg Pro Leu Ile Asp Lys His Ile Tyr Ile Arg Val Cys Gln
            245                   250                  255

Arg Pro Ala Ser Val Asp Val Leu Ala Pro Pro Val Leu Ser Gly Glu
            260                   265                  270

Asn Tyr Lys Ala Ser Cys Ile Val Arg His Phe Tyr Pro Pro Gly Ser
        275                   280                  285

Val Tyr Val Ser Trp Arg Gln Asn Gly Asn Ile Ala Thr Pro Arg Lys
    290                   295                  300

Asp Arg Asp Gly Ser Phe Trp Trp Phe Glu Ser Gly Arg Gly Ala Thr
305                   310                  315                       320

Leu Val Ser Thr Ile Thr Leu Gly Asn Ser Gly Ile Asp Phe Pro Pro
            325                   330                  335

Lys Ile Ser Cys Leu Val Ala Trp Lys Gln Gly Asp Met Ile Ser Thr
            340                   345                  350

Thr Asn Ala Thr Ala Ile Pro Thr Val Tyr His His Pro Arg Leu Ser
        355                   360                  365

Leu Ala Phe Lys Asp Gly Tyr Ala Ile Cys Thr Ile Glu Cys Val Pro
    370                   375                  380

Ser Glu Ile Thr Val Arg Trp Leu Val His Asp Glu Ala Gln Pro Asn
385                   390                  395                       400

Thr Thr Tyr Asn Thr Val Val Thr Gly Leu Cys Arg Thr Ile Asp Arg
                405                   410                  415

His Arg Asn Leu Leu Ser Arg Ile Pro Val Trp Asp Asn Trp Thr Lys
            420                   425                  430

Thr Lys Tyr Thr Cys Arg Leu Ile Gly Tyr Pro Phe Asp Glu Asp Lys
        435                   440                  445

Phe Gln Asp Ser Glu Tyr Tyr Asp Ala Thr Pro Ser Ala Arg Gly Thr

|     |     |     |     | 450 |     |     |     |     | 455 |     |     |     |     | 460 |     |     |
| --- | --- | --- | --- | --- | --- | --- | --- | --- | --- | --- | --- | --- | --- | --- | --- | --- |
| Pro | Met | Val | Ile | Thr | Val | Thr | Ala | Val | Leu | Gly | Leu | Ala | Val | Ile | Leu |     |
| 465 |     |     |     |     | 470 |     |     |     |     | 475 |     |     |     |     | 480 |     |

| Gly | Met | Gly | Ile | Ile | Met | Thr | Ala | Leu | Cys | Leu | Tyr | Asn | Ser | Thr | Arg |
| --- | --- | --- | --- | --- | --- | --- | --- | --- | --- | --- | --- | --- | --- | --- | --- |
|     |     |     |     | 485 |     |     |     |     | 490 |     |     |     |     | 495 |     |

| Lys | Asn | Ile | Arg | Leu |
| --- | --- | --- | --- | --- |
|     |     |     |     | 500 |

( 2 ) INFORMATION FOR SEQ ID NO:10:

( i ) SEQUENCE CHARACTERISTICS:
        ( A ) LENGTH: 1734 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..1734

( x i ) SEQUENCE DESCRIPTION: SEQ ID NO:10:

| ATG | GAC | CGC | GCC | GTT | AGC | CAA | GTT | GCG | TTA | GAG | AAT | GAT | GAA | AGA | GAG | 48 |
| --- | --- | --- | --- | --- | --- | --- | --- | --- | --- | --- | --- | --- | --- | --- | --- | --- |
| Met | Asp | Arg | Ala | Val | Ser | Gln | Val | Ala | Leu | Glu | Asn | Asp | Glu | Arg | Glu |     |
| 1   |     |     |     | 5   |     |     |     |     | 10  |     |     |     |     | 15  |     |     |
| GCA | AAA | AAT | ACA | TGG | CGC | TTG | ATA | TTC | CGG | ATT | GCA | ATC | TTA | TTC | TTA | 96 |
| Ala | Lys | Asn | Thr | Trp | Arg | Leu | Ile | Phe | Arg | Ile | Ala | Ile | Leu | Phe | Leu |     |
|     |     |     | 20  |     |     |     |     | 25  |     |     |     |     | 30  |     |     |     |
| ACA | GTA | GTG | ACC | TTG | GCT | ATA | TCT | GTA | GCC | TCC | CTT | TTA | TAT | AGC | ATG | 144 |
| Thr | Val | Val | Thr | Leu | Ala | Ile | Ser | Val | Ala | Ser | Leu | Leu | Tyr | Ser | Met |     |
|     |     |     | 35  |     |     |     |     | 40  |     |     |     |     | 45  |     |     |     |
| GGG | GCT | AGC | ACA | CCT | AGC | GAT | CTT | GTA | GGC | ATA | CCG | ACT | AGG | ATT | TCC | 192 |
| Gly | Ala | Ser | Thr | Pro | Ser | Asp | Leu | Val | Gly | Ile | Pro | Thr | Arg | Ile | Ser |     |
|     | 50  |     |     |     |     | 55  |     |     |     |     | 60  |     |     |     |     |     |
| AGG | GCA | GAA | GAA | AAG | ATT | ACA | TCT | ACA | CTT | GGT | TCC | AAT | CAA | GAT | GTA | 240 |
| Arg | Ala | Glu | Glu | Lys | Ile | Thr | Ser | Thr | Leu | Gly | Ser | Asn | Gln | Asp | Val |     |
| 65  |     |     |     |     | 70  |     |     |     |     | 75  |     |     |     |     | 80  |     |
| GTA | GAT | AGG | ATA | TAT | AAG | CAA | GTG | GCC | CTT | GAG | TCT | CCA | TTG | GCA | TTG | 288 |
| Val | Asp | Arg | Ile | Tyr | Lys | Gln | Val | Ala | Leu | Glu | Ser | Pro | Leu | Ala | Leu |     |
|     |     |     |     | 85  |     |     |     |     | 90  |     |     |     |     | 95  |     |     |
| TTA | AAT | ACT | GAG | ACC | ACA | ATT | ATG | AAC | GCA | ATA | ACA | TCT | CTC | TCT | TAT | 336 |
| Leu | Asn | Thr | Glu | Thr | Thr | Ile | Met | Asn | Ala | Ile | Thr | Ser | Leu | Ser | Tyr |     |
|     |     |     | 100 |     |     |     |     | 105 |     |     |     |     | 110 |     |     |     |
| CAG | ATT | AAT | GGA | GCT | GCA | AAC | AAC | AGC | GGG | TGG | GGG | GCA | CCT | ATT | CAT | 384 |
| Gln | Ile | Asn | Gly | Ala | Ala | Asn | Asn | Ser | Gly | Trp | Gly | Ala | Pro | Ile | His |     |
|     |     |     | 115 |     |     |     |     | 120 |     |     |     |     | 125 |     |     |     |
| GAC | CCA | GAT | TAT | ATA | GGG | GGG | ATA | GGC | AAA | GAA | CTC | ATT | GTA | GAT | GAT | 432 |
| Asp | Pro | Asp | Tyr | Ile | Gly | Gly | Ile | Gly | Lys | Glu | Leu | Ile | Val | Asp | Asp |     |
|     | 130 |     |     |     |     | 135 |     |     |     |     | 140 |     |     |     |     |     |
| GCT | AGT | GAT | GTC | ACA | TCA | TTC | TAT | CCC | TCT | GCA | TTT | CAA | GAA | CAT | CTG | 480 |
| Ala | Ser | Asp | Val | Thr | Ser | Phe | Tyr | Pro | Ser | Ala | Phe | Gln | Glu | His | Leu |     |
| 145 |     |     |     |     | 150 |     |     |     |     | 155 |     |     |     |     | 160 |     |
| AAT | TTT | ATC | CCG | GCG | CCT | ACT | ACA | GGA | TCA | GGT | TGC | ACT | CGA | ATA | CCC | 528 |
| Asn | Phe | Ile | Pro | Ala | Pro | Thr | Thr | Gly | Ser | Gly | Cys | Thr | Arg | Ile | Pro |     |
|     |     |     |     | 165 |     |     |     |     | 170 |     |     |     |     | 175 |     |     |
| TCA | TTT | GAC | ATG | AGT | GCT | ACC | CAT | TAC | TGC | TAC | ACC | CAT | AAT | GTA | ATA | 576 |
| Ser | Phe | Asp | Met | Ser | Ala | Thr | His | Tyr | Cys | Tyr | Thr | His | Asn | Val | Ile |     |
|     |     |     | 180 |     |     |     |     | 185 |     |     |     |     | 190 |     |     |     |

```
TTG TCT GGA TGC AGA GAT CAC TCA CAC TCA CAT CAG TAT TTA GCA CTT          624
Leu Ser Gly Cys Arg Asp His Ser His Ser His Gln Tyr Leu Ala Leu
        195                     200                 205

GGT GTG CTC CGG ACA TCT GCA ACA GGG AGG GTA TTC TTT TCT ACT CTG          672
Gly Val Leu Arg Thr Ser Ala Thr Gly Arg Val Phe Phe Ser Thr Leu
        210                     215                 220

CGT TCC ATC AAC CTG GAC GAC ACC CAA AAT CGG AAG TCT TGC AGT GTG          720
Arg Ser Ile Asn Leu Asp Asp Thr Gln Asn Arg Lys Ser Cys Ser Val
225                     230                 235                 240

AGT GCA ACT CCC CTG GGT TGT GAT ATG CTG TGC TCG AAA GCC ACG GAG          768
Ser Ala Thr Pro Leu Gly Cys Asp Met Leu Cys Ser Lys Ala Thr Glu
                245                 250                 255

ACA GAG GAA GAA GAT TAT AAC TCA GCT GTC CCT ACG CGG ATG GTA CAT          816
Thr Glu Glu Glu Asp Tyr Asn Ser Ala Val Pro Thr Arg Met Val His
                    260                 265                 270

GGG AGG TTA GGG TTC GAC GGC CAA TAT CAC GAA AAG GAC CTA GAT GTC          864
Gly Arg Leu Gly Phe Asp Gly Gln Tyr His Glu Lys Asp Leu Asp Val
            275                 280                 285

ACA ACA TTA TTC GGG GAC TGG GTG GCC AAC TAC CCA GGA GTA GGG GGT          912
Thr Thr Leu Phe Gly Asp Trp Val Ala Asn Tyr Pro Gly Val Gly Gly
Thr 290                     295                 300

GGA TCT TTT ATT GAC AGC CGC GTG TGG TTC TCA GTC TAC GGA GGG TTA          960
Gly Ser Phe Ile Asp Ser Arg Val Trp Phe Ser Val Tyr Gly Gly Leu
305                     310                 315                 320

AAA CCC AAT ACA CCC AGT GAC ACT GTA CAG GAA GGG AAA TAT GTG ATA         1008
Lys Pro Asn Thr Pro Ser Asp Thr Val Gln Glu Gly Lys Tyr Val Ile
                325                 330                 335

TAC AAG CGA TAC AAT GAC ACA TGC CCA GAT GAG CAA GAC TAC CAG ATT         1056
Tyr Lys Arg Tyr Asn Asp Thr Cys Pro Asp Glu Gln Asp Tyr Gln Ile
            340                 345                 350

CGA ATG GCC AAG TCT TCG TAT AAG CCT GGA CGG TTT GGT GGG AAA CGC         1104
Arg Met Ala Lys Ser Ser Tyr Lys Pro Gly Arg Phe Gly Gly Lys Arg
        355                 360                 365

ATA CAG CAG GCT ATC TTA TCT ATC AAA GTG TCA ACA TCC TTA GGC GAA         1152
Ile Gln Gln Ala Ile Leu Ser Ile Lys Val Ser Thr Ser Leu Gly Glu
    370                 375                 380

GAC CCG GTA CTG ACT GTA CCG CCC AAC ACA GTC ACA CTC ATG GGG GCC         1200
Asp Pro Val Leu Thr Val Pro Pro Asn Thr Val Thr Leu Met Gly Ala
385                 390                 395                 400

GAA GGC AGA ATT CTC ACA GTA GGG ACA TCC CAT TTC TTG TAT CAG CGA         1248
Glu Gly Arg Ile Leu Thr Val Gly Thr Ser His Phe Leu Tyr Gln Arg
                405                 410                 415

GGG TCA TCA TAC TTC TCT CCC GCG TTA TTA TAT CCT ATG ACA GTC AGC         1296
Gly Ser Ser Tyr Phe Ser Pro Ala Leu Leu Tyr Pro Met Thr Val Ser
            420                 425                 430

AAC AAA ACA GCC ACT CTT CAT AGT CCT TAT ACA TTC AAT GCC TTC ACT         1344
Asn Lys Thr Ala Thr Leu His Ser Pro Tyr Thr Phe Asn Ala Phe Thr
        435                 440                 445

CGG CCA GGT AGT ATC CCT TGC CAG GCT TCA GCA AGA TGC CCC AAC TCA         1392
Arg Pro Gly Ser Ile Pro Cys Gln Ala Ser Ala Arg Cys Pro Asn Ser
    450                 455                 460

TGT GTT ACT GGA GTC TAT ACA GAT CCA TAT CCC CTA ATC TTC TAT AGA         1440
Cys Val Thr Gly Val Tyr Thr Asp Pro Tyr Pro Leu Ile Phe Tyr Arg
465                 470                 475                 480

AAC CAC ACC TTG CGA GGG GTA TTC GGG ACA ATG CTT GAT GGT GAA CAA         1488
Asn His Thr Leu Arg Gly Val Phe Gly Thr Met Leu Asp Gly Glu Gln
                485                 490                 495

GCA AGA CTT AAC CCT GCG TCT GCA GTA TTC GAT AGC ACA TCC CGC AGT         1536
Ala Arg Leu Asn Pro Ala Ser Ala Val Phe Asp Ser Thr Ser Arg Ser
            500                 505                 510
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| CGC | ATA | ACT | CGA | GTG | AGT | TCA | AGC | AGC | ATC | AAA | GCA | GCA | TAC | ACA | ACA | 1584 |
| Arg | Ile | Thr | Arg | Val | Ser | Ser | Ser | Ser | Ile | Lys | Ala | Ala | Tyr | Thr | Thr |      |
|     |     | 515 |     |     |     |     | 520 |     |     |     |     |     | 525 |     |     |      |
| TCA | ACT | TGT | TTT | AAA | GTG | GTC | AAG | ACC | AAT | AAG | ACC | TAT | TGT | CTC | AGC | 1632 |
| Ser | Thr | Cys | Phe | Lys | Val | Val | Lys | Thr | Asn | Lys | Thr | Tyr | Cys | Leu | Ser |      |
|     | 530 |     |     |     |     | 535 |     |     |     |     | 540 |     |     |     |     |      |
| ATT | GCT | GAA | ATA | TCT | AAT | ACT | CTC | TTC | GGA | GAA | TTC | AGA | ATC | GTC | CCG | 1680 |
| Ile | Ala | Glu | Ile | Ser | Asn | Thr | Leu | Phe | Gly | Glu | Phe | Arg | Ile | Val | Pro |      |
| 545 |     |     |     |     | 550 |     |     |     |     | 555 |     |     |     |     | 560 |      |
| TTA | CTA | GTT | GAG | ATC | CTC | AAA | GAT | GAC | GGG | GTT | AGA | GAA | GCC | AGG | TCT | 1728 |
| Leu | Leu | Val | Glu | Ile | Leu | Lys | Asp | Asp | Gly | Val | Arg | Glu | Ala | Arg | Ser |      |
|     |     |     |     | 565 |     |     |     |     | 570 |     |     |     |     | 575 |     |      |
| GGC | TAG |     |     |     |     |     |     |     |     |     |     |     |     |     |     | 1734 |
| Gly |     |     |     |     |     |     |     |     |     |     |     |     |     |     |     |      |

( 2 ) INFORMATION FOR SEQ ID NO:11:

( i ) SEQUENCE CHARACTERISTICS:
    ( A ) LENGTH: 577 amino acids
    ( B ) TYPE: amino acid
    ( D ) TOPOLOGY: linear ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
| Met | Asp | Arg | Ala | Val | Ser | Gln | Val | Ala | Leu | Glu | Asn | Asp | Glu | Arg | Glu |
| 1 | | | | 5 | | | | | 10 | | | | | 15 | |
| Ala | Lys | Asn | Thr | Trp | Arg | Leu | Ile | Phe | Arg | Ile | Ala | Ile | Leu | Phe | Leu |
| | | | 20 | | | | | 25 | | | | | 30 | | |
| Thr | Val | Val | Thr | Leu | Ala | Ile | Ser | Val | Ala | Ser | Leu | Leu | Tyr | Ser | Met |
| | | | 35 | | | | | 40 | | | | | 45 | | |
| Gly | Ala | Ser | Thr | Pro | Ser | Asp | Leu | Val | Gly | Ile | Pro | Thr | Arg | Ile | Ser |
| | | 50 | | | | | 55 | | | | | 60 | | | |
| Arg | Ala | Glu | Glu | Lys | Ile | Thr | Ser | Thr | Leu | Gly | Ser | Asn | Gln | Asp | Val |
| 65 | | | | | 70 | | | | | 75 | | | | | 80 |
| Val | Asp | Arg | Ile | Tyr | Lys | Gln | Val | Ala | Leu | Glu | Ser | Pro | Leu | Ala | Leu |
| | | | | 85 | | | | | 90 | | | | | 95 | |
| Leu | Asn | Thr | Glu | Thr | Thr | Ile | Met | Asn | Ala | Ile | Thr | Ser | Leu | Ser | Tyr |
| | | | 100 | | | | | 105 | | | | | 110 | | |
| Gln | Ile | Asn | Gly | Ala | Ala | Asn | Ser | Gly | Trp | Gly | Ala | Pro | Ile | His |
| | | 115 | | | | | 120 | | | | | 125 | | | |
| Asp | Pro | Asp | Tyr | Ile | Gly | Gly | Ile | Gly | Lys | Glu | Leu | Ile | Val | Asp | Asp |
| | 130 | | | | | 135 | | | | | 140 | | | | |
| Ala | Ser | Asp | Val | Thr | Ser | Phe | Tyr | Pro | Ser | Ala | Phe | Gln | Glu | His | Leu |
| 145 | | | | | 150 | | | | | 155 | | | | | 160 |
| Asn | Phe | Ile | Pro | Ala | Pro | Thr | Thr | Gly | Ser | Gly | Cys | Thr | Arg | Ile | Pro |
| | | | 165 | | | | | 170 | | | | | 175 | | |
| Ser | Phe | Asp | Met | Ser | Ala | Thr | His | Tyr | Cys | Tyr | Thr | His | Asn | Val | Ile |
| | | | 180 | | | | | 185 | | | | | 190 | | |
| Leu | Ser | Gly | Cys | Arg | Asp | His | Ser | His | Ser | His | Gln | Tyr | Leu | Ala | Leu |
| | | 195 | | | | | 200 | | | | | 205 | | | |
| Gly | Val | Leu | Arg | Thr | Ser | Ala | Thr | Gly | Arg | Val | Phe | Phe | Ser | Thr | Leu |
| | 210 | | | | | 215 | | | | | 220 | | | | |
| Arg | Ser | Ile | Asn | Leu | Asp | Asp | Thr | Gln | Asn | Arg | Lys | Ser | Cys | Ser | Val |
| 225 | | | | | 230 | | | | | 235 | | | | | 240 |
| Ser | Ala | Thr | Pro | Leu | Gly | Cys | Asp | Met | Leu | Cys | Ser | Lys | Ala | Thr | Glu |
| | | | | 245 | | | | | 250 | | | | | 255 | |
| Thr | Glu | Glu | Glu | Asp | Tyr | Asn | Ser | Ala | Val | Pro | Thr | Arg | Met | Val | His |

|  |  |  |  |  | 260 |  |  |  | 265 |  |  |  | 270 |  |
|---|---|---|---|---|---|---|---|---|---|---|---|---|---|---|
| Gly | Arg | Leu 275 | Gly | Phe | Asp | Gly | Gln 280 | Tyr | His | Glu | Lys | Asp 285 | Leu | Asp | Val |
| Thr | Thr 290 | Leu | Phe | Gly | Asp | Trp 295 | Val | Ala | Asn | Tyr | Pro 300 | Gly | Val | Gly | Gly |
| Gly 305 | Ser | Phe | Ile | Asp | Ser 310 | Arg | Val | Trp | Phe | Ser 315 | Val | Tyr | Gly | Gly | Leu 320 |
| Lys | Pro | Asn | Thr | Pro 325 | Ser | Asp | Thr | Val | Gln 330 | Glu | Gly | Lys | Tyr | Val 335 | Ile |
| Tyr | Lys | Arg | Tyr 340 | Asn | Asp | Thr | Cys | Pro 345 | Asp | Glu | Gln | Asp | Tyr 350 | Gln | Ile |
| Arg | Met | Ala 355 | Lys | Ser | Ser | Tyr | Lys 360 | Pro | Gly | Arg | Phe | Gly 365 | Gly | Lys | Arg |
| Ile | Gln 370 | Gln | Ala | Ile | Leu | Ser 375 | Ile | Lys | Val | Ser | Thr 380 | Ser | Leu | Gly | Glu |
| Asp 385 | Pro | Val | Leu | Thr | Val 390 | Pro | Pro | Asn | Thr | Val 395 | Thr | Leu | Met | Gly | Ala 400 |
| Glu | Gly | Arg | Ile | Leu 405 | Thr | Val | Gly | Thr | Ser 410 | His | Phe | Leu | Tyr | Gln 415 | Arg |
| Gly | Ser | Ser | Tyr 420 | Phe | Ser | Pro | Ala | Leu 425 | Leu | Tyr | Pro | Met | Thr 430 | Val | Ser |
| Asn | Lys | Thr 435 | Ala | Thr | Leu | His | Ser 440 | Pro | Tyr | Thr | Phe | Asn 445 | Ala | Phe | Thr |
| Arg | Pro 450 | Gly | Ser | Ile | Pro | Cys 455 | Gln | Ala | Ser | Ala | Arg 460 | Cys | Pro | Asn | Ser |
| Cys 465 | Val | Thr | Gly | Val | Tyr 470 | Thr | Asp | Pro | Tyr | Pro 475 | Leu | Ile | Phe | Tyr | Arg 480 |
| Asn | His | Thr | Leu | Arg 485 | Gly | Val | Phe | Gly | Thr 490 | Met | Leu | Asp | Gly | Glu 495 | Gln |
| Ala | Arg | Leu | Asn 500 | Pro | Ala | Ser | Ala | Val 505 | Phe | Asp | Ser | Thr | Ser 510 | Arg | Ser |
| Arg | Ile | Thr 515 | Arg | Val | Ser | Ser | Ser 520 | Ile | Lys | Ala | Ala 525 | Tyr | Thr | Thr |
| Ser | Thr 530 | Cys | Phe | Lys | Val | Val 535 | Lys | Thr | Asn | Lys | Thr 540 | Tyr | Cys | Leu | Ser |
| Ile 545 | Ala | Glu | Ile | Ser | Asn 550 | Thr | Leu | Phe | Gly | Glu 555 | Phe | Arg | Ile | Val | Pro 560 |
| Leu | Leu | Val | Glu | Ile 565 | Leu | Lys | Asp | Asp | Gly 570 | Val | Arg | Glu | Ala | Arg 575 | Ser |
| Gly |  |  |  |  |  |  |  |  |  |  |  |  |  |  |  |

( 2 ) INFORMATION FOR SEQ ID NO:12:

( i ) SEQUENCE CHARACTERISTICS:
        ( A ) LENGTH: 1662 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..1662

( x i ) SEQUENCE DESCRIPTION: SEQ ID NO:12:

| | | | | | | | | | | | | | | | | |
|---|---|---|---|---|---|---|---|---|---|---|---|---|---|---|---|---|
| ATG | GGC | TCC | AGA | CCT | TCT | ACC | AAG | AAC | CCA | GCA | CCT | ATG | ATG | CTG | ACT | 48 |
| Met | Gly | Ser | Arg | Pro | Ser | Thr | Lys | Asn | Pro | Ala | Pro | Met | Met | Leu | Thr | |
| 1 | | | | 5 | | | | | 10 | | | | | 15 | | |
| ATC | CGG | GTC | GCG | CTG | GTA | CTG | AGT | TGC | ATC | TGT | CCG | GCA | AAC | TCC | ATT | 96 |
| Ile | Arg | Val | Ala | Leu | Val | Leu | Ser | Cys | Ile | Cys | Pro | Ala | Asn | Ser | Ile | |
| | | | 20 | | | | | 25 | | | | | 30 | | | |
| GAT | GGC | AGG | CCT | CTT | GCA | GCT | GCA | GGA | ATT | GTG | GTT | ACA | GGA | GAC | AAA | 144 |
| Asp | Gly | Arg | Pro | Leu | Ala | Ala | Ala | Gly | Ile | Val | Val | Thr | Gly | Asp | Lys | |
| | | 35 | | | | | 40 | | | | | 45 | | | | |
| GCA | GTC | AAC | ATA | TAC | ACC | TCA | TCC | CAG | ACA | GGA | TCA | ATC | ATA | GTT | AAG | 192 |
| Ala | Val | Asn | Ile | Tyr | Thr | Ser | Ser | Gln | Thr | Gly | Ser | Ile | Ile | Val | Lys | |
| | 50 | | | | | 55 | | | | | 60 | | | | | |
| CTC | CTC | CCG | AAT | CTG | CCA | AAG | GAT | AAG | GAG | GCA | TGT | GCG | AAA | GCC | CCC | 240 |
| Leu | Leu | Pro | Asn | Leu | Pro | Lys | Asp | Lys | Glu | Ala | Cys | Ala | Lys | Ala | Pro | |
| 65 | | | | | 70 | | | | | 75 | | | | | 80 | |
| TTG | GAT | GCA | TAC | AAC | AGG | ACA | TTG | ACC | ACT | TTG | CTC | ACC | CCC | CTT | GGT | 288 |
| Leu | Asp | Ala | Tyr | Asn | Arg | Thr | Leu | Thr | Thr | Leu | Leu | Thr | Pro | Leu | Gly | |
| | | | | 85 | | | | | 90 | | | | | 95 | | |
| GAC | TCT | ATC | CGT | AGG | ATA | CAA | GAG | TCT | GTG | ACT | ACA | TCT | GGA | GGG | GGG | 336 |
| Asp | Ser | Ile | Arg | Arg | Ile | Gln | Glu | Ser | Val | Thr | Thr | Ser | Gly | Gly | Gly | |
| | | | 100 | | | | | 105 | | | | | 110 | | | |
| AGA | CAG | GGG | CGC | CTT | ATA | GGC | GCC | ATT | ATT | GGC | GGT | GTG | GCT | CTT | GGG | 384 |
| Arg | Gln | Gly | Arg | Leu | Ile | Gly | Ala | Ile | Ile | Gly | Gly | Val | Ala | Leu | Gly | |
| | | 115 | | | | | 120 | | | | | 125 | | | | |
| GTT | GCA | ACT | GCC | GCA | CAA | ATA | ACA | GCG | GCC | GCA | GCT | CTG | ATA | CAA | GCC | 432 |
| Val | Ala | Thr | Ala | Ala | Gln | Ile | Thr | Ala | Ala | Ala | Ala | Leu | Ile | Gln | Ala | |
| | | 130 | | | | | 135 | | | | | 140 | | | | |
| AAA | CAA | AAT | GCT | GCC | AAC | ATC | CTC | CGA | CTT | AAA | GAG | AGC | ATT | GCC | GCA | 480 |
| Lys | Gln | Asn | Ala | Ala | Asn | Ile | Leu | Arg | Leu | Lys | Glu | Ser | Ile | Ala | Ala | |
| 145 | | | | | 150 | | | | | 155 | | | | | 160 | |
| ACC | AAT | GAG | GCT | GTG | CAT | GAG | GTC | ACT | GAC | GGA | TTA | TCG | CAA | CTA | GCA | 528 |
| Thr | Asn | Glu | Ala | Val | His | Glu | Val | Thr | Asp | Gly | Leu | Ser | Gln | Leu | Ala | |
| | | | | 165 | | | | | 170 | | | | | 175 | | |
| GTG | GCA | GTT | GGG | AAG | ATG | CAG | CAG | TTC | GTT | AAT | GAC | CAA | TTT | AAT | AAA | 576 |
| Val | Ala | Val | Gly | Lys | Met | Gln | Gln | Phe | Val | Asn | Asp | Gln | Phe | Asn | Lys | |
| | | | 180 | | | | | 185 | | | | | 190 | | | |
| ACA | GCT | CAG | GAA | TTA | GAC | TGC | ATC | AAA | ATT | GCA | CAG | CAA | GTT | GGT | GTA | 624 |
| Thr | Ala | Gln | Glu | Leu | Asp | Cys | Ile | Lys | Ile | Ala | Gln | Gln | Val | Gly | Val | |
| | | 195 | | | | | 200 | | | | | 205 | | | | |
| GAG | CTC | AAC | CTG | TAC | CTA | ACC | GAA | TCG | ACT | ACA | GTA | TTC | GGA | CCA | CAA | 672 |
| Glu | Leu | Asn | Leu | Tyr | Leu | Thr | Glu | Ser | Thr | Thr | Val | Phe | Gly | Pro | Gln | |
| | 210 | | | | | 215 | | | | | 220 | | | | | |
| ATC | ACT | TCA | CCT | GCC | TTA | AAC | AAG | CTG | ACT | ATT | CAG | GCA | CTT | TAC | AAT | 720 |
| Ile | Thr | Ser | Pro | Ala | Leu | Asn | Lys | Leu | Thr | Ile | Gln | Ala | Leu | Tyr | Asn | |
| 225 | | | | | 230 | | | | | 235 | | | | | 240 | |
| CTA | GCT | GGT | GGG | AAT | ATG | GAT | TAC | TTA | TTG | ACT | AAG | TTA | GGT | ATA | GGG | 768 |
| Leu | Ala | Gly | Gly | Asn | Met | Asp | Tyr | Leu | Leu | Thr | Lys | Leu | Gly | Ile | Gly | |
| | | | | 245 | | | | | 250 | | | | | 255 | | |
| AAC | AAT | CAA | CTC | AGC | TCA | TTA | ATC | GGT | AGC | GGC | TTA | ATC | ACC | GGT | AAC | 816 |
| Asn | Asn | Gln | Leu | Ser | Ser | Leu | Ile | Gly | Ser | Gly | Leu | Ile | Thr | Gly | Asn | |
| | | | 260 | | | | | 265 | | | | | 270 | | | |
| CCT | ATT | CTA | TAC | GAC | TCA | CAG | ACT | CAA | CTC | TTG | GGT | ATA | CAG | GTA | ACT | 864 |
| Pro | Ile | Leu | Tyr | Asp | Ser | Gln | Thr | Gln | Leu | Leu | Gly | Ile | Gln | Val | Thr | |
| | | 275 | | | | | 280 | | | | | 285 | | | | |
| CTA | CCT | TCA | GTC | GGG | AAC | CTA | AAT | AAT | ATG | CGT | GCC | ACC | TAC | TTG | GAA | 912 |
| Leu | Pro | Ser | Val | Gly | Asn | Leu | Asn | Asn | Met | Arg | Ala | Thr | Tyr | Leu | Glu | |
| | | 290 | | | | | 295 | | | | | 300 | | | | |
| ACC | TTA | TCC | GTA | AGC | ACA | ACC | AGG | GGA | TTT | GCC | TCG | GCA | CTT | GTC | CCA | 960 |
| Thr | Leu | Ser | Val | Ser | Thr | Thr | Arg | Gly | Phe | Ala | Ser | Ala | Leu | Val | Pro | |

```
                    305                             310                             315                             320
AAA  GTG  GTG  ACA  CGG  GTC  GGT  TCT  GTG  ATA  GAA  GAA  CTT  GAC  ACC  TCA      1008
Lys  Val  Val  Thr  Arg  Val  Gly  Ser  Val  Ile  Glu  Glu  Leu  Asp  Thr  Ser
               325                             330                             335

TAC  TGT  ATA  GAA  ACT  GAC  TTA  GAT  TTA  TAT  TGT  ACA  AGA  ATA  GTA  ACG      1056
Tyr  Cys  Ile  Glu  Thr  Asp  Leu  Asp  Leu  Tyr  Cys  Thr  Arg  Ile  Val  Thr
               340                             345                             350

TTC  CCT  ATG  TCC  CCT  GGT  ATT  TAC  TCC  TGC  TTG  AGC  GGC  AAT  ACA  TCG      1104
Phe  Pro  Met  Ser  Pro  Gly  Ile  Tyr  Ser  Cys  Leu  Ser  Gly  Asn  Thr  Ser
               355                             360                             365

GCC  TGT  ATG  TAC  TCA  AAG  ACC  GAA  GGC  GCA  CTT  ACT  ACA  CCA  TAT  ATG      1152
Ala  Cys  Met  Tyr  Ser  Lys  Thr  Glu  Gly  Ala  Leu  Thr  Thr  Pro  Tyr  Met
               370                             375                             380

ACT  ATC  AAA  GGC  TCA  GTC  ATC  GCT  AAC  TGC  AAG  ATG  ACA  ACA  TGT  AGA      1200
Thr  Ile  Lys  Gly  Ser  Val  Ile  Ala  Asn  Cys  Lys  Met  Thr  Thr  Cys  Arg
385                             390                             395                  400

TGT  GTA  AAC  CCC  CCG  GGT  ATC  ATA  TCG  CAA  AAC  TAT  GGA  GAA  GCC  GTG      1248
Cys  Val  Asn  Pro  Pro  Gly  Ile  Ile  Ser  Gln  Asn  Tyr  Gly  Glu  Ala  Val
               405                             410                             415

TCT  CTA  ATA  GAT  AAA  CAA  TCA  TGC  AAT  GTT  TTA  TCC  TTA  GGC  GGG  ATA      1296
Ser  Leu  Ile  Asp  Lys  Gln  Ser  Cys  Asn  Val  Leu  Ser  Leu  Gly  Gly  Ile
               420                             425                             430

ACT  TTA  AGG  CTC  AGT  GGG  GAA  TTC  GAT  GTA  ACT  TAT  CAG  AAG  AAT  ATC      1344
Thr  Leu  Arg  Leu  Ser  Gly  Glu  Phe  Asp  Val  Thr  Tyr  Gln  Lys  Asn  Ile
               435                             440                             445

TCA  ATA  CAA  GAT  TCT  CAA  GTA  ATA  ATA  ACA  GGC  AAT  CTT  GAT  ATC  TCA      1392
Ser  Ile  Gln  Asp  Ser  Gln  Val  Ile  Ile  Thr  Gly  Asn  Leu  Asp  Ile  Ser
               450                             455                             460

ACT  GAG  CTT  GGG  AAT  GTC  AAC  AAC  TCG  ATC  AGT  AAT  GCC  TTG  AAT  AAG      1440
Thr  Glu  Leu  Gly  Asn  Val  Asn  Asn  Ser  Ile  Ser  Asn  Ala  Leu  Asn  Lys
465                             470                             475                  480

TTA  GAG  GAA  AGC  AAC  AGA  AAA  CTA  GAC  AAA  GTC  AAT  GTC  AAA  CTG  ACC      1488
Leu  Glu  Glu  Ser  Asn  Arg  Lys  Leu  Asp  Lys  Val  Asn  Val  Lys  Leu  Thr
               485                             490                             495

AGC  ACA  TCT  GCT  CTC  ATT  ACC  TAT  ATC  GTT  TTG  ACT  ATC  ATA  TCT  CTT      1536
Ser  Thr  Ser  Ala  Leu  Ile  Thr  Tyr  Ile  Val  Leu  Thr  Ile  Ile  Ser  Leu
               500                             505                             510

GTT  TTT  GGT  ATA  CTT  AGC  CTG  ATT  CTA  GCA  TGC  TAC  CTA  ATG  TAC  AAG      1584
Val  Phe  Gly  Ile  Leu  Ser  Leu  Ile  Leu  Ala  Cys  Tyr  Leu  Met  Tyr  Lys
               515                             520                             525

CAA  AAG  GCG  CAA  CAA  AAG  ACC  TTA  TTA  TGG  CTT  GGG  AAT  AAT  ACC  CTA      1632
Gln  Lys  Ala  Gln  Gln  Lys  Thr  Leu  Leu  Trp  Leu  Gly  Asn  Asn  Thr  Leu
               530                             535                             540

GAT  CAG  ATG  AGA  GCC  ACT  ACA  AAA  ATG  TGA                                    1662
Asp  Gln  Met  Arg  Ala  Thr  Thr  Lys  Met
545                             550
```

(2) INFORMATION FOR SEQ ID NO:13:

(i) SEQUENCE CHARACTERISTICS:
        (A) LENGTH: 553 amino acids
        (B) TYPE: amino acid
        (D) TOPOLOGY: linear (ii) MOLECULE TYPE: protein (xi) SEQUENCE DESCRIPTION: SEQ ID NO:13:

```
Met  Gly  Ser  Arg  Pro  Ser  Thr  Lys  Asn  Pro  Ala  Pro  Met  Met  Leu  Thr
 1                  5                            10                           15

Ile  Arg  Val  Ala  Leu  Val  Leu  Ser  Cys  Ile  Cys  Pro  Ala  Asn  Ser  Ile
                    20                           25                           30
```

-continued

| | | | | | | | | | | | | | | |
|---|---|---|---|---|---|---|---|---|---|---|---|---|---|---|
|Asp|Gly|Arg|Pro|Leu|Ala|Ala|Ala|Gly|Ile|Val|Val|Thr|Gly|Asp|Lys|
| | |35| | | |40| | | | |45| | | |
|Ala|Val|Asn|Ile|Tyr|Thr|Ser|Ser|Gln|Thr|Gly|Ser|Ile|Ile|Val|Lys|
| |50| | | | |55| | | |60| | | | |
|Leu|Leu|Pro|Asn|Leu|Pro|Lys|Asp|Lys|Glu|Ala|Cys|Ala|Lys|Ala|Pro|
|65| | | | |70| | | |75| | | | |80|
|Leu|Asp|Ala|Tyr|Asn|Arg|Thr|Leu|Thr|Thr|Leu|Leu|Thr|Pro|Leu|Gly|
| | | | |85| | | |90| | | | |95| |
|Asp|Ser|Ile|Arg|Arg|Ile|Gln|Glu|Ser|Val|Thr|Thr|Ser|Gly|Gly|Gly|
| | | |100| | | |105| | | | |110| | |
|Arg|Gln|Gly|Arg|Leu|Ile|Gly|Ala|Ile|Ile|Gly|Gly|Val|Ala|Leu|Gly|
| | |115| | | |120| | | | |125| | | |
|Val|Ala|Thr|Ala|Ala|Gln|Ile|Thr|Ala|Ala|Ala|Leu|Ile|Gln|Ala|
| |130| | | |135| | | | |140| | | | |
|Lys|Gln|Asn|Ala|Ala|Asn|Ile|Leu|Arg|Leu|Lys|Glu|Ser|Ile|Ala|Ala|
|145| | | | |150| | | |155| | | | |160|
|Thr|Asn|Glu|Ala|Val|His|Glu|Val|Thr|Asp|Gly|Leu|Ser|Gln|Leu|Ala|
| | | | |165| | | |170| | | | |175| |
|Val|Ala|Val|Gly|Lys|Met|Gln|Gln|Phe|Val|Asn|Asp|Gln|Phe|Asn|Lys|
| | | |180| | | |185| | | | |190| | |
|Thr|Ala|Gln|Glu|Leu|Asp|Cys|Ile|Lys|Ile|Ala|Gln|Gln|Val|Gly|Val|
| | |195| | | |200| | | | |205| | | |
|Glu|Leu|Asn|Leu|Tyr|Leu|Thr|Glu|Ser|Thr|Thr|Val|Phe|Gly|Pro|Gln|
| |210| | | | |215| | | |220| | | | |
|Ile|Thr|Ser|Pro|Ala|Leu|Asn|Lys|Leu|Thr|Ile|Gln|Ala|Leu|Tyr|Asn|
|225| | | | |230| | | |235| | | | |240|
|Leu|Ala|Gly|Gly|Asn|Met|Asp|Tyr|Leu|Leu|Thr|Lys|Leu|Gly|Ile|Gly|
| | | | |245| | | |250| | | | |255| |
|Asn|Asn|Gln|Leu|Ser|Ser|Leu|Ile|Gly|Ser|Gly|Leu|Ile|Thr|Gly|Asn|
| | | |260| | | |265| | | | |270| | |
|Pro|Ile|Leu|Tyr|Asp|Ser|Gln|Thr|Gln|Leu|Leu|Gly|Ile|Gln|Val|Thr|
| | |275| | | |280| | | | |285| | | |
|Leu|Pro|Ser|Val|Gly|Asn|Leu|Asn|Asn|Met|Arg|Ala|Thr|Tyr|Leu|Glu|
| |290| | | | |295| | | |300| | | | |
|Thr|Leu|Ser|Val|Ser|Thr|Thr|Arg|Gly|Phe|Ala|Ser|Ala|Leu|Val|Pro|
|305| | | | |310| | | |315| | | | |320|
|Lys|Val|Val|Thr|Arg|Val|Gly|Ser|Val|Ile|Glu|Glu|Leu|Asp|Thr|Ser|
| | | |325| | | |330| | | | |335| | |
|Tyr|Cys|Ile|Glu|Thr|Asp|Leu|Asp|Leu|Tyr|Cys|Thr|Arg|Ile|Val|Thr|
| | | |340| | | |345| | | | |350| | |
|Phe|Pro|Met|Ser|Pro|Gly|Ile|Tyr|Ser|Cys|Leu|Ser|Gly|Asn|Thr|Ser|
| | |355| | | |360| | | | |365| | | |
|Ala|Cys|Met|Tyr|Ser|Lys|Thr|Glu|Gly|Ala|Leu|Thr|Thr|Pro|Tyr|Met|
| |370| | | | |375| | | |380| | | | |
|Thr|Ile|Lys|Gly|Ser|Val|Ile|Ala|Asn|Cys|Lys|Met|Thr|Thr|Cys|Arg|
|385| | | | |390| | | |395| | | | |400|
|Cys|Val|Asn|Pro|Pro|Gly|Ile|Ile|Ser|Gln|Asn|Tyr|Gly|Glu|Ala|Val|
| | | | |405| | | |410| | | | |415| |
|Ser|Leu|Ile|Asp|Lys|Gln|Ser|Cys|Asn|Val|Leu|Ser|Leu|Gly|Gly|Ile|
| | | |420| | | |425| | | | |430| | |
|Thr|Leu|Arg|Leu|Ser|Gly|Glu|Phe|Asp|Val|Thr|Tyr|Gln|Lys|Asn|Ile|
| | |435| | | |440| | | | |445| | | |
|Ser|Ile|Gln|Asp|Ser|Gln|Val|Ile|Ile|Thr|Gly|Asn|Leu|Asp|Ile|Ser|
| |450| | | | |455| | | |460| | | | |

```
Thr  Glu  Leu  Gly  Asn  Val  Asn  Asn  Ser  Ile  Ser  Asn  Ala  Leu  Asn  Lys
465                      470                 475                      480

Leu  Glu  Glu  Ser  Asn  Arg  Lys  Leu  Asp  Lys  Val  Asn  Val  Lys  Leu  Thr
                    485                      490                      495

Ser  Thr  Ser  Ala  Leu  Ile  Thr  Tyr  Ile  Val  Leu  Thr  Ile  Ile  Ser  Leu
               500                      505                      510

Val  Phe  Gly  Ile  Leu  Ser  Leu  Ile  Leu  Ala  Cys  Tyr  Leu  Met  Tyr  Lys
          515                      520                      525

Gln  Lys  Ala  Gln  Gln  Lys  Thr  Leu  Leu  Trp  Leu  Gly  Asn  Asn  Thr  Leu
     530                      535                      540

Asp  Gln  Met  Arg  Ala  Thr  Thr  Lys  Met
545                      550
```

(2) INFORMATION FOR SEQ ID NO:14:

(i) SEQUENCE CHARACTERISTICS:
       (A) LENGTH: 3489 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (ix) FEATURE:
       (A) NAME/KEY: CDS
       (B) LOCATION: 1..3489

(xi) SEQUENCE DESCRIPTION: SEQ ID NO:14:

```
ATG  TTG  GTA  ACA  CCT  CTT  TTA  CTA  GTG  ACT  CTT  TGT  GTA  CTA  TGT         48
Met  Leu  Val  Thr  Pro  Leu  Leu  Leu  Val  Thr  Leu  Leu  Cys  Val  Leu  Cys
  1                    5                        10                       15

AGT  GCT  GCT  TTG  TAT  GAC  AGT  AGT  TCT  TAC  GTT  TAC  TAC  TAC  CAA  AGT    96
Ser  Ala  Ala  Leu  Tyr  Asp  Ser  Ser  Ser  Tyr  Val  Tyr  Tyr  Tyr  Gln  Ser
               20                        25                        30

GCC  TTT  AGA  CCA  CCT  AAT  GGT  TGG  CAT  TTA  CAC  GGG  GGT  GCT  TAT  GCG   144
Ala  Phe  Arg  Pro  Pro  Asn  Gly  Trp  His  Leu  His  Gly  Gly  Ala  Tyr  Ala
          35                        40                        45

GTA  GTT  AAT  ATT  TCT  AGC  GAA  TCT  AAT  AAT  GCA  GGC  TCT  TCA  CCT  GGG   192
Val  Val  Asn  Ile  Ser  Ser  Glu  Ser  Asn  Asn  Ala  Gly  Ser  Ser  Pro  Gly
     50                        55                        60

TGT  ATT  GTT  GGT  ACT  ATT  CAT  GGT  GGT  CGT  GTT  GTT  AAT  GCT  TCT  TCT   240
Cys  Ile  Val  Gly  Thr  Ile  His  Gly  Gly  Arg  Val  Val  Asn  Ala  Ser  Ser
 65                        70                        75                   80

ATA  GCT  ATG  ACG  GCA  CCG  TCA  TCA  GGT  ATG  GCT  TGG  TCT  AGC  AGT  CAG   288
Ile  Ala  Met  Thr  Ala  Pro  Ser  Ser  Gly  Met  Ala  Trp  Ser  Ser  Ser  Gln
                    85                        90                        95

TTT  TGT  ACT  GCA  CAC  TGT  AAC  TTT  TCA  GAT  ACT  ACA  GTG  TTT  GTT  ACA   336
Phe  Cys  Thr  Ala  His  Cys  Asn  Phe  Ser  Asp  Thr  Thr  Val  Phe  Val  Thr
               100                      105                      110

CAT  TGT  TAT  AAA  TAT  GAT  GGG  TGT  CCT  ATA  ACT  GGC  ATG  CTT  CAA  AAG   384
His  Cys  Tyr  Lys  Tyr  Asp  Gly  Cys  Pro  Ile  Thr  Gly  Met  Leu  Gln  Lys
          115                      120                      125

AAT  TTT  TTA  CGT  GTT  TCT  GCT  ATG  AAA  AAT  GGC  CAG  CTT  TTC  TAT  AAT   432
Asn  Phe  Leu  Arg  Val  Ser  Ala  Met  Lys  Asn  Gly  Gln  Leu  Phe  Tyr  Asn
     130                      135                      140

TTA  ACA  GTT  AGT  GTA  GCT  AAG  TAC  CCT  ACT  TTT  AAA  TCA  TTT  CAG  TGT   480
Leu  Thr  Val  Ser  Val  Ala  Lys  Tyr  Pro  Thr  Phe  Lys  Ser  Phe  Gln  Cys
145                      150                      155                      160
```

| | | | | | | | | | | | | | | | | |
|---|---|---|---|---|---|---|---|---|---|---|---|---|---|---|---|---|
| GTT | AAT | AAT | TTA | ACA | TCC | GTA | TAT | TTA | AAT | GGT | GAT | CTT | GTT | TAC | ACC | 528 |
| Val | Asn | Asn | Leu | Thr 165 | Ser | Val | Tyr | Leu 170 | Asn | Gly | Asp | Leu | Val 175 | Tyr | Thr | |
| TCT | AAT | GAG | ACC | ACA | GAT | GTT | ACA | TCT | GCA | GGT | GTT | TAT | TTT | AAA | GCT | 576 |
| Ser | Asn | Glu | Thr 180 | Thr | Asp | Val | Thr | Ser 185 | Ala | Gly | Val | Tyr | Phe 190 | Lys | Ala | |
| GGT | GGA | CCT | ATA | ACT | TAT | AAA | GTT | ATG | AGA | AAA | GTT | AAA | GCC | CTG | GCT | 624 |
| Gly | Gly | Pro 195 | Ile | Thr | Tyr | Lys | Val | Met 200 | Arg | Lys | Val | Lys | Ala 205 | Leu | Ala | |
| TAT | TTT | GTT | AAT | GGT | ACT | GCA | CAA | GAT | GTT | ATT | TTG | TGT | GAT | GGA | TCA | 672 |
| Tyr | Phe 210 | Val | Asn | Gly | Thr | Ala 215 | Gln | Asp | Val | Ile | Leu 220 | Cys | Asp | Gly | Ser | |
| CCT | AGA | GGC | TTG | TTA | GCA | TGC | CAG | TAT | AAT | ACT | GGC | AAT | TTT | TCA | GAT | 720 |
| Pro 225 | Arg | Gly | Leu | Leu | Ala 230 | Cys | Gln | Tyr | Asn | Thr 235 | Gly | Asn | Phe | Ser | Asp 240 | |
| GGC | TTT | TAT | CCT | TTT | ATT | AAT | AGT | AGT | TTA | GTT | AAG | CAG | AAG | TTT | ATT | 768 |
| Gly | Phe | Tyr | Pro | Phe 245 | Ile | Asn | Ser | Ser | Leu 250 | Val | Lys | Gln | Lys | Phe 255 | Ile | |
| GTC | TAT | CGT | GAA | AAT | AGT | GTT | AAT | ACT | ACT | TTT | ACG | TTA | CAC | AAT | TTC | 816 |
| Val | Tyr | Arg | Glu 260 | Asn | Ser | Val | Asn | Thr 265 | Thr | Phe | Thr | Leu | His 270 | Asn | Phe | |
| ACT | TTT | CAT | AAT | GAG | ACT | GGC | GCC | AAC | CCT | AAT | CCT | AGT | GGT | GTT | CAG | 864 |
| Thr | Phe | His 275 | Asn | Glu | Thr | Gly | Ala 280 | Asn | Pro | Asn | Pro | Ser 285 | Gly | Val | Gln | |
| AAT | ATT | CTA | ACT | TAC | CAA | ACA | CAA | ACA | GCT | CAG | AGT | GGT | TAT | TAT | AAT | 912 |
| Asn | Ile | Leu 290 | Thr | Tyr | Gln | Thr | Gln 295 | Thr | Ala | Gln | Ser | Gly 300 | Tyr | Tyr | Asn | |
| TTT | AAT | TTT | TCC | TTT | CTG | AGT | AGT | TTT | GTT | TAT | AAG | GAG | TCT | AAT | TTT | 960 |
| Phe 305 | Asn | Phe | Ser | Phe | Leu 310 | Ser | Ser | Phe | Val | Tyr 315 | Lys | Glu | Ser | Asn | Phe 320 | |
| ATG | TAT | GGA | TCT | TAT | CAC | CCA | AGT | TGT | AAT | TTT | AGA | CTA | GAA | ACT | ATT | 1008 |
| Met | Tyr | Gly | Ser | Tyr 325 | His | Pro | Ser | Cys | Asn 330 | Phe | Arg | Leu | Glu | Thr 335 | Ile | |
| AAT | AAT | GGC | TTG | TGG | TTT | AAT | TCA | CTT | TCA | GTT | TCA | ATT | GCT | TAC | GGT | 1056 |
| Asn | Asn | Gly | Leu 340 | Trp | Phe | Asn | Ser | Leu 345 | Ser | Val | Ser | Ile | Ala 350 | Tyr | Gly | |
| CCT | CTT | CAA | GGT | GGT | TGC | AAG | CAA | TCT | GTC | TTT | AGT | GGT | AGA | GCA | ACT | 1104 |
| Pro | Leu | Gln 355 | Gly | Gly | Cys | Lys | Gln 360 | Ser | Val | Phe | Ser | Gly 365 | Arg | Ala | Thr | |
| TGT | TGT | TAT | GCT | TAT | TCA | TAT | GGA | GGT | CCT | TCG | CTG | TGT | AAA | GGT | GTT | 1152 |
| Cys | Cys 370 | Tyr | Ala | Tyr | Ser | Tyr 375 | Gly | Gly | Pro | Ser | Leu 380 | Cys | Lys | Gly | Val | |
| TAT | TCA | GGT | GAG | TTA | GAT | CTT | AAT | TTT | GAA | TGT | GGA | CTG | TTA | GTT | TAT | 1200 |
| Tyr | Ser 385 | Gly | Glu | Leu | Asp 390 | Leu | Asn | Phe | Glu | Cys 395 | Gly | Leu | Leu | Val | Tyr 400 | |
| GTT | ACT | AAG | AGC | GGT | GGC | TCT | CGT | ATA | CAA | ACA | GCC | ACT | GAA | CCG | CCA | 1248 |
| Val | Thr | Lys | Ser | Gly 405 | Gly | Ser | Arg | Ile | Gln 410 | Thr | Ala | Thr | Glu | Pro 415 | Pro | |
| GTT | ATA | ACT | CGA | CAC | AAT | TAT | AAT | AAT | ATT | ACT | TTA | AAT | ACT | TGT | GTT | 1296 |
| Val | Ile | Thr | Arg 420 | His | Asn | Tyr | Asn | Asn 425 | Ile | Thr | Leu | Asn | Thr 430 | Cys | Val | |
| GAT | TAT | AAT | ATA | TAT | GGC | AGA | ACT | GGC | CAA | GGT | TTT | ATT | ACT | AAT | GTA | 1344 |
| Asp | Tyr | Asn | Ile | Tyr 435 | Gly | Arg | Thr | Gly | Gln 440 | Gly | Phe | Ile | Thr | Asn 445 | Val | |
| ACC | GAC | TCA | GCT | GTT | AGT | TAT | AAT | TAT | CTA | GCA | GAC | GCA | GGT | TTG | GCT | 1392 |
| Thr | Asp | Ser | Ala 450 | Val | Ser | Tyr | Asn | Tyr 455 | Leu | Ala | Asp | Ala | Gly 460 | Leu | Ala | |
| ATT | TTA | GAT | ACA | TCT | GGT | TCC | ATA | GAC | ATC | TTT | GTT | GTA | CAA | GGT | GAA | 1440 |
| Ile | Leu | Asp | Thr 465 | Ser | Gly | Ser | Ile | Asp 470 | Ile | Phe | Val | Val | Gln 475 | Gly | Glu 480 | |

```
TAT  GGT  CTT  ACT  TAT  TAT  AAG  GTT  AAC  CCT  TGC  GAA  GAT  GTC  AAC  CAG    1488
Tyr  Gly  Leu  Thr  Tyr  Tyr  Lys  Val  Asn  Pro  Cys  Glu  Asp  Val  Asn  Gln
               485                      490                      495

CAG  TTT  GTA  GTT  TCT  GGT  GGT  AAA  TTA  GTA  GGT  ATT  CTT  ACT  TCA  CGT    1536
Gln  Phe  Val  Val  Ser  Gly  Gly  Lys  Leu  Val  Gly  Ile  Leu  Thr  Ser  Arg
               500                      505                      510

AAT  GAG  ACT  GGT  TCT  CAG  CTT  CTT  GAG  AAC  CAG  TTT  TAC  ATT  AAA  ATC    1584
Asn  Glu  Thr  Gly  Ser  Gln  Leu  Leu  Glu  Asn  Gln  Phe  Tyr  Ile  Lys  Ile
               515                      520                      525

ACT  AAT  GGA  ACA  CGT  CGT  TTT  AGA  CGT  TCT  ATT  ACT  GAA  AAT  GTT  GCA    1632
Thr  Asn  Gly  Thr  Arg  Arg  Phe  Arg  Arg  Ser  Ile  Thr  Glu  Asn  Val  Ala
     530                      535                      540

AAT  TGC  CCT  TAT  GTT  AGT  TAT  GGT  AAG  TTT  TGT  ATA  AAA  CCT  GAT  GGT    1680
Asn  Cys  Pro  Tyr  Val  Ser  Tyr  Gly  Lys  Phe  Cys  Ile  Lys  Pro  Asp  Gly
545                      550                      555                      560

TCA  ATT  GCC  ACA  ATA  GTA  CCA  AAA  CAA  TTG  GAA  CAG  TTT  GTG  GCA  CCT    1728
Ser  Ile  Ala  Thr  Ile  Val  Pro  Lys  Gln  Leu  Glu  Gln  Phe  Val  Ala  Pro
               565                      570                      575

TTA  CTT  AAT  GTT  ACT  GAA  AAT  GTG  CTC  ATA  CCT  AAC  AGT  TTT  AAT  TTA    1776
Leu  Leu  Asn  Val  Thr  Glu  Asn  Val  Leu  Ile  Pro  Asn  Ser  Phe  Asn  Leu
               580                      585                      590

ACT  GTT  ACA  GAT  GAG  TAC  ATA  CAA  ACG  CGT  ATG  GAT  AAG  GTC  CAA  ATT    1824
Thr  Val  Thr  Asp  Glu  Tyr  Ile  Gln  Thr  Arg  Met  Asp  Lys  Val  Gln  Ile
               595                      600                      605

AAT  TGT  CTG  CAG  TAT  GTT  TGT  GGC  AAT  TCT  CTG  GAT  TGT  AGA  GAT  TTG    1872
Asn  Cys  Leu  Gln  Tyr  Val  Cys  Gly  Asn  Ser  Leu  Asp  Cys  Arg  Asp  Leu
          610                      615                      620

TTT  CAA  CAA  TAT  GGG  CCT  GTT  TGT  GAC  AAC  ATA  TTG  TCT  GTA  GTA  AAT    1920
Phe  Gln  Gln  Tyr  Gly  Pro  Val  Cys  Asp  Asn  Ile  Leu  Ser  Val  Val  Asn
625                      630                      635                      640

AGT  ATT  GGT  CAA  AAA  GAA  GAT  ATG  GAA  CTT  TTG  AAT  TTC  TAT  TCT  TCT    1968
Ser  Ile  Gly  Gln  Lys  Glu  Asp  Met  Glu  Leu  Leu  Asn  Phe  Tyr  Ser  Ser
                    645                      650                      655

ACT  AAA  CCG  GCT  GGT  TTT  AAT  ACA  CCA  TTT  CTT  AGT  AAT  GTT  AGC  ACT    2016
Thr  Lys  Pro  Ala  Gly  Phe  Asn  Thr  Pro  Phe  Leu  Ser  Asn  Val  Ser  Thr
               660                      665                      670

GGT  GAG  TTT  AAT  ATT  TCT  CTT  CTG  TTA  ACA  ACT  CCT  AGT  AGT  CCT  AGA    2064
Gly  Glu  Phe  Asn  Ile  Ser  Leu  Leu  Leu  Thr  Thr  Pro  Ser  Ser  Pro  Arg
               675                      680                      685

AGG  CGT  TCT  TTT  ATT  GAA  GAC  CTT  CTA  TTT  ACA  AGC  GTT  GAA  TCT  GTT    2112
Arg  Arg  Ser  Phe  Ile  Glu  Asp  Leu  Leu  Phe  Thr  Ser  Val  Glu  Ser  Val
690                      695                      700

GGA  TTA  CCA  ACA  GAT  GAC  GCA  TAC  AAA  AAT  TGC  ACT  GCA  GGA  CCT  TTA    2160
Gly  Leu  Pro  Thr  Asp  Asp  Ala  Tyr  Lys  Asn  Cys  Thr  Ala  Gly  Pro  Leu
705                      710                      715                      720

GGT  TTT  CTT  AAG  GAC  CTT  GCG  TGT  GCT  CGT  GAA  TAT  AAT  GGT  TTG  CTT    2208
Gly  Phe  Leu  Lys  Asp  Leu  Ala  Cys  Ala  Arg  Glu  Tyr  Asn  Gly  Leu  Leu
               725                      730                      735

GTG  TTG  CCT  CCC  ATT  ATA  ACA  GCA  GAA  ATG  CAA  ACT  TTG  TAT  ACT  AGT    2256
Val  Leu  Pro  Pro  Ile  Ile  Thr  Ala  Glu  Met  Gln  Thr  Leu  Tyr  Thr  Ser
               740                      745                      750

TCT  CTA  GTA  GCT  TCT  ATG  GCT  TTT  GGT  GGT  ATT  ACT  GCA  GCT  GGT  GCT    2304
Ser  Leu  Val  Ala  Ser  Met  Ala  Phe  Gly  Gly  Ile  Thr  Ala  Ala  Gly  Ala
               755                      760                      765

ATA  CCT  TTT  GCC  ACA  CAA  CTG  CAG  GCT  AGA  ATT  AAT  CAC  TTG  GGT  ATT    2352
Ile  Pro  Phe  Ala  Thr  Gln  Leu  Gln  Ala  Arg  Ile  Asn  His  Leu  Gly  Ile
     770                      775                      780

ACC  CAG  TCA  CTT  TTG  TTG  AAG  AAT  CAA  GAA  AAA  ATT  GCT  GCT  TCC  TTT    2400
Thr  Gln  Ser  Leu  Leu  Leu  Lys  Asn  Gln  Glu  Lys  Ile  Ala  Ala  Ser  Phe
785                      790                      795                      800
```

| | | | | | | | | | | | | | | | | |
|---|---|---|---|---|---|---|---|---|---|---|---|---|---|---|---|---|
| AAT<br>Asn | AAG<br>Lys | GCC<br>Ala | ATT<br>Ile | GGT<br>Gly<br>805 | CGT<br>Arg | ATG<br>Met | CAG<br>Gln | GAA<br>Glu | GGT<br>Gly<br>810 | TTT<br>Phe | AGA<br>Arg | AGT<br>Ser | ACA<br>Thr | TCT<br>Ser<br>815 | CTA<br>Leu | 2448 |
| GCA<br>Ala | TTA<br>Leu | CAA<br>Gln | CAA<br>Gln<br>820 | ATT<br>Ile | CAA<br>Gln | GAT<br>Asp | GTT<br>Val | GTT<br>Val<br>825 | AAT<br>Asn | AAG<br>Lys | CAG<br>Gln | AGT<br>Ser | GCT<br>Ala<br>830 | ATT<br>Ile | CTT<br>Leu | 2496 |
| ACT<br>Thr | GAG<br>Glu | ACT<br>Thr<br>835 | ATG<br>Met | GCA<br>Ala | TCA<br>Ser | CTT<br>Leu | AAT<br>Asn<br>840 | AAA<br>Lys | AAT<br>Asn | TTT<br>Phe | GGT<br>Gly | GCT<br>Ala<br>845 | ATT<br>Ile | TCT<br>Ser | TCT<br>Ser | 2544 |
| GTG<br>Val | ATT<br>Ile<br>850 | CAA<br>Gln | GAA<br>Glu | ATC<br>Ile | TAC<br>Tyr | CAG<br>Gln<br>855 | CAA<br>Gln | CTT<br>Leu | GAC<br>Asp | GCC<br>Ala | ATA<br>Ile<br>860 | CAA<br>Gln | GCA<br>Ala | AAT<br>Asn | GCT<br>Ala | 2592 |
| CAA<br>Gln<br>865 | GTG<br>Val | GAT<br>Asp | CGT<br>Arg | CTT<br>Leu | ATA<br>Ile<br>870 | ACT<br>Thr | GGT<br>Gly | AGA<br>Arg | TTG<br>Leu | TCA<br>Ser<br>875 | TCA<br>Ser | CTT<br>Leu | TCT<br>Ser | GTT<br>Val | TTA<br>Leu<br>880 | 2640 |
| GCA<br>Ala | TCT<br>Ser | GCT<br>Ala | AAG<br>Lys | CAG<br>Gln<br>885 | GCG<br>Ala | GAG<br>Glu | CAT<br>His | ATT<br>Ile | AGA<br>Arg<br>890 | GTG<br>Val | TCA<br>Ser | CAA<br>Gln | CAG<br>Gln | CGT<br>Arg<br>895 | GAG<br>Glu | 2688 |
| TTA<br>Leu | GCT<br>Ala | ACT<br>Thr | CAG<br>Gln<br>900 | AAA<br>Lys | ATT<br>Ile | AAT<br>Asn | GAG<br>Glu | TGT<br>Cys<br>905 | GTT<br>Val | AAG<br>Lys | TCA<br>Ser | CAG<br>Gln | TCT<br>Ser<br>910 | ATT<br>Ile | AGG<br>Arg | 2736 |
| TAC<br>Tyr | TCC<br>Ser | TTT<br>Phe<br>915 | TGT<br>Cys | GGT<br>Gly | AAT<br>Asn | GGA<br>Gly | CGA<br>Arg<br>920 | CAT<br>His | GTT<br>Val | CTA<br>Leu | ACC<br>Thr | ATA<br>Ile<br>925 | CCG<br>Pro | CAA<br>Gln | AAT<br>Asn | 2784 |
| GCA<br>Ala | CCT<br>Pro | AAT<br>Asn<br>930 | GGT<br>Gly | ATA<br>Ile | GTG<br>Val | TTT<br>Phe | ATA<br>Ile<br>935 | CAC<br>His | TTT<br>Phe | TCT<br>Ser | TAT<br>Tyr | ACT<br>Thr<br>940 | CCA<br>Pro | GAT<br>Asp | AGT<br>Ser | 2832 |
| TTT<br>Phe<br>945 | GTT<br>Val | AAT<br>Asn | GTT<br>Val | ACT<br>Thr | GCA<br>Ala<br>950 | ATA<br>Ile | GTG<br>Val | GGT<br>Gly | TTT<br>Phe | TGT<br>Cys<br>955 | GTA<br>Val | AAG<br>Lys | CCA<br>Pro | GCT<br>Ala | AAT<br>Asn<br>960 | 2880 |
| GCT<br>Ala | AGT<br>Ser | CAG<br>Gln | TAT<br>Tyr | GCA<br>Ala<br>965 | ATA<br>Ile | GTA<br>Val | CCC<br>Pro | GCT<br>Ala | AAT<br>Asn<br>970 | GGT<br>Gly | AGG<br>Arg | GGT<br>Gly | ATT<br>Ile | TTT<br>Phe<br>975 | ATA<br>Ile | 2928 |
| CAA<br>Gln | GTT<br>Val | AAT<br>Asn | GGT<br>Gly<br>980 | AGT<br>Ser | TAC<br>Tyr | TAC<br>Tyr | ATC<br>Ile | ACA<br>Thr<br>985 | GCA<br>Ala | CGA<br>Arg | GAT<br>Asp | ATG<br>Met | TAT<br>Tyr<br>990 | ATG<br>Met | CCA<br>Pro | 2976 |
| AGA<br>Arg | GCT<br>Ala | ATT<br>Ile<br>995 | ACT<br>Thr | GCA<br>Ala | GGA<br>Gly | GAT<br>Asp | ATA<br>Ile<br>1000 | GTT<br>Val | ACG<br>Thr | CTT<br>Leu | ACT<br>Thr | TCT<br>Ser<br>1005 | TGT<br>Cys | CAA<br>Gln | GCA<br>Ala | 3024 |
| AAT<br>Asn | TAT<br>Tyr | GTA<br>Val<br>1010 | AGT<br>Ser | GTA<br>Val | AAT<br>Asn | AAG<br>Lys | ACC<br>Thr<br>1015 | GTC<br>Val | ATT<br>Ile | ACT<br>Thr | ACA<br>Thr | TTC<br>Phe<br>1020 | GTA<br>Val | GAC<br>Asp | AAT<br>Asn | 3072 |
| GAT<br>Asp<br>1025 | GAT<br>Asp | TTT<br>Phe | GAT<br>Asp | TTT<br>Phe | AAT<br>Asn<br>1030 | GAC<br>Asp | GAA<br>Glu | TTG<br>Leu | TCA<br>Ser | AAA<br>Lys<br>1035 | TGG<br>Trp | TGG<br>Trp | AAT<br>Asn | GAC<br>Asp | ACT<br>Thr<br>1040 | 3120 |
| AAG<br>Lys | CAT<br>His | GAG<br>Glu | CTA<br>Leu | CCA<br>Pro<br>1045 | GAC<br>Asp | TTT<br>Phe | GAC<br>Asp | AAA<br>Lys | TTC<br>Phe<br>1050 | AAT<br>Asn | TAC<br>Tyr | ACA<br>Thr | GTA<br>Val | CCT<br>Pro<br>1055 | ATA<br>Ile | 3168 |
| CTT<br>Leu | GAC<br>Asp | ATT<br>Ile | GAT<br>Asp<br>1060 | AGT<br>Ser | GAA<br>Glu | ATT<br>Ile | GAT<br>Asp | CGT<br>Arg<br>1065 | ATT<br>Ile | CAA<br>Gln | GGC<br>Gly | GTT<br>Val | ATA<br>Ile<br>1070 | CAG<br>Gln | GGT<br>Gly | 3216 |
| CTT<br>Leu | AAT<br>Asn | GAC<br>Asp<br>1075 | TCT<br>Ser | TTA<br>Leu | ATA<br>Ile | GAC<br>Asp | CTT<br>Leu<br>1080 | GAA<br>Glu | AAA<br>Lys | CTT<br>Leu | TCA<br>Ser | ATA<br>Ile<br>1085 | CTC<br>Leu | AAA<br>Lys | ACT<br>Thr | 3264 |
| TAT<br>Tyr | ATT<br>Ile | AAG<br>Lys<br>1090 | TGG<br>Trp | CCT<br>Pro | TGG<br>Trp | TAT<br>Tyr | GTG<br>Val<br>1095 | TGG<br>Trp | TTA<br>Leu | GCC<br>Ala | ATA<br>Ile | GCT<br>Ala<br>1100 | TTT<br>Phe | GCC<br>Ala | ACT<br>Thr | 3312 |
| ATT<br>Ile<br>1105 | ATC<br>Ile | TTC<br>Phe | ATC<br>Ile | TTA<br>Leu | ATA<br>Ile<br>1110 | CTA<br>Leu | GGA<br>Gly | TGG<br>Trp | GTT<br>Val | TTC<br>Phe<br>1115 | TTC<br>Phe | ATG<br>Met | ACT<br>Thr | GGA<br>Gly | TGT<br>Cys<br>1120 | 3360 |

-continued

| | | | | | | | | | | | | | | | | |
|---|---|---|---|---|---|---|---|---|---|---|---|---|---|---|---|---|
| TGT | GGT | TGT | TGT | TGT | GGA | TGC | TTT | GGC | ATT | ATG | CCT | CTA | ATG | AGT | AAG | 3408 |
| Cys | Gly | Cys | Cys | Cys | Gly | Cys | Phe | Gly | Ile | Met | Pro | Leu | Met | Ser | Lys | |
| | | | | 1125 | | | | 1130 | | | | | | 1135 | | |
| TGT | GGT | AAG | AAA | TCT | TCT | TAT | TAC | ACG | ACT | TTT | GAT | AAC | GAT | GTG | GTA | 3456 |
| Cys | Gly | Lys | Lys | Ser | Ser | Tyr | Tyr | Thr | Thr | Phe | Asp | Asn | Asp | Val | Val | |
| | | | 1140 | | | | | 1145 | | | | | 1150 | | | |
| ACT | GAA | CAA | AAC | AGA | CCT | AAA | AAG | TCT | GTT | TAA | | | | | | 3489 |
| Thr | Glu | Gln | Asn | Arg | Pro | Lys | Lys | Ser | Val | | | | | | | |
| | | 1155 | | | | | 1160 | | | | | | | | | |

( 2 ) INFORMATION FOR SEQ ID NO:15:

( i ) SEQUENCE CHARACTERISTICS:
( A ) LENGTH: 1162 amino acids
( B ) TYPE: amino acid
( D ) TOPOLOGY: linear ( i i ) MOLECULE TYPE: protein ( x i ) SEQUENCE DESCRIPTION: SEQ ID NO:15:

| | | | | | | | | | | | | | | |
|---|---|---|---|---|---|---|---|---|---|---|---|---|---|---|
| Met | Leu | Val | Thr | Pro | Leu | Leu | Leu | Val | Thr | Leu | Leu | Cys | Val | Leu | Cys |
| 1 | | | | 5 | | | | | 10 | | | | | 15 |
| Ser | Ala | Ala | Leu | Tyr | Asp | Ser | Ser | Ser | Tyr | Val | Tyr | Tyr | Tyr | Gln | Ser |
| | | | | 20 | | | | | 25 | | | | | 30 |
| Ala | Phe | Arg | Pro | Pro | Asn | Gly | Trp | His | Leu | His | Gly | Gly | Ala | Tyr | Ala |
| | | | 35 | | | | | 40 | | | | | 45 |
| Val | Val | Asn | Ile | Ser | Ser | Glu | Ser | Asn | Asn | Ala | Gly | Ser | Ser | Pro | Gly |
| | | | 50 | | | | | 55 | | | | | 60 |
| Cys | Ile | Val | Gly | Thr | Ile | His | Gly | Gly | Arg | Val | Val | Asn | Ala | Ser | Ser |
| 65 | | | | | 70 | | | | | 75 | | | | | 80 |
| Ile | Ala | Met | Thr | Ala | Pro | Ser | Ser | Gly | Met | Ala | Trp | Ser | Ser | Ser | Gln |
| | | | | 85 | | | | | 90 | | | | | 95 |
| Phe | Cys | Thr | Ala | His | Cys | Asn | Phe | Ser | Asp | Thr | Thr | Val | Phe | Val | Thr |
| | | | | 100 | | | | | 105 | | | | | 110 |
| His | Cys | Tyr | Lys | Tyr | Asp | Gly | Cys | Pro | Ile | Thr | Gly | Met | Leu | Gln | Lys |
| | | | 115 | | | | | 120 | | | | | 125 |
| Asn | Phe | Leu | Arg | Val | Ser | Ala | Met | Lys | Asn | Gly | Gln | Leu | Phe | Tyr | Asn |
| | | | 130 | | | | | 135 | | | | | 140 |
| Leu | Thr | Val | Ser | Val | Ala | Lys | Tyr | Pro | Thr | Phe | Lys | Ser | Phe | Gln | Cys |
| 145 | | | | | 150 | | | | | 155 | | | | | 160 |
| Val | Asn | Asn | Leu | Thr | Ser | Val | Tyr | Leu | Asn | Gly | Asp | Leu | Val | Tyr | Thr |
| | | | | 165 | | | | | 170 | | | | | 175 |
| Ser | Asn | Glu | Thr | Thr | Asp | Val | Thr | Ser | Ala | Gly | Val | Tyr | Phe | Lys | Ala |
| | | | 180 | | | | | 185 | | | | | 190 |
| Gly | Gly | Pro | Ile | Thr | Tyr | Lys | Val | Met | Arg | Lys | Val | Lys | Ala | Leu | Ala |
| | | | 195 | | | | | 200 | | | | | 205 |
| Tyr | Phe | Val | Asn | Gly | Thr | Ala | Gln | Asp | Val | Ile | Leu | Cys | Asp | Gly | Ser |
| | | 210 | | | | | 215 | | | | | 220 |
| Pro | Arg | Gly | Leu | Leu | Ala | Cys | Gln | Tyr | Asn | Thr | Gly | Asn | Phe | Ser | Asp |
| 225 | | | | | 230 | | | | | 235 | | | | | 240 |
| Gly | Phe | Tyr | Pro | Phe | Ile | Asn | Ser | Ser | Leu | Val | Lys | Gln | Lys | Phe | Ile |
| | | | | 245 | | | | | 250 | | | | | 255 |
| Val | Tyr | Arg | Glu | Asn | Ser | Val | Asn | Thr | Thr | Phe | Thr | Leu | His | Asn | Phe |
| | | | 260 | | | | | 265 | | | | | 270 |
| Thr | Phe | His | Asn | Glu | Thr | Gly | Ala | Asn | Pro | Asn | Pro | Ser | Gly | Val | Gln |
| | | | 275 | | | | | 280 | | | | | 285 |
| Asn | Ile | Leu | Thr | Tyr | Gln | Thr | Gln | Thr | Ala | Gln | Ser | Gly | Tyr | Tyr | Asn |
| | | | 290 | | | | | 295 | | | | | 300 |

-continued

| | | | | | | | | | | | | | | | |
|---|---|---|---|---|---|---|---|---|---|---|---|---|---|---|---|
| Phe | Asn | Phe | Ser | Phe | Leu | Ser | Ser | Phe | Val | Tyr | Lys | Glu | Ser | Asn | Phe |
| 305 | | | | 310 | | | | 315 | | | | | | | 320 |
| Met | Tyr | Gly | Ser | Tyr | His | Pro | Ser | Cys | Asn | Phe | Arg | Leu | Glu | Thr | Ile |
| | | | | 325 | | | | 330 | | | | | 335 | | |
| Asn | Asn | Gly | Leu | Trp | Phe | Asn | Ser | Leu | Ser | Val | Ser | Ile | Ala | Tyr | Gly |
| | | | 340 | | | | 345 | | | | | 350 | | | |
| Pro | Leu | Gln | Gly | Gly | Cys | Lys | Gln | Ser | Val | Phe | Ser | Gly | Arg | Ala | Thr |
| | | 355 | | | | | 360 | | | | | 365 | | | |
| Cys | Cys | Tyr | Ala | Tyr | Ser | Tyr | Gly | Gly | Pro | Ser | Leu | Cys | Lys | Gly | Val |
| | 370 | | | | | 375 | | | | | 380 | | | | |
| Tyr | Ser | Gly | Glu | Leu | Asp | Leu | Asn | Phe | Glu | Cys | Gly | Leu | Leu | Val | Tyr |
| 385 | | | | | 390 | | | | 395 | | | | | | 400 |
| Val | Thr | Lys | Ser | Gly | Gly | Ser | Arg | Ile | Gln | Thr | Ala | Thr | Glu | Pro | Pro |
| | | | | 405 | | | | 410 | | | | | 415 | | |
| Val | Ile | Thr | Arg | His | Asn | Tyr | Asn | Asn | Ile | Thr | Leu | Asn | Thr | Cys | Val |
| | | | 420 | | | | | 425 | | | | | 430 | | |
| Asp | Tyr | Asn | Ile | Tyr | Gly | Arg | Thr | Gly | Gln | Gly | Phe | Ile | Thr | Asn | Val |
| | | 435 | | | | | 440 | | | | | 445 | | | |
| Thr | Asp | Ser | Ala | Val | Ser | Tyr | Asn | Tyr | Leu | Ala | Asp | Ala | Gly | Leu | Ala |
| 450 | | | | | 455 | | | | | 460 | | | | | |
| Ile | Leu | Asp | Thr | Ser | Ser | Ile | Asp | Ile | Phe | Val | Val | Gln | Gly | Glu |
| 465 | | | | | 470 | | | | 475 | | | | | 480 |
| Tyr | Gly | Leu | Thr | Tyr | Tyr | Lys | Val | Asn | Pro | Cys | Glu | Asp | Val | Asn | Gln |
| | | | | 485 | | | | | 490 | | | | | 495 | |
| Gln | Phe | Val | Val | Ser | Gly | Gly | Lys | Leu | Val | Gly | Ile | Leu | Thr | Ser | Arg |
| | | | 500 | | | | | 505 | | | | 510 | | | |
| Asn | Glu | Thr | Gly | Ser | Gln | Leu | Leu | Glu | Asn | Gln | Phe | Tyr | Ile | Lys | Ile |
| | | 515 | | | | | 520 | | | | | 525 | | | |
| Thr | Asn | Gly | Thr | Arg | Arg | Phe | Arg | Arg | Ser | Ile | Thr | Glu | Asn | Val | Ala |
| | | 530 | | | | | 535 | | | | | 540 | | | |
| Asn | Cys | Pro | Tyr | Val | Ser | Tyr | Gly | Lys | Phe | Cys | Ile | Lys | Pro | Asp | Gly |
| 545 | | | | | 550 | | | | | 555 | | | | | 560 |
| Ser | Ile | Ala | Thr | Ile | Val | Pro | Lys | Gln | Leu | Glu | Gln | Phe | Val | Ala | Pro |
| | | | | 565 | | | | | 570 | | | | | 575 | |
| Leu | Leu | Asn | Val | Thr | Glu | Asn | Val | Leu | Ile | Pro | Asn | Ser | Phe | Asn | Leu |
| | | | 580 | | | | | 585 | | | | | 590 | | |
| Thr | Val | Thr | Asp | Glu | Tyr | Ile | Gln | Thr | Arg | Met | Asp | Lys | Val | Gln | Ile |
| | | | 595 | | | | | 600 | | | | 605 | | | |
| Asn | Cys | Leu | Gln | Tyr | Val | Cys | Gly | Asn | Ser | Leu | Asp | Cys | Arg | Asp | Leu |
| | 610 | | | | | 615 | | | | | 620 | | | | |
| Phe | Gln | Gln | Tyr | Gly | Pro | Val | Cys | Asp | Asn | Ile | Leu | Ser | Val | Val | Asn |
| 625 | | | | | 630 | | | | | 635 | | | | | 640 |
| Ser | Ile | Gly | Gln | Lys | Glu | Asp | Met | Glu | Leu | Leu | Asn | Phe | Tyr | Ser | Ser |
| | | | | 645 | | | | | 650 | | | | | 655 | |
| Thr | Lys | Pro | Ala | Gly | Phe | Asn | Thr | Pro | Phe | Leu | Ser | Asn | Val | Ser | Thr |
| | | | 660 | | | | | 665 | | | | | 670 | | |
| Gly | Glu | Phe | Asn | Ile | Ser | Leu | Leu | Leu | Thr | Thr | Pro | Ser | Ser | Pro | Arg |
| | | 675 | | | | | 680 | | | | | 685 | | | |
| Arg | Arg | Ser | Phe | Ile | Glu | Asp | Leu | Leu | Phe | Thr | Ser | Val | Glu | Ser | Val |
| | 690 | | | | | 695 | | | | | 700 | | | | |
| Gly | Leu | Pro | Thr | Asp | Asp | Ala | Tyr | Lys | Asn | Cys | Thr | Ala | Gly | Pro | Leu |
| 705 | | | | | 710 | | | | | 715 | | | | | 720 |
| Gly | Phe | Leu | Lys | Asp | Leu | Ala | Cys | Ala | Arg | Glu | Tyr | Asn | Gly | Leu | Leu |

-continued

|  |  |  | 725 |  |  |  |  |  | 730 |  |  |  |  |  | 735 |  |
|---|---|---|---|---|---|---|---|---|---|---|---|---|---|---|---|---|

Val Leu Pro Pro Ile Ile Thr Ala Glu Met Gln Thr Leu Tyr Thr Ser
           740                745                750

Ser Leu Val Ala Ser Met Ala Phe Gly Gly Ile Thr Ala Ala Gly Ala
           755                760                765

Ile Pro Phe Ala Thr Gln Leu Gln Ala Arg Ile Asn His Leu Gly Ile
           770                775                780

Thr Gln Ser Leu Leu Leu Lys Asn Gln Glu Lys Ile Ala Ala Ser Phe
785                790                795                800

Asn Lys Ala Ile Gly Arg Met Gln Glu Gly Phe Arg Ser Thr Ser Leu
           805                810                815

Ala Leu Gln Gln Ile Gln Asp Val Val Asn Lys Gln Ser Ala Ile Leu
           820                825                830

Thr Glu Thr Met Ala Ser Leu Asn Lys Asn Phe Gly Ala Ile Ser Ser
           835                840                845

Val Ile Gln Glu Ile Tyr Gln Gln Leu Asp Ala Ile Gln Ala Asn Ala
           850                855                860

Gln Val Asp Arg Leu Ile Thr Gly Arg Leu Ser Ser Leu Ser Val Leu
865                870                875                880

Ala Ser Ala Lys Gln Ala Glu His Ile Arg Val Ser Gln Gln Arg Glu
           885                890                895

Leu Ala Thr Gln Lys Ile Asn Glu Cys Val Lys Ser Gln Ser Ile Arg
           900                905                910

Tyr Ser Phe Cys Gly Asn Gly Arg His Val Leu Thr Ile Pro Gln Asn
           915                920                925

Ala Pro Asn Gly Ile Val Phe Ile His Phe Ser Tyr Thr Pro Asp Ser
           930                935                940

Phe Val Asn Val Thr Ala Ile Val Gly Phe Cys Val Lys Pro Ala Asn
945                950                955                960

Ala Ser Gln Tyr Ala Ile Val Pro Ala Asn Gly Arg Gly Ile Phe Ile
           965                970                975

Gln Val Asn Gly Ser Tyr Tyr Ile Thr Ala Arg Asp Met Tyr Met Pro
           980                985                990

Arg Ala Ile Thr Ala Gly Asp Ile Val Thr Leu Thr Ser Cys Gln Ala
           995                1000               1005

Asn Tyr Val Ser Val Asn Lys Thr Val Ile Thr Thr Phe Val Asp Asn
           1010               1015               1020

Asp Asp Phe Asp Phe Asn Asp Glu Leu Ser Lys Trp Trp Asn Asp Thr
1025               1030               1035               1040

Lys His Glu Leu Pro Asp Phe Asp Lys Phe Asn Tyr Thr Val Pro Ile
           1045               1050               1055

Leu Asp Ile Asp Ser Glu Ile Asp Arg Ile Gln Gly Val Ile Gln Gly
           1060               1065               1070

Leu Asn Asp Ser Leu Ile Asp Leu Glu Lys Leu Ser Ile Leu Lys Thr
           1075               1080               1085

Tyr Ile Lys Trp Pro Trp Tyr Val Trp Leu Ala Ile Ala Phe Ala Thr
           1090               1095               1100

Ile Ile Phe Ile Leu Ile Leu Gly Trp Val Phe Phe Met Thr Gly Cys
1105               1110               1115               1120

Cys Gly Cys Cys Cys Gly Cys Phe Gly Ile Met Pro Leu Met Ser Lys
           1125               1130               1135

Cys Gly Lys Lys Ser Ser Tyr Tyr Thr Thr Phe Asp Asn Asp Val Val
           1140               1145               1150

```
Thr Glu Gln Asn Arg Pro Lys Lys Ser Val
    1155                1160
```

(2) INFORMATION FOR SEQ ID NO:16:

(i) SEQUENCE CHARACTERISTICS:
        (A) LENGTH: 1846 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1846

(xi) SEQUENCE DESCRIPTION: SEQ ID NO:16:

```
ATG TTG GTG AAG TCA CTG TTT CTA GTG ACC ATT TTG TTT GCA CTA TGT        48
Met Leu Val Lys Ser Leu Phe Leu Val Thr Ile Leu Phe Ala Leu Cys
 1               5                  10                  15

AGT GCT AAT TTA TAT GAC AAC GAA TCT TTT GTG TAT TAC TAC CAG AGT        96
Ser Ala Asn Leu Tyr Asp Asn Glu Ser Phe Val Tyr Tyr Tyr Gln Ser
                20                  25                  30

GCT TTT AGG CCA GGA CAT GGT TGG CAT TTA CAT GGA GGT GCT TAT GCA       144
Ala Phe Arg Pro Gly His Gly Trp His Leu His Gly Gly Ala Tyr Ala
             35                  40                  45

GTA GTT AAT GTG TCT AGT GAA AAT AAT AAT GCA GGT ACT GCC CCA AGT       192
Val Val Asn Val Ser Ser Glu Asn Asn Asn Ala Gly Thr Ala Pro Ser
         50                  55                  60

TGC ACT GCT GGT GCT ATT GGC TAC AGT AAG AAT TTC AGT GCG GCC TCA       240
Cys Thr Ala Gly Ala Ile Gly Tyr Ser Lys Asn Phe Ser Ala Ala Ser
 65                  70                  75                  80

GTA GCC ATG ACT GCA CCA CTA AGT GGT ATG TCA TGG TCT GCC TCA TCT       288
Val Ala Met Thr Ala Pro Leu Ser Gly Met Ser Trp Ser Ala Ser Ser
                 85                  90                  95

TTT TGT ACA GCT CAC TGT AAT TTT ACT TCT TAT ATA GTG TTT GTT ACA       336
Phe Cys Thr Ala His Cys Asn Phe Thr Ser Tyr Ile Val Phe Val Thr
                100                 105                 110

CAT TGT TTT AAG AGC GGA TCT AAT AGT TGT CCT TTG ACA GGT CTT ATT       384
His Cys Phe Lys Ser Gly Ser Asn Ser Cys Pro Leu Thr Gly Leu Ile
            115                 120                 125

CCA AGC GGT TAT ATT CGT ATT GCT GCT ATG AAA CAT GGA AGT CGT ACG       432
Pro Ser Gly Tyr Ile Arg Ile Ala Ala Met Lys His Gly Ser Arg Thr
        130                 135                 140

CCT GGT CAC TTA TTT TAT AAC TTA ACA GTT TCT GTG ACT AAA TAT CCT       480
Pro Gly His Leu Phe Tyr Asn Leu Thr Val Ser Val Thr Lys Tyr Pro
145                 150                 155                 160

AAG TTT AGA TCG CTA CAA TGT GTT AAT AAT CAT ACT TCT GTA TAT TTA       528
Lys Phe Arg Ser Leu Gln Cys Val Asn Asn His Thr Ser Val Tyr Leu
                165                 170                 175

AAT GGT GAC CTT GTT TTC ACA TCT AAC TAT ACT GAA GAT GTT GTA GCT       576
Asn Gly Asp Leu Val Phe Thr Ser Asn Tyr Thr Glu Asp Val Val Ala
            180                 185                 190

GCA GGT GTC CAT TTT AAA AGT GGT GGA CCT ATA ACT TAT AAA GTT ATG       624
Ala Gly Val His Phe Lys Ser Gly Gly Pro Ile Thr Tyr Lys Val Met
        195                 200                 205

AGA GAG GTT AAA GCC TTG GCT TAT TTT GTC AAT GGT ACT GCA CAT GAT       672
Arg Glu Val Lys Ala Leu Ala Tyr Phe Val Asn Gly Thr Ala His Asp
210                 215                 220
```

-continued

| | | | | | | | | | | | | | | | | |
|---|---|---|---|---|---|---|---|---|---|---|---|---|---|---|---|---|
| GTC | ATT | CTA | TGT | GAT | GAC | ACA | CCT | AGA | GGT | TTG | TTA | GCA | TGC | CAA | TAT | 720 |
| Val | Ile | Leu | Cys | Asp | Asp | Thr | Pro | Arg | Gly | Leu | Leu | Ala | Cys | Gln | Tyr | |
| 225 | | | | 230 | | | | | 235 | | | | | | 240 | |
| AAT | ACT | GGC | AAT | TTT | TCA | GAT | GGC | TTC | TAT | CCT | TTT | ACT | AAT | ACT | AGT | 768 |
| Asn | Thr | Gly | Asn | Phe | Ser | Asp | Gly | Phe | Tyr | Pro | Phe | Thr | Asn | Thr | Ser | |
| | | | | 245 | | | | | 250 | | | | | 255 | | |
| ATT | GTT | AAG | GAT | AAG | TTT | ATT | GTT | TAT | CGT | GAA | AGT | AGT | GTC | AAT | ACT | 816 |
| Ile | Val | Lys | Asp | Lys | Phe | Ile | Val | Tyr | Arg | Glu | Ser | Ser | Val | Asn | Thr | |
| | | | 260 | | | | | 265 | | | | | 270 | | | |
| ACT | TTG | ACA | TTA | ACT | AAT | TTC | ACG | TTT | AGT | AAT | GAA | AGT | GGT | GCC | CCT | 864 |
| Thr | Leu | Thr | Leu | Thr | Asn | Phe | Thr | Phe | Ser | Asn | Glu | Ser | Gly | Ala | Pro | |
| | | 275 | | | | | 280 | | | | | 285 | | | | |
| CCT | AAT | ACA | GGT | GGT | GTT | GAC | AGT | TTT | ATT | TTA | TAC | CAG | ACA | CAA | ACA | 912 |
| Pro | Asn | Thr | Gly | Gly | Val | Asp | Ser | Phe | Ile | Leu | Tyr | Gln | Thr | Gln | Thr | |
| | 290 | | | | | 295 | | | | | 300 | | | | | |
| GCT | CAG | AGT | GGT | TAT | TAT | AAT | TTT | AAT | TTT | TCA | TTT | CTG | AGT | AGT | TTT | 960 |
| Ala | Gln | Ser | Gly | Tyr | Tyr | Asn | Phe | Asn | Phe | Ser | Phe | Leu | Ser | Ser | Phe | |
| 305 | | | | | 310 | | | | | 315 | | | | | 320 | |
| GTT | TAT | AGG | GAA | AGT | AAT | TAT | ATG | TAT | GGA | TCT | TAC | CAT | CCG | GCT | TGT | 1008 |
| Val | Tyr | Arg | Glu | Ser | Asn | Tyr | Met | Tyr | Gly | Ser | Tyr | His | Pro | Ala | Cys | |
| | | | | 325 | | | | | 330 | | | | | 335 | | |
| AGT | TTT | AGA | CCT | GAA | ACC | CTT | AAT | GGT | TTG | TGG | TCT | AAT | TCC | CTT | TCT | 1056 |
| Ser | Phe | Arg | Pro | Glu | Thr | Leu | Asn | Gly | Leu | Trp | Ser | Asn | Ser | Leu | Ser | |
| | | | 340 | | | | | 345 | | | | | 350 | | | |
| GTT | TCA | TTA | ATA | TAC | GGT | CCC | ATT | CAA | GGT | GGT | TGT | AAG | CAA | TCT | GTA | 1104 |
| Val | Ser | Leu | Ile | Tyr | Gly | Pro | Ile | Gln | Gly | Gly | Cys | Lys | Gln | Ser | Val | |
| | | 355 | | | | | 360 | | | | | 365 | | | | |
| TTT | AAT | GGT | AAA | GCA | ACT | TGT | TGT | TAT | GCT | TAT | TCA | TAC | GGA | GGA | CCT | 1152 |
| Phe | Asn | Gly | Lys | Ala | Thr | Cys | Cys | Tyr | Ala | Tyr | Ser | Tyr | Gly | Gly | Pro | |
| | 370 | | | | | 375 | | | | | 380 | | | | | |
| CGT | GCT | TGT | AAA | GGT | GTC | TAT | AGA | GGT | GAG | CTA | ACA | CAG | CAT | TTT | GAA | 1200 |
| Arg | Ala | Cys | Lys | Gly | Val | Tyr | Arg | Gly | Glu | Leu | Thr | Gln | His | Phe | Glu | |
| 385 | | | | | 390 | | | | | 395 | | | | | 400 | |
| TGT | GGT | TTG | TTA | GTT | TAT | GTT | ACT | AAG | AGC | GAT | GGC | TCC | CGT | ATA | CAA | 1248 |
| Cys | Gly | Leu | Leu | Val | Tyr | Val | Thr | Lys | Ser | Asp | Gly | Ser | Arg | Ile | Gln | |
| | | | | 405 | | | | | 410 | | | | | 415 | | |
| ACT | GCA | ACA | CAA | CCA | CCT | GTA | TTA | ACC | CAA | AAT | TTT | TAT | AAT | AAC | ATC | 1296 |
| Thr | Ala | Thr | Gln | Pro | Pro | Val | Leu | Thr | Gln | Asn | Phe | Tyr | Asn | Asn | Ile | |
| | | | 420 | | | | | 425 | | | | | 430 | | | |
| ACT | TTA | GGT | AAG | TGT | GTT | GAT | TAT | AAT | GTT | TAT | GGT | AGA | ACT | GGA | CAA | 1344 |
| Thr | Leu | Gly | Lys | Cys | Val | Asp | Tyr | Asn | Val | Tyr | Gly | Arg | Thr | Gly | Gln | |
| | | 435 | | | | | 440 | | | | | 445 | | | | |
| GGT | TTT | ATT | ACT | AAT | GTA | ACT | GAT | TTA | GCT | ACT | TCC | CAT | AAT | TAC | TTA | 1392 |
| Gly | Phe | Ile | Thr | Asn | Val | Thr | Asp | Leu | Ala | Thr | Ser | His | Asn | Tyr | Leu | |
| | 450 | | | | | 455 | | | | | 460 | | | | | |
| GCG | GAG | GGA | GGA | TTA | GCT | ATT | TTA | GAT | ACA | TCT | GGT | GCC | ATA | GAC | ATC | 1440 |
| Ala | Glu | Gly | Gly | Leu | Ala | Ile | Leu | Asp | Thr | Ser | Gly | Ala | Ile | Asp | Ile | |
| 465 | | | | | 470 | | | | | 475 | | | | | 480 | |
| TTC | GTT | GTA | CAA | GGT | GAA | TAT | GGC | CCT | AAC | TAC | TAT | AAG | GTT | AAT | CTA | 1488 |
| Phe | Val | Val | Gln | Gly | Glu | Tyr | Gly | Pro | Asn | Tyr | Tyr | Lys | Val | Asn | Leu | |
| | | | | 485 | | | | | 490 | | | | | 495 | | |
| TGT | GAA | GAT | GTT | AAC | CAA | CAG | TTT | GTA | GTT | TCT | GGT | GGT | AAA | TTA | GTA | 1536 |
| Cys | Glu | Asp | Val | Asn | Gln | Gln | Phe | Val | Val | Ser | Gly | Gly | Lys | Leu | Val | |
| | | | 500 | | | | | 505 | | | | | 510 | | | |
| GGT | ATT | CTC | ACT | TCA | CGT | AAT | GAA | ACT | GGT | TCT | CAG | CCT | CTT | GAA | AAC | 1584 |
| Gly | Ile | Leu | Thr | Ser | Arg | Asn | Glu | Thr | Gly | Ser | Gln | Pro | Leu | Glu | Asn | |
| | | 515 | | | | | 520 | | | | | 525 | | | | |
| CAG | TTT | TAC | ATT | AAG | ATC | ACT | AAT | GGA | ACA | CAT | CGT | TCT | AGA | CGT | TCT | 1632 |
| Gln | Phe | Tyr | Ile | Lys | Ile | Thr | Asn | Gly | Thr | His | Arg | Ser | Arg | Arg | Ser | |
| | 530 | | | | | 535 | | | | | 540 | | | | | |

```
GTT  AAT  GAA  AAT  GTT  ACG  AAT  TGC  CCT  TAT  GTT  AGT  TAT  GGC  AAG  TTT    1680
Val  Asn  Glu  Asn  Val  Thr  Asn  Cys  Pro  Tyr  Val  Ser  Tyr  Gly  Lys  Phe
545                550                     555                     560

TGT  ATA  AAA  CCT  GAT  GGT  TCA  GTT  TCT  CCT  ATA  GTA  CCA  AAA  GAA  CTT    1728
Cys  Ile  Lys  Pro  Asp  Gly  Ser  Val  Ser  Pro  Ile  Val  Pro  Lys  Glu  Leu
               565                     570                     575

GAA  CAG  TTT  GTG  GCA  CCT  TTA  CTT  AAT  GTT  ACT  GAA  AAT  GTG  CTC  ATA    1776
Glu  Gln  Phe  Val  Ala  Pro  Leu  Leu  Asn  Val  Thr  Glu  Asn  Val  Leu  Ile
               580                     585                     590

CCT  AAC  AGT  TTT  AAC  TTA  ACT  GTT  ACA  GAT  GAG  TAC  ATA  CAA  ACG  CGT    1824
Pro  Asn  Ser  Phe  Asn  Leu  Thr  Val  Thr  Asp  Glu  Tyr  Ile  Gln  Thr  Arg
          595                     600                     605

ATG  GAT  AAG  GTC  CAA  ATT  AGG  A                                               1846
Met  Asp  Lys  Val  Gln  Ile  Arg
610                     615
```

( 2 ) INFORMATION FOR SEQ ID NO:17:

( i ) SEQUENCE CHARACTERISTICS:
        ( A ) LENGTH: 615 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met  Leu  Val  Lys  Ser  Leu  Phe  Leu  Val  Thr  Ile  Leu  Phe  Ala  Leu  Cys
1                   5                   10                      15

Ser  Ala  Asn  Leu  Tyr  Asp  Asn  Glu  Ser  Phe  Val  Tyr  Tyr  Tyr  Gln  Ser
               20                  25                      30

Ala  Phe  Arg  Pro  Gly  His  Gly  Trp  His  Leu  His  Gly  Gly  Ala  Tyr  Ala
          35                  40                      45

Val  Val  Asn  Val  Ser  Ser  Glu  Asn  Asn  Asn  Ala  Gly  Thr  Ala  Pro  Ser
     50                       55                      60

Cys  Thr  Ala  Gly  Ala  Ile  Gly  Tyr  Ser  Lys  Asn  Phe  Ser  Ala  Ala  Ser
65                  70                      75                              80

Val  Ala  Met  Thr  Ala  Pro  Leu  Ser  Gly  Met  Ser  Trp  Ser  Ala  Ser  Ser
               85                      90                              95

Phe  Cys  Thr  Ala  His  Cys  Asn  Phe  Thr  Ser  Tyr  Ile  Val  Phe  Val  Thr
               100                     105                     110

His  Cys  Phe  Lys  Ser  Gly  Ser  Asn  Ser  Cys  Pro  Leu  Thr  Gly  Leu  Ile
          115                     120                     125

Pro  Ser  Gly  Tyr  Ile  Arg  Ile  Ala  Ala  Met  Lys  His  Gly  Ser  Arg  Thr
     130                     135                     140

Pro  Gly  His  Leu  Phe  Tyr  Asn  Leu  Thr  Val  Ser  Val  Thr  Lys  Tyr  Pro
145                     150                     155                     160

Lys  Phe  Arg  Ser  Leu  Gln  Cys  Val  Asn  Asn  His  Thr  Ser  Val  Tyr  Leu
               165                     170                     175

Asn  Gly  Asp  Leu  Val  Phe  Thr  Ser  Asn  Tyr  Thr  Glu  Asp  Val  Val  Ala
               180                     185                     190

Ala  Gly  Val  His  Phe  Lys  Ser  Gly  Gly  Pro  Ile  Thr  Tyr  Lys  Val  Met
          195                     200                     205

Arg  Glu  Val  Lys  Ala  Leu  Ala  Tyr  Phe  Val  Asn  Gly  Thr  Ala  His  Asp
     210                     215                     220

Val  Ile  Leu  Cys  Asp  Asp  Thr  Pro  Arg  Gly  Leu  Leu  Ala  Cys  Gln  Tyr
225                     230                     235                     240

Asn  Thr  Gly  Asn  Phe  Ser  Asp  Gly  Phe  Tyr  Pro  Phe  Thr  Asn  Thr  Ser
                    245                     250                     255
```

| | | | | | | | | | | | | | | |
|---|---|---|---|---|---|---|---|---|---|---|---|---|---|---|
| Ile | Val | Lys | Asp 260 | Lys | Phe | Ile | Val 265 | Tyr | Arg | Glu | Ser | Ser 270 | Val | Asn | Thr |
| Thr | Leu | Thr 275 | Leu | Thr | Asn | Phe 280 | Thr | Phe | Ser | Asn | Glu 285 | Ser | Gly | Ala | Pro |
| Pro | Asn 290 | Thr | Gly | Gly | Val | Asp 295 | Ser | Phe | Ile | Leu | Tyr 300 | Gln | Thr | Gln | Thr |
| Ala 305 | Gln | Ser | Gly | Tyr | Tyr 310 | Asn | Phe | Asn | Phe | Ser 315 | Phe | Leu | Ser | Ser | Phe 320 |
| Val | Tyr | Arg | Glu | Ser 325 | Asn | Tyr | Met | Tyr | Gly 330 | Ser | Tyr | His | Pro | Ala 335 | Cys |
| Ser | Phe | Arg | Pro 340 | Glu | Thr | Leu | Asn | Gly 345 | Leu | Trp | Ser | Asn | Ser 350 | Leu | Ser |
| Val | Ser | Leu 355 | Ile | Tyr | Gly | Pro | Ile 360 | Gln | Gly | Gly | Cys | Lys 365 | Gln | Ser | Val |
| Phe | Asn 370 | Gly | Lys | Ala | Thr | Cys 375 | Cys | Tyr | Ala | Tyr | Ser 380 | Tyr | Gly | Gly | Pro |
| Arg 385 | Ala | Cys | Lys | Gly | Val 390 | Tyr | Arg | Gly | Glu | Leu 395 | Thr | Gln | His | Phe | Glu 400 |
| Cys | Gly | Leu | Leu | Val 405 | Tyr | Val | Thr | Lys | Ser 410 | Asp | Gly | Ser | Arg | Ile 415 | Gln |
| Thr | Ala | Thr | Gln 420 | Pro | Pro | Val | Leu | Thr 425 | Gln | Asn | Phe | Tyr | Asn 430 | Asn | Ile |
| Thr | Leu | Gly 435 | Lys | Cys | Val | Asp | Tyr 440 | Asn | Val | Tyr | Gly | Arg 445 | Thr | Gly | Gln |
| Gly | Phe 450 | Ile | Thr | Asn | Val | Thr 455 | Asp | Leu | Ala | Thr | Ser 460 | His | Asn | Tyr | Leu |
| Ala 465 | Glu | Gly | Gly | Leu | Ala 470 | Ile | Leu | Asp | Thr | Ser 475 | Gly | Ala | Ile | Asp | Ile 480 |
| Phe | Val | Val | Gln | Gly 485 | Glu | Tyr | Gly | Pro | Asn 490 | Tyr | Tyr | Lys | Val | Asn 495 | Leu |
| Cys | Glu | Asp | Val | Asn 500 | Gln | Gln | Phe | Val 505 | Val | Ser | Gly | Gly | Lys 510 | Leu | Val |
| Gly | Ile | Leu 515 | Thr | Ser | Arg | Asn | Glu 520 | Thr | Gly | Ser | Gln | Pro 525 | Leu | Glu | Asn |
| Gln | Phe 530 | Tyr | Ile | Lys | Ile | Thr 535 | Asn | Gly | Thr | His | Arg 540 | Ser | Arg | Arg | Ser |
| Val 545 | Asn | Glu | Asn | Val | Thr 550 | Asn | Cys | Pro | Tyr | Val 555 | Ser | Tyr | Gly | Lys | Phe 560 |
| Cys | Ile | Lys | Pro | Asp 565 | Gly | Ser | Val | Ser | Pro 570 | Ile | Val | Pro | Lys | Glu 575 | Leu |
| Glu | Gln | Phe | Val 580 | Ala | Pro | Leu | Leu | Asn 585 | Val | Thr | Glu | Asn | Val 590 | Leu | Ile |
| Pro | Asn | Ser 595 | Phe | Asn | Leu | Thr | Val 600 | Thr | Asp | Glu | Tyr | Ile 605 | Gln | Thr | Arg |
| Met | Asp 610 | Lys | Val | Gln | Ile | Arg 615 | | | | | | | | | |

( 2 ) INFORMATION FOR SEQ ID NO:18:

( i ) SEQUENCE CHARACTERISTICS:
        ( A ) LENGTH: 2116 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:18:

| | | | | | | |
|---|---|---|---|---|---|---|
| TATAATTATC | TAGCAGACGC | AGGTATGGCT | ATTTTAGATA | CATCTGGTTC | CATAGACATC | 60 |
| TTTGTTGCAC | AAGGTGAATA | TGGCCTTACT | TATTATAAGG | CTAACCCTTG | CGAAGACGTC | 120 |
| AACCAGCAGT | TTGTAGTTTC | TGGTGGTAAA | TTAGTAGGTA | TTCTTACTTC | ACGTAATGAG | 180 |
| ACTGGTTCTC | AGCTTCTTGA | GAACCAGTTT | TACATTAAAA | TCACTAATGG | AACACGTCGT | 240 |
| TCTAGACGTT | CTATTACTGC | AAATGTHACA | AATYGCCCTT | ATGTTAGCTA | TGGCAAGTTT | 300 |
| TGTCTAAAAC | CTGATGGYTC | AGYTTCTGYT | ATAGCACCAC | NNNNNNNNN | NNNNNNNNN | 360 |
| NNNNNNNNN | NNNNNNNNN | NNNNNNNNN | NNNNNNNNN | NNNNNNNNN | NNNNNNNNN | 420 |
| NNNNNNNNN | NNNNNNNNN | NNNNNNNNN | NNNNNNNNN | NNNNNNNNN | NNNNNNNNT | 480 |
| GTTTGTGGCA | ATTCTCTGGA | TTGTAGAAAG | TTGYTTCAAC | AATATGGGCC | TGTTTGBGAC | 540 |
| AACATATTGT | CTGTGGTAAA | TAGTGTTGGT | CAAAAGAAG | ATATGGAACT | TCUAAATCTC | 600 |
| TATTCTTCTA | CTAAACCATC | TGGCTTTAAT | ACACCAGTTT | TTAGTAATCT | YAGCACTGGC | 660 |
| GATTTYAATA | TTTCTCTTYT | GGTTGACACC | TCCAGTAGTA | CTACTGGGCG | CTCTTTTATT | 720 |
| GAAGATCTTT | TATTTACAAG | TGTTGAATCT | GTTGGATTAC | CAACAGATGA | AGCTTATAAA | 780 |
| AAGTGCACTG | CAGGACCTTT | AGGCTTCCTT | AAGGACCTBG | CGTGTGCTCG | TGAATATAAT | 840 |
| GGCTTGCTTG | YNNNNNCCC | TATTATAACA | GCAGAAATGC | AAACCTTGTA | TACTAGTTCT | 900 |
| TTAGTAGCTT | CTATGGCTTT | TGGTGGGATT | ACTGCAGCTG | GTGCTATACC | TTTTGCCACA | 960 |
| CAACTGCAGG | CTAGAATTAA | TCACTTGGGT | ATTACCCAGT | CACTTTTGCA | GAAAAATCAA | 1020 |
| GAAAAAATTG | CTGCCTCCTT | TAATAAGGCC | ATTGGCCATA | TGCAGGAAGG | TTTTAGAAGT | 1080 |
| ACATCTCTAG | CATTACAACA | AGTYCAMGAT | GTTGTTAATA | AGCAGAGTGC | TATTCTTACT | 1140 |
| GAGACTATGG | CATCACTTAA | TAAAAATTTK | GGTGCTATTT | CTTCTGTGAT | TCAAGATATC | 1200 |
| TACCAGCAAC | TTGACGCCAT | ACAAGCAAAT | GCTCAAGTGG | ATCGTCTTAT | AACTGGTAGA | 1260 |
| TTGTCATCAC | TTTCTGTTTT | AGCATCTGCT | AAGCAGGCGG | AGTATATTAG | AGTGTCACAA | 1320 |
| CAGCGTGAGT | TAGCTACTCA | GAAAATTAAT | GAGTGTGTTA | AATCACAGTC | TATTAGGTAC | 1380 |
| TCCTTTTGTG | GTAATGGACG | ACACGTTCTA | ACTATACCGC | AAAATGCACC | TAATGGTATA | 1440 |
| GTGTTTATAC | ACTTTACTTA | TACTCCAGAG | AGTTTTGKTA | ATGTTACTGC | AATAGTGGGT | 1500 |
| TTTTGTAARG | CCGCTAATGC | TAGTCAGTAT | GCAATAGTGC | CTGCTAATGG | CAGAGGTATT | 1560 |
| TCTATACAAG | TTAATGGTAG | TCACTACATC | ACTGCACGAG | ATATGTATAT | GCCAAGAGAT | 1620 |
| ATTACTGCAG | GAGATATAGT | TACGCTTACT | TCTTGTCAAG | CAAATTATGT | AAGTGTAMMT | 1680 |
| AAGACCGTCA | TTACYACATT | HGTAGACAAT | GATGATTTTG | ATTTTGATGA | CGAATTGTCA | 1740 |
| AAATGGTGGA | ATGATACTAA | GCATGAGCTA | CCAGACTTTG | ACGAATTCAA | TTACACAGTA | 1800 |
| CCTATACTTG | ACATTGGTAG | TGAAATTGAT | CGTATTCAAG | GCGTTATACA | GGGCCTTAAT | 1860 |
| GACTCTCTAA | TAGACCTTGA | AACACTATCA | ATACTCAAAA | CTTATATTAA | GTGGCCTTGG | 1920 |
| TATGTGTGGT | TAGCCATAGC | TTTTGSCACT | ATTATCTTCA | TCCTAATATT | AGGGTGGGTG | 1980 |
| TTTTTCATGA | CTGGTTGTTG | TGGTTGTTGT | TGTGGATGCT | TTGGCATTAT | TCCTCTAATG | 2040 |
| AGCAAGTGTG | GTAAGAAATC | TTCTTATTAC | ACGACTTTGG | ATAATGATGT | GGTAACTGAA | 2100 |
| CAAWACAGAC | CYAAAA | | | | | 2116 |

( 2 ) INFORMATION FOR SEQ ID NO:19:

( i ) SEQUENCE CHARACTERISTICS:
    ( A ) LENGTH: 705 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:19:

| Tyr | Asn | Tyr | Leu | Ala | Asp | Ala | Gly | Met | Ala | Ile | Leu | Asp | Thr | Ser | Gly |
|---|---|---|---|---|---|---|---|---|---|---|---|---|---|---|---|
| 1 | | | | 5 | | | | 10 | | | | | | 15 | |
| Ser | Ile | Asp | Ile | Phe | Val | Ala | Gln | Gly | Glu | Tyr | Gly | Leu | Thr | Tyr | Tyr |
| | | | 20 | | | | 25 | | | | | 30 | | | |
| Lys | Ala | Asn | Pro | Cys | Glu | Asp | Val | Asn | Gln | Gln | Phe | Val | Val | Ser | Gly |
| | | 35 | | | | 40 | | | | | 45 | | | | |
| Gly | Lys | Leu | Val | Gly | Ile | Leu | Thr | Ser | Arg | Asn | Glu | Thr | Gly | Ser | Gln |
| | 50 | | | | | 55 | | | | | 60 | | | | |
| Leu | Leu | Glu | Asn | Gln | Phe | Tyr | Ile | Lys | Ile | Thr | Asn | Gly | Thr | Arg | Arg |
| 65 | | | | | 70 | | | | | 75 | | | | | 80 |
| Ser | Arg | Arg | Ser | Ile | Thr | Ala | Asn | Val | Thr | Asn | Xaa | Pro | Tyr | Val | Ser |
| | | | | 85 | | | | | 90 | | | | | 95 | |
| Tyr | Gly | Lys | Phe | Cys | Leu | Lys | Pro | Asp | Gly | Ser | Xaa | Ser | Xaa | Ile | Ala |
| | | | 100 | | | | | 105 | | | | | 110 | | |
| Pro | Xaa | Xaa | Xaa | Xaa | Xaa | Xaa | Xaa | Xaa | Xaa | Xaa | Xaa | Xaa | Xaa | Xaa | Xaa |
| | | 115 | | | | 120 | | | | | 125 | | | | |
| Xaa | Xaa | Xaa | Xaa | Xaa | Xaa | Xaa | Xaa | Xaa | Xaa | Xaa | Xaa | Xaa | Xaa | Xaa | Xaa |
| | 130 | | | | | 135 | | | | | 140 | | | | |
| Xaa | Xaa | Xaa | Xaa | Xaa | Xaa | Xaa | Xaa | Xaa | Xaa | Xaa | Xaa | Xaa | Xaa | Xaa | Xaa |
| 145 | | | | | 150 | | | | | 155 | | | | | 160 |
| Val | Cys | Gly | Asn | Ser | Leu | Asp | Cys | Arg | Lys | Leu | Xaa | Gln | Gln | Tyr | Gly |
| | | | | 165 | | | | | 170 | | | | | 175 | |
| Pro | Val | Xaa | Asp | Asn | Ile | Leu | Ser | Val | Val | Asn | Ser | Val | Gly | Gln | Lys |
| | | | 180 | | | | | 185 | | | | | 190 | | |
| Glu | Asp | Met | Glu | Leu | Leu | Asn | Leu | Tyr | Ser | Ser | Thr | Lys | Pro | Ser | Gly |
| | | | 195 | | | | | 200 | | | | | 205 | | |
| Phe | Asn | Thr | Pro | Val | Phe | Ser | Asn | Leu | Ser | Thr | Gly | Asp | Phe | Asn | Ile |
| | | 210 | | | | | 215 | | | | | 220 | | | |
| Ser | Leu | Leu | Val | Asp | Thr | Ser | Ser | Thr | Thr | Gly | Arg | Ser | Phe | Ile |
| 225 | | | | | 230 | | | | | 235 | | | | | 240 |
| Glu | Asp | Leu | Leu | Phe | Thr | Ser | Val | Glu | Ser | Val | Gly | Leu | Pro | Thr | Asp |
| | | | | 245 | | | | | 250 | | | | | 255 | |
| Glu | Ala | Tyr | Lys | Lys | Cys | Thr | Ala | Gly | Pro | Leu | Gly | Phe | Leu | Lys | Asp |
| | | | 260 | | | | | 265 | | | | | 270 | | |
| Leu | Ala | Cys | Ala | Arg | Glu | Tyr | Asn | Gly | Leu | Leu | Xaa | Xaa | Xaa | Pro | Ile |
| | | 275 | | | | | 280 | | | | | 285 | | | |
| Ile | Thr | Ala | Glu | Met | Gln | Thr | Leu | Tyr | Thr | Ser | Ser | Leu | Val | Ala | Ser |
| | | 290 | | | | | 295 | | | | | 300 | | | |
| Met | Ala | Phe | Gly | Gly | Ile | Thr | Ala | Ala | Gly | Ala | Ile | Pro | Phe | Ala | Thr |
| 305 | | | | | 310 | | | | | 315 | | | | | 320 |
| Gln | Leu | Gln | Ala | Arg | Ile | Asn | His | Leu | Gly | Ile | Thr | Gln | Ser | Leu | Leu |
| | | | | 325 | | | | | 330 | | | | | | 335 |
| Gln | Lys | Asn | Gln | Glu | Lys | Ile | Ala | Ala | Ser | Phe | Asn | Lys | Ala | Ile | Gly |
| | | | 340 | | | | | 345 | | | | | 350 | | |

| His | Met | Gln 355 | Glu | Gly | Phe | Arg | Ser 360 | Thr | Ser | Leu | Ala | Leu 365 | Gln | Gln | Val |
|---|---|---|---|---|---|---|---|---|---|---|---|---|---|---|---|
| Xaa | Asp 370 | Val | Val | Asn | Lys | Gln 375 | Ser | Ala | Ile | Leu | Thr 380 | Glu | Thr | Met | Ala |
| Ser 385 | Leu | Asn | Lys | Asn | Xaa 390 | Gly | Ala | Ile | Ser | Ser 395 | Val | Ile | Gln | Asp | Ile 400 |
| Tyr | Gln | Gln | Leu | Asp 405 | Ala | Ile | Gln | Ala | Asn 410 | Ala | Gln | Val | Asp | Arg 415 | Leu |
| Ile | Thr | Gly | Arg 420 | Leu | Ser | Ser | Leu | Ser 425 | Val | Leu | Ala | Ser | Ala 430 | Lys | Gln |
| Ala | Glu | Tyr 435 | Ile | Arg | Val | Ser | Gln 440 | Arg | Glu | Leu | Ala 445 | Thr | Gln | Lys | |
| Ile | Asn | Glu 450 | Cys | Val | Lys | Ser 455 | Gln | Ser | Ile | Arg | Tyr 460 | Ser | Phe | Cys | Gly |
| Asn 465 | Gly | Arg | His | Val | Leu 470 | Thr | Ile | Pro | Gln | Asn 475 | Ala | Pro | Asn | Gly | Ile 480 |
| Val | Phe | Ile | His | Phe 485 | Thr | Tyr | Thr | Pro | Glu 490 | Ser | Phe | Xaa | Asn | Val 495 | Thr |
| Ala | Ile | Val | Gly 500 | Phe | Cys | Lys | Ala | Ala 505 | Asn | Ala | Ser | Gln | Tyr 510 | Ala | Ile |
| Val | Pro | Ala 515 | Asn | Gly | Arg | Gly | Ile 520 | Ser | Ile | Gln | Val | Asn 525 | Gly | Ser | His |
| Tyr | Ile 530 | Thr | Ala | Arg | Asp | Met 535 | Tyr | Met | Pro | Arg | Asp 540 | Ile | Thr | Ala | Gly |
| Asp 545 | Ile | Val | Thr | Leu | Thr 550 | Ser | Cys | Gln | Ala | Asn 555 | Tyr | Val | Ser | Val | Xaa 560 |
| Lys | Thr | Val | Ile | Thr 565 | Thr | Xaa | Val | Asp | Asn 570 | Asp | Phe | Asp | Phe 575 | Asp | |
| Asp | Glu | Leu | Ser 580 | Lys | Trp | Trp | Asn | Thr 585 | Lys | His | Glu | Leu 590 | Pro | Asp | |
| Phe | Asp | Glu 595 | Phe | Asn | Tyr | Thr | Val 600 | Pro | Ile | Leu | Asp | Ile 605 | Gly | Ser | Glu |
| Ile | Asp 610 | Arg | Ile | Gln | Gly | Val 615 | Ile | Gln | Gly | Leu | Asn 620 | Asp | Ser | Leu | Ile |
| Asp 625 | Leu | Glu | Thr | Leu | Ser 630 | Ile | Leu | Lys | Thr | Tyr 635 | Ile | Lys | Trp | Pro | Trp 640 |
| Tyr | Val | Trp | Leu | Ala 645 | Ile | Ala | Phe | Xaa | Thr 650 | Ile | Ile | Phe | Ile | Leu 655 | Ile |
| Leu | Gly | Trp | Val 660 | Phe | Phe | Met | Thr | Gly 665 | Cys | Cys | Gly | Cys 670 | Cys | Gly | |
| Cys | Phe | Gly 675 | Ile | Ile | Pro | Leu | Met 680 | Ser | Lys | Cys | Gly | Lys 685 | Lys | Ser | Ser |
| Tyr | Tyr 690 | Thr | Thr | Leu | Asp | Asn 695 | Asp | Val | Val | Thr | Glu 700 | Gln | Xaa | Arg | Pro |
| Lys 705 | | | | | | | | | | | | | | | |

( 2 ) INFORMATION FOR SEQ ID NO:20:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: DNA (genomic)

(iii) HYPOTHETICAL: NO (iv) ANTI-SENSE: NO (xi) SEQUENCE DESCRIPTION: SEQ ID NO:20:

```
GAATTCGAGC TCGCCCGGGG ATCCTCTAGA GTCGAC                                    36
```

(2) INFORMATION FOR SEQ ID NO:21:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 13..57

(xi) SEQUENCE DESCRIPTION: SEQ ID NO:21:

```
CACAGCTCAA CA ATG AAG TGG GCA ACG TGG ATC GAT CCC GTC GTT TTA              48
              Met Lys Trp Ala Thr Trp Ile Asp Pro Val Val Leu
               1               5                   10

CAA CGT CGT                                                                57
Gln Arg Arg
       15
```

(2) INFORMATION FOR SEQ ID NO:22:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:22:

```
Met Lys Trp Ala Thr Trp Ile Asp Pro Val Val Leu Gln Arg Arg
 1               5                   10                  15
```

(2) INFORMATION FOR SEQ ID NO:23:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

```
ACTCGGGCAG CGTTGGGTCC TGGGACTCTA GAGGATCGAT CCCCTATGGC GATCATC             57
```

(2) INFORMATION FOR SEQ ID NO:24:

(i) SEQUENCE CHARACTERISTICS:
        (A) LENGTH: 99 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:24:

GCGCCCACGT GGCCTGGTAC AATTCGAGCT CGCCCGGGGA TCCTCTAGAG TCGACTCTAG 60

AGGATCGATC CTCTAGAGTC GGCGGGACGA GCCCGCGAT 99

(2) INFORMATION FOR SEQ ID NO:25:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:25:

TCCACAGGAC CTGCAGCGAC CCGCTTAACA GCGTCAACAG CGTGCCGCAG ATCGGGG 57

(2) INFORMATION FOR SEQ ID NO:26:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:26:

GTTGATCCCG GGAGATGGGG GAGGCTAACT GAAAC 35

(2) INFORMATION FOR SEQ ID NO:27:

(i) SEQUENCE CHARACTERISTICS:
        (A) LENGTH: 103 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:27:

GCTCATGGTG GCCCCCGGGC GGTTCAACGA GGGCCAGTAC CGGCGCCTGG TGTCCGTCGA 60

CCTGCAGGTC GACTCTAGAG GATCCCCGGG CGAGCTCGAA TTC 103

(2) INFORMATION FOR SEQ ID NO:28:

(i) SEQUENCE CHARACTERISTICS:
        (A) LENGTH: 66 base pairs
        (B) TYPE: nucleic acid
        (C) STRANDEDNESS: double
        (D) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:28:

GAATTCGAGC TCGCCCGGGG ATCCTCTAGA GTCGACGTCT GGGGCGCGGG GGTGGTGCTC    60

TTCGAG    66

( 2 ) INFORMATION FOR SEQ ID NO:29:

( i ) SEQUENCE CHARACTERISTICS:
                        ( A ) LENGTH: 66 base pairs
                        ( B ) TYPE: nucleic acid
                        ( C ) STRANDEDNESS: double
                        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
                        ( A ) NAME/KEY: CDS
                        ( B ) LOCATION: 16..66

( x i ) SEQUENCE DESCRIPTION: SEQ ID NO:29:

CTCCACAGCT CAACA ATG AAG TGG GCA ACG TGG ATC GAT CCC GTC GTT TTA    51
                Met Lys Trp Ala Thr Trp Ile Asp Pro Val Val Leu
                 1               5                  10

CAA CGT CGT GAC TGG    66
Gln Arg Arg Asp Trp
        15

( 2 ) INFORMATION FOR SEQ ID NO:30:

( i ) SEQUENCE CHARACTERISTICS:
                        ( A ) LENGTH: 17 amino acids
                        ( B ) TYPE: amino acid
                        ( D ) TOPOLOGY: linear ( i i ) MOLECULE TYPE: protein ( x i ) SEQUENCE DESCRIPTION: SEQ ID NO:30:

Met Lys Trp Ala Thr Trp Ile Asp Pro Val Val Leu Gln Arg Arg Asp
 1               5                  10                  15
Trp ( 2 ) INFORMATION FOR SEQ ID NO:31:

( i ) SEQUENCE CHARACTERISTICS:
                        ( A ) LENGTH: 132 base pairs
                        ( B ) TYPE: nucleic acid
                        ( C ) STRANDEDNESS: double
                        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
                        ( A ) NAME/KEY: CDS
                        ( B ) LOCATION: 1..93

( x i ) SEQUENCE DESCRIPTION: SEQ ID NO:31:

GAC GAC TCC TGG AGC CCG TCA GTA TCG GCG AAA ATC CAG CTG AGC GCC    48

```
Asp  Asp  Ser  Trp  Ser  Pro  Ser  Val  Ser  Ala  Glu  Ile  Gln  Leu  Ser  Ala
 1              5                        10                          15

GGT  CGC  TAC  CAT  TAC  CAG  TTG  GTC  TGG  TGT  CAA  AAA  GAT  CTA  GAA              93
Gly  Arg  Tyr  His  Tyr  Gln  Leu  Val  Trp  Cys  Gln  Lys  Asp  Leu  Glu
               20                       25                    30

TAAGCTAGAG GATCGATCCC CTATGGCGAT CATCAGGGC                                             132
```

( 2 ) INFORMATION FOR SEQ ID NO:32:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Asp  Asp  Ser  Trp  Ser  Pro  Ser  Val  Ser  Ala  Glu  Ile  Gln  Leu  Ser  Ala
 1              5                        10                          15

Gly  Arg  Tyr  His  Tyr  Gln  Leu  Val  Trp  Cys  Gln  Lys  Asp  Leu  Glu
               20                       25                    30
```

( 2 ) INFORMATION FOR SEQ ID NO:33:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:33:

```
AACGAGGGCC AGTACCGGCG CCTGGTGTCC GTCGACTCTA GAGGATCCCC GGGCGAGCTC           60

GAATTC                                                                     66
```

( 2 ) INFORMATION FOR SEQ ID NO:34:

( i ) SEQUENCE CHARACTERISTICS:
        ( A ) LENGTH: 65 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:34:

```
CAGGTCGAAG CTTGGGCGCT GCCTATGTAG TGAAATCTAT ACTGGGATTT ATCATAACTA           60

GTTTA                                                                      65
```

( 2 ) INFORMATION FOR SEQ ID NO:35:

( i ) SEQUENCE CHARACTERISTICS:
        ( A ) LENGTH: 65 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:35:

AATAATCTAT CACTTTGTCA TGGAGATGCC CAAGCTTCGA CGACTCCCTT GGCCATGATG 60

AATGG 65

( 2 ) INFORMATION FOR SEQ ID NO:36:

( i ) SEQUENCE CHARACTERISTICS:
        ( A ) LENGTH: 65 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:36:

TATACCAGCT ACGGCGCTAG CATTCATGGT ATCCGTGAT TGCTCGATGC TTTCCTTCTG 60

AATTC 65

( 2 ) INFORMATION FOR SEQ ID NO:37:

( i ) SEQUENCE CHARACTERISTICS:
        ( A ) LENGTH: 65 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:37:

AAGCTTGGCC TCGTCGTTAA TTAACCCAAT TCGAGCTCGC CCAGCTTGGG CTGCAGGTCG 60

GGAAC 65

( 2 ) INFORMATION FOR SEQ ID NO:38:

( i ) SEQUENCE CHARACTERISTICS:
        ( A ) LENGTH: 65 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:38:

TGTTTCAGTT AGCCTCCCCC ATCTCCCGAC TCTAGAGGAT CTCGACATAG CGAATACATT 60

TATGG 65

( 2 ) INFORMATION FOR SEQ ID NO:39:

( i ) SEQUENCE CHARACTERISTICS:
        ( A ) LENGTH: 130 base pairs
        ( B ) TYPE: nucleic acid
        ( C ) STRANDEDNESS: double (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:39:

| AACGTATATA | TTTTTCACGA | CGTAGACCAC | TATTGCCATG | GACTCTAGAG | GATCGGGTAC | 60 |
| CGAGCTCGAA | TTGGGAAGCT | TGTCGACTTA | ATTAAGCGGC | CGCGTTTAAA | CGGCCCTCGA | 120 |
| GGCCAAGCTT | | | | | | 130 |

(2) INFORMATION FOR SEQ ID NO:40:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:40:

| GTCGACGTCT | GGGGCGCGGG | GGTGGTGCTC | TTCGAGACGC | TGCCTACCCC | AAGACGATCG | 60 |

(2) INFORMATION FOR SEQ ID NO:41:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:41:

| AGCTCAACAA | TGAAGTGGGC | AACGTGGATC | GATCCCGTCG | TTTTACAACG | TCGTGACTGG | 60 |

(2) INFORMATION FOR SEQ ID NO:42:

(i) SEQUENCE CHARACTERISTICS:
        (A) LENGTH: 120 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:42:

| GAGCCCGTCA | GTATCGGCGG | AAATCCAGCT | GAGCGCCGGT | CGCTACCATT | ACCAGTTGGT | 60 |
| GTTGGTCTGG | TGTCAAAAAG | ATCCGGACCG | CGCCGTTAGC | CAAGTTGCGT | TAGAGAATGA | 120 |

(2) INFORMATION FOR SEQ ID NO:43:

(i) SEQUENCE CHARACTERISTICS:
        (A) LENGTH: 60 base pairs (B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:43:

ACACAGTCAC ACTCATGGGG GCCGAAGGCA GAATTCGTAA TCATGGTCAT AGCTGTTTCC    60

(2) INFORMATION FOR SEQ ID NO:44:

(i) SEQUENCE CHARACTERISTICS:
(A) LENGTH: 60 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:44:

AAACCTGTCG TGCCAGCGAG CTCGGGATCC TCTAGAGGAT CCCCGGGCCC CGCCCCTGC    60

(2) INFORMATION FOR SEQ ID NO:45:

(i) SEQUENCE CHARACTERISTICS:
(A) LENGTH: 60 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:45:

TCGTCCACAC GGAGCGCGGC TGCCGACACG GATCCCGGTT GGCGCCCTCC AGGTGCAGGA    60

(2) INFORMATION FOR SEQ ID NO:46:

(i) SEQUENCE CHARACTERISTICS:
(A) LENGTH: 60 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:46:

AACCCCCCCC CCCCCCCCCC CCCCCCCCTG CAGGCATCGT GGTGTCACGC TCGTCGTTTG    60

(2) INFORMATION FOR SEQ ID NO:47:

(i) SEQUENCE CHARACTERISTICS:
(A) LENGTH: 60 base pairs
(B) TYPE: nucleic acid
(C) STRANDEDNESS: double
(D) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:47:

| TGTCATGCCA | TCCGTAAGAT | GCTTTTCTGT | GACTGGTGAG | TCGGATCCTC | TAGAGTCGAC | 60 |

( 2 ) INFORMATION FOR SEQ ID NO:48:

( i ) SEQUENCE CHARACTERISTICS:
        ( A ) LENGTH: 2681 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 146..481

( i x ) FEATURE:
        ( A ) NAME/KEY: CDS
        ( B ) LOCATION: complement (602..1402)

( i x ) FEATURE:
        ( A ) NAME/KEY: CDS
        ( B ) LOCATION: 1599..2135

( i x ) FEATURE:
        ( A ) NAME/KEY: CDS
        ( B ) LOCATION: complement (2308..2634)

( x i ) SEQUENCE DESCRIPTION: SEQ ID NO:48:

| TTTATCGGAC | CTTGGGTATT | CAGGGGAACC | CATCTGGTTG | AAATGCATCC | GACCCTGCAC | 60 |
| TTGATCCTGG | TTACCCCGAC | CCAANTTTTA | AGCCGGCTGG | CGCGGTCCCT | AGATAACCCC | 120 |
| CCGCTTAAAA | CTAGCCCCAA | TATTGATGTG | CAGATATAAC | ACAGNNANCC | GATCAATGGA | 180 |
| AGACATGCTA | CGGCGGTCAT | CTCCCGAAGA | CATCACCGAT | TCCCTAACAA | TGTGCCTGAT | 240 |
| TATGTTATCG | CGCATTCGTC | GTACCATGCG | CACCGCAGGA | AATAAATATA | GCTATATGAT | 300 |
| AGATCCAATG | AATCGTATGT | CTAATTACAC | TCCAGGCGAA | TGTATGACAG | GTATATTGCG | 360 |
| ATATATTGAC | GAACATGCTA | GAAGGTGTCC | TGATCACATA | TGTAATTTGT | ATATCACATG | 420 |
| TACACTTATG | CCGATGTATG | TGCACGGGCG | ATATTTCTAT | TGTAATTCAT | TTTTTTGKTA | 480 |
| GTAAACTACC | ACAGGCTGTC | CGGAAATCTA | AGTAATGAA | TAAAGTAGAT | GGTTAATACT | 540 |
| CATTGCTTAG | AATTGGACTA | CTTTTAATYC | TCTTTAATGT | TCGTATTAAA | TAAAAACATC | 600 |
| TTTAATAAAC | TTCAGCCTCT | TCGCTTATTG | TAGAAATTGA | GTATTCAMAA | TCATGTTCAA | 660 |
| AGCCGTCTTC | GGAGAGTGTA | CTCGCCACGG | TGGTTGGAAC | ATCACTATGT | CTACACGTCA | 720 |
| AATTTAAGCA | CGTCAGGTCT | GTCGAGGACA | AGAAATGGTT | AACTAGTGTT | TCAATTATTC | 780 |
| TTATAAACGT | TAAGCATTGT | AAGCCCCCCG | GCCGTCCGCA | GCAACAATTT | ACTAGTATGC | 840 |
| CGTGGGCTCC | GGGACTATCA | CGGATGTCCA | ATTCGCACAT | GCATATAATT | TTTCTAGGGT | 900 |
| CTCTCATTTC | GAGAAATCTT | CGGGGATCCA | TCAGCAATGC | GGGCTGTAGT | CCCGATTCCC | 960 |
| GTTTCAAATG | AAGGTGCTCC | AACACGGTCT | TCAAAGCAAC | CGGCATACCA | GCAAACACAG | 1020 |
| ACTGCAACTC | CCCGCTGCAA | TGATTGGTTA | TAAACAGTAA | TCTGTCTTCT | GGAAGTATAT | 1080 |
| TTCGCCCGAC | AATCCACGGC | GCCCCCAAAG | TTAAAAACCA | TCCATGTGTA | TTTGCGTCTT | 1140 |

```
CTCTGTTAAA AGAATATTGA CTGGCATTTT CCCGTTGACC GCCAGATATC CAAAGTACAG    1200

CACGATGTTG CACGGACGAC TTTGCAGTCA CCAGCCTTCC TTTCCACCCC CCCACCAACA    1260

AAATGTTTAT CGTAGGACCC ATATCCGTAA TAAGGATGGG TCTGGCAGCA ACCCCATAGG    1320

CGCCTCGGCG TGGTAGTTCT CGAGGATACA TCCAAAGAGG TTGAGTATTC TCTCTACACT    1380

TCTTGTTAAA TGGAAAGTGC ATTTGCTTGT TCTTACAATC GGCCCGAGTC TCGTTCACAG    1440

CGCCTCGTTC ACACTTAAAC CACAAATAGT CTACAGGCTA TATGGGAGCC AGACTGAAAC    1500

TCACATATGA CTAATATTCG GGGGTGTTAG TCACGTGTAG CCCATTGTGT GCATATAACG    1560

ATGTTGGACG CGTCCTTATT CGCGGTGTAC TTGATACTAT GGCAGCGAGC ATGGGATATT    1620

CATCCTCGTC ATCGTTAACA TCTCTACGGG TTCAGAATGT TTGGCATGTC GTCGATCCTT    1680

TGCCCATCGT TGCAAATTAC AAGTCCGATC GCCATGACCG CGATAAGCCT GTACCATGTG    1740

GCATTAGGGT GACATCTCGA TCATACATTA TAAGACCAAC GTGCGAGTCT TCCAAAGACC    1800

TGCACGCCTT CTTCTTCGGA TTGTCAACGG GTTCTTCAGA ATCTATGCCC ATATCTGGCG    1860

TTGAGACCAT TGTGCGTTTA ATGAACAATA AAGCGGCATG CCATGGAAAG GAGGGCTGCA    1920

GATCTCCATT TTCTCACGCC ACTATCCTGG ACGCTGTAGA CGATAATTAT ACCATGAATA    1980

TAGAGGGGGT ATGTTTCCAC TGCCACTGTG ATGATAAGTT TTCTCCAGAT TGTTGGATAT    2040

CTGCATTTTC TGCTGCCGAA CAAACTTCAT CGCTATGCAA AGAGATGCGT GTGTACACGC    2100

GCCGGTGGAG TATACGGGAA ACTAAATGTT CATAGAGGTC TTTGGGCTAT ATGTTATTAA    2160

ATAAAATAAT TGACCAGTGA ACAATTTGTT TAATGTTAGT TTATTCAATG CATTGGTTGC    2220

AAATATTCAT TACTTCTCCA ATCCCAGGTC ATTCTTTAGC GAGATGATGT TATGACATTG    2280

CTGTGAAAAT TACTACAGGA TATATTTTTA AGATGCAGGA GTAACAATGT GCATAGTAGG    2340

CGTAGTTATC GCAGACGTGC AACGCTTCGC ATTTGAGTTA CCGAAGTGCC CAACAGTGCT    2400

GCGGTTATGG TTTATGCGCA CAGAATCCAT GCATGTCCTA ATTGAACCAT CCGATTTTTC    2460

TTTTAATCGC GATCGATGTT TGGGCAACTG CGTTATTTCA GATCTAAAAA ATTTACCCTY    2520

TATGACCATC ACATCTCTCT GGYTCATACC CCGCTTGGGN TAAGATATCA TGTAGATTCC    2580

GCCCCTAAGA AATTGCAAAC TAACATNATT GNCGGGTTCC ATATACAATC CCATCTTGTC    2640

CNCTCGAAAT TACAAACTCG CGCAATAGAC CCCCGTACAT T                        2681
```

(2) INFORMATION FOR SEQ ID NO:49:

(i) SEQUENCE CHARACTERISTICS:
        (A) LENGTH: 111 amino acids
        (B) TYPE: amino acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:49:

```
Met Cys Arg Tyr Asn Thr Xaa Xaa Arg Ser Met Glu Asp Met Leu Arg
 1               5                  10                  15

Arg Ser Ser Pro Glu Asp Ile Thr Asp Ser Leu Thr Met Cys Leu Ile
            20                  25                  30

Met Leu Ser Arg Ile Arg Arg Thr Met Arg Thr Ala Gly Asn Lys Tyr
        35                  40                  45

Ser Tyr Met Ile Asp Pro Met Asn Arg Met Ser Asn Tyr Thr Pro Gly
```

|    |     | 50  |     |     |     |     | 55  |     |     |     |     | 60  |     |     |
|----|-----|-----|-----|-----|-----|-----|-----|-----|-----|-----|-----|-----|-----|-----|
| Glu | Cys | Met | Thr | Gly | Ile | Leu | Arg | Tyr | Ile | Asp | Glu | His | Ala | Arg | Arg |
| 65 |     |     |     |     | 70  |     |     |     |     | 75  |     |     |     |     | 80 |
| Cys | Pro | Asp | His | Ile | Cys | Asn | Leu | Tyr | Ile | Thr | Cys | Thr | Leu | Met | Pro |
|    |     |     |     | 85  |     |     |     |     | 90  |     |     |     |     | 95  |     |
| Met | Tyr | Val | His | Gly | Arg | Tyr | Phe | Tyr | Cys | Asn | Ser | Phe | Phe | Xaa |
|    |     |     |     | 100 |     |     |     |     | 105 |     |     |     |     | 110 |

( 2 ) INFORMATION FOR SEQ ID NO:50:

( i ) SEQUENCE CHARACTERISTICS:
        ( A ) LENGTH: 266 amino acids
        ( B ) TYPE: amino acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:50:

| Met | His | Phe | Pro | Phe | Asn | Lys | Lys | Cys | Arg | Glu | Asn | Thr | Gln | Pro | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Trp | Met | Tyr | Pro | Arg | Glu | Leu | Pro | Arg | Arg | Gly | Ala | Tyr | Gly | Val | Ala |
|     |     |     | 20  |     |     |     |     | 25  |     |     |     |     | 30  |     |     |
| Ala | Arg | Pro | Ile | Leu | Ile | Thr | Asp | Met | Gly | Pro | Thr | Ile | Asn | Ile | Leu |
|     |     | 35  |     |     |     |     | 40  |     |     |     |     | 45  |     |     |     |
| Leu | Val | Gly | Gly | Trp | Lys | Gly | Arg | Leu | Val | Thr | Ala | Lys | Ser | Ser | Val |
|     |     | 50  |     |     |     |     | 55  |     |     |     |     | 60  |     |     |     |
| Gln | His | Arg | Ala | Val | Leu | Trp | Ile | Ser | Gly | Gly | Gln | Arg | Glu | Asn | Ala |
| 65  |     |     |     |     | 70  |     |     |     |     | 75  |     |     |     |     | 80  |
| Ser | Gln | Tyr | Ser | Phe | Asn | Arg | Glu | Asp | Ala | Asn | Thr | His | Gly | Trp | Phe |
|     |     |     |     | 85  |     |     |     |     | 90  |     |     |     |     | 95  |     |
| Leu | Thr | Leu | Gly | Ala | Pro | Trp | Ile | Val | Gly | Arg | Asn | Ile | Leu | Pro | Glu |
|     |     |     | 100 |     |     |     |     | 105 |     |     |     |     | 110 |     |     |
| Asp | Arg | Leu | Leu | Phe | Ile | Thr | Asn | His | Cys | Ser | Gly | Glu | Leu | Gln | Ser |
|     |     | 115 |     |     |     |     | 120 |     |     |     |     | 125 |     |     |     |
| Val | Phe | Ala | Gly | Met | Pro | Val | Ala | Leu | Lys | Thr | Val | Leu | Glu | His | Leu |
|     |     | 130 |     |     |     |     | 135 |     |     |     |     | 140 |     |     |     |
| His | Leu | Lys | Arg | Glu | Ser | Gly | Leu | Gln | Pro | Ala | Leu | Leu | Met | Asp | Pro |
| 145 |     |     |     |     | 150 |     |     |     |     | 155 |     |     |     |     | 160 |
| Arg | Arg | Phe | Leu | Glu | Met | Arg | Asp | Pro | Arg | Lys | Ile | Ile | Cys | Met | Cys |
|     |     |     |     | 165 |     |     |     |     | 170 |     |     |     |     | 175 |     |
| Glu | Leu | Asp | Ile | Arg | Asp | Ser | Pro | Gly | Ala | His | Gly | Ile | Leu | Val | Asn |
|     |     |     | 180 |     |     |     |     | 185 |     |     |     |     | 190 |     |     |
| Cys | Cys | Cys | Gly | Arg | Pro | Gly | Gly | Leu | Gln | Cys | Leu | Thr | Phe | Ile | Arg |
|     |     | 195 |     |     |     |     | 200 |     |     |     |     | 205 |     |     |     |
| Ile | Ile | Glu | Thr | Leu | Val | Asn | His | Phe | Leu | Ser | Ser | Thr | Asp | Leu | Thr |
|     |     | 210 |     |     |     |     | 215 |     |     |     |     | 220 |     |     |     |
| Cys | Leu | Asn | Leu | Thr | Cys | Arg | His | Ser | Asp | Val | Pro | Thr | Thr | Val | Ala |
| 225 |     |     |     |     | 230 |     |     |     |     | 235 |     |     |     |     | 240 |
| Ser | Thr | Leu | Ser | Glu | Asp | Gly | Phe | Glu | His | Asp | Xaa | Glu | Tyr | Ser | Ile |
|     |     |     |     | 245 |     |     |     |     | 250 |     |     |     |     | 255 |     |
| Ser | Thr | Ile | Ser | Glu | Glu | Ala | Glu | Val | Tyr |
|     |     |     | 260 |     |     |     |     | 265 |     |

(2) INFORMATION FOR SEQ ID NO:51:

(i) SEQUENCE CHARACTERISTICS:
        (A) LENGTH: 178 amino acids
        (B) TYPE: amino acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:51:

```
Met Ala Ala Ser Met Gly Tyr Ser Ser Ser Ser Ser Leu Thr Ser Leu
 1               5                  10                 15

Arg Val Gln Asn Val Trp His Val Val Asp Pro Leu Pro Ile Val Ala
                 20                 25                 30

Asn Tyr Lys Ser Asp Arg His Asp Arg Asp Lys Pro Val Pro Cys Gly
             35              40                 45

Ile Arg Val Thr Ser Arg Ser Tyr Ile Ile Arg Pro Thr Cys Glu Ser
         50              55                 60

Ser Lys Asp Leu His Ala Phe Phe Phe Gly Leu Ser Thr Gly Ser Ser
 65                  70                 75                 80

Glu Ser Met Pro Ile Ser Gly Val Glu Thr Ile Val Arg Leu Met Asn
                 85                 90                 95

Asn Lys Ala Ala Cys His Gly Lys Glu Gly Cys Arg Ser Pro Phe Ser
             100                 105                110

His Ala Thr Ile Leu Asp Ala Val Asp Asp Asn Tyr Thr Met Asn Ile
         115                 120                125

Glu Gly Val Cys Phe His Cys His Cys Asp Asp Lys Phe Ser Pro Asp
     130                 135                140

Cys Trp Ile Ser Ala Phe Ser Ala Ala Glu Gln Thr Ser Ser Leu Cys
145                 150                155                160

Lys Glu Met Arg Val Tyr Thr Arg Arg Trp Ser Ile Arg Glu Thr Lys
                 165                170                175

Cys Ser
```

(2) INFORMATION FOR SEQ ID NO:52:

(i) SEQUENCE CHARACTERISTICS:
        (A) LENGTH: 108 amino acids
        (B) TYPE: amino acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:52:

```
Met Gly Leu Tyr Met Glu Pro Xaa Asn Xaa Val Ser Leu Gln Phe Leu
 1               5                  10                 15

Arg Gly Gly Ile Tyr Met Ile Ser Xaa Pro Lys Arg Gly Met Xaa Gln
                 20                 25                 30

Arg Asp Val Met Val Ile Xaa Gly Lys Phe Phe Arg Ser Glu Ile Thr
             35              40                 45

Gln Leu Pro Lys His Arg Ser Arg Leu Lys Glu Lys Ser Asp Gly Ser
         50              55                 60
```

| Ile | Arg | Thr | Cys | Met | Asp | Ser | Val | Arg | Ile | Asn | His | Asn | Arg | Ser | Thr |
| 65 | | | | | 70 | | | | 75 | | | | | | 80 |

| Val | Gly | His | Phe | Gly | Asn | Ser | Asn | Ala | Lys | Arg | Cys | Thr | Ser | Ala | Ile |
| | | | | 85 | | | | | 90 | | | | | 95 | |

| Thr | Thr | Pro | Thr | Met | His | Ile | Val | Thr | Pro | Ala | Ser |
| | | | 100 | | | | | 105 | | | |

( 2 ) INFORMATION FOR SEQ ID NO:53:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA Oligonucleotide Primer ( i i i ) HYPOTHETICAL: NO ( i v ) ANTI-SENSE: YES ( x i ) SEQUENCE DESCRIPTION: SEQ ID NO:53:

CTCGCTCGCC CATGATCATT AAGCAAGAAT TCCGTCG        37

( 2 ) INFORMATION FOR SEQ ID NO:54:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA Oligonucleotide Primer ( i i i ) HYPOTHETICAL: NO ( i v ) ANTI-SENSE: NO ( x i ) SEQUENCE DESCRIPTION: SEQ ID NO:54:

CTGGTTCGGC CCATGATCAG ATGACAAACC TGCAAGATC        39

( 2 ) INFORMATION FOR SEQ ID NO:55:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:55:

CTCGGCGTGG TAGTTCTCGA GGCCTTAATT AAGGCCCTCG AGGATACATC CAAAGAG        57

( 2 ) INFORMATION FOR SEQ ID NO:56:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO (xi) SEQUENCE DESCRIPTION: SEQ ID NO:56:

CGGCGTGGTA GTTCTCGAGG CCTTAAGCGG CCGCTTAAGG CCCTCGAGGA TACATCCAAA 60

GAG 63

RECOMBINANT HERPESVIRUS OF TURKEYS AND USES THEREOF

This application is a continuation application of U.S. Ser. No. 08/288,065, filed Aug. 9, 1994, which is a continuation-in-part of PCT International Application No. PCT/US93/05681, filed Jun. 14, 1993, which is a continuation-in-part of U.S. Ser. No. 08/023,610, filed Feb. 26, 1993, the contents of which are hereby incorporated by reference.

BACKGROUND OF THE INVENTION

The ability to isolate DNA and clone such isolated DNA into bacterial plasmids has greatly expanded the approaches available to make viral vaccines. The methods used to make the present invention involve modifying cloned DNA sequences from various viral pathogens of animals, by insertions, deletions, single or multiple base changes, and subsequent insertions of these modified sequences into the genome of the virus. One utility of the addition of a foreign sequence is achieved when the foreign sequence encodes a foreign protein that is expressed during viral infection of the animal. The resulting live virus may then be used in a vaccine to elicit an immune response in a host animal and provide protection to the animal against disease. A virus with these characteristics is referred to as a viral vector, because it becomes a living vector that will carry and express the foreign protein in the host animal. In effect it becomes an elaborate delivery system for the foreign protein(s).

More specifically, the present invention relates to the use of herpesvirus of turkeys (HVT) as a viral vector for vaccination of birds against disease. The group of herpesviruses comprise various pathogenic agents that infect and cause disease in a number of target species: swine, cattle, chickens, horses, dogs, cats, etc. Each herpesvirus is specific for its host species, but they are all related in the structure of their genomes, their mode of replication, and to some extent in the pathology they cause in the host animal and in the mechanism of the host immune response to the virus infection.

The application of recombinant DNA techniques to animal viruses has a relatively recent history. The first viruses to be engineered have been those with the smallest genomes. In the case of the papovaviruses, because these viruses are so small and cannot accommodate much extra DNA, their use in genetic engineering has been as defective replicons. Foreign gene expression from these viruses requires a wild-type helper virus and is limited to cell culture systems. For adenoviruses, there is a small amount of nonessential DNA that can be replaced by foreign sequences. The only foreign DNA that seems to have been expressed in adenoviruses are the T-antigen genes from papovaviruses (Mansour, et al., *Proc. Natl. Acad. Sci. US*, 1985; Thummel, et al., *Cell*, 1983; Scolnick, et al., *Cell*, 1981; Thummel, et al., *Cell*, 1981), and the herpes simplex virus (HSV) thymidine kinase gene (Haj-Ahmed and Graham, *J. of Virology*, 1986). These publications do not identify the nonessential regions in HVT wherein foreign DNA may be inserted, nor do they teach how to achieve the expression of foreign genes in HVT, e.g., which promoter sequence and termination sequence to use.

Another group of viruses that have been engineered are the poxviruses. One member of this group, vaccinia, has been the subject of much research on foreign gene expression. Poxviruses are large DNA-containing viruses that replicate in the cytoplasm of the infected cell. They have a structure that is unique in that they do not contain any capsid that is based upon icosahedral symmetry or helical symmetry. The poxviruses are most likely to have evolved from bacterial-like microorganisms through the loss of function and degeneration. In part due to this uniqueness, the advances made in the genetic engineering of poxviruses cannot be directly extrapolated to other viral systems, including herpesviruses and HVT. Vaccinia recombinant virus constructs have been made in a number of laboratories that express the following inserted foreign genes: HSV thymidine kinase gene (Mackett, et al., *Proc. Natl. Acad. Sci. USA*, 1982; Panicali and Paoletti, *Proc. Natl. Acad. Sci. USA*, 1982, hepatitis B surface antigen (Paoletti, et al., *Proc. Natl. Acad. Sci. USA*, 1984; Smith et al., *Nature*, 1983), HSV glycoprotein D gene, influenzae hemagglutinin gene (Panicali, et al., *Proc. Natl. Acad. Sci. USA*, 1983; Smith, et al., *Proc. Natl. Acad. Sci. USA*, 1983), malaria antigen gene (Smith, et al., *Science*, 1984, and vesicular stomatitis glycoprotein G gent (Mackett, et al., *Science*, 1986). The general overall features of vaccinia recombinant DNA work are similar to the techniques used for all the viruses, especially as they relate to the techniques in reference (Maniatis, et al., *Molecular Cloning*, 1982). However in detail, the vaccinia techniques are not applicable to herpesviruses and HVT. The utility of vaccinia as a vaccine vector is in question because of its close relationship to human smallpox and its known pathogenicity to humans. Thus, the use of the host-specific herpesvirus HVT is a better solution to vaccination of poultry.

Among the primate herpesviruses, only HSV of humans and, to a limited extent, herpes saimiri of monkeys have been engineered to contain foreign DNA sequences. The first use of recombinant DNA to manipulate HSV involved cloning a piece of DNA from the L-S junction region into the unique long region of HSV DNA, specifically into the thymidine kinase gene (Moccarski, et al., *Cell*, 1980). This insert was not a foreign piece of DNA, rather it was a naturally occurring piece of herpesvirus DNA that was duplicated at another place in the genome. This piece of DNA was not engineered to specifically express a protein, and thus this work does not involve expression of protein in herpesviruses. The next manipulation of HSV involved the creation of deletions in the virus genome by a combination of recombinant DNA techniques and thymidine kinase selection. Using this approach, the HSV alpha-22 gene has been deleted (Post, et al., *Cell*, 1981), and a 15,000 basepair sequence of DNA has been deleted from the internal repeat of HSV (Poffenberger, et al., *Proc. Natl. Acad. Sci. USA*, 1981).

The following cases involve insertion of genes that encode protein into herpesviruses: the insertion of HSV glycoprotein C into a naturally occurring deletion mutant of this gene in HSV (Gibson and Spear, *J. of Virology*, 1983); the insertion of glycoprotein D of HSV type 2 into HSV type 1 (Lee, et al., *Proc. Natl. Acad. Sci. USA*, 1982), with no manipulation of promoter sequences since the gene is not 'foreign'; the insertion of hepatitis B surface antigen into HSV under the control of the HSV ICP4 promoter (Shih, et al., *Proc. Natl. Acad. Sci. USA*, 1984); and the insertion of bovine growth hormone into herpes saimiri virus with an SV40 promoter (the promoter did not work in this system and an endogenous upstream promoter served to transcribe the gene) (Desrosiers, et al., 1984). Two additional foreign genes (chicken ovalbumin gene and Epstein-Barr virus nuclear antigen) have been inserted into HSV (Arsenakis and Roizman, 1984), and glycoprotein X of pseudorabies virus has been inserted into HSV (Post, et al., 1985).

These cases of deletion or insertion of genes into herpesviruses demonstrate that it is possible to genetically engineer herpesvirus genomes by recombinant DNA techniques. The methods that have been used to insert genes involve homologous recombination between the viral DNA cloned in plasmids and purified viral DNA transfected into the same animal cell. However, the extent to which one can generalize the location of the deletion and the sites for insertion of foreign genes is not known from these previous studies.

One object of the present invention is a vaccine for Marek's disease. Marek's disease virus (MDV) is the causative agent of Marek's disease which encompasses fowl paralysis, a common lymphoproliferative disease of chickens. The disease occurs most commonly in young chickens between 2 and 5 months of age. The prominent clinical signs are progressive paralysis of one or more of the extremities, incoordination due to paralysis of legs, drooping of the limb due to wing involvement, and a lowered head position due to involvement of the neck muscles. In acute cases, severe depression may result. In the case of highly oncogenic strains, there is characteristic bursal and thymic atrophy. In addition, there are lymphoid tumors affecting the gonads, lungs, liver, spleen, kidney and thymus (Mohanty and Dutta, 1981).

Most chickens are vaccinated against MDV at one day of age to protect the bird against MDV for life. Prior to the present invention, the principal vaccination method for MDV involved using naturally occurring strains of turkey herpesvirus (HVT). It would be advantageous to incorporate other antigens into this vaccination at one day of age, but efforts to combine conventional vaccines have not proven satisfactory to date due to competition and immunosuppression between pathogens. The multivalent HVT-based vaccines engineered in this invention represent a novel way to simultaneously vaccinate against a number of different pathogens. For the first time, a recombinant HVT with a foreign gene inserted into a non-essential region of the HVT genome is disclosed.

The types of genetic engineering that have been performed on these herpesviruses consist of cloning parts of the virus DNA into plasmids in bacteria, reconstructuring the virus DNA while in the cloned state so that the DNA contains deletions of certain sequences, and furthermore adding foreign DNA sequences either in place of the deletions or at sites removed from the deletions.

A foreign gene of interest targeted for insertion into the genome of HVT may be obtained from any pathogenic organism of interest. Typically, the gene of interest will be derived from pathogens that in poultry cause diseases that have an economic impact on the poultry industry. The genes may be derived from organisms for which there are existing vaccines, and because of the novel advantages of the vectoring technology the HVT derived vaccines will be superior. Also, the gene of interest may be derived from pathogens for which there is currently no vaccine but where there is a requirement for control of the disease. Typically, the gene of interest encodes immunogenic polypeptides of the pathogen, and may represent surface proteins, secreted proteins and structural proteins.

A relevant avian pathogen that is a target for HVT vectoring is Infectious Laryngotracheitis virus (ILTV). ILTV is a member of the herpesviridiae family, and this pathogen causes an acute disease of chickens which is characterized by respiratory depression, gasping and expectoration of bloody exudate. Viral replication is limited to cells of the respiratory tract, where in the trachea the infection gives rise to tissue erosion and hemorrhage. In chickens, no drug has been effective in reducing the degree of lesion formation or in decreasing clinical signs. Vaccination of birds with various modified forms of the ILT virus derived by cell passage and/or tedious regimes of administration have conferred acceptable protection in susceptible chickens. Because of the degree of attenuation of current ILT vaccines care must be taken to assure that the correct level of virus is maintained; enough to provide protection, but not enough to cause disease in the flock.

An additional target for the HVT vectoring approach is Newcastle disease, an infectious highly contagious and debilitating disease that is caused by the Newcastle disease virus (NDV). NDV is a single-stranded RNA virus of the paramyxovirus family. The various pathotypes of NDV (velogenic, mesogenic, lentogenic) differ with regard to the severity of the disease, the specificity and symptoms, but most types seem to infect the respiratory system and the nervous system. NDV primarily infects chickens, turkeys and other avian species. Historically vaccination has been used to prevent disease, but because of maternal antibody interferences, life-span of the bird and route of administration, the producer needs to adapt immunization protocols to fit specific needs.

SUMMARY OF THE INVENTION

The present invention provides a recombinant herpesvirus of turkeys designated S-HVT-050 (ATCC Accession No. VR 2400). The present invention further provides a vaccine which comprises an effective immunizing amount of S-HVT-050 and a suitable carrier. A method of immunizing a fowl against disease caused by Marek's disease virus and Newcastle disease virus is also provided which comprises administering to the fowl an effective immunizing dose of the vaccine of the present invention.

BRIEF DESCRIPTION OF FIGURES

FIG. 1A shows BamHI restriction fragment map of the HVT genome. Fragments are numbered in order of decreasing size; letters refer to small fragments whose comparative size has not been determined.

FIG. 1B shows BamHI #16 fragment of the HVT genome showing location of β-galactosidase gene insertion in S-HVT-001.

FIG. 1C shows BamHI #19 fragment of the HVT genome showing location of β-galactosidase gene insertion. Legend: B=BamHI; X=XhoI; H=HindIII; P=PstI; S=SalI; N=NdeI; R=EcoRI.

FIG. 2A contains a diagram showing the orientation of DNA fragments assembled in plasmid 191-47. FIGS. 2A to 2D show the sequences located at each of the junctions between the DNA fragments in plasmid 191-47. (SEQ ID NOs: 20, 21, 22, 23, 24, 25, 26, and 27).

FIGS. 3A and 3B show details of S-HVT-003 Construction.

FIG. 3A shows restriction map of HVT DNA in the region of the BamHI #16 fragment. This fragment is contained within large HindIII fragment. FIG. 3A also shows the XhoI site which was first changed to an EcoRI (R) site by use of a "linker" and standard cloning procedures. FIG. 3A also shows details of the construction of the beta-gal gene and IBVD gene inserted into the BamHI #16 fragment for use in homologous recombination. Both genes were under the control of the PRV gX gene promoter (gX).

FIG. 3B shows the S-HVT-003 genome, including the location of the two inserted foreign genes, β-gal and IBDV.

In FIG. 3: H=HindIII; B=BamHI; X=XhoI; R=EcoRI; Xb=XbaI; Hp=HpaI; S=SmaI; UL=unique long region; US=unique short region; IR=internal repeat region; TR=terminal repeat region.

FIG. 4 shows a Western blot indicating the differential expression of the IBDV 32 kD antigen in cellular lysates of S-HVT-003 infected cells (32 kD present) and S-HVT-001 infected cells (32 kD negative). IBDV specific polypeptides were identified by probing the blot with hyper-immune rat antiserum directed against denatured IBDV virions. This serum reacts primarily with the immunodominant 32 kD antigen (IBDV VP3). The lanes on the blot contain: 1) protein molecular weight standards, 2) uninfected CEF cells, 3) S-HVT-001 infected CEF's, 4) 5) & 6) S-HVT-003 and 7) IBDV virion polypeptides.

FIGS. 6A, GB, and 6C provide details of S-HVT-004 Construction.

FIG. 6A is a restriction map of HVT DNA in the region of the BamHI #16 fragment. This fragment is contained within a large HindIII fragment. Shown also is the XhoI site (X) where applicants have made their insertion. Before the insertion, the XhoI was first changed to EcoRI (R) site by use of a "linker" and standard cloning procedures.

FIG. 6B provides details of the construction of the β-gal gene and MDV gA gene inserted into the BamHI #16 fragment for use in homologous recombination. Beta-gal was under the control of the PRV gX gene promoter (gX), while the MDV gA gene was under the control of its own promoter.

FIG. 6C is of S-HVT-004 genome showing the location of the two inserted foreign genes, β-gal and MDV gA.

In FIG. 6, H=HindIII; B=BamHI; X=XhoI; R=EcoRI; Xb=XbaI; UL=unique long region; US=unique short region; IR=internal repeat region; TR=terminal repeat region.

FIGS. 7A and 7B provide a detailed description of the β-galactosidase (lacZ) marker gene insertion in homology vector 467-22.A12. FIG. 7A shows a diagram indicating the orientation of DNA fragments assembled in the marker gene. The origin of each fragment is described in the Materials and Methods section. FIGS. 7A and 7B show the DNA sequences located at the junctions between DNA fragments and at the ends of the marker gene (SEQ ID NOs: 28, 29, 30, 31, 32, and 33). FIGS. 7A and 7B further show the restriction sites used to generate each DNA fragment at the appropriate junction and the location of the lacZ gene coding region. Numbers in parenthesis ( ) refer to amino acids, and-restriction sites in brackets [ ] indicate the remnants of sites which were destroyed during construction. The following abbreviations are used, pseudorabies virus (PRV), lactose operon Z gene (lacZ), *Escherichia coli* (*E.Coli*), polyadenylation signal (pA), and glycoprotein X (gpx).

FIG. 10A and 10B show a diagram indicating the orientation of DNA fragments assembled in the cassette and the location of the MDV gA and gB genes. The origin of each fragment is described in the Materials and Methods section. The sequences located at the junctions between each fragment and at the ends of the marker gene are shown in FIGS. 10A and 10B, including junction A (SEQ ID NO: 34), junction B (SEQ ID NO: 35), and junction C (SEQ ID NO: 36). The restriction sites used to generate each fragment are indicated at the appropriate junction. Numbers in parenthesis ( ) refer to amino acids, and restriction sites in brackets [ ] indicate the remnants of sites which were destroyed during construction.

FIG. 11A and 11B provide a detailed description of the HindIII fragment insert in Homology Vector 556-41.5. The diagram of FIGS. 11A and 11B show the orientation of DNA fragments assembled in the cassette. The origin of each fragment is described in the Materials and Methods section. FIGS. 11A and 11B further show the DNA sequences located at the junctions between each DNA fragment of the plasmid and at the ends of the marker gene, including junction A (SEQ ID NO: 37), junction B (SEQ ID NO: 38), and junction C (SEQ ID NO: 39). The restriction sites used to generate each fragment are indicated at the appropriate junction. The location of the MDV gD and a portion of the gI gene is also given. Numbers in parenthesis ( ) refer to amino acids, and restriction sites in brackets [ ] indicate the remnants of sites which were destroyed during construction.

FIGS. 12A, 12B, and 12C provide a detailed description of the SalI fragment insert in Homology Vector 255-18.B16. FIG. 12A shows a diagram indicating the orientation of DNA fragments assembled in the cassette. The origin of each fragment is described in the Materials and Methods section. FIGS. 12A to 12C further show the DNA sequences located at the junctions between each fragment and at the ends of the marker gene are shown, including junction A (SEQ ID NO: 40), junction B (SEQ ID NO: 41), junction C (SEQ ID NO: 42), junction D (SEQ ID NO: 43), junction E (SEQ ID NO: 44), junction F (SEQ ID NO: 45), junction G (SEQ ID NO: 46), and junction H (SEQ ID NO: 47). The restriction sites used to generate each fragment are indicated at the appropriate junction. The location of the NDV F and lacZ-NDV HN hybrid gene are shown. Numbers in parenthesis ( ) refer to amino acids, and restriction sites in brackets [ ] indicate the remnants of sites which were destroyed during construction.

FIGS. 13A and 13B show how the unique XhoI site of the BamHI #10 fragment of the HVT genome was converted into a PacI site and a NotI site by insertion of the synthetic DNA sequence at the XhoI site (Nucleotides #1333–1338; SEQ ID NO. 48). FIG. 13A shows the XhoI site converted into a PacI site to generate Plasmid 654-45.1 (SEQ ID NO. 55) and FIG. 13B shows the XhoI site converted into a NotI site to generate Plasmid 686-63.A1 (SEQ ID NO. 56).

FIG. 15 shows a restriction map of cosmids 407-32.1C1, 672-01.A40, 672-07.C40, and 654-45.1. The overlap of HVT genomic DNA fragments EcoRI #9 and BamHI #10 is illustrated. A unique XhoI site within the EcoRI #9 and BamHI #10 fragments has been converted to a unique PacI site in Plasmid 654-45.1 or a unique NotI site in Plasmid 686-63.A1.

DETAILED DESCRIPTION OF THE INVENTION

Figure 1A:
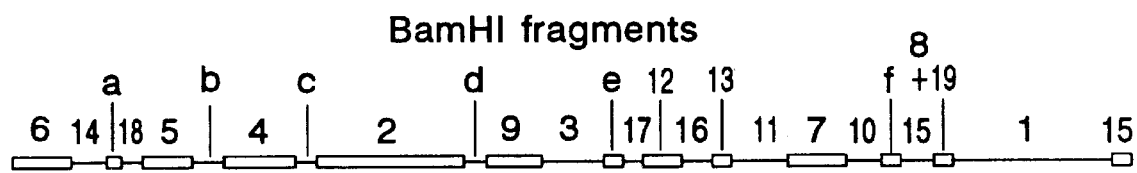
FIGS. 1A, 1B, and 1C show details of HVT Construction and Map Data.

The present invention provides a recombinant herpesvirus of turkeys (HVT) comprising a foreign DNA sequence inserted into a non-essential site in the HVT genome. The foreign DNA sequence is capable of being expressed in a host cell infected with the recombinant HVT and its expression is under control of a promoter located upstream of the foreign DNA sequence.

For purposes of this invention "a non-essential site in the HVT genome" means a region in the HVT genome which is not necessary for the viral infection or replication.

For purposes of this invention, "a foreign DNA sequence" means DNA which codes for a gene or part thereof that does not naturally in the HVT genome.

In one embodiment of the present invention, the foreign DNA sequence inserted into the HVT genome encodes a polypeptide. Preferably, the polypeptide is antigenic in the animal into which the recombinant HVT is introduced. Preferably, this antigenic polypeptide is a linear polymer of more than 10 amino acids linked by peptide bonds which stimulates the animal to produce antibodies.

Also provided are several appropriate insertion sites in the HVT genome useful for constructing the recombinant herpesvirus of the present invention. One such site is the BamHI #16 fragment of the HVT genome. A preferred insertion site within the BamHI #16 fragment lies within an open reading frame encoding HVT UL43 and a preferred insertion site within that open reading frame is a XhoI restriction endonuclease site.

Two other insertion sites are the EcoRI #9 fragment and the BamHI #10 fragment of the HVT genome, a preferred insertion site within both of those fragments being a XhoI restriction endonuclease site.

Yet another insertion site is the HVT US2 gene, with a preferred insertion site within it being a StuI restriction endonuclease site.

In one embodiment of the present invention, the recombinant herpesvirus of turkeys (HVT) contains a foreign DNA sequence encoding a detectable marker. Preferably, the detectable marker is $E.$ $coli$ B-galactosidase. Preferably, such recombinant HVT is designated S-HVT-001, S-HVT-014, or S-HVT-012.

S-HVT-012 has been deposited on Oct. 15, 1992 pursuant to the Budapest Treaty on the International Deposit of Microorganism for the Purposes of Patent Procedure with the Patent Culture Depository of the American Type Culture Collection, 12301 Parklawn Drive, Rockville, Md. 20852 U.S.A. under ATCC Accession No. VR 2382.

S-HVT-014 has been deposited on Dec. 7, 1993 pursuant to the Budapest Treaty on the International Deposit of Microorganisms for the Purpose of Patent Procedure with the Patent Culture Depository of the American Type Culture Collection, 12301 Parklawn Drive, Rockville, Md. 20852 U.S.A. under ATCC Accession No. VR 2440.

In one embodiment of the present invention, the recombinant herpesvirus (HVW) contains a foreign DNA sequence encoding an antigenic polypeptide from infectious bursal disease virus (IBDV), Marek's disease virus (MDV), Newcastle disease virus (NDV), infectious laryngotracheitis virus (ILTV), or infectious bronchitis virus (IBV).

When the foreign DNA sequence of the recombinant HVT of the present invention encodes an antigenic polypeptide from infectious bursal disease virus (IBDV), it is preferred that the antigenic polypeptide is IBDV VP2, VP3 or VP4 protein. Such recombinant HVT can be further engineered to contain a foreign DNA sequence encoding a detectable marker, such as $E.$ $coli$ B-galactosidase.

Recombinant HVT designated S-HVT-003 and S-HVT-096 are each an embodiment of a recombinant HVT comprising foreign DNA sequence encoding an antigenic polypeptide from IBDV and encoding a detectable marker. S-HVT-003 has been deposited on Jul. 21, 1987 pursuant to the Budapest Treaty on the International Deposit of Microorganism for the Purposes of Patent Procedure with the Patent Culture Depository of the American Type Culture Collection, 12301 Parklawn Drive, Rockville, Md. 20852 U.S.A. under ATCC Accession No. VR 2178).

The present invention also provides a recombinant HVT which contains one or more foreign DNA sequence encoding an antigenic polypeptide from IBDV as well as one or more foreign DNA sequence encoding an antigenic polypeptide from MDV. Preferably, the IBDV antigenic polypeptide is IBDV VP2, VP3, or VP4 and the MDV antigenic polypeptide is MDV glycoprotein B (gB), glycoprotein D (gD), or glycoprotein A (gA).

In one embodiment, a recombinant HVT contains foreign DNA sequence encoding IBDV VP2, MDV gA, MDV gD, and MDV gB. Preferably, such recombinant virus is designated S-HVT-137 or S-HVT-143.

The present invention provides a recombinant HVT which contains a foreign DNA sequence encoding an antigenic polypeptide from MDV. Preferably, the antigenic polypeptide is MDV gB, gA, or gD.

One embodiment of a recombinant HVT containing a foreign DNA sequence encoding MDV gA is a recombinant HVT designated S-HVT-004.

An embodiment of a recombinant HVT containing a foreign DNA sequence encoding MDV gB is also provided and this recombinant HVT is designated S-HVT-045. S-HVT-045 has been deposited on Oct. 15, 1992 pursuant to the Budapest Treaty on the International Deposit of Microorganism for the Purposes of Patent Procedure with the Patent Culture Depository of the American Type Culture Collection, 12301 Parklawn Drive, Rockville, Md. 20852 U.S.A. under ATCC Accession No. VR 2383.

The present also invention includes recombinant HVTs engineered to contain more than one foreign DNA sequence encoding an MDV antigen. For example, a foreign DNA sequence encoding MDV gA and gB can both be vectored into the HVT genome. Furthermore, a recombinant HVT can be constructed to include a foreign DNA sequence encoding MDV gA, gB and gD.

Recombinant HVT designated S-HVT-046 and S-HVT-047 provide embodiments of a recombinant HVT containing foreign DNA sequence encoding MDV gA and gB; recombinant HVT designated S-HVT-048 and S-HVT-062 provide embodiments of a recombinant HVT containing foreign DNA sequence encoding MDV gA, gB and gD. S-HVT-062 has been deposited on Feb. 23, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2401.

The present invention provides a recombinant HVT containing a foreign DNA sequence encoding an antigenic polypeptide from Newcastle disease virus (NDV). In such case, it is preferred that the antigenic polypeptide is NDV fusion (F) protein or NDV hemagglutinin-neuraminidase (HN) or a recombinant protein comprising $E.$ $coli$ B-galactosidase fused to NDV HN. One such virus is a recombinant HVT designated S-HVT-007.

The present invention also provides a recombinant HVT which contains one or more foreign DNA sequences encoding an antigenic polypeptide from MDV as well as one or more foreign DNA sequences encoding an antigenic polypeptide from NDV. Preferably, the MDV antigenic polypeptide is MDV gB, gD, or gA and the NDV antigenic polypeptide is NDV F or HN.

In one embodiment of the invention, the recombinant HVT contains foreign DNA sequence encoding MDV gB, MDV gA, and NDV F. Preferably, this recombinant HVT is designated S-HVT-048.

In one embodiment of the invention, the recombinant HVT contains foreign DNA sequence encoding MDV gB, MDV gA, and NDV HN. Preferably, this recombinant HVT is designated S-HVT-049.

In another embodiment of the invention, the recombinant HVT contains foreign DNA sequence encoding MDV gB, MDV gA, NDV F and NDV HN. Preferably, such recombinant HVT is designated S-HVT-050. S-HVT-050 has been deposited on Feb. 23, 1993 pursuant to the Budapest Treaty on the International Deposit of Microorganisms for the Purpose of Patent Procedure with the Patent Culture Depository of the American Type Culture Collection, 12301 Parklawn Drive, Rockville, Md. 20852 U.S.A. under ATCC Accession No. VR 2400.

In yet another embodiment of the invention, the recombinant HVT contains foreign DNA sequence encoding MDV gB, MDV gA, MDV gD, NDV F and NDV HN. Preferably, such recombinant HVT is designated S-HVT-106 or S-HVT-128.

The present invention further provides a recombinant HVT which contains a foreign DNA sequence encoding an antigenic polypeptide from infectious laryngotracheitis virus (ILTV). It is preferred that the antigenic polypeptide is ILTV glycoprotein B (gB), ILTV glycoprotein D (gD), or ILTV glycoprotein I (gI).

Also provided are recombinant HVTs which are engineered to contained more than one foreign DNA sequence encoding an ILTV antigen. For example, ILTV gB and gD can be vectored together into the HVT genome, so can ILTV gD and gI, and ILTV gB, gD and gI. Recombinant HVT designated S-HVT-051, S-HVT-052 and S-HVT-138 are embodiments of such recombinant virus.

The present invention also provides a recombinant HVT which contains one or more foreign DNA sequence encoding an antigenic polypeptide from MDV as well as one or more foreign DNA sequence encoding an antigenic polypeptide from ILTV. Preferably, the MDV antigenic polypeptide is MDV gB, gD, or gA and the ILTV antigenic polypeptide is ILTV gB, gD or gI.

In one embodiment of the invention, the recombinant HVT contains foreign DNA sequence encoding MDV gB, MDV gA, MDV gD, ILTV gD and ILTV gB. Preferably, this recombinant HVT is designated S-HVT-123.

In another embodiment of the invention, the recombinant HVT contains foreign DNA sequence encoding MDV gB, MDV gA, MDV gD, ILTV gI and ILTV gD. Preferably, this recombinant HVT is designated S-HVT-139 or S-HVT-140.

The present invention further provides a recombinant HVT which contains a foreign DNA sequence encoding an antigenic polypeptide from infectious bronchitis virus (IBV). Preferably, the antigenic polypeptide is IBV spike protein or IBV matrix protein.

The present invention also provides a recombinant HVT which contains one or more foreign DNA sequence encoding an antigenic polypeptide from IBV as well as one or more foreign DNA sequence encoding an antigenic polypeptide from MDV. Preferably, the IBV antigenic polypeptide is IBV spike protein or IBV matrix protein, and the MDV antigenic polypeptide is MDV gB, gD, or gA. One embodiment of such recombinant virus is designated S-HVT-066.

The expression of the inserted foreign DNA sequence is under control of a promoter located upstream of the foreign DNA sequence. Preferably, the promoter is a herpesvirus promoter. Preferably, the promoter is selected from a group consisting of PRV gX promoter, MDV gB promoter, MDV gA promoter, MDV gD promoter, ILTV gB promoter, ILTV gD promoter, HSV-1 alpha 4 promoter and HCMV immediate early promoter.

The present invention further provides for a homology vector for producing a recombinant herpesvirus of turkeys by inserting foreign DNA sequence into the HVT genome. The homology vector comprises a double-stranded DNA molecule consisting essentially of a double-stranded foreign DNA sequence, with at one end of the foreign DNA sequence, double-stranded DNA homologous to the genomic DNA located at one side of a non-essential site of the HVT genome, and at the other end of the foreign DNA sequence, double-stranded DNA homologous to the HVT genomic DNA sequence located at the other side of the same site. DNA sequence corresponding to a promoter is located upstream of the foreign DNA sequence and controls its expression.

In one embodiment of the invention, the foreign DNA sequence of the homology vector encodes a polypeptide. In one embodiment of the invention, the polypeptide is antigenic in the animal into which the recombinant herpesvirus of turkeys is introduced. Preferably, the antigenic polypeptide is from infectious bursal disease virus, Marek's disease virus, Newcastle disease virus, infectious laryngotracheitis virus, or infectious bronchitis virus. Preferably, the antigenic polypeptide is selected from a group consisting essentially of infectious bursal disease virus VP2 protein, infectious bursal disease virus VP3 protein, infectious bursal disease virus VP4 protein, Marek's disease virus glycoprotein gB, Marek's disease virus glycoprotein gA, Marek's disease virus glycoprotein gD, Newcastle disease virus fusion (F) protein, Newcastle disease virus hemagglutinin-neuraminidase (HN), infectious laryngotracheitis virus glycoprotein I, infectious laryngotracheitis virus glycoprotein D, infectious laryngotracheitis virus glycoprotein B, infectious bronchitis virus spike protein, or infectious bronchitis virus matrix protein.

In one embodiment of the invention, the polypeptide is a detectable marker. Preferably, the detectable marker is *E. coli* β-galactosidase.

In one embodiment of the invention, the double-stranded herpesvirus of turkeys DNA is homologous to DNA sequence present within the BamHI #16 fragment of the herpesvirus of turkeys genome. Preferably, the double-stranded herpesvirus of turkeys DNA is homologous to DNA sequences present within the open reading frame encoding UL 43 protein of the herpesvirus of turkeys genome. Preferably, this homology vector is designated 172-29.31.

For purposes of this invention, a "homology vector" is a plasmid constructed to insert foreign DNA sequence in a specific site on the genome of a herpesvirus of turkeys.

In one embodiment of the invention, the double-stranded herpesvirus of turkeys DNA is homologous to DNA sequences present within the EcoRI #9 fragment or BamHI #10 fragment of the herpesvirus of turkeys genome. Preferably, this homology vector is designated 172-63.1.

In one embodiment of the invention, the double-stranded herpesvirus of turkeys DNA is homologous to DNA sequence present within the US2 gene coding region of the herpesvirus of turkeys genome. Preferably, this homology vector is designated 435-47.1.

The invention further provides a vaccine which comprises an effective immunizing amount of a recombinant herpesvirus of turkeys of the present invention and a suitable carrier.

Suitable carriers for the herpesvirus of turkeys vaccine are well known in the art and include proteins, sugars, etc. One example of such suitable carrier is a physiologically balanced culture medium containing one or more stabilizing agents such as stabilized, hydrolyzed proteins, lactose, etc.

For purpose of this invention, an "effective immunizing amount" of recombinant herpesvirus of the present invention is within the range of $10^2$ to $10^9$ PFU/dose.

The present invention further provides a method of immunizing a fowl. The present invention also provides a method of immunizing a fowl in ovo. For purposes of this invention, this includes immunizing a fowl against infectious bursal disease virus, Marek's disease virus, Newcastle disease virus, infectious laryngotracheitis virus, or infectious bronchitis virus. The method comprises administering to the fowl an effective immunizing dose of the vaccine of the present invention. The vaccine may be administered by any of the methods well known to those skilled in the art, for example, by intramuscular, subcutaneous, intraperitoneal or intravenous, injection. Alternatively, the vaccine may be administered intranasally, orally or intraocularly.

The present invention also provides a host cell infected with a recombinant herpesvirus of turkeys of the present invention. Preferably, the host cell is an avian cell.

For purposes of this invention, a "host cell" is a cell used to propagate a vector and its insert. Infecting the cell was accomplished by methods well known to those skilled in the art, for example, as set forth in DNA TRANSFECTION FOR GENERATING RECOMBINANT HERPESVIRUS in Materials and Methods.

A recombinant herpesvirus of turkeys of the present invention provides a way for distinguishing an animal vaccinated with the vaccine of the present invention from an animal infected with a naturally-occurring, wild-type infectious bursal disease virus, Marek's disease virus, Newcastle disease virus, infectious laryngotracheitis virus, or infectious bronchitis virus. This is possible because recombinant herpesvirus of turkeys contain foreign DNA which encodes a limited number of antigens from the above mentioned viruses that are needed to confer protective immunity to the corresponding pathogens. Consequently, host animals vaccinated with those recombinant herpesviruses of turkeys can be distinguished from ones which have been infected with wild-type infectious bursal disease virus, Marek's disease virus, Newcastle disease virus, infectious laryngotracheitis virus, or infectious bronchitis virus by the absence of antigens that are normally present in the wild type viruses.

Methods for constructing, selecting and purifying recombinant herpesvirus of turkeys are detailed below in Materials and Methods.

MATERIALS AND METHODS

PREPARATION OF HERPESVIRUS OF TURKEYS STOCK SAMPLES. Herpesvirus of turkeys stock samples were prepared by infecting tissue culture cells at a multiplicity of infection of 0.01 PFU/cell in Dulbecco's Modified Eagle Medium (DMEM) containing 2 mM glutamine, 100 units/ml penicillin, 100 units/ml streptomycin (these components are obtained from Irvine Scientific or an equivalent supplier, and hereafter are referred to as complete DME medium) plus 1% fetal bovine serum. After cytopathic effect was complete, the medium and cells were harvested and the cells were pelleted at 3000 rpm for 5 minutes in a clinical centrifuge. Infected cells were resuspended in complete medium containing 20% fetal bovine serum, 10% DMSO and stored frozen at −70° C.

PREPARATION OF HERPESVIRUS OF TURKEY DNA. All manipulations of herpesvirus of turkey (HVT) were made using strain FC-126 (ATCC #584-C). For the preparation of HVT viral DNA from the cytoplasm of infected cells, primary chicken embryo fibroblasts were infected at a MOI sufficient to cause extensive cytopathic effect before the cells overgrew. All incubations were carried out at 39° C. in a humidified incubator with 5% $CO_2$ in air. Best DNA yields were obtained by harvesting monolayers which were maximally infected, but showing incomplete cell lysis (typically 5–7 days). Infected cells were harvested by scraping the cells into the medium using a cell scraper (Costar brand). The cell suspension was centrifuged at 3000 rpm for 10 minutes at 5° C. in a GS-3 rotor (Sorvall Instruments). The resultant pellet was resuspended in cold PBS (20 ml/Roller Bottle) and subjected to another centrifugation for 10 minutes at 3000 rpm in the cold. After decanting the PBS, the cellular pellet was resuspended in 4 ml/roller bottle of RSB buffer (10 mM Tris pH 7.5, 1 mM EDTA, and 1.5 MM $MgCl_2$). NP40 (Nonidet P-40™;Sigma) was added to the sample to a final concentration of 0.5% minutes with occasional mixing. The sample was centrifuged for 10 minutes at 3000 rpm in the cold to pellet the nuclei and remove cellular debris. The supernatant fluid was carefully transferred to a 15 ml Corex centrifuge tube. Both EDTA (0.5M pH 8.0) and SDS (sodium dodecyl sulfate; stock 20%) were added to the sample to final concentrations of 5 mM and 1%, respectively. One hundred $\mu l$ of proteinase-K (10 mg/ml; Boehringer Mannheim) was added per 4 ml of sample, mixed, and incubated at 45° C. for 1–2 hours. After this period, an equal volume of water-saturated phenol was added to the sample and gently mixed by hand. The sample was spun in a clinical centrifuge for 5 minutes at 3000 rpm to separate the phases. NaAc was added to the aqueous phase to a final concentration of 0.3M (stock solution 3M pH 5.2), and the nucleic acid precipitated at −70° C. for 30 minutes after the addition of 2.5 volumes of cold absolute ethanol. DNA in the sample was-pelleted by spinning for 20 minutes to 8000 rpm in an HB-4 rotor at 5° C. The supernatant was carefully removed and the DNA pellet washed once with 25 ml of 80% ethanol. The DNA pellet was dried briefly by vacuum (2–3 minutes), and resuspended in 50 μl/roller bottle of infected cells of TE buffer (10 mM Tris pH 7.5, 1 mM EDTA). Typically, yields of viral DNA ranged between 5–10 μg/roller bottle of infected cells. All viral DNA was stored at approximately 10° C.

POLYMERASE FILL-IN REACTION. DNA was resuspended in buffer containing 50 mM Tris pH 7.4, 50 mM KCl, 5 mM $MgCl_2$, and 400 micromolar each of the four deoxynucleotides. Ten units of Klenow DNA polymerase (BRL) were added and the reaction was allowed to proceed for 15 minutes at room temperature. The DNA was then phenol extracted and ethanol precipitated as above.

DNA SEQUENCING. Sequencing was performed using the USB Sequenase Kit and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone and Supersee programs from Coral Software.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al (1982) and Sambrook et al (1989). The polymerase chain reaction (PCR) was used to introduce restriction sites convenient for the manipulation of various DNAs. The procedures used are described by Innis et al (1990). In general amplified fragments were less than 500 base pairs in size and critical regions of amplified fragments were confirmed by DNA sequencing. Except as noted, these techniques were used with minor variation.

SOUTHERN BLOTTING OF DNA. The general procedure for Southern blotting was taken from Maniatis et al. (1982). DNA was blotted to nitrocellulose filters (S&S BA8S) in 20× SSC (1× ssc=0.15M NaCl, 0.015M sodium citrate, pH 7.0), and prehybridized in hybridization Solution consisting of 30% formamide, 1× Denhardt's solution (0.02% polyvinylpyrrolidone (PVP), 0.02% bovine serum albumin (BSA), 0.02% Ficoll), 6× SSC, 50 mM $NaH_2PO_4$, pH 6.8, 200 μg/ml salmon sperm DNA for 4–24 hours at 55° C. Labeled probe DNA was added that had been labeled by nick translation using a kit from Bethesda Research Laboratories (BRL) and one $^{32}$P-labeled nucleotide. The probe DNA was separated from the unincorporated nucleotides by NACS column (BRL) or on a Sephadex G50 column (Pharmacia). After overnight hybridization at 55° C., the filter was washed once with 2× SSC at room temperature followed by two washes with 0.1× SSC, 0.1% sodium dodecyl sulfate (SDS) for 30 minutes at 55° C. The filter was dried and autoradiographed.

cDNA CLONING PROCEDURE. cDNA cloning refers to the methods used to convert RNA molecules into DNA molecules following state of the art procedures. Applicants' methods are described in (Gubler and Hoffman, 1983). Bethesda Research Laboratories (Gaithersburg, Md.) have designed a cDNA Cloning Kit that is very similar to the procedures used by applicants, and contains a set of reagents and protocols that may be used to duplicate our results.

For cloning virus mRNA species, a host cell line sensitive to infection by the virus was infected at 5–10 plaque forming units per cell. When cytopathic effect was evident, but before total destruction, the medium was removed and the cells were lysed in 10 mls lysis buffer (4M guanidine thiocyanate, 0.1% antifoam A, 25 mM sodium citrate pH 7.0, 0.5% N-lauroyl sarcosine, 0.1M beta-metcaptoethanol). The cell lysate was poured into a sterilized Dounce homogenizer and homogenized on ice 8–10 times until the solution was homogenous. For RNA purification, 8 mls of cell lysate were gently layered over 3.5 mls of CsCl solution (5.7M CsCl, 25 mM sodium citrate pH 7.0) in Beckman SW41 centrifuge tube. The samples were centrifuged for 18 hrs at 20° C. at 36000 rpm in a Beckman SW41 rotor. The tubes were put on ice and the supernatants from the tubes were carefully removed by aspiration to leave the RNA pellet undisturbed. The pellet was resuspended in 400 μl glass distilled water, and 2.6 mls of guanidine solution (7.5M guanidine-HCL, 25 mM sodium citrate pH 7.0, 5 mM dithiothreitol) were added. The 0.37 volumes of 1M acetic acid were added, followed by 0.75 volumes of cold ethanol and the sample was put at −20° C. for 18 hrs to precipitate RNA. The precipitate was collected by centrifugation in a Sorvall centrifuge for 10 min a 4° C. at 10000 rpm in an SS34 rotor. The pellet was dissolved in 1.0 ml distilled water, recentrifuged at 13000 rpm, and the supernatant saved. RNA was re-extracted from the pellet 2 more times as above with 0.5 ml distilled water, and the supernatants were pooled. A 0.1 volume of 2M potassium acetate solution was added to the sample followed by 2 volumes of cold ethanol and the sample was put at −20° C. for 18 hrs. The precipitated RNA was collected by centrifugation in the SS34 rotor at 40 C for 10 min at 10000 rpm. The pellet was dissolved in 1 ml distilled water and the concentration taken by absorption at A260/280. The RNA was stored at −70° C.

mRNA containing polyadenylate tails (poly-A) was selected using oligo-dT cellulose (Pharmacia #27 5543-0). Three mg of total RNA was boiled and chilled and applied to the 100 mg oligo-dT cellulose column in binding buffer (0.1M Tris pH 7.5, 0.5M LiCl, 5 mM EDTA pH 8.0, 0.1% lithium dodecyl sulfate). The retained poly-A RNA was eluted from the column with elution buffer (5 mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mM sodium acetate and 2 volumes cold ethanol at −20° C. for 18 hrs. The RNA was resuspended in 50 μl distilled water.

Ten μg poly-A RNA was denatured in 20 mM methyl mercury hydroxide for 6 min at 22° C. β-mercaptoethanol was added to 75 mM and the sample was incubated for 5 min at 22° C. The reaction mixture for first strand cDNA synthesis in 0.25 ml contained 1 μg oligo-dT primer (P-L Bio-chemicals) or 1 μg synthetic primer, 28 units placental ribonuclease inhibitor (Bethesda Research Labs #5518SA), 100 mM Tris pH 8.3, 140 mM KCl, 10 mM $MgCl_2$, 0.8 mM DATP, dCTP, dGTP, and dTTP (Pharmacia), 100 microcuries $^{32}$p-labeled dCTP (New England Nuclear #NEG-013H), and 180 units AMV reverse transcriptase (Molecular Genetics Resources #MG 101). The reaction was incubated at 42° C. for 90 min, and then was terminated with 20 mM EDTA pH 8.0. The sample was extracted with an equal volume of phenol/chloroform (1:1) and precipitated with 2M ammonium acetate and 2 volumes of cold ethanol −20° C. for 3 hrs. After precipitation and centrifugation, the pellet was dissolved in 100 µl distilled water. The sample was loaded onto a 15 ml G-100 Sephadex column (Pharmacia) in buffer (100 mM Tris pH 7.5, 1 mM EDTA pH 8.0, 100 mM NaCl). The leading edge of the eluted DNA fractions was pooled, and DNA was concentrated by lyophilization until the volume was about 100 µl, then the DNA was precipitated with ammonium acetate plus ethanol as above.

The entire first strand sample was used for second strand reaction which followed the Gubler and Hoffman (1983) method except that 50 µg/ml dNTP's, 5.4 units DNA polymerase I (Boerhinger Mannheim #642-711), and 100 units/ml E. coli DNA ligase (New England Biolabs #205) in a total volume of 50 microliters were used. After second strand synthesis, the cDNA was phenol/chloroform extracted and precipitated. The DNA was resuspended in 10 µl distilled water, treated with 1 µg RNase A for 10 min at 22° C., and electrophoresed through a it agarose gel (sigma Type II agarose) in 40 mM Tris-acetate pH 6.85. The gel was stained with ethidium bromide, and DNA in the expected size range was excised from the gel and electroeluted in 8 mM Tris-acetate pH 6.85. Electroeluted DNA was lyophilized to about 100 microliters, and precipitated with ammonium acetate and ethanol as above. The DNA was resuspended in 20 µl water.

Oligo-dC tails were added to the DNA to facilitate cloning. The reaction contained the DNA, 100 mM potassium cacodylate pH 7.2, 0.2 mM dithiothreitol, 2 mM CaCl$_2$, 80 µmoles dCTP, and 25 units terminal deoxynucleotidyl transferase (Molecular Genetic Resources #S1001) in 50 µl. After 30 min at 37° C., the reaction was terminated with 10 mM EDTA, and the sample was phenol/chloroform extracted and precipitated as above.

The dC-tailed DNA sample was annealed to 200 ng plasmid vector pBR322 that contained oligo-dG tails (Bethesda Research Labs #5355 SA/SB) in 200 µl of 0.01M Tris pH 7.5, 0.1M NaCl, 1 mM EDTA pH 8.0 at 65° C. for 2 min and then 57° C. for 2 hrs. Fresh competent E. coli DH-1 cells were prepared and transformed as described by Hanahan (1983) using half the annealed cDNA sample in twenty 200 µl aliquots of cells. Transformed cells were plated on L-broth agar plates plus 10 µg/ml tetracycline. Colonies were screened for the presence of inserts into the ampicillin gene using Ampscreen (Bethesda Research Labs #5537 UA), and the positive colonies were picked for analysis.

DNA TRANSFECTION FOR GENERATING RECOMBINANT HERPESVIRUS. The method is based upon the polybrene-DMSO procedure of Kawai and Nishizawa (1984) with the following modifications. Generation of recombinant HVT virus is dependent upon homologous recombination between HVT viral DNA and the plasmid homology vector containing the desired foreign DNA flanked by the appropriate herpesvirus cloned sequences. Transfections were carried out in 6 cm plates (Corning plastic) of 50% confluent primary chick embryo fibroblast (CEF) cells. The cells were plated out the day before in CEF growth media (1× F10/199, 5% fetal calf serum, 2% glutamine, 1% non-essential amino acids, and 2% penicillin/streptomycin) containing 4 µg/ml polybrene (stock 4 mg/ml in 1× HBSS). For cotransfections into CEF cells, 5 µg of intact HVT DNA, and suspended in 1 ml of CEF media containing 30 µg/ml polybrene (stock 4 mg/ml in 1× HBSS). The DNA-polybrene suspension (1 ml) was then added to a 6 cm plate of CEF cells from which the media had been aspirated, and incubated at 39° C. for 30 minutes. The plates were rocked periodically during this time to redistribute the inoculum. After this period, 4 ml of CEF growth media was added directly to wash plate, and incubated an additional 2.5 hours a 39° C. At this time, the media was removed from each plate, and the cells shocked with 2 ml of 30% DMSO (Dimethyl Sulfoxide, J. T. Baker Chemical Co.) in 1× HBSS for 4 minutes at room temperature. The 30% DMSO was carefully removed and the monolayers washed once with 1× HBSS at room temperature. The cells were then incubated at 39° C. after the addition of 5 mls of CEF growth media. The next day, the media was changed to remove any last traces of DMSO and to stimulate cell growth. Cytopathic effect from the virus becomes apparent within 6 days. Generation of a high titer stock (80%–90% CPE) can usually be made within 1 week from this date. HVT stock samples were prepared by resuspending the infected cells in CEF growth media containing 20% fetal calf serum, 10% DMSO and stored at −70° C.

PROCEDURE FOR GENERATING RECOMBINANT HERPESVIRUS FROM SUBGENOMIC DNA FRAGMENTS. The ability to generate herpesviruses by cotransfection of cloned overlapping subgenmoic fragments has been demonstrated for pseudorabies S virus (Zijl et al., 1988). If deletions and/or insertions are engineered directly into the subgenomic fragments prior to the cotransfection, this procedure results in a high frequency of viruses containing the genomic alteration, greatly reducing the amount of screening required to purify the recombinant virus. We have used this procedure to construct recombinant HVT.

A library of subclones containing overlapping HVT subgenomic fragments was generated as follows. HVT DNA was obtained from the American Type Culture Collection (FC-126("Calnek")). It was sheared and then size selected on a glycerol gradient as described by van Zijl et al., (1988) with 40–50 kb fragments chosen as the insert population. The pooled fractions were diluted twofold with TE, one-tenth volume of 3M NaAc and 2.5 volumes of ethanol were added, and the DNA was precipitated at 30K rpm in a Beckman SW41 rotor for 1 hr. The sheared fragments were given blunt ends by initial treatment with T4 DNA polymerase, using low DNTP concentrations to promote 3' overhang removal, followed by treatment with Klenow polymerase to fill in recessed 3' ends. These insert fragments were then ligated to a pWE15 (Strategene) cosmid vector, which had been digested with BamHI, treated with calf intestinal phosphatase, and made blunt by treatment with Klenow polymerase. The ligated mixture was then packaged using Gigapack XL packaging extracts (Stratagene). Ligation and packaging was as recommended by the manufacturer.

Published restriction maps for the enzymes BamHI, HindIII, and XhoI permitted the use of subcloned fragments as specific probes to screen the Cosmid library for subclones spanning the genome. Probes were generated from subcloned restriction fragments. The fragments were then labeled using a non-radioactive system (Genius, Boehringer Mannheim). Screening was facilitated by picking colonies to media followed by growth overnight. Sets of five filters and a master plate were stamped from microtiter dish and again grown overnight. Glycerol was added to the wells to 15% and the plates were frozen at −20° C. to provide stock cultures of each colony. Filters were BioRad Colony Lift Membranes and were treated and hybridized per manufacturer's instructions, and washed in 0.1× SSC, 0.1% SDS, 65° C. Clones which hybridized with the non-radioactive probe were detected according to the Genius kit directions.

Colonies were selected for further analysis on the basis of their hybridization to two or more of the specific probes. These were then digested with BamHI, and compared to published maps of HVT (Buckmaster et al., 1988). The three cosmids (407-32.2C3, 407-32.IG7, and 407-32.5G6) were obtained in this manner. A detailed description of each clone is given below. It was found that chloramphenicol amplification (Maniatis et al., 1982) was necessary to achieve reasonable yields of DNA from these clones. In addition, one cosmid clone (407-32.5G6) was unstable and had to be grown from the original frozen stock in order to obtain satisfactory DNA preparations.

The pWE15 vector allows the inserts to be excised with NotI. However, four NotI sites are present in the HVT genome, so that inserts spanning these sites cannot be excised with NotI. Two of the NotI sites are present in the BamHI #2 fragment of HVT, this fragment was cloned directly in pSP64. The other two sites are present in the unique short region within the BamHI #1 fragment. This fragment was cloned directly in the pWE15 vector. The three sheared cosmids and the two BamHI fragments cover all but a small portion of the ends of the HVT genome. Because these regions are repeated in the internal portions of the genome, all of the genetic information is available.

A StuI site within the HVT US2 gene was established as a useful site for foreign DNA insertion utilizing the HOMOLOGOUS RECOMBINATION PROCEDURE FOR GENERATING RECOMBINANT HERPESVIRUSES (see Example 6). The HVT US2 gene is located within the BamHI #1 fragment which contains five StuI sites. To facilitate the use of this site for insertion of foreign DNA by the StuI site within the US2 gene was converted to a unique HindIII site. This was accomplished by partially digesting the BamHI #1 subclone with StuI, and then inserting a 10 kb fragment conferring kanomycin resistance ($Neo^R$) into the site using HindIII linkers. The kanomycin resistance gene allowed positive selection of recombinant clones. The $Neo^R$ fragment was removed by digestion with HindIII followed by religation generating clone 430-84.215.

DNA was prepared for reconstruction experiments by restriction digestion with enzymes which cut the subclones outside or flanking the HVT insertions. In some instances, one cosmid in a reconstruction was used undigested. Digested DNAs were extracted once with phenol and precipitated with ethanol. DNA was resuspended at a concentration of 0.5 to 1 $\mu$g/ml. Viral reconstruction experiments were performed using Lipofectin (BRL) to mediate transfection. Two to three micrograms each of subclone were added to 0.5 ml of MEM media (Earle's salts) supplemented with It non-essential amino acids and 2% penicillin/Streptomycin (MEM+). Controls consisted of MEM+ with no DNA, with several ug of HVT DNA, or with 4 out of 5 of the subclones. Separately, 30 $\mu$l of the Lipofectin were added to another 0.5 ml. of MEM+. These two mixtures were then combined and incubated at RT for 15 minutes.

Chick embryo fibroblast (CEF) cells were prepared for transfection in the following manner. CEFs (Spafas) were grown in 6 well dishes at 39° C. in F10/M199 (1:1) media containing 1% non-essential amino acids, 2% penicillin/streptomycin, and 5% feral calf serum (CEF+). Cells were transfected at a confluence of 90–95%. For transfection, wells were aspirated and rinsed 3 times with MEM+, and then incubated 4 hours at 39° C. with the 1 ml lipofectin/DNA mixture above. One ml more of CEF+ was then added to the wells, and cells were incubated overnight and fed with CEF+. Plates were then examined daily for the appearance of plaques.

Lipofectin with control HVT DNA resulted in the appearance of plaques within 5 days. When only four of the five subclones were used, no plaques were obtained. When the five overlapping genomic fragments of HVT were used to reconstruct the virus, plaques appeared anywhere from 5 to 19 days after the initial lipofection. In the case of plaques appearing late, plaques were not initially seen on the infected monolayer, and it was only after passaging the monolayer and replating on a larger surface that plaques appeared. After passaging, plaques generally appeared within 3 days. Recombinant viruses were plaque purified approximately three and then analyzed for insertion of foreign DNAs.

BLUOGAL SCREEN FOR RECOMBINANT HERPESVIRUS. When the foreign gene encoded the enzyme β-galactosidase, the plaques that contained the gene were visualized more easily. The chemical Bluogal™ (Bethesda Research Labs) was incorporated at the level of 200–300 $\mu$g/ml into the agarose overlay during the plaque assay, and the plaques that expressed active β-galactosidase turned blue. The blue plaques were then picked and purified by further blue plaque isolations. Other foreign genes were inserted by homologous recombination such that they replaced the β-galactosidase gene; in this instance non-blue plaques were picked for purification of the recombinant virus.

SCREEN FOR FOREIGN GENE EXPRESSION IN RECOMBINANT HVT USING BLACK PLAQUE ASSAYS. To analyze expression of foreign antigens expressed by recombinant HVT viruses, monolayers of CEF cells are infected with recombinant HVT, overlaid with nutrient agarose media and incubated for 4–5 days at 39° C. Once plaques have developed, the agarose overlay is removed from the dish, the monolayer rinsed 1× with PBS, fixed with 100% methanol for 10 minutes at room temperature and the cells air dried. After re-hydrating the plate with PBS, the primary antibody is diluted to the appropriate dilution with PBS and incubated with the cell monolayer for 2 hours to overnight at room temperature. Unbound antibody is then removed from the cells by washing three times with PBS at room temperature. An alkaline phosphatase conjugated secondary antibody is diluted with PBS and incubated with the cells for 2 hours at room temperature. Unbound secondary antibody is then removed by washing the cells three times with PBS at room temperature. Next, the monolayer is rinsed in color development buffer (100mM Tris pH 9.5/100 mM NaCl/5 mM MgCl2), and then incubated 10 minutes to overnight at room temperature with freshly prepared substrate solution (0.3 mg/ml Nitro Blue tetrazolium+0.15 mg/ml 5-Bromo-4-Chloro-3-Indolyl Phosphatase in color development buffer.) Finally, the reaction is stopped by replacing the substrate solution with TE (10 mM Tris, pH7.5/1 mM EDTA). Plaques expressing the correct antigen will stain black.

PLAQUE HYBRIDIZATION PROCEDURE FOR ASSESSING THE PURITY OF RECOMBINANT HVT STOCKS. When no suitable immunological reagent exists to detect the presence of a particular antigen in a recombinant HVT virus, plaque hybridization can be used to assess the purity of a stock. Initially, CEF cell monolayers are infected with various dilutions of the viral stocks to give ~50–100 plaques/10 cm.dish, overlaid with nutrient agarose media and incubated for 4–5 days at 39° C. Once plaque development occurs, the position of each plaque is marked on bottom of the dish. The agarose overlay is then removed, the plate washed with PBS, and the remaining CEF monolayer is transferred to a NC membrane or BioRad nylon membrane pre-wetted with PBS (making note of the membrane position relative to the dish). Cells contained on the NC membranes are then lysed by placing the membranes in 1.5 mls of 1.5M NaCl and 0.5M NaOH for five minutes. The membranes are neutralized by placing them in 1.5 mls of 3M Sodium acetate (pH 5.2) for five minutes. DNA from the lysed cells is then bound to the NC membranes by baking at 80° C. for one hour. After this period the membranes are prehybridized in a solution containing 6× SSC, 3% skim milk, 0.5% SDS, (±) salmon sperm DNA (50 μg/ml) for one hour at 65° C. Radio-labeled probe DNA (alpha 32P-dCTP) is then added and the membranes incubated at 65° C. overnight (~12 hours). After hybridization the NC membranes are washed two times (30 minutes each) with 2× SSC at 65° C., followed by two additional washes at 65° C. with 0.5× SSC. The NC membranes are then dried and exposed to X-ray film (Kodak X-OMAT,AR) at −70° C. for 12 hours. Positive signals are then aligned with the position of the plaques on the dish and purity of the stock is recorded as the percentage of positive plaques over the total.

Figure 7B:
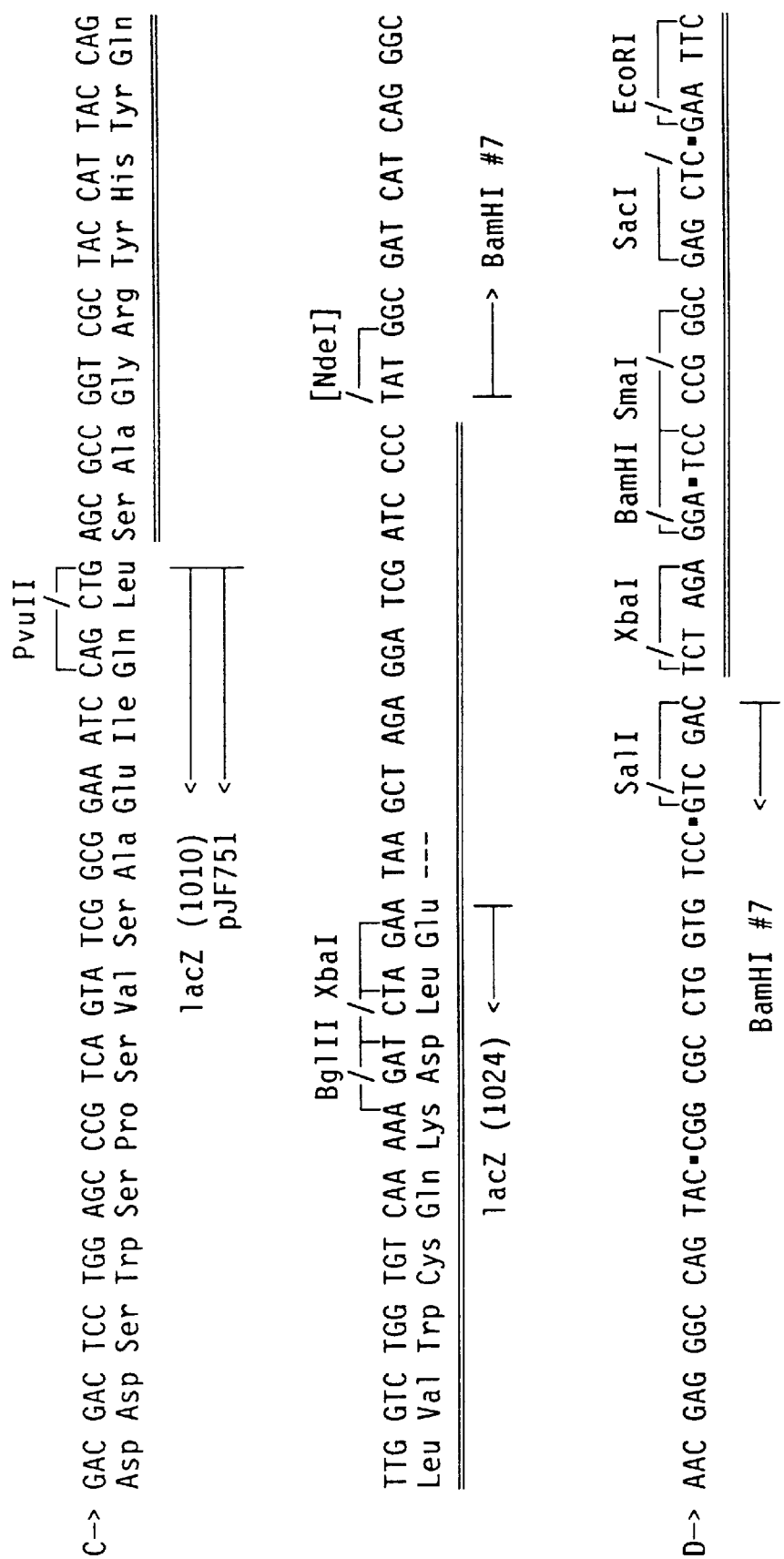
Figure 8:
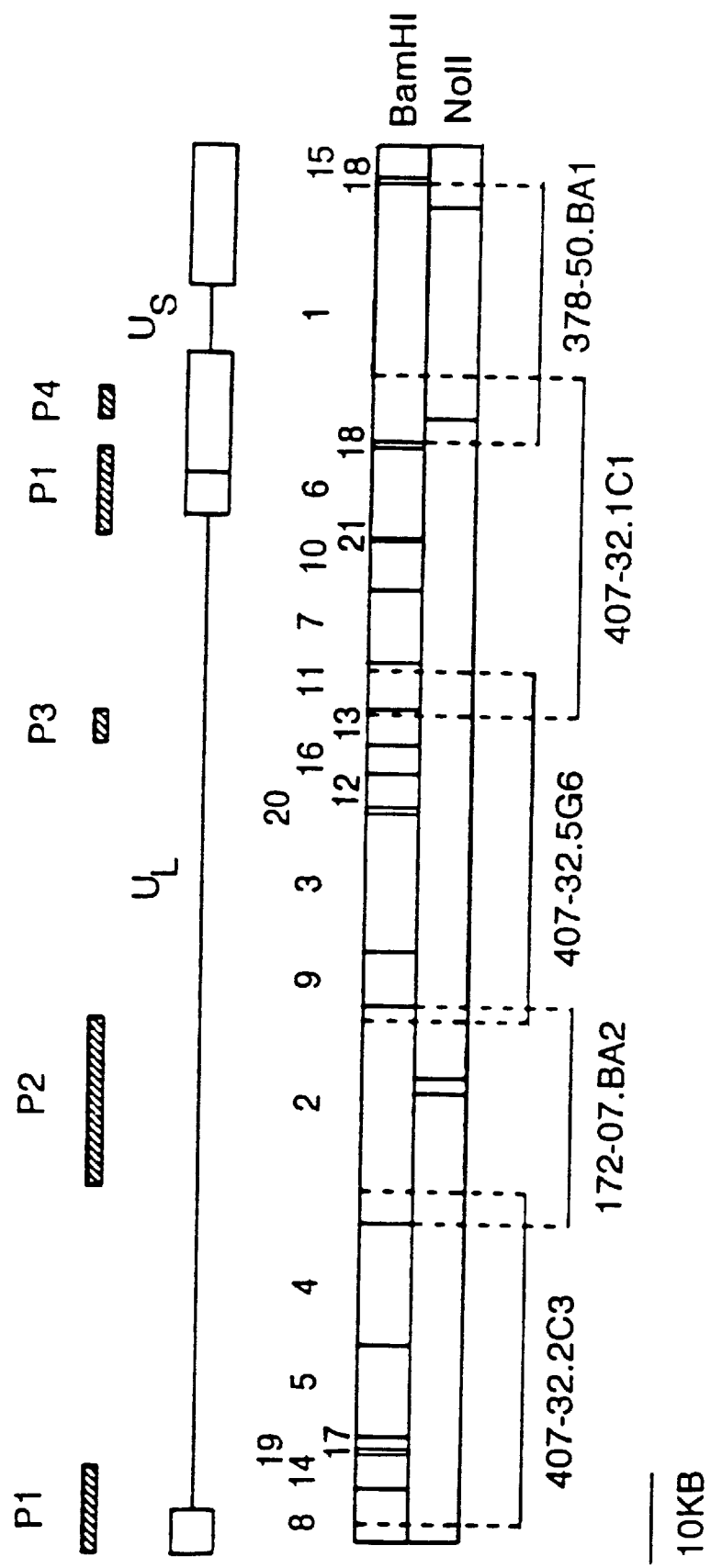
FIG. 8 is a BamHI, NotI restriction map of the HVT genome. The unique long (UL) and unique short (US) regions are shown. The long and short region repeats are indicated by boxes. The BamHI fragments are numbered in decreasing order of size. The location of probes P1–P4 are indicated. The origin of each probe is as follows: P1-BaMHI #6, P2-BamHI #2, P3-BamHI #13, and P4-4.0 kb BgIII to StuI sub-fragment of HVT genomic XbaI fragment #5 (8.0 kb).
Figure 9:
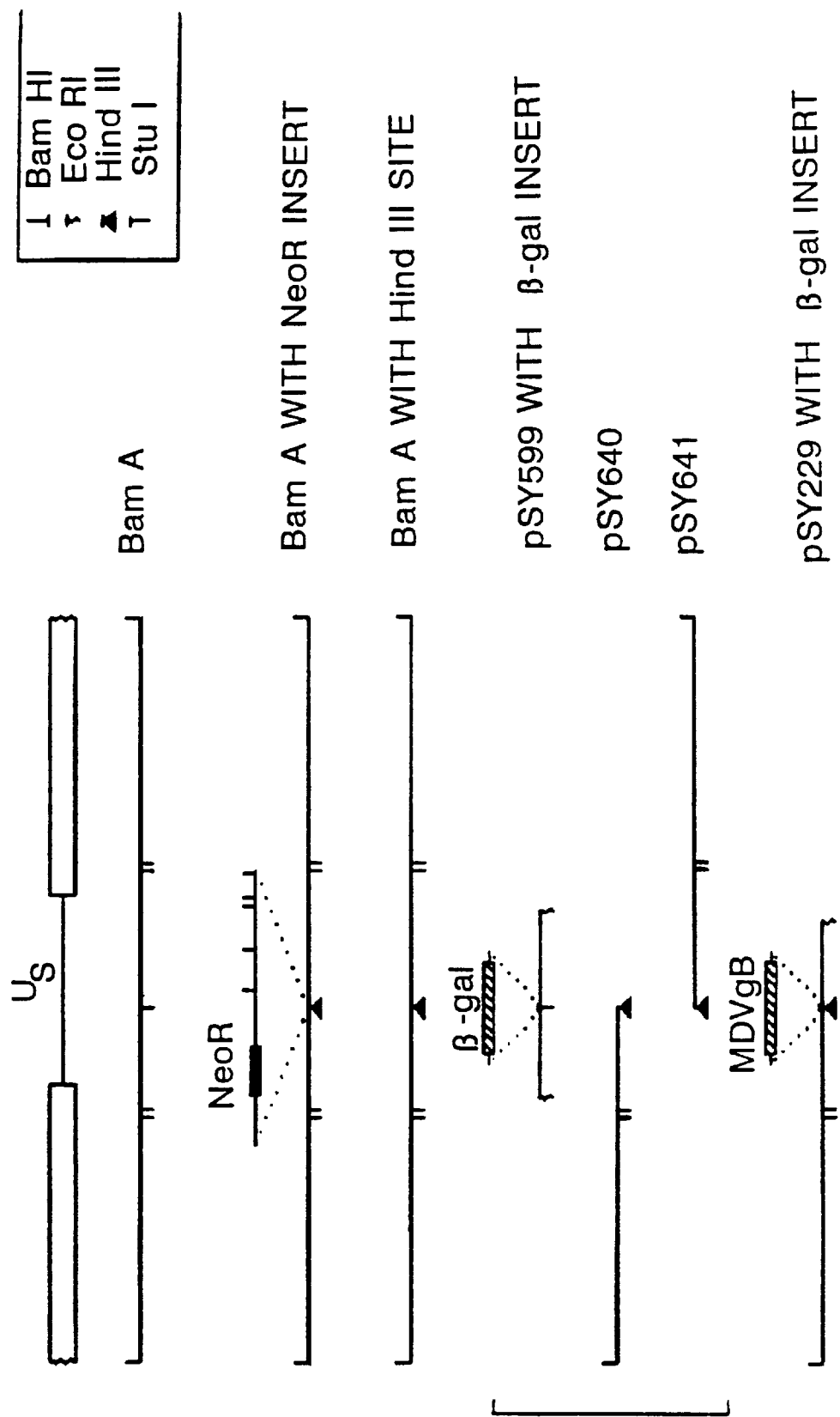
FIG. 9 outlines the procedure for construction of plasmid pSY229.

CONSTRUCTION OF HOMOLOGY VECTOR FOR INSERTION OF THE BETA-GALACTOSIDASE GENE INTO HVT US2 GENE. The beta-galactosidase (lacZ) gene was inserted into the HVT EcoRI #7 fragment at the unique StuI site. The marker gene is oriented in the same direction as the US2 gene. A detailed description of the marker gene is given in FIGS. 7A and 7B. It is constructed utilizing standard recombinant DNA techniques (Maniatis et al, 1982 and Sambrook et al, 1989), by joining restriction fragments from the following sources with the synthetic DNA sequences indicated in FIGS. 7A and 7B. Fragment 1 is an approximately 413 base pair SalI to BamHI restriction sub-fragment of the PRV BamHI restriction fragment 10 (Lomniczi et al., 1984). Fragment 2 is an approximately 3010 base pair BamHI to PvuII restriction fragment of plasmid pJF751 (Ferrari et al., 1985). Fragment 3 is an approximately 754 base pair NdeI to SalI restriction sub-fragment of the PRV BamHI restriction fragment #7 (Lomniczi et al., 1984).

SUBGENOMIC CLONE 172-07.BA2. Plasmid 172-07.BA2 was constructed for the purpose of generating recombinant HVT. It contains an approximately 25,000 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 2999 base pair BamHI to BamHI restriction fragment of pSP64 (Promega). The second fragment is the approximately 25,000 base pair BamHI #2 fragment of HVT (Buckmaster et al., 1988).

HOMOLOGY VECTOR 172-29.31. The plasmid 172-29.31 was constructed for the purpose of inserting foreign DNA into HVT. It contains a unique XhoI restriction enzyme site into which foreign DNA may be inserted. When a plasmid containing a foreign DNA insert at the XhoI site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair BamHI to BamHII restriction fragment of pSP64 (Promega). The second fragment is the approximately 3300 base pair BamHI #16 fragment of HVT (Buckmaster et al., 1988). The complete sequence of the BamHI #16 fragment is given in SEQ ID NO:3. Note that the fragment was cloned such that the UL43 ORF is in the opposite transcriptional orientation to the pSP64 β-lacatamase gene.

HOMOLOGY VECTOR 172-63.1. The plasmid 172-63.1 was constructed for the purpose of inserting foreign DNA into HVT. It contains a unique XhoI restriction enzyme site into which foreign DNA may be inserted. When a plasmid containing a foreign DNA insert at the XhoI site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair EcoRI to EcoRI restriction fragment of pSP64 (Promega). The second fragment is the approximately 5500 base pair EcoRI #9 fragment of HVT. Note that the EcoRI fragment was cloned such that the unique XhoI site is closest to the unique HindIII site in the pSP64 vector.

Figure 12B:
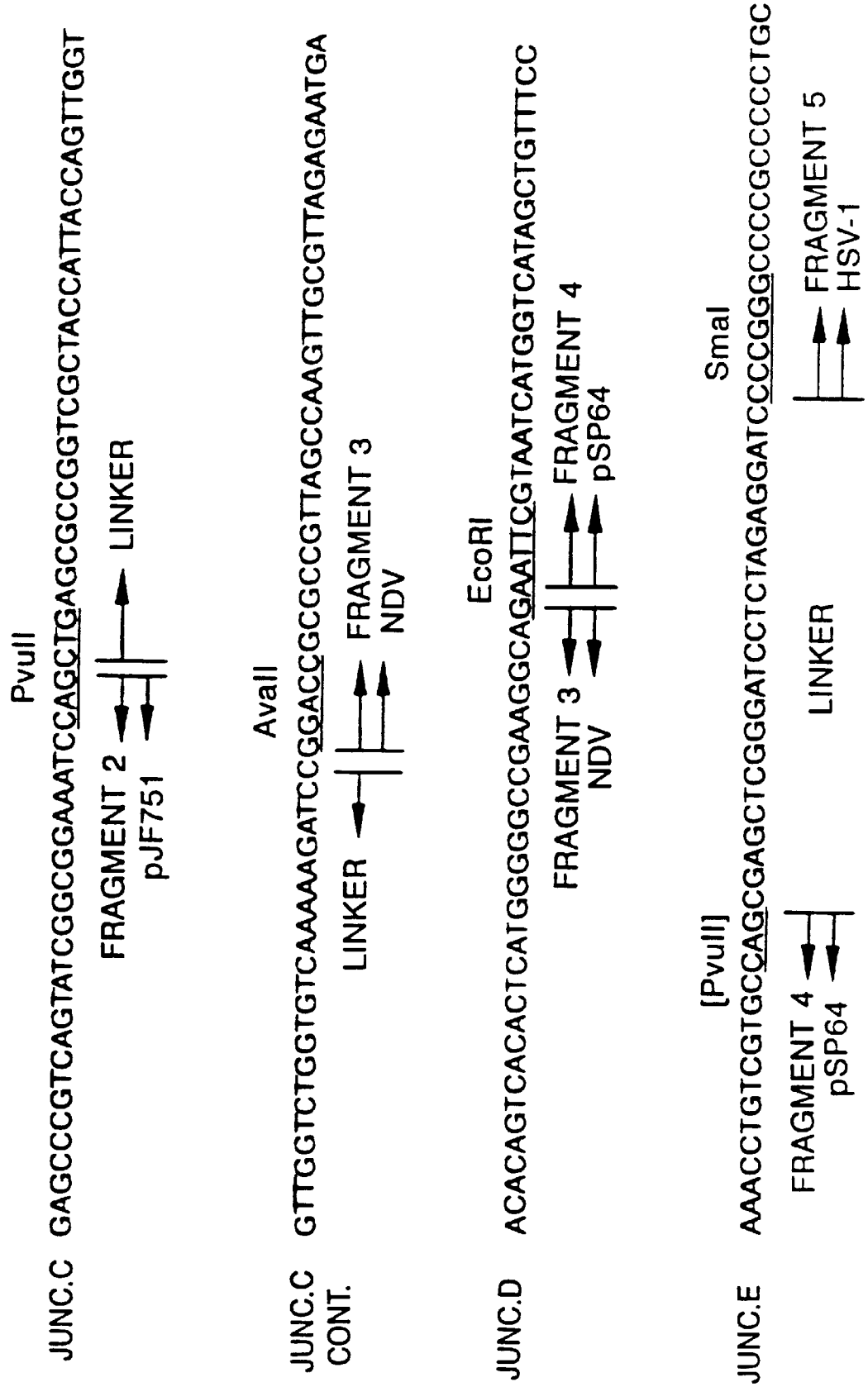
Figure 12C:
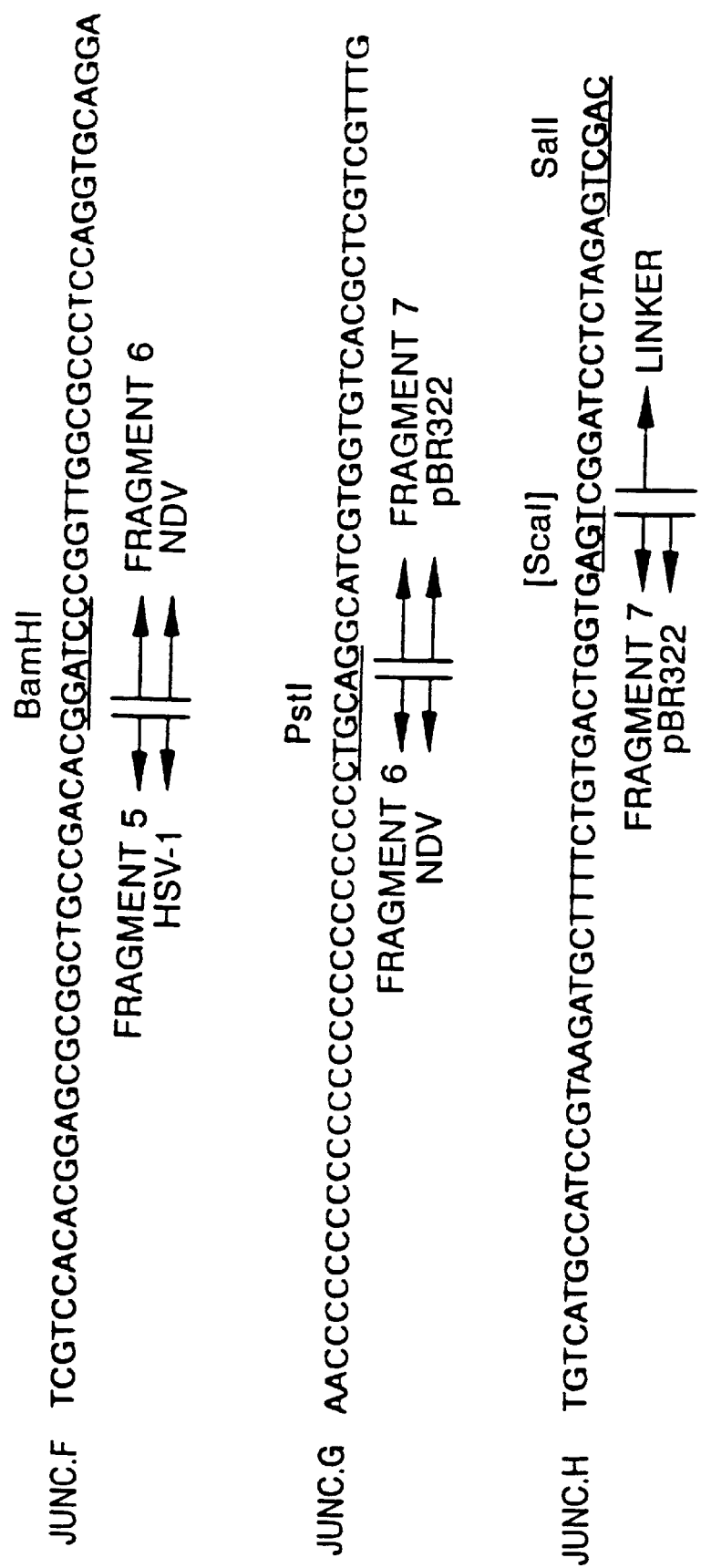

HOMOLOGY VECTORS 255-18.B16. The plasmid 255-18.B16 was constructed for the purpose of inserting the NDV HN and F genes into HVT. The NDV HN and F genes were inserted as a SalI fragment into the homology vector 172-29.31 at the XhoI site. The NDV HN and F genes were inserted in the same transcriptional orientation the UL43 ORF in the parental homology vector. A detailed description of the SalI fragment is shown in FIGS. 12A, 12B and 12C. The inserted SalI fragment may be constructed utilizing standard recombinant DNA techniques (Maniatis et al, 1982 and Sambrook et al, 1989), by joining restriction fragments from the following sources with the synthetic DNA sequences indicated in FIGS. 12A, 12B and 12C. Fragment 1 is an approximately 416 base pair SalI to BamHI restriction sub-fragment of the PRV BamHI restriction fragment 10 (Lomniczi et al., 1984). Fragment 2 is an approximately 3009 base pair BamHI to PvuII fragment of the plasmid pJF751 (Ferrari et al., 1985). Fragment 3 is an approximately 1200 base pair AvaII to EcoRI restriction fragment of full length NDV HN cDNA. Fragment 4 is an approximately 179 base pair EcoRI to PvuII restriction fragment of the plasmid pSP64 (Promega). Fragment 5 is an approximately 357 base pair SmaI to BamHI restriction sub-fragment of the HSV-1 BamHI restriction fragment N. Fragment 6 is an approximately 1812 base pair BamHI to PstI restriction fragment of the full length NDV F cDNA. Fragment 7 is an approximately 235 base pair PstI to ScaI restriction fragment of the plasmid pBR322.

SUBGEMOMIC CLONE 378-50.BA1. Cosmid 378-50.BA1 was constructed for the purpose of generating recombinant HVT. It contains an approximately 29,500 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid may be constructed by joining two restriction fragments from the following sources. The first fragment is an approximately 8164 base pair BamHI to BamHI restriction fragment of pWE15 (Stratagene). The second fragment is the approximately 29,500 base pair BamHI #1 fragment of HVT (Buckmaster et al., 1988).

SUBGEMOMIC CLONE 407-32.1C1. Cosmid 407-32.1C1 was constructed for the purpose of generating recombinant HVT. It contains an approximately 38,850 base pair region of genomic HVT DNA (see FIG. 8). This region includes BamHI fragments 11, 7, 8, 21, 6, 18, approximately 1250 base pairs of fragment 13, and approximately 6,700 base pairs of fragment 1. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid maybe constructed as described above in the PROCEDURE FOR GENERATING RECOMBINANT HERPESVIRUS FROM OVERLAPPING SUBGENOMIC FRAGMENTS. It was isolated from the sheared DNA library by screening with the probes P1 and P4 (described in FIG. 8). A bacterial strain containing this cosmid has been deposited on Mar. 3, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 75428.

SUBGEMOMIC CLONE 407-32.2C3. Cosmid 407-32.2C3 was constructed for the purpose of generating recombinant HVT. It contains an approximately 40,170 base pair region of genomic HVT DNA (see FIG. 8). This region includes BamHI fragments 10, 14, 19, 17, 5, and approximately 2,100 base pairs of fragment 2. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid may be constructed as described above in the PROCEDURE FOR GENERATING RECOMBINANT HERPESVIRUS FROM OVERLAPPING SUBGENOMIC FRAGMENTS. It was isolated from the sheared DNA library by screening with the probes P1 and P2 (described in FIG. 8). A bacterial strain containing this cosmid has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 75430.

SUBGEMOMIC CLONE 407-32.5G6. Cosmid 407-32.5G6 was constructed for the purpose of generating recombinant HVT. It contains an approximately 40,000 base pair region of genomic HVT DNA (see FIG. 8). This region includes BamHI fragments 9, 3, 20, 12, 16, 13, approximately 1,650 base pairs of fragment 2, and approximately 4,000 base pairs of fragment 11. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid may be constructed as described above in the PROCEDURE FOR GENERATING RECOMBINANT HERPESVIRUS FROM OVERLAPPING SUBGENOMIC FRAGMENTS. It was isolated from the sheared DNA library by screening with the probes P2 and P3 (described in FIG. 8). A bacterial strain containing this cosmid has been deposited on Mar. 3, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 75427.

HOMOLOGY VECTOR 435-47.1. The plasmid 435-47.1 was constructed for the purpose of inserting foreign DNA into HVT. It contains a unique HindIII restriction enzyme site into which foreign DNA may be inserted. When a plasmid containing a foreign DNA insert at the HindIII site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair EcORI to EcoRI restriction fragment of pSP64 (Promega). The second fragment is the approximately 7300 base pair EcoRI #7 fragment of HVT. Note that the HindIII site of the pSP64 vector was removed by digesting the subclone with HindIII followed by a Klenow fill in reaction and religation. A synthetic HindIII linker (CAAGCTTG) was then inserted into the unique StuI site of the EcoRI #7 fragment.

SUBGEMOMIC CLONE 437-26.24. Plasmid 437-26.24 was constructed for the purpose of generating recombinant HVT. It contains an approximately 13,600 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 2970 base pair HindIII to BamHI restriction fragment of pSP64 (Promega). The second fragment is the approximately 13,600 base pair BamHI to StuI sub-fragment of the BamHI #2 fragment of HVT (Buckmaster et al., 1988). Note that the BamHI #2 fragment contains five StuI sites, the site utilized in this subcloning was converted to a HindIII site as described in the PROCEDURE FOR GENERATING RECOMBINANT HERPESVIRUS FROM OVERLAPPING SUBGENOMIC FRAGMENTS.

SUBGEMOMIC CLONE 437-26.26. Plasmid 437-26.26 was constructed for the purpose of generating recombinant HVT. It contains an approximately 15,300 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 2970 base pair HindIII to BamHI restriction fragment of pSP64

(Promega). The second fragment is the approximately 15,300 base pair BamHI to StuI sub-fragment of the BamHI #2 fragment of HVT (Buckmaster et al., 1988). Note that the BamHI #2 fragment contains five StuI sites, the site utilized in this subcloning was converted to a HindIII site as described in the PROCEDURE FOR GENERATING RECOMBINANT HERPESVIRUS FROM OVERLAPPING SUBGENOMIC FRAGMENTS.

HOMOLOGY VECTORS 456-18.18 and 456-17.22. The plasmids 456-18.18 and 456-17.22 were constructed for the purpose of inserting the MDV gA and gB genes into HVT. The MDV genes were inserted as a cassette into the homology vector 435-47.1 at the unique HindIII site. The MDV genes were inserted at the blunt ended HindIII site as a blunt ended PstI to EcoRI fragment (see FIGS. 10A and 10B). The HindIII and EcoRI sites were blunted by the Klenow fill in reaction. The PstI site was blunted by the T4 DNA polymerase reaction. Note that the MDV cassette was inserted in both orientations. Plasmid 456-18.18 contains the MDV genes inserted in the opposite transcriptional orientation to the US2 gene in the parental homology vector. Plasmid 456-17.22 contains the MDV genes inserted in the same transcriptional orientation as the US2 gene in the parental homology vector. A detailed description of the MDV cassette is given in FIGS. 10A and 10B. It may be constructed utilizing standard recombinant DNA techniques (Maniatis et al, 1982 and Sambrook et al, 1989), by joining restriction fragments from the following sources with the synthetic DNA sequences indicated in FIGS. 10A and 10B. Fragment 1 is an approximately 2178 base pair PvuII to EcoRV restriction sub-fragment of the MDV EcoRI 6.9 KB genomic restriction fragment (Ihara et al., 1989). Fragment 2 is an approximately 3898 base pair SalI to EcoRI genomic MDV fragment (Ross, et al., 1989).

HOMOLOGY VECTOR 528-03.37. The plasmid 528-03.37 was constructed for the purpose of inserting the infectious laryngotracheitis (ILT) virus gD gene into HVT. The gD gene followed by the PRV gX poly adenylation signal was inserted as a cassette into the homology vector 435-47.1 at the unique HindIII site. The cassette may be constructed utilizing standard recombinant DNA techniques (Maniatis et al, 1982 and Sambrook et al, 1989), by joining restriction fragments from the following sources. The first fragment is an approximately 2060 base pair EcoRI to BclI restriction sub-fragment of the ILT KpnI genomic restriction fragment #8 (10.6 KB). The second fragment is an approximately 754 base pair NdeI to SalI restriction sub-fragment of the PRV BamHI restriction fragment #7 (Lomniczi et al., 1984). Note that the fragments are oriented such that BclI and NdeI sites are contiguous.

HOMOLOGY VECTOR 528-11.43. The plasmid 528-11.43 was constructed for the purpose of inserting the infectious laryngotracheitis (ILT) virus gB gene (A. M. Grifin, 1991) into HVT. The gB gene was inserted as an EcoRI fragment into the homology vector 435-47.1 at the unique HindIII site. The gB gene was inserted at the blunt ended HindIII site as a blunt ended EcoRI fragment. The HindIII and EcoRI sites were blunted by the Klenow fill in reaction. The gB gene was inserted in the same transcriptional orientation as the US2 gene in the parental homology vector. The EcoRI fragment may be obtained as a 3.0 KB ILT virus genomic fragment.

HOMOLOGY VECTOR 518-46.B3. The plasmid 518-46.B3 was constructed for the purpose of inserting foreign DNA into HVT. It contains a unique HindIII restriction enzyme site into which foreign DNA may be inserted. When a plasmid containing a foreign DNA insert at the HindIII site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining three restriction fragments from the following sources. The first fragment is an approximately 1649 base pair PvuI to SalI restriction fragment of pSP64 (Promega). The second fragment is an approximately 1368 base pair PvuI to SalI restriction fragment of pSP65 (Promega). The third fragment is the approximately 3400 base pair XhoI to XhoI fragment of plasmid 437-47.1.

HOMOLOGY VECTOR 535-70.3. The plasmid 535-70.3 was constructed for the purpose of inserting the MDV gB, and gA genes and the NDV F gene into HVT. The F gene was inserted as a cassette into homology vector 456-17.22 at the HindIII site located between the MDV gA and gB genes (see Junction B, FIG. 10A). The F gene is under the control of the HCMV immediate early promoter and followed by the HSV-1 TK poly adenylation signal. The F gene was inserted in the same transcriptional orientation as the US2 gene in the parental homology vector. The cassette may be constructed utilizing standard recombinant DNA techniques (Maniatis et al, 1982 and Sambrook et al, 1989), by joining restriction fragments from the following sources. The first fragment is an approximately 1191 base pair PstI to AvaII restriction sub-fragment of the HCMV genomic XbaI E fragment (D. R. Thomsen, et al., 1981). The second fragment is an approximately 1812 base pair BamHI to PstI restriction fragment of the full length NDV F cDNA clone (B1 strain). The last fragment is an approximately 784 base pair SmaI to SmaI restriction sub-fragment of the HSV-1 BamHI restriction fragment Q (McGeoch, et al., 1985).

HOMOLOGY VECTOR 549-24.15. The plasmid 549-24.15 was constructed for the purpose of inserting the MDV gB, and gA genes and the NDV HN and F genes into HVT. The HN and F genes were inserted as a cassette into homolgy vector 456-17.22 at the HindIII site located between the MDV gA and gB genes (see Junction B, FIG. 10A). The HN and F genes are under the control of the PRV gpX and HCMV immediate early promoters respectively. The HN and F genes are followed by the PRV gX poly and HSV-1 TK adenylation signals respectively. The cassette may be constructed utilizing standard recombinant DNA techniques (Maniatis et al, 1982 and Sambrook et al, 1989), by joining restriction fragments from the following sources. The first fragment is an approximately 413 base pair SalI to BamHI restriction sub-fragment of the PRV BamHI fragment #10 (Lomniczi, et al., 1984) The second fragment is an approximately 1811 base pair AvaII to NaeI restriction fragment of the full length NDV HN cDNA clone (B1 strain). The third fragment is an approximately 754 base pair NdeI to Sail restriction sub-fragment of the PRV BamHI restriction fragment #7 (Lomniczi, et al., 1984). The fourth fragment is an approximately 1191 base pair PstI to AvaII restriction sub-fragment of the HCMV genomic XbaI E fragment (D. R. Thomsen, et al., 1981). The fifth fragment is an approximately 1812 base pair BamHI to PstI restriction fragment of the full length NDV F cDNA clone (B1 strain). The last fragment is an approximately 784 base pair SmaI to SmaI restriction sub-fragment of the HSV-1 BamHI restriction fragment Q (McGeoch, et al., 1985).

HOMOLOGY VECTOR 549-62.10. The plasmid 549-62.10 was constructed for the purpose of inserting the MDV gB, and gA genes and the NDV HN gene into HVT. The HN gene was inserted as a cassette into homology vector 456-17.22 at the HindIII site located between the MDV gA and gB genes (see Junction B, FIG. 10A). The HN gene is under the control of the PRV gpX promoter and followed by the PRV gX poly adenylation signal. The HN gene was inserted in the same transcriptional orientation as the US2 gene in the parental homology vector. The cassette may be constructed utilizing standard recombinant DNA techniques (Maniatis et al, 1982 and Sambrook et al, 1989), by joining restriction fragments from the following sources. The first fragment is an approximately 413 base pair SalI to BamHI restriction sub-fragment of the PRV BamHI fragment #10 (Lomniczi, et al., 1984) The second fragment is an approximately 1811 base pair AvaII to NaeI restriction fragment of the full length NDV HN cDNA clone (B1 strain). The last fragment is an approximately 754 base pair NdeI to SalI restriction sub-fragment of the PRV BamHI restriction fragment #7 (Lonniczi, et al., 1984).

SUBGENOMIC CLONE 550-60.6 Plasmid 550-60.6 was constructed for the purpose of generating recombinant HVT. It contains an approximately 12,300 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 4176 base pair EcoRV to BamHI restriction fragment of pBR322. The second fragment is the approximately 12,300 base pair sub-fragment of the BamHI X2 fragment of HVT (Buckmaster et al., 1988). This fragment was generated in the following manner. Plasmid 437-26.26 was linearized with HindIII and then resected with the ExoIII Mung Bean Deletion Kit (Stratagene). Samples from the 3 and 4 minute reactions were combined and digested with BamHI resulting in a population of fragments containing the desired 12,300 base pair sub-fragment. This population was cloned into the pBR322 fragment and the resulting clones were screened for the appropriate size and restriction map. Fortuitously the resected sub-fragment that generated clone 550-60.6 ended in the nucleotides GG which generated a second BamHI site when ligated to the EcoRV site (ATCC) of pBR322. A bacterial strain containing this plasmid has been deposited on Mar. 3, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 75429.

HOMOLOGY VECTORS 566-41.5. The plasmid 566-41.5 was constructed for the purpose of inserting the MDV gA, gB and gD genes into HVT. The MDV gD gene was inserted as a HindIII fragment into the homology vector 456-17.22 at the HindIII site located between MDV gA and gB (see FIGS. 10A and 10B). The MDV gene was inserted in the same transcriptional orientation as gA and gB in the parental homology vector. A detailed description of the HindIII fragment containing the MDV gD gene is shown in FIG. 11A and 11B. Note that a herpesvirus polyadenation signal was added to the gD gene cassette. The inserted HindIII fragment may be constructed utilizing standard recombinant DNA techniques (Maniatis et al, 1982 and Sambrook et al, 1989), by joining restriction fragments from the following sources with the synthetic DNA sequences indicated in FIGS. 11A and 11B. Fragment 1 is an approximately 784 base pair SmaI to SmaI restriction sub-fragment of the HSV-1 BamHI restriction fragment Q (McGeoch et al., 1988). Note that this fragment is oriented such that the polyadenylation sequence (AATAAA) is located closest to junction B. Fragment 2 is an approximately 2177 base pair SalI to NcoI sub-fragment of the MDV BglII 4.2 KB genomic restriction fragment (Ross, et al., 1991).

HOMOLOGY VECTOR 567-72.1D. The plasmid 567-72.1D was constructed for the purpose of inserting the MDV gB, gA, and gD genes and the infectious bronchitis virus (IBV) matrix and spike genes into HVT. The IBV genes were inserted as a cassette into homolgy vector 566-41.5 at the unique NotI site located upstream of the MDV gD gene (see Junction C, FIG. 11B). The IBV spike and matrix genes are under the control of the HCMV immediate early and PRV gpX promoters respectively. The IBV spike and matrix genes are followed by the HSV-1 TK and PRV gX poly adenylation signals respectively. The IBV genes were inserted in the same transcriptional orientation as the US2 gene in the parental homology vector. The cassette may be constructed utilizing standard recombinant DNA techniques (Maniatis et al, 1982 and Sambrook et al, 1989), by joining restriction fragments from the following sources. The first fragment is an approximately 413 base pair SalI to BamHI restriction sub-fragment of the PRV BamHI fragment #10 (Lomniczi, et al., 1984) The second fragment contains amino acids 1 to 223 of the IBV matrix gene. The coding region was obtained from a cDNA clone of the Arkansas strain of IBV. The third fragment is an approximately 754 base pair NdeI to SalI restriction sub-fragment of the PRV BamHI restriction fragment #7 (Lomniczi, et al., 1984). The fourth fragment is an approximately 1191 base pair PstI to AvaII restriction sub-fragment of the HCMV genomic xbaI E fragment (D. R. Thomsen, et al., 1981). The fifth fragment contains amino acids 4 to 1162 of the IBV spike gene. The coding region was obtained from a cDNA clone of the Arkansas strain of IBV. The last fragment is an approximately 784 base pair SmaI to SmaI restriction sub-fragment of the HSV-1 BamHI restriction fragment Q (McGeoch, et al., 1985).

HOMOLOGY VECTOR 603-57.F1. The plasmid 603-57.F1 was constructed for the purpose of inserting the IBDV VP2 gene into HVT. The IBDV VP2 gene was inserted as a cassette into homolgy vector 435-47.1 at the unique HindIII site. The VP2 gene is under the control of the HCMV immediate early promoter and is followed by the HSV-1 TK poly adenylation signal. The VP2 gene was inserted in the same transcriptional orientation as the US2 in the parental homology vector. The cassette may be constructed utilizing standard recombinant DNA techniques (Maniatis et al, 1982 and Sambrook et al, 1989), by joining restriction fragments from the following sources. The first fragment is an approximately 1191 base pair PstI to AvaII restriction sub-fragment of the HCMV genomic XbaI E fragment (D. R. Thomsen, et al., 1981). The second fragment is an approximately 1081 base pair BclI to BamHI restriction sub-fragment of the full length IBDV cDNA clone (see SEQ ID NO:1). Note that the BclI site was introduced into the cDNA clone directly upstream of the VP2 initiator methionine by converting the sequence CGCAGC to TGATCA. The first and second fragments are oriented such that AvaII and BclI sites are contiguous. The third fragment is an approximately 784 base pair SmaI to SmaI restriction sub-fragment of the HSV-1 BamHI restriction fragment Q (McGeoch, et al., 1985).

HOMOLOGY VECTOR 633-13.27. The plasmid 633-13.27 was constructed for the purpose of inserting the MDV gB, gA and gD genes and the NDV HN and F genes into HVT. The HN and F genes are under the control of the PRV gpX and HCMV immediate early promoters respectively. The HN and F genes are followed by the PRV gX poly and HSV-1 TK adenylation signals respectively. All five genes were inserted in the same transcriptional orientation as the US2 gene in the parental homology vector. The genes were inserted in the following order MDV gA, NDV HN, NDV F,MDV gD, and MDV gB.

HOMOLOGY VECTOR 634-29.16. The plasmid 634-29.16 was constructed for the purpose of inserting the ILT virus gB and gD genes into HVT. The lacZ marker gene followed by the ILT gB and gD genes inserted as a cassette into the homology vector 172-29.31 at the unique XhoI site. The cassette may be constructed utilizing standard recombinant DNA techniques (Maniatis et al, 1982 and Sambrook et al, 1989), by joining restriction fragments from the following sources. The first fragment is an approximately 4229 base pair SalI to SalI restriction fragment derived from the lacZ marker gene described above and shown in FIGS. 7A and 7B. The second fragment is an approximately 2060 base pair EcoRI to BclI restriction sub-fragment of the ILT KpnI genomic restriction fragment #8 (10.6 KB). The third fragment is an approximately 754 base pair NdeI to SalI restriction sub-fragment of the PRV BamHI restriction fragment #7 (Lomniczi et al., 1984). Note that the second and third fragments are oriented such that BclI and NdeI sites are contiguous. The fourth fragment is the 3.0 KB ILT virus genomic EcoRI fragment containing the gB gene. All three genes are in the same transcriptional orientation as the UL43 gene.

SUBGENOMIC CLONE 415-09.BA1. Cosmid 415-09.BA1 was constructed for the purpose of generating recombinant HVT. It contains an approximately 29,500 base pair BamHI #1 fragment of genomic HVT DNA. It was used in conjuction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid was constructed by joining two restriction fragments (Sambrook, et al., 1989) from the following sources. The vector is an approximately 4430 base pair BamHI to BamHI restriction fragment of pSY1005 derived from pHC79 (Bethesda Research Labs, Inc.) and pWE15 (Stratagene, Inc.). The first fragment is the approximately 29,500 base pair BamHI #1 fragment of the HVT genome (Buckmaster et al., 1988).

SUBGENOMIC CLONE 672-01.A40. Cosmid 672-01.A40 was constructed for the purpose of generating recombinant HVT. It was isolated as a subclone of cosmid 407-32.1C1 (see FIGS. 8 and 15). Cosmid 672-01.A40 contains an approximately 14,000 base pair NotI to AscI subfragment and an approximately 1300 base pair AscI to BamHI subfragment of cosmid 407-32.1C1. The cosmid was constructed by joining restriction fragments (Sambrook, et al., 1989) from the following sources. The vector is an approximately 2700 base pair NotI to BamHI fragment constructed from pNEB193 (New England Biolabs, Inc.) which contains a NotI linker inserted into the SmaI site. Fragment 1 is an approximately 15,300 base pair region of genomic HVT DNA. This region includes BamHI fragments 11 and 7, and approximately 1250 base pairs of fragment 13. It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 654-45.1. Plasmid 654-45.1 was constructed for the purpose of generating recombinant HVT. It was isolated as an AscI subclone of cosmid 407-32.1.C1 (see FIGS. 8 and 15). The cosmid was constructed by joining restriction fragments (Sambrook, et al., 1989) from the following sources. The vector is an approximately 2000 base pair AscI fragment constructed from a 2000 base pair AatII to PvuII fragment of pNEB 193 (New England Biolabs, Inc.) blunt ended with Klenow DNA polymerase and AscI linkers inserted. Fragment 1 is an approximately 8600 base pair AscI to AscI fragment of genomic HVT DNA. This region includes BamHI fragments 10 and 21, and approximately 1100 base pairs of fragment 6 and approximately 1300 base pairs of fragment 7. The XhoI site (Nucleotide #1333–1338; SEQ ID NO. 48) has been converted to a unique PacI site using synthetic DNA linkers. The PacI site was used for the insertion and expression of foreign genes in HVT. (See FIG. 13A). It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 686-63.A1. Plasmid 686-63.A1 was constructed for the purpose of generating recombinant HVT. It was isolated as an AscI subclone of cosmid 407-32.1 C1 (see FIGS. 8, 15). The cosmid was constructed by joining restriction fragments (Sambrook, et al., 1989) from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. Fragment 1 is an approximately 8600 base pair AscI to AscI fragment of genomic HVT DNA. This region includes BamHI fragments 10 and 21, and approximately 1100 base pairs of fragment 6 and approximately 1300 base pairs of fragment 7. The XhoI site (Nucleotide #1333–1338; SEQ ID NO. 48) has been converted to a unique NotI site using synthetic DNA linkers. The NotI site was used for the insertion and expression of foreign genes in HVT. (See FIG. 13B) It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 672-07.C40. Cosmid 672-07.C40 was constructed for the purpose of generating recombinant HVT. It was isolated as a subclone of cosmid 407-32.1C1 (see FIGS. 8 and 15). Cosmid 672-07.C40 contains an approximately 1100 base pair BamHI to AscI subfragment and an approximately 13,000 base pair AscI to NotI subfragment of cosmid 407-32.1C1. The cosmid was constructed by joining restriction fragments (Sambrook, et al., 1989) from the following sources. The vector is an approximately 2700 base pair NotI to BamHI fragment constructed from pNEB193 (New England Biolabs, Inc.) which contains a NotI linker inserted into the SmaI site. Fragment 1 is an approximately 14,100 base pair region of genomic HVT DNA. This region includes BamHI fragments 6 and 18, and an approximately 2600 base pair BamHI to NotI fragment within BamHI fragment #1. It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 706-57.A3. Plasmid 706-57.A3 was constructed for the purpose of generating recombinant HVT. Plasmid 706-57.A3 contains the IBDV VP2 gene inserted into the PacI site of plasmid 654-45.1. The IBDV VP2 gene uses the IBRV VP8 promoter and ILTV US3 polyadenylation signal. The cosmid was constructed utilizing standard recombinant DNA techniques (Sambrook, et al., 1989) by joining restriction fragments from the following sources. The vector is an approximately 2000 base pair AscI fragment constructed from a 2000 base pair AatII to PvuII fragment of PNEB193 (New England Biolabs, Inc.) blunt ended with Klenow DNA polymerase and AscI linkers inserted. The first fragment is a 208 base pair HindIII to BamHI fragment coding for the IBRV VP8 promoter (Carpenter et al., 1991). The second fragment is an approximately 1626 base pair fragment coding for the IBDV VP2 gene derived by reverse transcription and polymerase chain reaction (PCR) (Sambrook, et al., 1989) of IBDV standard challenge strain (USDA) genomic RNA (Kibenge et al., 1990). The antisense primer used for reverse transcription and PCR was 5'-CTCGCTCGCCCATGATCATTAAGCAAGAATTC-CGTCG-3' (SEQ ID NO: 53). The sense primer used for PCR was 5'-CTGGTTCGGCCCATGATCAGATGACAAACCTGC-AAGATC-3' (SEQ ID NO: 54). The DNA fragment generated by PCR was cloned into the PCR-Direct™ vector (Clontech Laboratories, Inc., Palo Alto, Calif.). The IBDV VP2 fragment was subcloned next to the VP8 promoter using BclI sites generated by the PCR primers. The DNA sequence at this junction adds amino acids methionine, aspartate and glutamine before the native initiator methionine of VP2. The DNA fragment contains the coding sequence from amino acid 1 to amino acid 536 of the IBDV polyprotein (SEQ ID NO. 2) which includes the entire coding sequence of the VP2 protein. The third fragment is an approximately 494 base pair fragment coding for the ILTV US3 polyadenylation signal.

SUBGENOMIC CLONE 711-92.1A. Plasmid 711-92.1A was constructed for the purpose of generating recombinant HVT. Plasmid 711-92.1A contains the ILTV gD and gI genes inserted into the PacI site of plasmid 654-45.1. The ILTV gD and gI genes use their respective endogenous ILTV promoters and single shared endogenous polyadenylation signal. The plasmid was constructed utilizing standard recombinant DNA techniques (Sambrook, et al., 1989) by joining restriction fragments from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. The first fragment is an approximately 3556 base pair SalI to HindIII restriction subfragment of the ILTV Asp718I genomic fragment #8 (10.6 kb).

SUBGENOMIC CLONE 717-38.12. Plasmid 717-38.12 was constructed for the purpose of generating recombinant HVT. Plasmid 717-38.12 contains the NDV HN and F genes inserted into the PacI site of plasmid 654-45.1. The NDV HN gene uses the PRV gX promoter and the PRV gX polyadenylation signal. The NDV F gene uses the HCKV immediate early promoter and the HSV TK polyadenylation signal. The plasmid was constructed utilizing standard recombinant DNA techniques (Sambrook, et al., 1989) by joining restriction fragments from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. The first fragment is an approximately 413 base pair SalI to BamHI restriction subfragment of the PRV BamHI fragment #10 (Lomniczi, et al., 1984). The second fragment is an approximately 1811 base pair AvaII to NaeI restriction fragment of the full length NDV EN cDNA clone (B1 strain; SEQ ID NO. 10). The third fragment is an approximately 754 base pair NdeI to SalI restriction subfragment of the PRV BamHI restriction fragment #7 (Lomniczi, et al., 1984). The fourth fragment is an approximately 1191 base pair PstI to AvaII restriction subfragment of the HCMV genomic XbaI E fragment (D. R. Thomsen, et al., 1981). The fifth fragment is an approximately 1812 base pair BamHI to PstI restriction fragment of the full length NDV F cDNA clone (B1 strain; SEQ ID NO. 12). The sixth fragment is an approximately 784 base pair SmaI to SmaI restriction subfragment of the HSV-1 BamHI restriction fragment Q (McGeoch, et al., 1985).

SUBGENOMIC CLONE 721-38.1J. Cosmid $_{721}$-38.1J was constructed for the purpose of inserting the MDV gA, gD, and gB genes into the unique short of HVT and for the purpose of generating recombinant HVT. Cosmid 721-38.1J contains the MDV gA, gD and gB genes inserted into a StuI site in the HVT US2 gene converted to a unique HindIII site within the BamHI #1 fragment of the unique short region of HVT. This region of the HVT BamHI #1 fragment containing the MDV genes was derived from S-HVT-062. Cosmid 721-38.1J was constructed by a partial restriction digest with BamHI of S-HVT-062 DNA and isolation of an approximately 39,300 base pair fragment. The cosmid was constructed utilizing standard recombinant DNA techniques (Sambrook, et al., 1989) by joining restriction fragments from the following sources. The vector is an approximately 8200 base pair BamHI fragment from cosmid vector pWE15. The first fragment is an approximately 900 base pair BamHI fragment from the repeat region of the HVT genome. The second fragment is an approximately 15,500 base pair BamHI to StuI subfragment of BamHI #1 of HVT. The third fragment is an approximately 8400 base pair cassette containing the MDV gA, gD, and gB genes (see FIGS. 10 and 11). The fourth fragment is an approximately 14,500 base pair HindIII to BamHI subfragment of the BamHI #1 of HVT.

SUBGENOMIC CLONE 722-60.E2. Cosmid 722-60.E2 was constructed for the purpose of inserting the MDV gA, gD, and gB genes and the NDV HN and F genes into the unique short of HVT and for the purpose of generating recombinant HVT. Cosmid 722-60.E2 contains the MDV gA, gD and gB genes and the NDV HN and F genes inserted into a StuI site in the HVT US2 gene converted to a unique HindIII site within the BamHI #1 fragment of the unique short region of HVT. All five genes were inserted in the same transcriptional orientation as the HVT US2 gene. This region of the HVT BamHI #1 fragment containing the MDV and NDV genes was derived from S-HVT-106. Cosmid 722-60.E2 was constructed by a partial restriction digest with BamHI of S-HVT-106 and isolation of an approximately 46,300 base pair fragment. The cosmid was constructed utilizing standard recombinant DNA techniques (Sambrook, et al., 1989) by joining restriction fragments from the following sources. The vector is an approximately 6100 base pair BamHI fragment from cosmid vector pSY1626 derived from PHC79 (Bethesda Research Labs, Inc.) and pWE15 (Strategene, Inc.). The first fragment is an approximately 900 base pair BamHI fragment from the repeat region of the HVT genome. The second fragment is an approximately 15,500 base pair BamHI to StuI subfragment of BamHI #1 of HVT. The third fragment is an approximately 15,400 base pair cassette containing the MDV gA gene, (FIGS. 10A and 10B, SEQ ID NO. 8), the

Figure 10A:
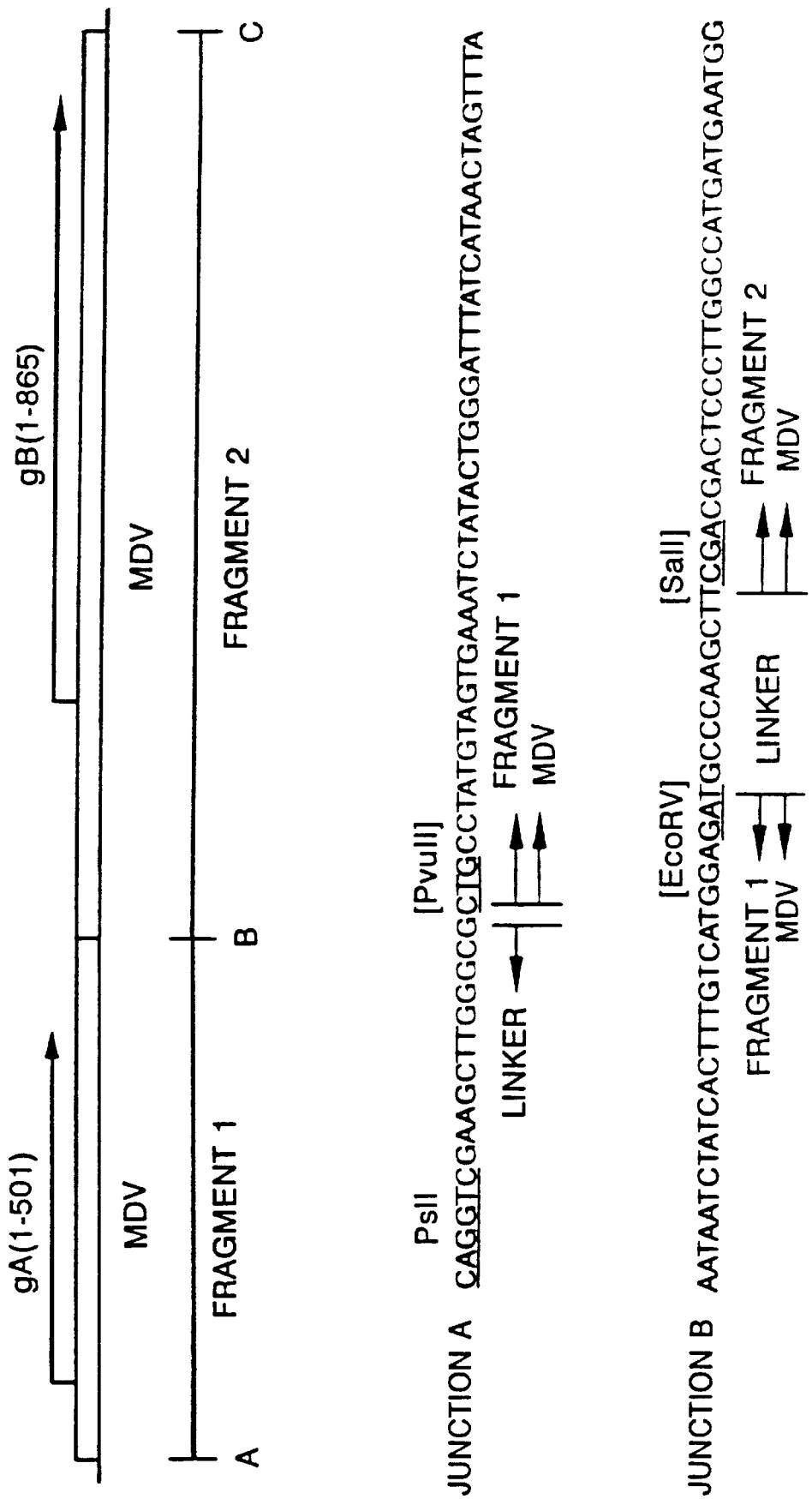
FIGS. 10A and 10B provide a detailed description of the MDV gene cassette insert in Homology Vectors 456-18.18 and 456-17.22.
Figure 10B:
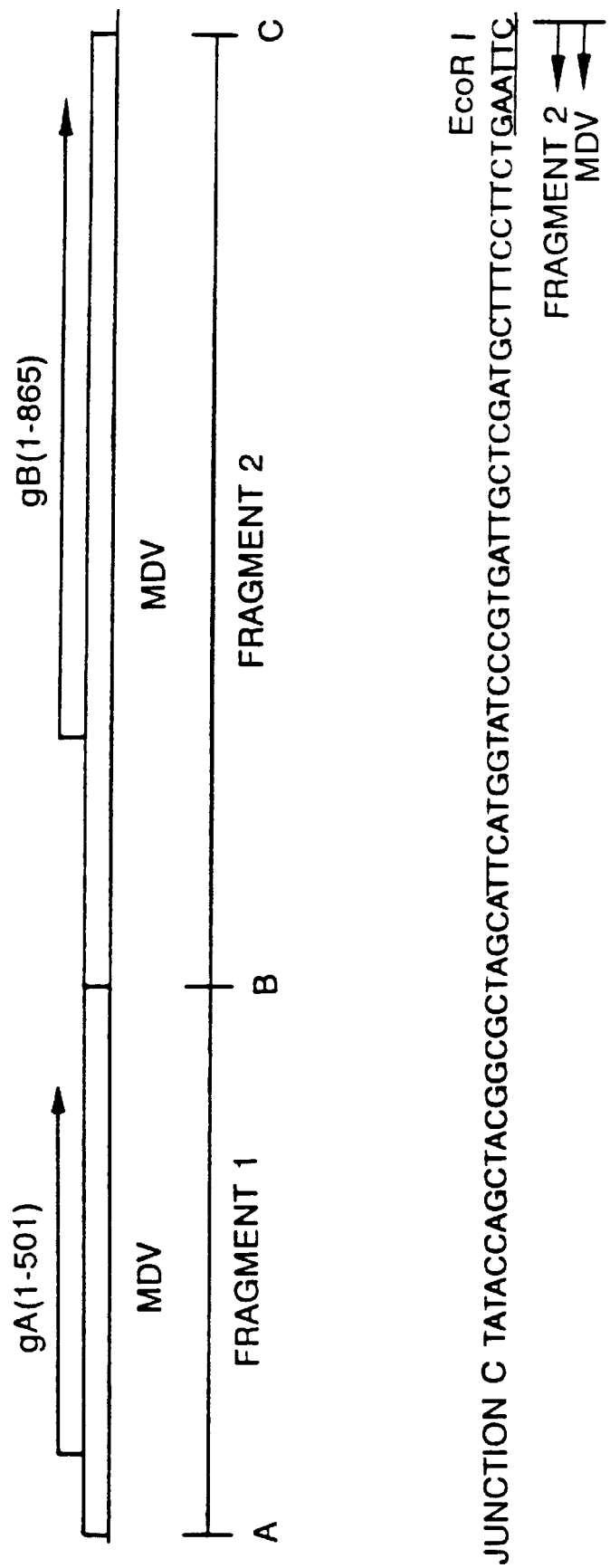
Figure 11A:
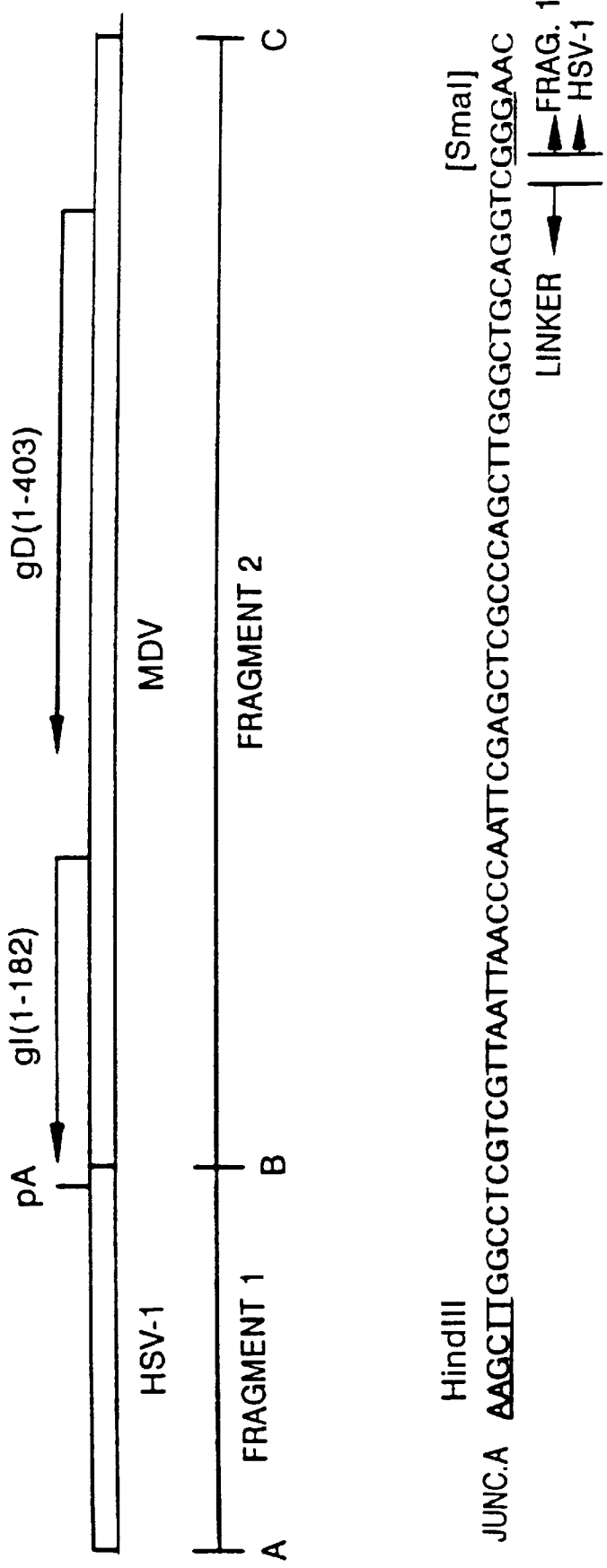

PRV gX promoter (Lomniczi et al., 1984), the NDV HN gene (SEQ ID NO. 10), the PRV gX polyadenylation site (Lomniczi et al., 1984), the HCMV immediate early promoter (D. R. Thomsen, et al., 1981), the NDV F gene (SEQ ID NO. 12), the HSV TK polyadenylation site (McGeoch, et al., 1985), the MDV gD gene (FIGS. 11A and 11B), the approximately 450 base pair ILTV US3 polyadenylation site, and the MDV gB gene (FIGS. 10A and 10B). The fourth fragment is an approximately 14,500 base pair StuI to BamHI subfragment of the BamHI #1 of HVT.

SUBGENOMIC CLONE 729-37.1. Plasmid 729-37.1 was constructed for the purpose of generating recombinant HVT. Plasmid 729-37.1 contains the ILTV gD and gB genes inserted into the NotI site of plasmid 686-63.A1. The ILTV gD and gB genes use their respective endogenous ILTV promoters, and the ILTV gD and gB gene are each followed by PRV gX polyadenylation signals. The ILTV gD and gB gene cassette was constructed utilizing standard recombinant DNA techniques (Sambrook, et al., 1989) by joining restriction fragments from the following sources. The vector is an approximately 2000 base pair ASCI fragment constructed from a 2000 base pair AatII to PvuII fragment of pNEB193 (New England Biolabs, Inc.) blunt ended with Klenow DNA polymerase and AscI linkers inserted. The first fragment is an approximately 2052 base pair SalI to XbaI restriction subfragment of the ILTV Asp718I genomic fragment #8 (10.6 kb). The second fragment is an approximately 572 base pair XbaI to Asp718I restriction subfragment of the PRV BamHI restriction fragment #7 (Lomniczi et al., 1984). The third fragment is an approximately 3059 base pair EcoRI to EcoRI restriction fragment of ILTV genomic DNA. The fourth fragment is an approximately 222 base pair EcoRI to SalI restriction subfragment of the PRV BamHI restriction fragment #7 (Lomniczi et al., 1984).

SUBGENOMIC CLONE 739-27.16. Cosmid 739-27.16 was constructed for the purpose of constructing a chimeric HVT/MDV virus containing the HVT genes of the unique long region and the MDV type 1 genes of the unique short region. Cosmid 739-27.16 contains the complete unique short region of MDV type 1. This region contains the entire SmaI B fragment and two SmaI K fragments. Cosmid 739-27.16 was constructed by a partial restriction digest with SmaI of MDV DNA and isolation of an approximately 29,000 to 33,000 base pair fragment. The cosmid was constructed utilizing standard recombinant DNA techniques (Sambrook, et al., 1989) by joining restriction fragments from the following sources. The vector is an approximately 8200 base pair BamHI fragment (made blunt-ended with Klenow DNA polymerase) from cosmid vector pWE15. The first fragment is an approximately 4050 base pair SmaI K fragment from the short internal repeat region of the MDV genome. The second fragment is an approximately 21,000 base pair fragment SmaI B of MDV. The third fragment is an approximately 3,650 base pair SmaI K fragment from the short terminal repeat region of the MDV genome (Fukuchi, et al., 1984, 1985).

EXAMPLES

Example 1

S-HVT-001

S-HVT-001 is a herpesvirus of turkeys (HVT) that contains the E. coli β-galactosidase gene inserted into the unique long region of the HVT genome. The restriction enzyme map of HVT has been published (T. Igarashi, et al., 1985). This information was used as a starting point to engineer the insertion of foreign genes into HVT. The BamHI restriction map of HVT is shown in FIG. 1A. From this data, several different regions of HVT DNA into which insertions of foreign genes could be made were targeted. The foreign gene chosen for insertion was the E. coli β-galactosidase (lacZ) gene, which we have used in PRV. The promoter was the PRV gpX promoter. The lacZ gene was inserted into the unique long region of HVT, specifically into the XhoI site in the BamHI #16 (3329 bp) fragment, and was shown to be expressed in an HVT recombinant by the formation of blue plaques using the substrate Bluogal™ (Bethesda Research Labs). Similarly, the lacZ gene has been inserted into the SalI site in the repeat region contained within the BamHI #19 (900 bp) fragment.

Figure 1B:
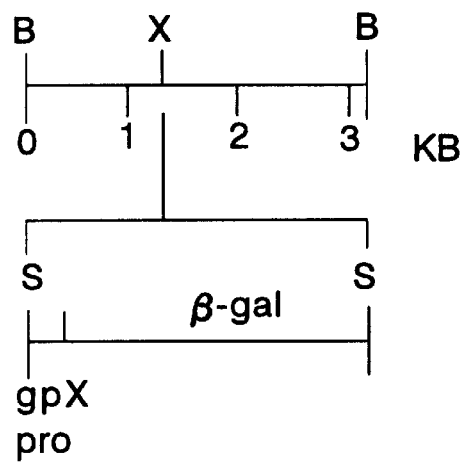
Figure 1C:
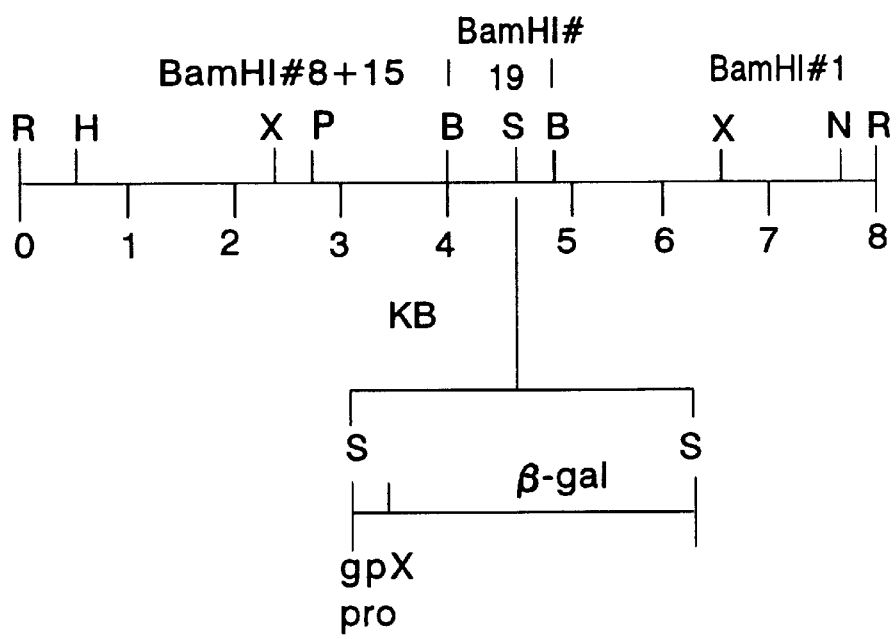
Figure 2A:
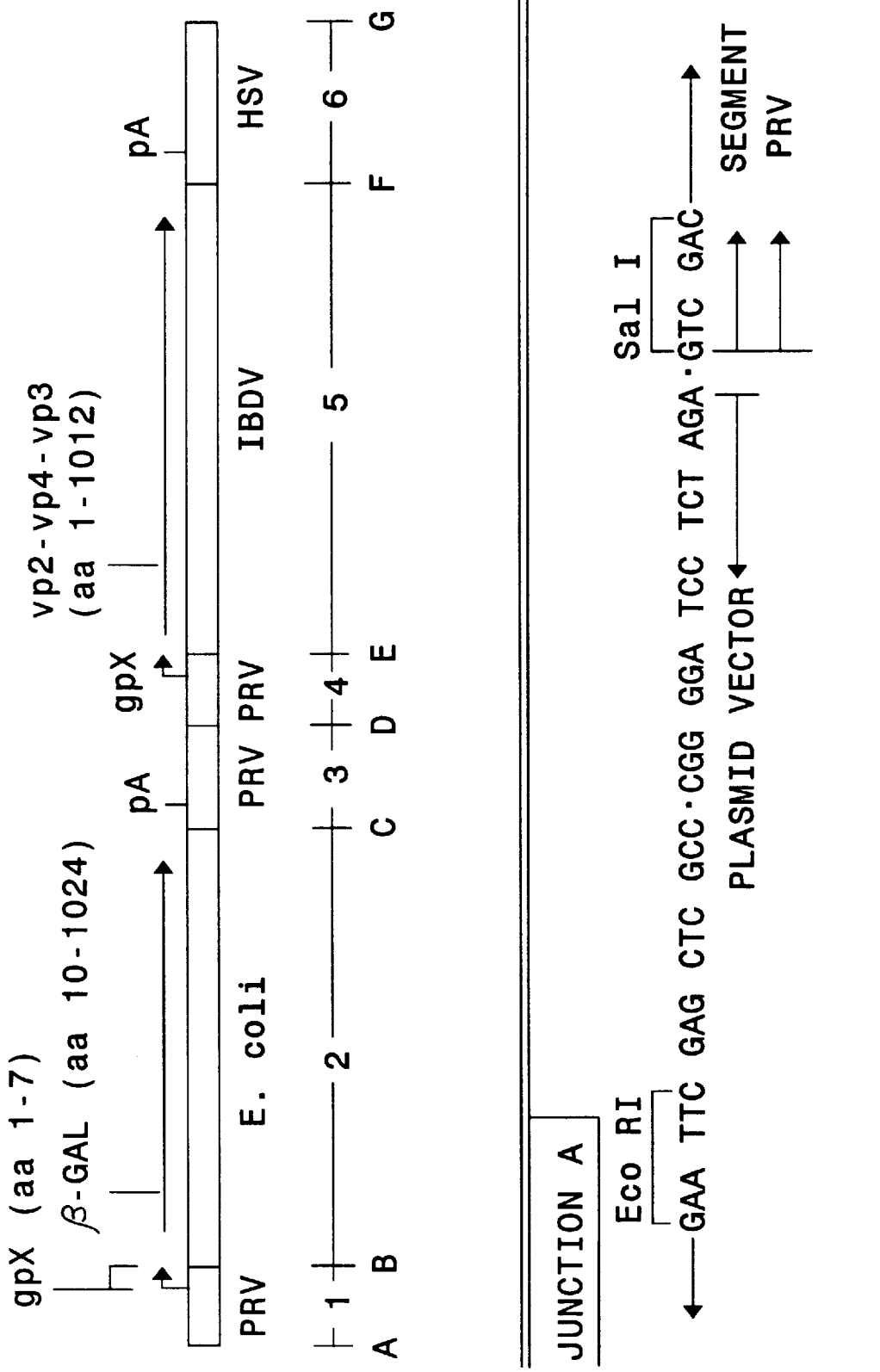
FIGS. 2A, 2B, 2C and 2D show insertion in Plasmid 191-47.
Figure 2B:
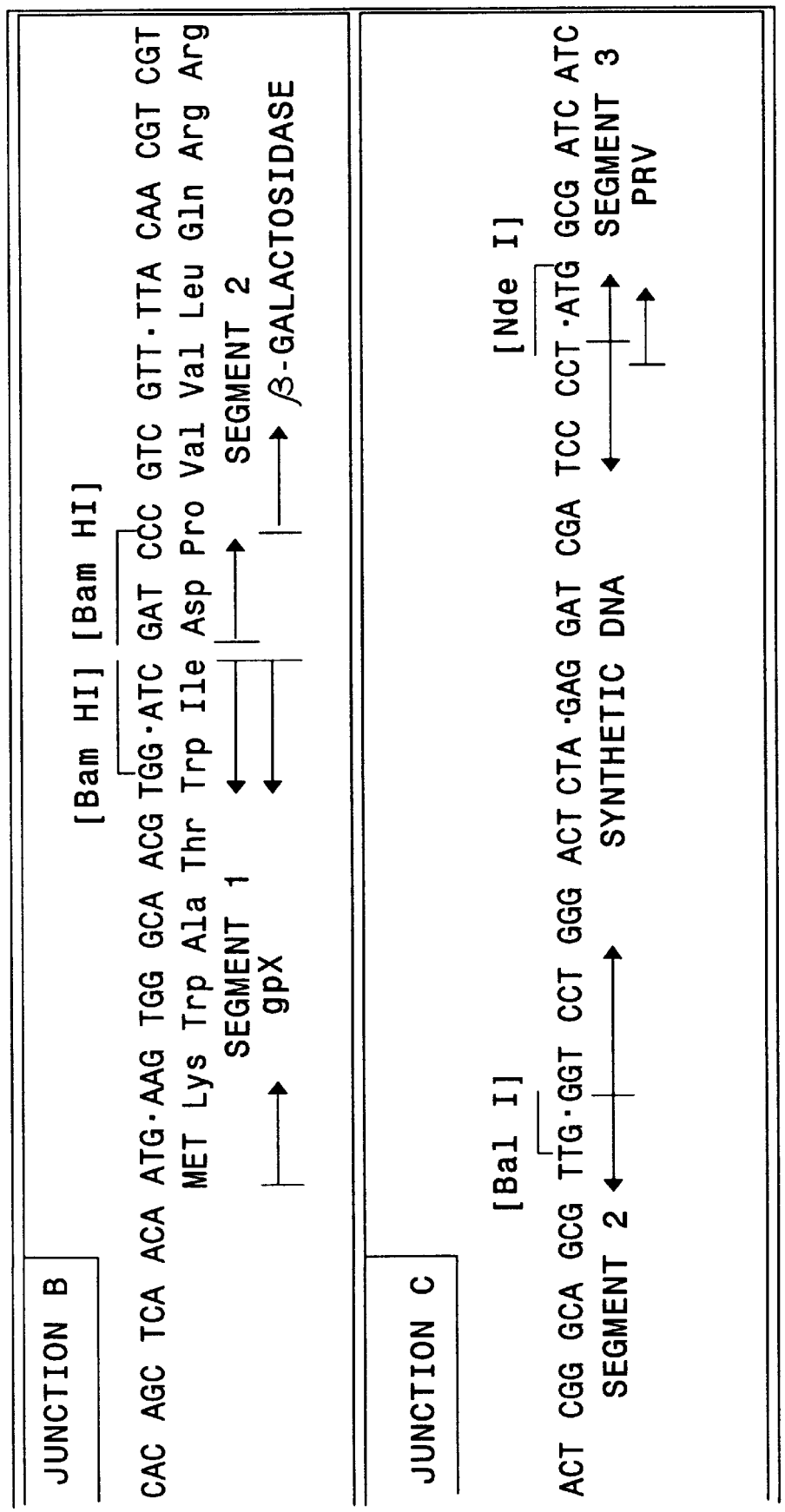
Figure 2C:
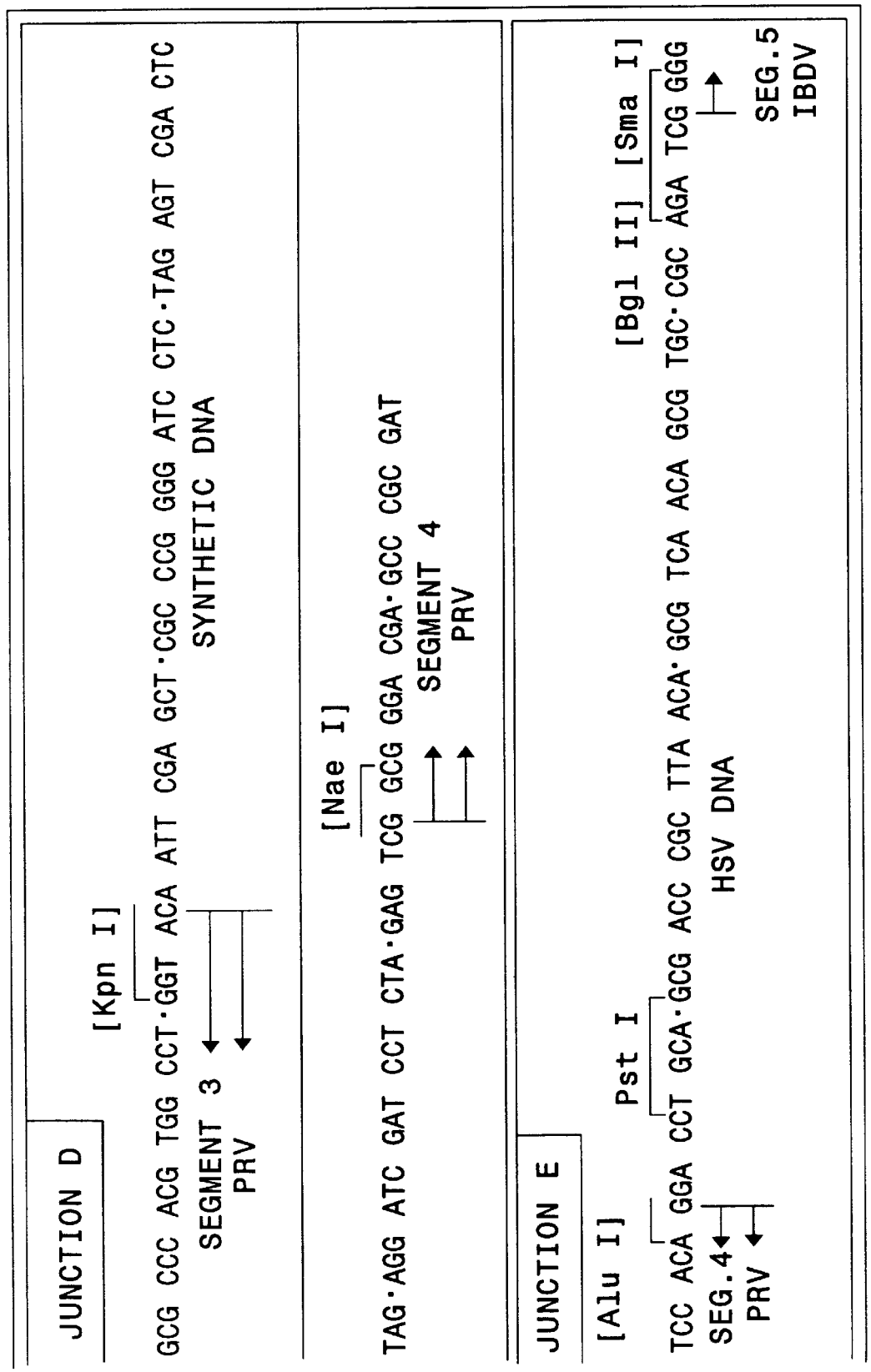
Figure 2D:
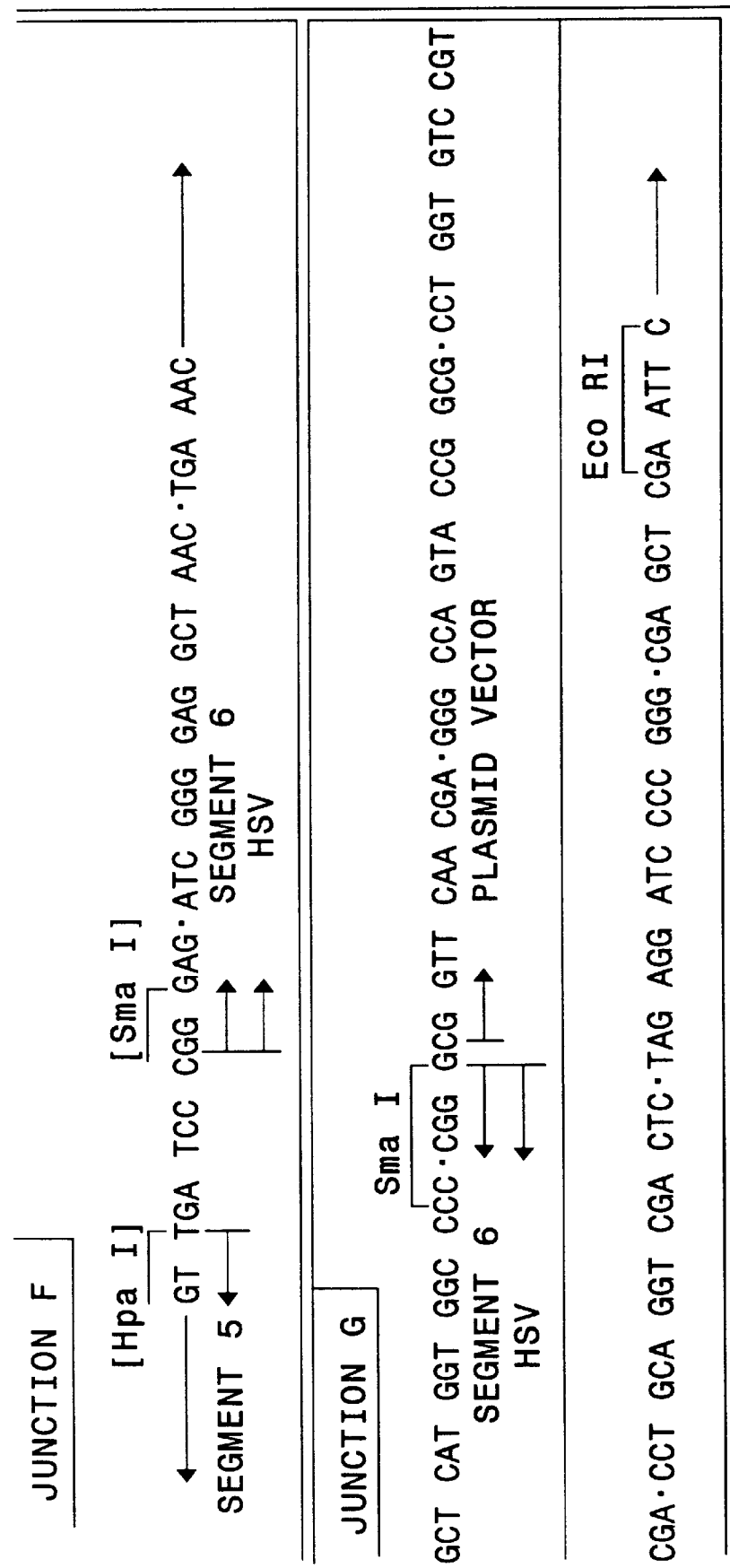

These experiments show that HVT is amenable to the procedures described within this application for the insertion and expression of foreign genes in herpesviruses. In particular, two sites for insertion of foreign DNA have been identified (FIGS. 1B and 1C).

Example 2

S-HVT-003

S-HVT-003 is a herpesvirus of turkeys (HVT) that contains the E. Coli β-galactosidase (lacZ) gene and the infectious bursal disease virus (IBDV) strain S40747 large segment of RNA (as a cDNA copy) (SEQ ID NO: 1) inserted into the unique long region of the HVT genome. This IBDV DNA contains one open reading frame that encodes three proteins (5'VP2-VP4-VP3 3') (SEQ ID NO: 2), two of which are antigens to provide protection against IBDV infections of chickens. Expression of the genes for both β-galactosidase and the IBDV polyprotein are under the control of the pseudorabies virus (PRV) gpX gene promoter. S-HVT-003 was made by homologous recombination. S-HVT-003 was deposited on Jul. 21, 1987 pursuant to the Budapest Treaty on the International Deposit of Microorganism for Purposes of Patent Procedure with the Patent Culture Depository of the American Type Culture Collection, 123C1 Parklawn Drive, Rockville, Md. 20852 U.S.A. under ATCC Accession No. VR 2178.

The IBDV genes were cloned by the cDNA CLONING PROCEDURE. Clones representing the genome of IBDV were screened by SOUTHERN BLOTTING OF DNA procedure against blots containing authentic IBDV RNA. Positive clones were then characterized by restriction mapping to identify groups of clones. Two such clones were identified, that together were found to represent the entire coding region of the IBDV large segment of RNA (3.3 kb dsRNA). One cDNA clone (2-84) contained an approximately 2500 base pair fragment representing the first half of the IBDV gene. The second clone (2-40) contained an approximately 2000 base pair fragment representing the distal half of the IBDV gene. Plasmid 2-84/2-40, representing the entire IBDV gene, was constructed by joining clone 2-84 and 2-40 at a unique PvuII site present in the overlapping sequences. The IBDV genome can be obtained from plasmid 2-84/2-40 as an approximately 3400 base pair SmaI to HpaI fragment. Confirmation of the nature of the proteins encoded by the IBDV gene was obtained by expressing the clone (2-84/2-40) in E. coli and detecting VP3 antigen using antiserum made against purified IBDV capsid proteins on Western blots. The cDNA of the IBDV large segment of RNA encoding the IBDV antigens show one open reading frame that will henceforth be referred to as the IBDV gene. The sequence of an Australian IBDV strain has been published which bears close homology to applicants' sequence (Hudson et al, 1986). Comparison of the amino acid differences between the two viruses revealed 29 amino acid changes within the 1012 amino acid coding region. There were only 3 amino acid differences deduced for VP4 and only 8 in VP3. In contrast, VP2 contained 18 amino acid changes, 14 of which were clustered between amino acids 139 to 332.

For insertion into the genome of HVT, the coding region for the IBDV gene was cloned between the PRV gpX promoter and the HSV TK poly-A signal sequence, creating plasmid 191-23. To aid in the identification of HVT recombinants made by homologous recombination containing the IBDV gene, the gpX promoted IBDV fragment from plasmid 191-23 was inserted behind (in tandem to) a lacZ gene controlled by a gpX promoter. The resultant plasmid, 191-47, contains the E.coli lacZ gene and the IBDV gene under the control of individual PRV gpX promoters. In constructing plasmid 191-47, various DNA fragments were joined by recombinant DNA techniques using either naturally occurring restriction sites or synthetic linker DNA. Details concerning the construction of these genes contained in plasmid 191-47 can be seen in FIGS. 2A, 2B, 2C and 2D.

The first segment of DNA (Segment 1, FIG. 2A) contains the gpX promoter region including the residues encoding the first seven amino acids of the gpX gene, and was derived from a subclone of the PRV BamHI #10 fragment as an approximately 800 base pair SalI to BamHI fragment. The second segment of DNA (Segment 2, FIG. 2A) contains the E. coli β-galactosidase coding region from amino acid 10 to amino acid 1024 and was derived from the plasmid pJF751 (obtained from Jim Hoch, Scripps Clinic and Research Foundation) as an approximately 3300 base pair BamHI to BalI fragment followed by an approximately 40 base pair Ava I to Sma I fragment. The third segment of DNA (Segment 3, FIG. 2A) contains the gpX poly A signal sequence and was derived from a subclone of the PRV BamHI #7 fragment as an approximately 700 base pair NdeI to StuI fragment. Segment three was joined to segment two by ligating the NdeI end which had been filled in according to the POLYMERASE FILL-IN REACTION, to the SmaI site. The fourth segment of DNA (Segment 4, FIG. 2A) contains the gpX promoter (TATA box and cap site) and was derived from a subclone of the PRV BamHI #10 fragment as an approximately 330 base pair NaeI to AluI fragment. Additionally, segment four contains approximately 36 base pairs of HSV TK 5' untranslated leader sequence as a PstI to BglII fragment in which the PstI site has been joined to the AluI site through the use of a synthetic DNA linker (McKnight and Kingbury, 1982). DNA segments four through six were inserted as a unit into the unique Kpn I site of segment three which is located 3' of the gpX poly A signal sequence. The fifth segment of DNA (Segment 5, FIG. 2A) contains the entire coding region of the IBDV large segment of RNA (cDNA clone) as an approximately 3400 base pair SmaI to HpaI fragment. The SmaI site of segment five was fused to the BglII site of segment four which had been filled in according to the POLYMERASE FILL IN REACTION. Expression of the IBDV gene (5'VP2-Vp4-VP3 3') is under the control of the gpX promoter (segment 4), but utilizes its own natural start and stop codons. The sixth segment of DNA (Segment 6, FIG. 2A) contains the HSV TK poly-A signal sequence as an approximately 800 base pair SmaI fragment (obtained from Bernard Roizman, Univ. of Chicago). The HpaI site of segment five was fused to the SmaI site of segment six through the use of a synthetic DNA linker.

In summary, the construct used to create S-HVT-003 (plasmid 191-47) contains (5' to 3') the PRV promoter, the gpX TATA box, the gpX cap site, the first seven amino acids of gpX, the E. coli β-galactosidase (lacZ) gene, the PRV poly-A signal sequence, the PRV gpX promoter, the gpX TATA box, the gpX cap site, a fusion within the gpX untranslated 5' leader to the IBDV gene, IBDV start codon, a fusion within the IBDV untranslated 3' end to HSV TK untranslated 3' end, and the TK poly-A signal sequence. The cassette containing these genes was engineered such that it was flanked by two EcoRI restriction endonuclease sites. As a result, an approximately 9100 base pair fragment containing both lacZ gene and the IBDV gene can be obtained by digestion with EcoRI. Henceforth, the 9161 base pair EcoRI fragment will be referred to as the IBDV/lacZ cassette. The following procedures were used to construct S-HVT-003 by homologous recombination. The IBDV/lacZ cassette was inserted into the unique XhoI site present within a subclone of the HVT BamHI #16 fragment. To achieve this, the XhoI site was first changed to an EcoRI site through the use of an EcoRI linker. This site had previously been shown to be nonessential in HVT by the insertion of lacZ (S-HVT-001). It was also shown that the flanking homology regions in BamHI #16 were efficient in homologous recombination. Shown in FIGS. 3A and 3B, the genomic location of the BamHI #16 fragment maps within the unique long region of HVT. The BamHI #16 fragment is approximately 3329 base pairs in length (SEQ ID NOs: 3, 4, 5, 6, and 7). HVT DNA was prepared by the PREPARATION OF HERPESVIRUS DNA procedure. Cotransfections of HVT DNA and plasmid DNA into primary chick embryo fibroblast (CEF) cells were done according to the DNA TRANSFECTION FOR GENERATING RECOMBINANT HERPESVIRUS. The recombinant virus resulting from the cotransfection stock was purified by three successive rounds of plaque purification using the BLUOGAL SCREEN FOR RECOMBINANT HERPESVIRUS procedure. When 100% of the plaques were blue, the DNA was analyzed for the presence of the IBDV gene by the SOUTHERN BLOTTING OF DNA procedure. Southern blots, probing EcoRI digested S-HVT-003 DNA with an IBDV specific nick translated probe (plasmid 2-84/2-40), confirmed the presence of the 9100 base pair EcoRI fragment. This result confirmed that S-HVT-003 contained both the lacZ gene and the IBDV gene incorporated into its genome. Additional Southern blots, using a probe specific for BamHI #16, confirmed that the homologous recombination occurred at the appropriate position in BamHI #16 and that no deletions were created. No differences in the growth of S-HVT-003 compared to wild type virus (S-HVT-000) were observed in vitro.

Figure 5:
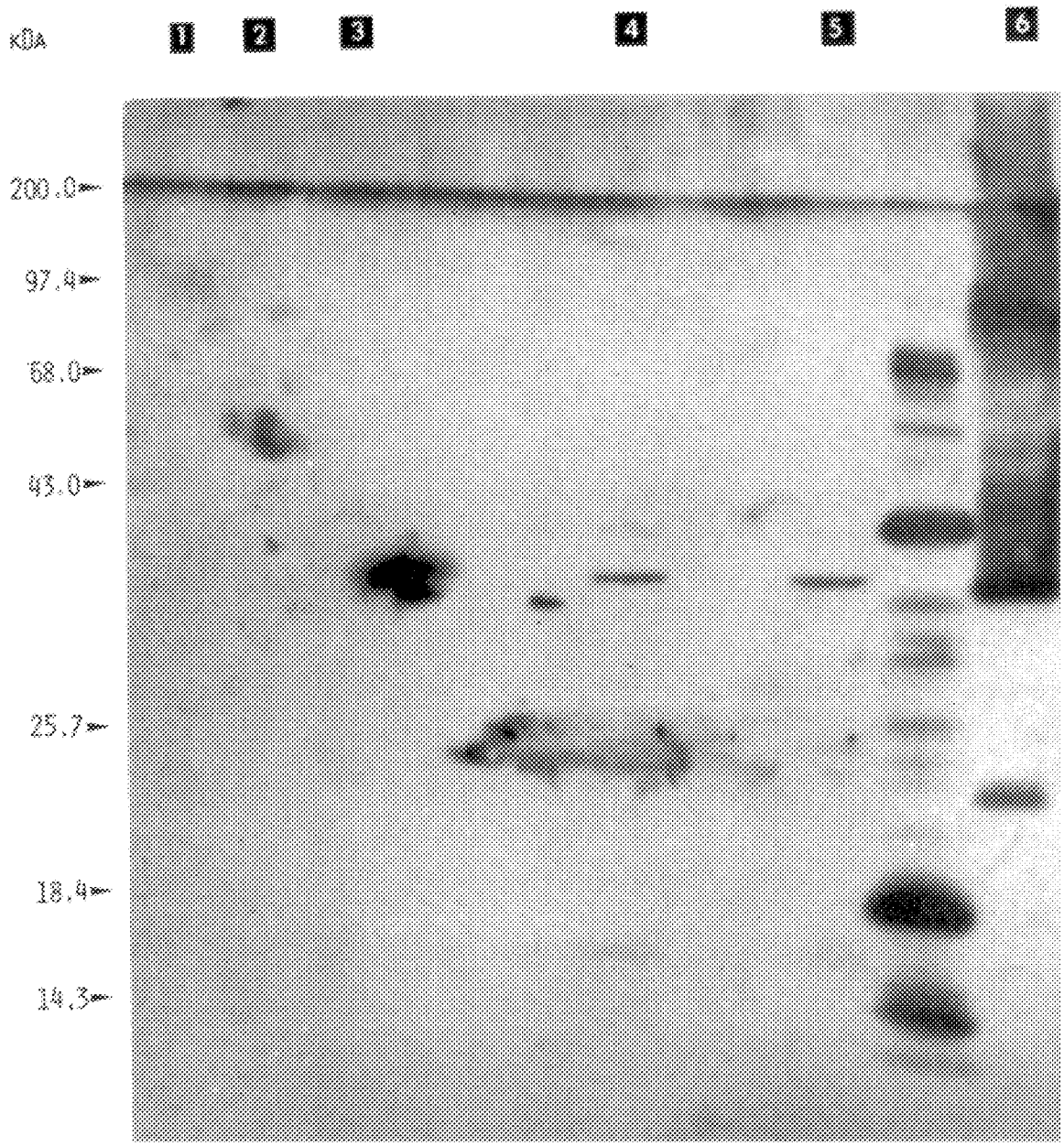
FIG. 5 shows a Western blot indicating the differential expression of the IBDV 42 kD (VP2) antigen in cellular lysates of S-HVT-003 infected cells (42 kD present) and S-HVT-001 infected cells (42 kD negative). IBDV specific polypeptides were identified using a VP2 specific rabbit anti-peptide antiserum. The lanes contain: 1) protein molecular weight standards, 2) wild-type HVT infected CEF's, 3) S-HVT-001 infected CEF's, 4) S-HVT-003 infected CEF's, 5) S-HVT-003 infected CEF's, and 6) IBDV virion polypeptides.

Expression of IBDV specific proteins from S-HVT-003 were assayed in vitro using the WESTERN BLOTTING PROCEDURE. Cellular lysates were prepared as described in PREPARATION OF HERPESVIRUS CELL LYSATES. Briefly, the proteins contained in the cellular lysates of S-HVT-003 were separated by polyacrylamide gel electrophoresis, transferred to nitrocellulose, and probed with either an antiserum made against denatured purified IBDV capsid proteins or antiserum made against a synthetic peptide corresponding to a predicted imuno dominant region of the IBDV 40 kd (VP2) capsid protein. The filters were washed and treated with [$^{125}$I] protein A to detect the position of the bound antibodies. FIG. 4 shows the results obtained using the antiserum made against denatured purified IBDV capsid proteins, which have been shown by the applicants to react primarily with VP3 (32 kd protein). As seen, S-HVT-003 produces a protein which is immunologically indistinguishable from the authentic VP3 protein from intact IBDV virions. Moreover, the polyprotein appears to be processed correctly, producing a VP3 species that comigrates with the authentic VP3 protein. Recent evidence using an Australian IBDV stain indicates that VP4 is involved in the processing of the precursor polyprotein into mature VP2 and VP3 protein species (Jagadish, et al., 1988). FIG. 5 shows the results obtained using a rabbit antiserum raised against a synthetic peptide that is homologous to a 14 amino acid region of the IBDV VP2 (40 kd) capsid protein. As seen, S-HVT-003 produces a protein that is immunologically indistinguishable from the authentic viral VP2 protein. In addition, the VP2 protein produced from S-HVT-003 comigrates with the 40 kd species of VP2 isolated from intact IBDV virions. This species represents a major component of infectious (complete) viral particles.

In summary, analysis of the expression of IBDV specific proteins from S-HVT-003 has shown that the polyprotein is processed in CEF cell culture, producing proteins of the appropriate size that react to immunological reagents specific for either VP2 or VP3 proteins on Western blots.

The following set of experiments was carried out in chickens to analyze the in vivo expression of the IBDV genes contained within S-HVT-003 as determined by seroconversion data, serum neutralization results, and protection from IBDV challenge.

The first experiment was designed to show the seroconversion of chickens to IBDV upon being vaccinated with S-HVT-003. Eleven 11-week-old chickens, seronegative to HVT and IBDV were obtained from SPAFAS Inc. Six birds were vaccinated subcutaneously in the abdominal region with 0.5 ml of a cellular suspension of CEF cells containing S-HVT-003 (40,000 PFU/ml). Serum samples were obtained every seven days for eight weeks for all birds in this study. On day 28 (4th week), three of these birds received a boost of S-HVT-003, while the other three birds received 0.5 ml of an inactivated IBDV vaccine inoculated subcutaneously in the cervical region. Three additional birds were given only the inactivated vaccine on day 28. Two birds served as contact controls and received no vaccinations. On day 56, all birds were sacrificed and necropsied. Table 1 show the results of the serum neutralization assay against IBDV. No detectable SN activity was observed in the birds given only S-HVT-003. Additionally, only one of the three birds that were given only the inactivated vaccine demonstrated low but detectable SN activity. SN titers were also detected in one of the three birds that received the S-HVT-003 followed by the inactivated IBDV vaccine boost; these titers were at a much higher level than with the inactivated IBDV vaccine alone. These results suggest that S-HVT-003 is priming the chicken for a secondary response against IBDV. In vitro analysis of the serum samples by WESTERN BLOTTING confirmed the seroconversion of the chickens to IBDV upon vaccination with S-HVT-003 both prior to and after boosts administered on day 28.

TABLE 1

| Vaccine Group | Bird No. | DAY 28 | 31 | 35 | 38 | 42 | 49 |
|---|---|---|---|---|---|---|---|
| HVT-003 | 265 | <2 | <2 | <2 | <2 | <2 | <2 |
| HVT-003 | 266 | <2 | <2 | <2 | <2 | <2 | <2 |
|  | 267 | <2 | <2 | <2 | <2 | <2 | <2 |
| HVT-003 | 260 | <2 | <2 | <2 | <2 | <2 | <2 |
| IBDV[a] | 264 | <2 | <2 | <2 | 1:64 | 1:256 | 1:512 |
|  | 269 | <2 | <2 | <2 | <2 | <2 | <2 |

TABLE 1-continued

| Vaccine Group | Bird No. | DAY 28 | 31 | 35 | 38 | 42 | 49 |
|---|---|---|---|---|---|---|---|
| C | 261 | <2 | <2 | <2 | <2 | <2 | <2 |
| IBDV[a] | 262 | <2 | <2 | <2 | <2 | 1:4 | 1:4 |
|  | 263 | <2 | <2 | <2 | <2 | <2 | <2 |
| C | 270 | <2 | <2 | <2 | <2 | <2 | <2 |
|  | 271 | <2 | <2 | <2 | <2 | <2 | <2 |

[a]Commercial

In the second experiment, twenty five 1-day old SPF chicks were vaccinated with S-HVT-003 (20 with 0.2 ml subcutaneously and 5 by bilateral eyedrop). Twenty chicks were kept as controls. On days four and seven postinfection, five vaccinates and two control birds were bled, sacrificed and their spleens removed for virus isolation. Spleen cell suspensions were made by standard method, and ~1×10$^6$ cells in 3 ml of chick embryo fibroblast (CEF) growth media were inoculated directly onto secondary cells. Cultures were incubated for 6–7 days and then scored for cytopathic effects (CPE) as determined by observing cell morphology. The cultures were passed a second time, and again scored for CPE. The results are shown in Table 2. All nonvaccinated control birds remained negative for HVT for both day 4 and 7 spleen cell isolations. Four out of the five birds vaccinated with S-HVT-003 were positive for HVT at day 4 for both the first and second passages. One bird did not produce virus, this may represent a vaccination failure. Five out of five birds were positive for HVT on day 7 at both passage one and two. Overall, the vector recovery experiment demonstrates that S-HVT-003 replicates as well as wild type HVT virus in vivo and that insertion of the IBDV/lacZ cassette into the XhoI site of BamHI #16 does not result in detectable attenuation of virus. Subsequent experiments examining the recovered virus by the BLUOGAL SCREEN FOR RECOMBINANT HERPESVIRUS procedure confirmed the in vivo stability of S-HVT-003, by demonstrating β-galactosidase expression in 100% of the viruses.

TABLE 2

| Sample | Harvest Date | | | |
|---|---|---|---|---|
|  | Day 4 | | Day 7 | |
|  | P1 | P2 | P1 | P2 |
| N 1 | – | – | | |
| N 2 | – | 3· | | |
| N 3 | | | – | – |
| N 4 | | | – | – |
| T 1 | – | – | | |
| T 2 | 2+ | 2+ | | |
| T 3 | 2+ | 2+ | | |
| T 4 | + | 4+ | | |
| T 5 | 3+ | 3+ | | |
| T 6 | | | 2+ | contaminated |
| T 7 | | | + | 5+ |
| T 8 | | | + | 5+ |
| T 8 | | | + | 5+ |
| T 9 | | | + | 5+ |
| T 10 | | | + | 5+ |

N = control, T = vaccinated
CPE ranged from negative (–) to 5+

At days 0, 4, 7, 14, 21, and 27 postinfection, blood samples were obtained from the rest of the chickens for determining serum ELISA titers against IBDV and HVT antigens as well as for virus neutralizing tests against IBDV. Additionally, at 21 days postinfection five control and fourteen vaccinated chicks were challenged with virulent IBDV by bi-lateral eyedrop ($10^{3.8}EID_{50}$). All birds were sacrificed 6-days post challenge and bursa to body weight ratios were calculated. A summary of the results is shown in tables 3 and 4, respectively. As presented in Table 3, no antibodies were detected against HVT antigens by ELISA prior to 21–27 days post vaccination. In chickens, the immune response during the first two weeks post hatch is both immature and parentally suppressed, and therefore these results are not totally unexpected. In contrast, IBDV ELISA's were negative up to day 21 post-vaccination, and were only detectable after challenge on day 27. The ELISA levels seen on day 27 post-vaccination indicate a primary response to IBDV. Table 4 comparing the Bursa-to-Body weight ratios for challenged controls and vaccinated/challenged groups show no significant differences. Vaccination with S-HVT-003 under these conditions did not prevent infection of the vaccinated birds by IBDV challenge, as indicated by the death of four vaccinated birds following challenge.

TABLE 3

| Sample Group | | ELISA | | VN |
| --- | --- | --- | --- | --- |
| | | HVT | IBDV | IBDV |
| C-0 | (n = 3) | 0 | 0 | <100 |
| C-4 | (n = 2) | 0 | 0 | nd |
| T-4 | (n = 5) | 0 | 0 | nd |
| C-7 | (n = 2) | 0 | 0 | <100 |
| T-7 | (n = 5) | 0 | 0 | <100 |
| C-14 | (n = 5) | 0 | 0 | nd |
| T-14 | (n = 14) | 0 | 0 | <100 |
| C-21 | (n = 5) | 0 | 0 | nd |
| T-21 | (n = 14) | 1 | 0 | <100 |
| C-27 | (n = 5) | 0 | 0 | nd |
| CC-27 | (n = 5) | 0 | 5 | nd |
| CT-27 | (n-10) | 3.2 | 2 | nd |

C = control
T = vaccinated
CC = challenged control
CT = Challenged & vaccinated.
ELISA titers are GMTs and they range from 0–9.

TABLE 4

| Sample Group | Body wt. | Bursa wt. | BBR |
| --- | --- | --- | --- |
| Control (n = 5) | 258.8 | 1.5088 | 0.0058 |
| Challenge | 209 | 0.6502 | 0.0031 |
| Control (n = 5) | | | |
| Challenge | 215.5 | 0.5944 | 0.0027 |
| Treated (n = 10) | | | |

Values are mean values. Body weights are different in control group because challenged birds did not feed well. Four challenged-treated birds died.

A third experiment was conducted repeating Experiment 2 but using immunologically responsive chicks (3 weeks of age). Six three week old SPF leghorn chickens were vaccinated intraperitoneally with 0.2 ml of S-HVT-003 (one drop in each eye). Serum samples were obtained every seven days for six-weeks and the birds were challenged with the virulent USDA standard challenge IBDV virus on day 43 post-vaccination. Six days post challenge, the control, vaccinated-challenged, and challenged groups were sacrificed and bursas were harvested for probing with anti-IBDV monoclonal antibodies (MAB) (provided by Dr. David Snyder, Virginia-Maryland Regional College of Veterinary Medicine). Bursal homogenates were prepared by mixing 1 ml of 0.5% NP40 with one bursa. Bursa were then ground and briefly sonicated. Supernatants from the homogenates were reacted with the R63 MAB which had been affixed to 96-well Elisa plates via a protein A linkage. After incubation, a biotin labeled preparation of the R63 MAB was added. After washing, an avidin-horse radish peroxidase conjugate was added and incubated. Tests were developed with Tris-malcate buffer (TMB)+$H_2O_2$ substrate. The test results are presented in Table 5. The data show the presence of high levels of IBDV antigen in all bursa in the vaccinate-challenged group and in the challenged group. No IBDV antigen was detected in the controls. IBDV specific antigen could be detected at dilutions of over 1/1000, and there does not appear to be differences between vaccinated and non-vaccinated challenged groups. HVT titers as determined by ELISA were first detectable at day 7 in four out of the six birds vaccinated. By day 14, six out of six vaccinated birds showed titers to HVT. All six birds continued to show HVT titers throughout the experiment. No IBDV SN titers were seen prior to the challenge. In contrast, analysis of these same serum samples by the WESTERN BLOTTING procedure demonstrated the seroconversion of chickens vaccinated with S-HVT-003 to IBDV prior to administration of the virus challenge. The level of response, however, remains small unless boosted by challenge. Comparison between the vaccinated/challenged and challenged only groups clearly demonstrates that the level of reactivity by Western blots is much higher in the vaccinated/challenged group. These results show that S-HVT-003 is seroconverting vaccinated birds to IBDV, and suggest that the level of IBDV specific expression are not high enough to induce a neutralizing response in the birds.

S-HVT-003 shows the merit of the vaccine approach the applicants have invented. HVT has been engineered to simultaneously express the foreign antigens (β-galactosidase and IBDV antigens) that are recognized in the host by an immune response directed to these proteins.

TABLE 5

Serology: Herpes/IBDV ELISA titer

| Bird # | Bleed Date | | | | | | | |
| --- | --- | --- | --- | --- | --- | --- | --- | --- |
| | 11/3 | 11/10 | 11/14 | 11/24 | 12/1 | 12/8 | 12/15 | 12/22 |
| Vaccinated and Challenged | | | | | | | | |
| 221 | 0/0 | 7/0 | 5/0 | 6/0 | 5/0 | 5/0 | 5/0 | 3/3 |
| 41 | 0/0 | 4/0 | 4/0 | 1/0 | 1/0 | 1/0 | 1/0 | 1/3 |
| 42 | 0/0 | 3/0 | 2/0 | 1/0 | 5/0 | 5/0 | 5/0 | 3/2 |
| 43 | 0/0 | 0/0 | 5/0 | 5/0 | 5/0 | 5/0 | 3/0 | 3/2 |
| 44 | 0/0 | 1/0 | 5/0 | 1/0 | 2/0 | 1/0 | 1/0 | 2/4 |
| 45 | 0/0 | 0/0 | 1/0 | 1/0 | 1/0 | 1/0 | 1/0 | 1/3 |
| Control | | | | | | | | |
| 28 | 0/0 | | | | | | | 0/0 |
| 38 | 0/0 | | | | | | | 0/0 |
| 73 | 0/0 | | | | | | | 0/0 |
| 75 | 0/0 | | | | | | | 0/0 |
| Challenged only | | | | | | | | |
| 40 | 0/0 | | | | | | | 0/3 |
| 74 | 0/0 | | | | | | | 0/5 |
| 39 | 0/0 | | | | | | | 0/3 |
| 72 | 0/0 | | | | | | | 0/3 |

Maximum titer level is 9

Example 3

S-HVT-004

S-HVT-004 is a recombinant herpesvirus of turkeys that contains the Marek's disease virus (MDV) glycoprotein A (gA) gene inserted into the long unique region, and the β-galactosidase (lacz) gene also inserted in the long unique region. The MDV antigen is more likely to elicit the proper antigentic response than the HVT equivalent antigen.

The MDV gA (SEQ ID NO: 8 and SEQ ID NO: 9) gene was cloned by standard DNA cloning gA procedures. An EcoRI restriction fragment had been reported to contain the MDV gA gene (Isfort et al., 1984) and this fragment was identified by size in the DNA clones. The region of the DNA reported to contain the gA gene was sequenced by applicants and found to contain a glycoprotein gene as expected. The DNA from this gene was used to find the corresponding gene in HVT by the SOUTHERN BLOTTING OF DNA procedure, and a gene in HVT was identified that contained a very similar sequence. This gene is the same gene previously called gA (Isfort et al., 1984).

For insertion into the genome of HVT, the MDV gA gene was used intact because it would have good herpesvirus signal sequences already. The lacZ gene was inserted into the XhoI fragment in BamHI fragment #16, and the MDV gA gene was inserted behind lacZ as shown in FIGS. 6A and 6B. Flanking regions in BamHI #16 were used for the homologous recombination. HVT DNA and plasmid DNA were co-transfected according to the DNA TRANSFECTION FOR GENERATING RECOMBINANT HERPESVIRUS procedure into primary chick embryo fibroblast (CEF) cells. The virus from the transfection stock was purified by successive plaque purifications using the BLUOGAL SCREEN FOR RECOMBINANT HERPESVIRUS procedure. At the end of this procedure, when 100% of the plaques were blue, the DNA was analyzed for the presence of the MDV gA gene. S-HVT-004 is a recombinant virus that contains both the β-galactosidase gene and the MDV gA gene incorporated into the genome.

FIG. 6C shows the structure of S-HVT-004.

Example 4

Newcastle Disease Virus

Newcastle disease virus (NDV) is closely related to PI-3 in overall structure. We have engineered the hemagglutinin (HN) and fusion (F) ones of PI-3 for expression in IBR (ref). Similarly we have cloned the hemagglutinin (HN) and fusion (F) genes from NDV for use in the herpesvirus delivery system (Herpesvirus of turkeys, HVT).

The procedures that we have utilized for construction of herpesvirus control sequences for expression have been applied to NDV.

Infectious Bronchitis Virus

Infectious bronchitis virus (IBV) is a virus of chickens closely related in overall structure to TGE. We have engineered the major neutralizing antigen of TGE for expression in PRV (ref). Similarly we have cloned the major neutralizing antigens from three strains of IBV: Massachusetts (SEQ ID NOs: 14 and 15), Connecticut (SEQ ID NOs: 18 and 19), and Arkansas-99 (SEQ ID NOs: 16 and 17) for use in a herpesvirus delivery system (HVT).

The procedures that we have utilized for the construction of herpesvirus control sequences for expression have been applied to IBV.

Example 5

S-HVT-045

S-HVT-045 is a recombinant herpesvirus of turkeys that contains the Marek's disease virus (MDV) glycoprotein B (gB) gene inserted into the short unique region. The MDV antigen is more likely to elicit the proper antigenic response than the HVT equivalent antigen. S-HVT-045 has been deposited on Oct. 15, 1992 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2383.

The MDV gB gene was cloned by standard DNA cloning procedures. The MDV gB gene was localized to a 3.9 kb EcoRI-SalI fragment using an oligonucleotide probe based on the HSV gB sequence in a region found to be conserved among known herpesvirus gB genes. The restriction map 3.9 kb EcoRI-SalI fragment is similar to the published map (Ross et al., 1989).

For insertion into the HVT genome, the MDV gB was used intact because it would have good herpesvirus signal sequences already. The MDV gB gene was inserted into a cloned 17.15 kb BamHI-EcoRI fragment derived from the HVT BamHI #1 fragment. The site used for insertion was the StuI site within HVT US2, previously utilized for the construction of S-HVT-012. The site was initially altered by insertion of a unique HindIII linker, and the MDV gB gene was inserted by standard DNA cloning procedures. Flanking regions in the 17.15 kb BamHI-EcoRI fragment were used, together with the remaining cloned HVT fragments using the PROCEDURE FOR GENERATING RECOMBINANT HERPESVIRUSES FROM OVERLAPPING SUBGENOMIC FRAGMENTS. The virus obtained from the transfection stock was plaque purified and the DNA was analyzed for the presence of the MDV gB gene. S-HVT-045 is a recombinant virus that contains the MDV gB gene incorporated into the genome at the StuI site in HVT US2 gene.

Testing of Recombinant S-HVT-045

Two studies were conducted to demonstrate the effectiveness of these recombinant HVT/MDV viruses in protecting against challenge with virulent Marek's disease virus. In Study A, one-day-old specific pathogen free (SPF) chicks were vaccinated with either S-HVT-045 or S-HVT-046. Seven days post-vaccination, vaccinated chicks, and non-vaccinated, control chicks were challenged with the highly virulent MD-5 strain of Marek's disease virus. Following a 6-week post-challenge observation period for clinical signs typical of Marek's disease, all chicks were necropsied and examined for lesions diagnostic of Marek's disease. The results, in Table 6, show that both recombinant viruses gave complete protection against a challenge that caused Marek's disease in 90% of non-vaccinated control chicks.

In a second study, one-day-old chicks were vaccinated either with S-HVT-045 or S-HVT-047. A third group of chicks were vaccinated with a USDA-licensed, conventional vaccine comprised of HVT and SB-1 viruses. Five days post-vaccination, the vaccinated chicks and a group of non-vaccinated, control chicks were challenged with virulent Marek's virus, strain RB1B. The chicks were observed for 8 weeks for clinical signs of Marek's disease, then necropsied and observed for Marek's lesions. This study demonstrated the ability of HVT-045 and HVT-047 to provide 100% protection against challenge (Table 1). The commercial vaccine gave 96% protection, and 79% of the non-vaccinated chicks developed Marek's disease.

TABLE 6

EFFICACY OF RECOMBINANT HVT/MDV VIRUSES TO PROTECT SUSCEPTIBLE CHICKS AGAINST VIRULENT MAREK'S DISEASE VIRUS

| | Marek's Protection | |
|---|---|---|
| Vaccine Group | MD-5 Challenge | RB1B Challenge |
| S-HVT-045 | 20/20 | 24/24 |
| S-HVT-046 | 20/20 | Not Tested |
| S-HVT-047 | Not Tested | 24/24 |

TABLE 6-continued

EFFICACY OF RECOMBINANT HVT/MDV VIRUSES TO
PROTECT SUSCEPTIBLE CHICKS AGAINST VIRULENT
MAREK'S DISEASE VIRUS

| | Marek's Protection | |
|---|---|---|
| Vaccine Group | MD-5 Challenge | RB1B Challenge |
| HVT[a] | Not Tested | 24/25 |
| Controls | 2/20 | 5/24 |

[a]Commercial

Example 6
S-HVT-012

S-HVT-012 is a recombinant herpesvirus of turkeys that contains the E. coli β-galactosidase (lacZ) gene inserted into the short unique region. The lacZ gene was used to determine the viability of this insertion site in HVT [ATCC F-126 ( "Calnek")]. S-HVT-012 has been deposited on Oct. 15, 1992 pursuant to the Budapest Treaty on the International Deposit of Microorganisms for the Purposes of Patent Procedure on with the Patent Culture Depository of the American Type Culture Collection, 12301 Parklawn Drive, Rockville, Md. 20852 U.S.A. under ATCC Accession No. VR 2382.

For insertion into the genome of HVT, the β-galactosidase gene was introduced into the unique StuI site of the cloned EcoRI fragment #7 of HVT, i.e., the fragment containing the StuI site within the US2 gene of HVT (as described in Methods and Materials). Flanking regions of EcoRI fragment #7 were used for homologous recombination. HVT DNA and plasmid DNA were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure, when 100% of the plaques were blue, the DNA was analyzed for the presence of the lacZ gene. S-HVT-012 is a recombinant virus that contains the lacZ gene incorporated into the genome at the StuI site within the US2 gene of HVT. S-HVT-012 may be formulated as a vaccine in the same manner as S-HVT-045. When administered to chickens, such a vaccine provides protection against Marek's disease virus.

Example 7
Sites for Insertion of Foreign DNA into HVT

In order to define appropriate insertion sites, a library of HVT BamHI and EcoRI restriction fragments was generated. Several of these restriction fragments (BaffEI fragments #16 and #13, and EcoRI fragments #6, #7, and #9 (see FIG. 1)) were subjected to restriction mapping analysis. One unique restriction site was identified in each fragment as a potential insertion site. These sites included XhoI in BamHI fragments #13 and #16, and EcoRI fragment #9 and SalI in EcoRI fragment #6 and StuI in EcoRI fragment #7. A β-galactosidase (lacZ) marker gene was inserted in each of the potential sites. A plasmid containing such a foreign DNA insert may be used according to the DNA COTRANSFECTION FOR GENERATING RECOMBINANT HERPESVIRUSES to CONSTRUCT a HVT containing the foreign DNA. For this procedure to be successful it is important that the insertion site be in a region non-essential to the replication of the RVT and that the site be flanked with HVT DNA appropriate for mediating homologous recombination between virus and plasmid DNAs. The plasmids containing the lacZ marker gene were utilized in the DNA COTRANSFECTION FOR GENERATING RECOMBINANT HERPESVIRUSES. The generation of recombinant virus was determined by the BLUOGAL SCREEN FOR RECOMBINANT HERPESVIRUS. Three of the five sites were successfully used to generate a recombinant virus. In each case the resulting virus was easily purified to 100%, clearly defining an appropriate site for the insertion of foreign DNA. The three homology vectors used to define these sites are described below.

Example 7A
Homology Vector 172-29.31

The homology vector 172-29.31 contains the HVT BamHI #16 fragment and is useful for the insertion of foreign DNA into HVT. Plasmid 172-29.31 contains a unique XboI restriction site into which foreign DNA may be cloned. We have demonstrated that the XhoI site in homology vector 172-29.31 may be used to insert foreign DNA into HVT by the construction of at least three recombinant HVT (see examples 1–3).

The homology vector 172-29.31 was further characterized by DNA sequence analysis. The complete sequences of the BamHI #16 fragment was determined. Approximately 2092 base pairs of the adjacent BamHI #13 fragment was also determined (see SEQ ID NO: 3). This sequence indicates that the open reading frame coding for HVT glycoprotein A (gA) spans the BamHI #16 –BamHI #13 junction. The HVT gA gene is homologous to the HSV-1 glycoprotein C (gC). The XhoI site interrupts an ORF which lies directly upstream of the HVT gA gene. This ORF shows amino acid sequence homology to the PRV p43 and the VZV gene 15. The PRV and VZV genes are the homologues of HSV-1 UL43. Therefore we have designated this ORF as HVT UL43 (SEQ ID NO: 5). It should be noted that the HVT UL43 does not exhibit direct homology to HSV-1 UL43. Although HVT UL43 is located upstream of the HVT gC homologue it is encoded on the same DNA strand as HVT gA, where as the HSV-1 UL43 is on the opposite strand relative to HSV-1 gC. The XhoI site interrupts UL43 at approximately amino acid 6, suggesting that the UL43 gene is non-essential for HVT replication.

Example 7B
Homology Vector 435-47.R17

The homology vector 435-47.R17 contains the HVT EcoRI #7 fragment and is useful for the insertion of foreign DNA into HVT. Plasmid 435-47.R17 contains a unique HindIII restriction site into which foreign DNA may be cloned. The HindIII restriction site in plasmid results from the insertion of a HindIII linker into the naturally occurring StuI site of EcoRI fragment #7. We have demonstrated that the HindIII site in homology vector 435-47.R17 may be used to insert foreign DNA into HVT by the construction of at least 25 recombinant HVT.

DNA sequence analysis at the StuI indicated that this fragment contains open reading frames coding for US10, US2, and US3. The StuI site interrupts US2 at approximately amino acid 124, suggesting that the US2 gene is non-essential for HVT replication.

Example 7C
Homology Vector 172-63.1

The homology vector 172-63.1 contains the HVT EcoRI #9 fragment and is useful for the insertion of foreign DNA into HVT. Plasmid 172-63.1 contains a unique xhoI restriction site into which foreign DNA may be cloned. We have demonstrated that the XhoI site in homology vector 172-63.1 may be used to insert foreign DNA into HVT by the construction of S-HVT-014 (see example 8).

Example 8
S-HVT-014

S-HVT-014 is a recombinant herpesvirus of turkeys that contains the E. coli β-galactosidase (lacZ) gene inserted into the long unique region. The lacZ gene was used to determine the viability of this insertion site in HVT [ATCC F-126 ("Calnek")].

For insertion into the genome of HVT, the β-galactosidase gene was introduced into the unique XhoI site of the cloned EcoRI fragment #9 (as described in Methods and Materials). The XhoI site within the EcoRI #9 fragment of the HVT genome is the same site as the XhoI site within the BamHI #10 fragment used for constructing recombinant herpesviruses of turkeys described in Examples 16 through 19. Flanking regions of EcoRI fragment #9 were used for homologous recombination. HVT DNA and plasmid DNA were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure when 100% of the plaques were blue. S-HVT-014 is a recombinant virus that contains the lacZ gene incorporated into the genome at the XhoI site within the EcoRI #9 fragment of HVT.

S-HVT-014 may be formulated as a vaccine in the same manner as S-HVT-045. When administered to chickens, such a vaccine provides protection against Marek's disease virus.

Example 9
S-HVT-005

S-HVT-005 is a recombinant herpesvirus of turkeys that contains the E. coli β-galactosidase (lacZ) gene inserted into the long unique region. The lacZ gene was used to determine the viability of this insertion site in HVT [ATCC F-126 ("Calnek")].

For insertion into the genome of HVT, the β-galactosidase gene was introduced into an approximately 1300 base pair deletion of the XhoI #9 fragment of HVT. The deletion which lies between the unique MluI and EcoRV sites removes the complete coding region of the HVT gA gene (see SEQ ID NO: 3). Flanking regions of XhoI fragment #9 were used for homologous recombination. HVT DNA and plasmid DNA were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure, when 100% of the plaques were blue, the DNA was analyzed for the presence of the lacZ gene. S-HVT-005 is a recombinant virus that contains the lacZ gene incorporated into the genome in place of the deleted gA gene of HVT.

S-HVT-005 may be formulated as a vaccine in the same manner as S-HVT-045. When administered to chickens, such a vaccine provides protection against Marek's disease virus.

Example 10
Marek's Disease Vaccines

Recombinant HVT expressing glycoproteins from Marek's Disease Virus make superior vaccines for Marek's Disease. We have constructed several recombinant HVT expressing MDV glycoproteins: S-HVT-004 (Example 3), S-HVT-045 (Example 5), S-HVT-046 (Example 10A), S-HVT-047 (Example 10B), S-HVT-062 (Example 10C).

Example 10A

S-HVT-046

S-HVT-046 is a recombinant herpesvirus of turkeys that contains the Marek's disease virus (MDV) glycoprotein B (gB) and glycoprotein A (gA) genes inserted into the short unique region. The MDV genes are inserted in the same transcriptional orientation as the US2 gene. The MDV antigens are more likely to elicit the proper antigenic response than the HVT equivalent antigen.

S-HVT-046 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 456-17.22 uncut. Insertion of the appropriate DNA was confirmed by southern blot analysis.

Example 10B

S-HVT-047

S-HVT-047 is a recombinant herpesvirus of turkeys that contains the MDV gB and gA genes inserted into the short unique region. The MDV genes are inserted in the opposite transcriptional orientation as the US2 gene. The MDV antigens are more likely to elicit the proper antigenic response than the HVT equivalent antigen.

S-HVT-047 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 456-17.18 uncut. Insertion of the appropriate DNA was confirmed by southern blot analysis.

Example 10C

S-HVT-062

S-HVT-062 is a recombinant herpesvirus of turkeys that contains the MDV gB, glycoprotein D (gD) and gA genes inserted into the short unique region. The MDV genes are inserted in the same transcriptional orientation as the US2 gene. The MDV antigens are more likely to elicit the proper antigenic response than the HVT equivalent antigen. S-HVT-062 has been deposited on Feb. 23, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2401.

S-HVT-062 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 556-60.6 with BamHI and HindIII, and 456-17.22 uncut. Insertion of the appropriate DNA was confirmed by southern blot analysis.

Testing of Recombinant HVT Expressing MDV Antigens

Two studies were conducted to demonstrate the effectiveness of these recombinant HVT/MDV viruses in protecting against challenge with virulent Marek's disease virus. In Study 1, one-day-old specific pathogen free (SPF) chicks were vaccinated with either S-HVT-045, S-HVT-046, or S-HVT-047. Five days post-vaccination, vaccinated chicks, and non-vaccinated, control chicks were challenged with MDV. Following a 6-week post-challenge observation period for clinical signs typical of Marek's disease, all chicks were necropsied and examined for lesions diagnostic of Marek's disease. The results, in Table 7, show these recombinant viruses gave complete protection against a challenge that caused Marek's disease in 84% of non-vaccinated control chicks.

In the second study, one-day-old chicks were vaccinated with S-HVT-062. Two more groups of chicks were vaccinated with a USDA-licensed, conventional vaccines comprised of HVT and a combination HVT and SB-1 viruses. Five days post-vaccination, the vaccinated chicks and a group of non-vaccinated, control chicks were challenged with MDV. The chicks were observed for 8 weeks for clinical signs of Marek's disease, then necropsied and observed for Marek's lesions. This study demonstrated the ability of S-HVT-062 to provide 100% protection against challenge (Table 7). The commercial vaccines gave 81% and 95% protection, respectively and 100% of the non-vaccinated chicks developed Marek's disease.

TABLE 7

EFFICACY OF RECOMBINANT HVT/MDV VIRU9SES AGAINST VIRULENT MAREK'S VIRUS CHALLENGE

| Study | Vaccine Group | Dose[a] | Protection[b] |
|---|---|---|---|
| 1 | S-HVT-045 | $2.2 \times 10^3$ | 24/24 (100%) |
| 1 | S-HVT-046 | $2.2 \times 10^3$ | 20/20 (100%) |
| 1 | S-HVT-047 | $2.2 \times 10^3$ | 24/24 (100%) |
| 1 | Controls | | 7/44 (16%) |
| 1 | HVT/SB-1 | | 24/25 (96%) |
| 2 | S-HVT-062 | $7.5 \times 10^2$ | 32/32 (100%) |
| 2 | S-HVT-062 | $1.5 \times 10^3$ | 22/22 (100%) |
| 2 | Controls | | 0/20 (0%) |
| 2 | HVT[c] | $7.5 \times 10^2$ | 17/21 (81%) |
| 2 | HVT/SB-1[c] | $7.5 \times 10^2$ | 21/22 (95%) |

[a]PFU/0.2 ml.
[b]No. protected/Total; Challange 5 days post-vaccination.
[c]Commercial vaccine.

Example 11
Bivalent Vaccines Against Newcastle Disease and Marek's Disease

Recombinant HVT expressing proteins from NDV make bivalent vaccines protecting against both Marek's Disease and Newcastle disease. We have constructed several recombinant HVT expressing NDV proteins S-HVT-007 (Example 11A), S-HVT-048 (Example 11B), S-HVT-049 (Example 11C), S-HVT-050 (Example 11D), and S-HVT-106 (Example 11E).

Example 11A
S-HVT-007

S-HVT-007 is a recombinant herpesvirus of turkeys that contains a E. coli lacZ NDV HN hybrid protein gene under the control of the PRV gX promoter and the NDV F gene under the control of the HSV-1α4 promoter inserted into the long unique region. The NDV genes are inserted in the same transcriptional orientation as the UL43 gene.

To construct S-HVT-007, HVT DNA and the plasmid 255-18.B16 were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure, when 100% of the plaques were blue.

Example 11B
S-HVT-048

S-HVT-048 is a recombinant herpesvirus of turkeys that contains the MDV gB and gA genes and the NDV F gene under the control of the HCMV immediate early promoter inserted into the short unique region. The MDV and NDV genes are inserted in the same transcriptional orientation as the US2 gene.

S-HVT-048 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 535-70.3 uncut. Insertion of the appropriate DNA was confirmed by southern blot analysis.

Example 11C
S-HVT-049

S-HVT-049 is a recombinant herpesvirus of turkeys that contains the MDV gB and gA genes and the NDV HN gene under the control of the PRV gX promoter inserted into the short unique region. The MDV and NDV genes are inserted in the same transcriptional orientation as the US2 gene.

S-HVT-049 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 549-62.10 uncut. Insertion of the appropriate DNA was confirmed by southern blot analysis.

Example 11D
S-HVT-050

S-HVT-050 is a recombinant herpesvirus of turkeys that contains the MDV gB and gA genes and the NDV HN (SEQ ID NOs: 10 and 11) and F (SEQ ID NOs: 12 and 13) genes. The NDV genes are under the control of the PRV gX and HCMV immediately promoters respectively. All four genes are inserted into the short unique region in the same transcriptional orientation as the US2 gene.

S-HVT-050 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 549-24.15 uncut. Insertion of the appropriate DNA was confirmed by southern blot analysis. S-HVT-050 has been deposited on Feb. 23, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2400.

Example 11E
S-HVT-106

S-HVT-106 is a recombinant herpesvirus of turkeys that contains the MDV gA, gB, gD genes and the NDV HN and F genes. The NDV genes are under the control of the PRV gX and HCMV immediately promoters respectively. All five genes are inserted into the short unique region in the same transcriptional orientation as the US2 gene.

S-HVT-106 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 633-13.27 uncut.

Testing of Recombinant HVT Expressing NDV Antigens

Two studies were conducted to demonstrate the effectiveness of these recombinant HVT/MDV/NDV viruses in protecting against challenge with virulent Newcastle and Marek's disease viruses. In Study 1, one-day-old specific pathogen free (SPF) chicks were vaccinated with either S-HVT-048, S-HVT-049, S-HVT-050, or a USDA-licensed, conventional vaccine comprised of NDV B1/B1 virus. Three weeks post-vaccination, vaccinated chicks, and non-vaccinated, control chicks were challenged with NDV. Birds were then observed for clinical signs of disease. The results, in Table 8, show these recombinant viruses (S-HVT-048 and S-HVT-050) gave complete protection against a challenge that caused Newcastle disease in 100% of non-vaccinated control chicks. Recombinant virus S-HVT-049 gave partial protection against Newcastle disease.

In the second study, one-day-old chicks were vaccinated with S-HVT-050. Two more groups of chicks were-vaccinated with a USDA-licensed, conventional vaccines comprised of HVT and a combination HVT and SB-1 viruses. Five days post-vaccination, the vaccinated chicks and a group of non-vaccinated, control chicks were challenged with MDV. The chicks were observed for 8 weeks for clinical signs of Marek's disease, then necropsied and observed for Marek's lesions. This study demonstrated the ability of S-HVT-050 to provide protection greater than the commercial Marek's disease vaccines.

TABLE 8

EFFICACY OF RECOMBINANT HVT/MDV/NDV VIRUSES AGAINST VIRULENT NEWCASTLE AND MAREK'S DISEASE VIRUS CHALLENGE

| Study | Vaccine Group | Dose[a] | Protection (%) NDV[b] | MDV[c] |
|---|---|---|---|---|
| 1 | S-HVT-048 | $4.0 \times 10^4$ | 19/19 (100) | |
| 1 | S-HVT-049 | $3.0 \times 10^4$ | 4/20 (20) | |
| 1 | S-HVT-050 | $1.5 \times 10^4$ | 20/20 (100) | |
| 1 | Controls | | 0/20 (0) | |
| 1 | NDV B1/B1[d] | | 18/18 (100) | |
| 2 | S-HVT-050 | $7.5 \times 10^2$ | | 13/14 (93) |
| 2 | S-HVT-050 | $1.5 \times 10^3$ | | 16/17 (94) |
| 2 | Controls | | | 5/23 (22) |
| 2 | HVT[d] | | | 20/26 (77) |
| 2 | HVT/SB-1[d] | | | 10/12 (83) |

[a]PFU/0.2 ml.
[b]No. protected/Total; Challenge 3 weeks post-vaccination.
[c]No. protected/Total; Challenge 5 days post-vaccination.
[d]Commercial vaccine.

Example 12
Bivalent Vaccines Against Infectious Laryngotracheitis and Marek's Disease Recombinant HVT expressing glycoproteins from ILT virus make bivalent vaccines protecting against both Marek's disease and infectious laryngotracheitis. We have constructed several recombinant HVT expressing ILT virus glycoproteins S-HVT-051 (Example 12A), S-HVT-052 (Example 12B), and S-HVT-104 (Example 11C).

Example 12A

S-HVT-051

S-HVT-051 is a recombinant herpesvirus of turkeys that contains the ILT virus gB gene inserted into the short unique region. The ILT gene is inserted in the same transcriptional orientation as the US2 gene.

S-HVT-051 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 528-11.34 uncut. Insertion of the appropriate DNA was confirmed by southern blot analysis.

Example 12B

S-HVT-052

S-HVT-052 is a recombinant herpesvirus of turkeys that contains the ILT virus gD gene inserted into the short unique region. The ILT gene is inserted in the opposite transcriptional orientation as the US2 gene.

S-HVT-052 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 528-03.37 uncut. Insertion of the appropriate DNA was confirmed by southern blot analysis.

Example 12C

S-HVT-104

S-HVT-104 is a recombinant herpesvirus of turkeys that contains six foreign genes. The MDV gA, gB, and gD genes are inserted in the unique short region in the same transcriptional orientation as the US2 gene. An E. coli lacZ marker gene and the ILT gB and gD-genes are inserted in BamHI #16 region in the same transcriptional orientation as the UL43 gene.

To construct S-HVT-104, DNA from S-HVT-062 and the plasmid 634-29.16 were co-transfected according to the DNA TRANSFECTION FOR GENERATING RECOMBINANT VIRUS procedure into primary chick embryo fibroblast (CEF) cells.

Testing of Recombinant HVT Expressing ILT Antigens

The following study was conducted to demonstrate the effectiveness of these recombinant HVT/ILT viruses in protecting against challenge with virulent Infectious Laryngotracheitis virus. One-day-old specific pathogen free (SPF) chicks were vaccinated with either S-HVT-051, S-HVT-052, a combination of S-HVT-051 and S-HVT-052, or a USDA-licensed, conventional vaccine comprised of ILT virus. Two to three weeks post-vaccination, vaccinated chicks, and non-vaccinated, control chicks were challenged with ILT. Birds were then observed for clinical signs of disease. The results, in Table 9, show these recombinant viruses (S-HVT-051 and S-HVT-052) gave protection against challenge with ILT virus comparable to a commercial ILT vaccine.

Animals vaccinated with the vaccines described here may be easily differentiated from animals infected with virulent ILT. This is accomplished by testing the suspect birds for antibodies to any ILT antigens other than gB or gD.

Examples of such antigens are ILT glycoproteins C, E, and G. Vaccinated, uninfected birds will be negative for these antigens whereas infected birds will be positive.

TABLE 9

EFFICACY OF RECOMBINANT HVT/ILT VIRUSES AGAINST VIRULENT INFECTIOUS LARYNGOTRACHEITIS VIRUS CHALLENGE

| Vaccine Group | Dose[a] | Protection[b] |
|---|---|---|
| S-HVT-051 | $2.1 \times 10^3$ | 28/30 (93%) |
| S-HVT-052 | $1.7 \times 10^3$ | 29/29 (100%) |
| S-HVT-051 + S-HVT-052 | $2.1 \times 10^3$ $1.7 \times 10^3$ | 24/24 (100%) |
| Controls | | 2/30 (7%) |
| ILT[c] | | 29/30 (97%) |

[a]PFU/0.2 ml.
[b]No. protected/Totals; Challenge 2–3 weeks post-vaccination.
[c]Commercial vaccine.

Example 13
Bivalent Vaccines Against Infectious Bursal Disease and Marek's Disease Recombinant HVT expressing proteins from IBDV make bivalent vaccines protecting against both Marek's Disease and infectious bursal disease. We have constructed several recombinant HVT expressing IBDV proteins. These viruses include S-HVT-003 (example 2) and S-HVT-096.

S-HVT-096 is a recombinant herpesvirus of turkeys that contains the IBDV VP2 gene, under the control of the HCMV immediate early promoter, inserted into the short unique region. The IBDV gene is inserted in the same transcriptional orientation as the US2 gene.

S-HVT-096 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 556-60.6 with BamHI, and 602-57.F1 uncut. Insertion of the appropriate DNA was confirmed by southern blot analysis.

S-HVT-096 was assayed for expression of VP2 by black plaque and western blot analysis. Both assays indicated that the virus was expressing high levels of protein which reacts specifically with an IBDV neutralizing monoclonal antibody. This virus will be useful as a vaccine against infectious bursal disease.

Example 14
Bivalent Vaccines Against Infectious Bronchitis and Marek's Disease

S-HVT-066 is a recombinant herpesvirus of turkeys that contains the MDV gB, gD and gA genes and the IBV spike and matrix genes. The IBV spike and matrix genes are under the control of the HCMV immediate early and PRV gX promoters respectively. All five genes are inserted into the short unique region. The MDV and IBV genes are inserted in the same transcriptional orientation as the US2 gene.

S-HVT-066 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 556-60.6 with BamHI, and 567-72.1D uncut. Insertion of the appropriate DNA was confirmed by southern blot analysis.

S-HVT-066 was assayed for expression of the IBV spike protein by black plaque and western blot analysis. Both assays indicated that the virus was expressing high levels of protein which reacts specifically with an IBV neutralizing monoclonal antibody. This virus will be useful as a vaccine against infectious bronchitis.

Example 15
Vaccines utilizing HVT to express antigens from various pathogens.

We also anticipate that antigens from the following pathogens may also be utilized to develop poultry vaccines: Chick anemia agent, Avian encephalomyelitis virus, Avian reovirus, Avian paramyxoviruses, Avian influenza virus, Avian adenovirus, Fowl pox virus, Avian coronavirus, Avian rotavirus, *Salmonella spp E. coli, Pasteurella spp, Haemophilus spp, Chlamydia spp, Mycoplasma spp, Campylobacter spp, Bordetella spp*, Poultry nematodes, cestodes, trematodes, Poultry mites/lice, Poultry protozoa (*Eimeria spp, Histomonas spp, Trichomonas spp*).

Example 16

Trivalent vaccines against Infectious Laryngotracheitis, Marek's Disease and Newcastle's Disease and bivalent vaccines against Infectious Laryngotracheitis and Marek's Disease are described. Superior protection against Infectious Laryngotracheitis is achieved with a vaccine combining S-HVT-123 (expressing ILTV gB and gD) with S-HVT-138, -139, or 140 (expressing ILTV gD and gI).

Example 16A
S-HVT-123

S-HVT-123 is a recombinant herpesvirus of turkeys that contains the ILT virus gB and gD genes inserted into a unique XhoI site converted to a NotI site in the BamHI #10 fragment of the HVT genome (FIGS. 13B and 15; SEQ ID NO. 48). S-HVT-123 further contains the MDV gA, gD, and gB genes inserted into a unique StuI site converted into a HindIII Site in the HVT US2 gene. The ILTV genes and the MDV genes each use their own respective promoters. S-HVT-123 is useful as a vaccine in poultry against Infectious Laryngotracheitis and Marek's Disease.

S-HVT-123 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 721-38.1J uncut, 729-37.1 with AscI.

Example 16B
S-HVT-138

Figure 14:
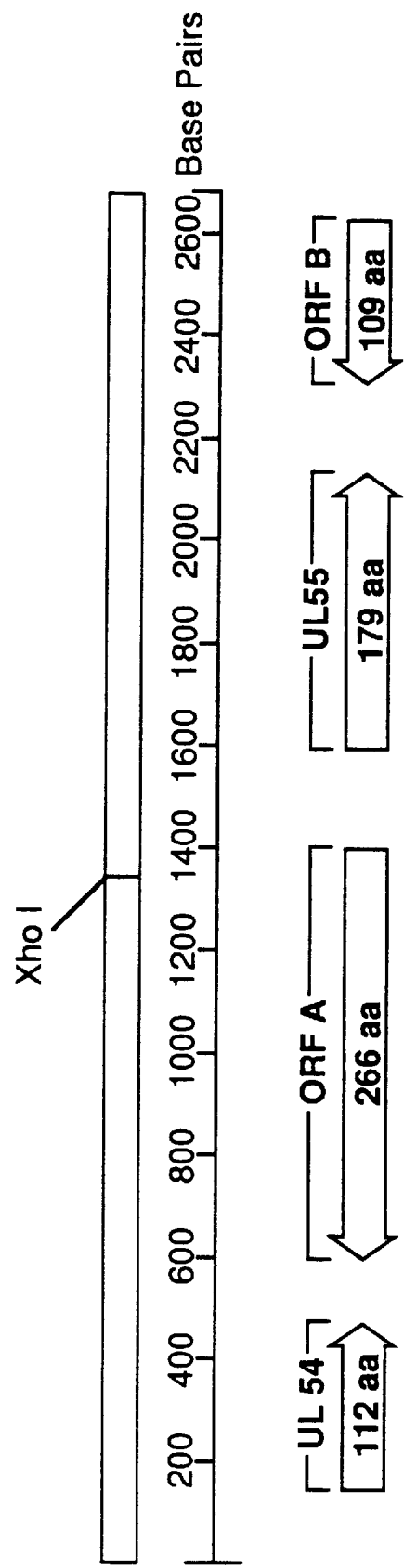
FIG. 14 shows a restriction map and open reading frames of the sequence surrounding the insertion site within the unique long of HVT (SEQ ID NO. 48). This map shows the XhoI restriction site (SEQ ID NO. 48; Nucl. 1333–1338) used for insertion of foreign genes. Also shown are four open reading frames within this sequence. ORF A is interrupted by insertion of DNA into the XhoI site. The ORF A amino acid sequence (SEQ ID NO. 50; Nucl. 1402 to 602; 267 amino acids) shows no significant sequence identity to any known amino acid sequence in the protein databases. UL 54 (SEQ ID NO. 49; Nucl. 146 to 481; 112 amino acids) and UL55 (SEQ ID NO. 51; Nucl. 1599 to 2135; 179 amino acids) show significant sequence identity to the herpes simplex virus type I UL54 and UL55 proteins, respectively. ORF B (SEQ ID NO. 52; Nucl. 2634 to 2308; 109 amino acids) shows no significant sequence identity to any known amino acid sequence in the protein databases. Searches were performed on NCBI databases using Blast software.

S-HVT-138 is a recombinant herpesvirus of turkeys that contains the ILT virus gD and gI genes inserted into a unique xhoI site converted to a PacI site in the BamHI #10 fragment of the HVT genome (FIGS. 13A and 15). The ILTV gD and gI genes are in the opposite transcriptional orientation to the open reading frame (ORF A) within the BamHI #10 fragment of the HVT genome (FIG. 14; SEQ ID NO. 48, 50). The ILTV gD and gI genes are expressed as overlapping transcripts from their own respective endogenous ILTV promoters, and share their own endogenous polyadenylation signal.

S-HVT-138 is useful as a vaccine in poultry against Infectious Laryngotracheitis and Marek's Disease.

S-HVT-138 was constructed according to the PROCEDURE FOR GENERATING RECOMBINANT HERPES- VIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 711-92.1A uncut, 415-09.BA1 with BamHI.

Example 16C

S-HVT-139

S-HVT-139 is a recombinant herpesvirus of turkeys that contains the ILT virus gD and gI genes inserted into a unique XhoI site converted to a PacI site in the BamHI #10 fragment of the HVT genome. The ILTV gD and gI genes are in the opposite transcriptional orientation to the open reading frame (ORF A) within the BamHI #10 fragment of the HVT genome (FIGS. 13A and 15; SEQ ID NO. 48, 50). S-HVT-139 further contains the MDV gA, gD, and gB genes inserted into a unique StuI site converted into a HindIII site in the HVT US2 gene. The ILTV gD and gI genes are expressed as overlapping transcripts from their own respective endogenous ILTV promoters, and the MDV genes are also expressed from their own endogenous promoters. S-HVT-139 is useful as a vaccine in poultry against Infectious Laryngotracheitis and Marek's Disease.

S-HVT-139 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 711-92.1A uncut, 721-38.1J uncut.

Example 16D

S-HVT-140

S-HVT-140 is a recombinant herpesvirus of turkeys that contains the ILT virus gD and gI genes inserted into a unique XhoI site converted to a PacI site in the BamHI #10 fragment of the HVT genome (FIGS. 13A and 15). The ILTV gD and gI genes are in the opposite transcriptional orientation to the open reading frame (ORF A) within the BamHI #10 fragment of the HVT genome (FIG. 14; SEQ ID NO. 48, 50). S-HVT-140 further contains the MDV gA, gD, and gB genes and the NDV F and HN genes inserted into a unique StuI site converted into a HindIII site in the HVT US2 gene. The ILTV gD and gI genes are expressed as overlapping transcripts from their own respective endogenous ILTV promoters, and the MDV genes are also expressed from their own respective endogenous MDV promoters. The NDV F gene is transcribed from the HCMV immediate early promoter, and the NDV HN gene is transcribed from the PRV gX promoter. S-HVT-140 is useful as a vaccine in poultry against Infectious Laryngotracheitis, Marek's Disease, and Newcastle's Disease.

S-HVT-140 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with Not5I, 172-07.BA2 with BamHI, 407-32.5G6 with NotI, 672-07.C40 with NotI, 672-01.A40 with NotI, 711-92.1A uncut, 722-60.E2 uncut.

Example 17

Trivalent vaccines against Infectious Bursal Disease, Marek's Disease and Newcastle's Disease and bivalent vaccines against Infectious Bursal Disease and Marek's Disease are described.

Example 17A

S-HVT-126

S-HVT-126 is a recombinant herpesvirus of turkeys that contains the IBDV VP2 gene inserted into a unique XhoI site converted to a PacI site in the BamHI #10 fragment in the HVT genome (FIGS. 13A and 15). The IBDV gene is in the same transcriptional orientation as the open reading frame (ORF A) within the BamRI #10 fragment of the HVT genome (FIG. 14; SEQ ID NO. 48, 50). The IBDV VP2 gene is expressed from an IBRV VP8 promoter. S-HVT-126 is useful as a vaccine in poultry against Infectious Bursal Disease and Marek's Disease.

S-HVT-126 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 706-57.A3 uncut, 415-09.BA1 with BamHI.

Example 17B

S-HVT-137

S-HVT-137 is a recombinant herpesvirus of turkeys that contains the IBDV VP2 gene inserted into a unique XhoI site converted to a PacI site in the BamHI #10 fragment in the HVT genome (FIGS. 13A and 15). The IBDV gene is in the same transcriptional orientation as the open reading frame (ORF A) within the BamRI #10 fragment of the HVT genome (FIG. 14; SEQ ID NO. 48, 50). S-HVT-137 further contains the MDV gA, gD, and gB genes inserted into a unique StuI site converted into a HindIII site in the HVT US2 gene. The IBDV VP2 gene is expressed from an IBRV VP8 promoter. The MDV genes are expressed from their own respective endogenous MDV promoters. S-HVT-137 is useful as a vaccine in poultry against Infectious Bursal Disease and Marek's Disease.

S-HVT-137 was constructed according to the PROCEDURE FUR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 706-57.A3 uncut, 721-38.1J uncut.

Example 17C

S-HVT-143

S-HVT-143 is a recombinant herpesvirus of turkeys that contains the IBDV VP2 gene inserted into a unique XhoI site converted to a PacI site in the BamHI #10 fragment of the HVT genome (FIGS. 13A and 15). The IBDV gene is in the same transcriptional orientation as the open reading frame (ORF A) within the BamHI #10 fragment of the HVT genome (FIG. 14; SEQ ID NO. 48, 50). S-HVT-143 further contains the MDV gA, gD, and gB genes and the NDV F and HN genes inserted into a unique StuI site converted into a HindIII site in the HVT US2 gene. The IBDV VP2 gene is expressed from an IBRV VPS promoter. The MDV genes are expressed from their own respective endogenous MDV promoters. The NDV F gene is transcribed from the HCMV immediate early promoter, and the NDV HN gene is transcribed from the PRV gX promoter. S-HVT-143 is useful as a vaccine in poultry against Infectious Bursal Disease, Marek's Disease, and Newcastle's Disease.

S-HVT-143 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with Ba HI, 407-32.5G6 with NotI, 672-07.C40 with NotI, 672-01.A40 with NotI, 706-57.A3 uncut, 722-60.E2 uncut Example 18

S-HVT-128

S-HVT-128 is a recombinant herpesvirus of turkeys that contains the NDV HN and F genes inserted into a unique XhoI site converted to a PacI site in the BamHI #10 fragment of the HVT genome (FIGS. 13A and 15). S-HVT-128 further contains the MDV gA, gD, and gB genes inserted into a unique StuI site converted into a HindIII site in the HVT US2 gene. The NDV HN gene is expressed from the PRV gX promoter and the NDV F gene is expressed from the HCMV immediate early promoter. The MDV genes are expressed from their own respective endogenous MDV promoters. S-HVT-128 is useful as a vaccine in poultry against Newcastle's Disease and Marek's Disease.

S-HVT-128 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, and 717-38.12 uncut. To a mixture of these six cosmids was added a limiting dilution of a recombinant HVT virus containing the MDV gA, gD, and gB genes inserted into the unique short region (see HVT-062) and the PRV gX promoter-lacZ gene inserted into an XhoI site converted to a NotI site in the BamHI #10 fragment within the unique long region of HVT. A recombinant virus S-HVT-128 was selected which was lac Z negative.

Example 19

HVT/MDV recombinant virus vaccine

A recombinant virus vaccine containing MDV and HVT genomic sequences which protects against Marek's disease is produced by combining cosmids of MDV genomic DNA containing genes coding for the relevant protective antigens of virulent MDV serotype 2 and cosmids of HVT genomic DNA according to the PROCEDURE FOR GENERATING RECOMBINANT HERPESVIRUS FROM OVERLAPPING SUBGENOMIC FRAGMENTS. The resulting virus is a vaccine that has the protective immune response to virulent MDV serotype 2 and the attenuated growth characteristics of the HVT. In one embodiment, a chimeric virus vaccine containing the MDV genes of the unique short and the HVT genes of the unique long is useful as a vaccine against Marek's disease in chickens. The MDV protective antigens within the unique short (gD, gE, and gI) elicit a protective immune response to MDV, while the virulence elements present in the unique long of MDV (55, 56, 57) are replaced by the attenuating unique long sequences of HVT. The result is an attenuated virus vaccine which protects against Marek's disease. Multivalent protection against Marek's disease, infectious laryngotracheitis, infectious bursal disease, Newcastle's disease, or another poultry pathogen is achieved by inserting the ILTV gB, gD, and gI genes, the IBDV VP2 gene, the NDV HN and F genes, or an antigen gene from a poultry pathogen into an XhoI site converted to a PacI site or NotI site in the B #10 fragment within the unique long region of HVT/MDV recombinant virus (FIGS. 13 and 15).

A cosmid was constructed containing the entire MDV unique short region. MDV genomic DNA contains several SmaI sites in the unique long and internal and terminal repeats of the virus, but no SmaI sites within the unique short of the virus. The entire unique short region of MDV was isolated by a partial restriction digestion of MDV genomic DNA with SmaI. A DNA fragment approximately 29,000 to 33,000 base pairs was isolated and cloned into a blunt ended site of the cosmid vector pWE15. To generate a recombinant HVT/MDV chimeric virus, the cosmid containing the MDV unique short region is combined with cosmids containing the HVT unique long region according to the PROCEDURE FOR GENERATING RECOMBINANT HERPESVIRUS FROM OVERLAPPING SUBGENOMIC FRAGMENTS. The following combination of subgenomic clones and enzymes are used: 407-32.2C3 with NotI, 172-07.BA2 with BamHI, 407-32.5G6 with NotI, 407-32.1C1 with NotI, and 739-27.16 with NotI.

The resulting virus vaccine provides superior protection against Marek's disease or as a multivalent vaccine against Marek's disease and infectious laryngotracheitis, infectious bursal disease, Newcastle's disease, or another poultry pathogen. This vaccine is superior because expression of MDV genes in the HVT/MDV chimera vaccine is safer and provides better protection against Marek's disease than vaccines presently available containing HVT and MDV type 1 (SB-1) or HVT alone. Secondly, one can demonstrate expression of the MDV glycoprotein genes in the absence of the homologous HVT genes for both diagnostic and regulatory purposes. This is useful since antibodies to an MDV glycoprotein will cross react with the homologous HVT glycoprotein. Finally, a recombinant HVT/MDV virus which contains a single copy of each glycoprotein gene is more stable that a recombinant virus containing two copies of a homologous glycoprotein gene from HVT and MDV which may delete by homologous recombination.

In an alternative embodiment, cosmids containing MDV protective antigen genes from the unique long (MDV gB and gC) are combined with cosmids containing HVT gene sequences from the unique short and the unique long, effectively avoiding the MDV virulence genes at the unique long/internal repeat junction and the unique long/terminal repeat junction (55, 56, and 57).

SB-1 strain is an MDV serotype 1 with attenuated pathogenicity. Vaccination with a combination of HVT and SB-1 live viruses protects against virulent MDV challenge better than vaccination with either virus alone. In an alternative embodiment of the present invention, a recombinant virus vaccine comprises the protective antigen genes of the virulent MDV serotype 2 combined with the attenuating genes of the non-virulent MDV serotypes 1 and 3, such as SB-1 and HVT. The genomic DNA corresponding to the unique long region of the recombinant virus is contributed by the SB-1 serotype. The genomic DNA corresponding to the unique short region is contributed by the HVT serotype. Three major glycoprotein antigens (gB, gA and gD) from the MDV serotype 2 are inserted into the unique short region of the virus.

The recombinant virus is constructed utilizing HVT subgenomic clones 672-01.A40, 672-07.C40 and 721-38.1J to reconstruct the unique short region. Subgenomic clone 721-38.1J contains an insertion of the MDV gB, gA, and gD genes. A large molar excess of these clones is cotransfected with a sub-infectious dose of SB-1 genomic DNA. To determine the appropriate sub-infectious dose, transfection of the SB-1 is titrated down to a dose which no longer yields virus plaques in cell culture. Such a dose contains subgenomic fragments spanning the unique long region of SB-1 which recombine with the HVT unique short subgenomic clones. Therefore, a virus resulting from recombination between overlapping homologous regions of the SB-1 and HVT subgenomic fragments is highly favored. Alternatively, SB-1 genomic fragments from the unique long region are subcloned into cosmid vectors. A recombinant virus containing the SB-1 unique long and the HVT unique short with the MDV, gB, gA, and gD genes is produced using the PROCEDURE FOR GENERATING RECOMBINANT HERPESVIRUS FROM OVERLAPPING SUBGENOMIC FRAGMENTS. This procedure is also used with an HVT subgenomic clone to insert antigen genes from other avian pathogens including but not limited to infectious laryngotracheitis virus, Newcastle's disease virus and infectious bursal disease virus.

References

1. Buckmaster et al., *J. Gen. Virol.* 69:2033, 1988.
2. F. A. Ferrari et al., *Journal of Bacteriology* 161, 556–562, 1985.
3. U. Gubler and B. J Hoffman, *Gene* 25, 263–269.
4. D. Hanahan, *Molecular Biology* 166, 557–580, 1983.
5. P. J. Hudson et al., *Nucleic Acid Research* 14, 5001–5012, 1986.
6. T. Igarashi et al., 10th *International Herpesvirus Workshop*, Abstract No. 17, Ann Arbor, Mich., Aug. 1985.
7. T. Ihara et al., *Virus Genes* 3, 127–140, 1989.
8. M. A. Innis et al., *PCR Protocols A Guide to Methods and Applications*, 84–91, Academic Press, Inc., San Diego, 1990.
9. R. J. Isfort et al., 9th *International Herpesvirus Workshop*, Abstract No. 146, Seattle, Wash., Aug. 1984.
10. M. N. Jagadish et al., *J. of Virol.* 62, 1084–1087, 1988.
11. Kawai and Nishizawa Mol. and *Cell Bio.* 4, 1172–1174, 1984.
12. B. Lomniczi et al., *Journal of Virology* 49, 970–979 1984.
13. Maniatis et al., *Molecular Cloning*, Cold Spring Harbor Laboratory, New York, 1982.
14. D. J. McGeoch et al., *Journal of Molecular Biology* 181, 1–13, 1985.
15. S. L. McKnight and R. Kingsbury, *Science* 217, 316–324, 1982.
16. L. J. N. Ross et al., *Journal of General Virology* 70, 1789–1804, 1989.
17. L. J. N. Ross et al., *Journal of General Virology* 72, 949–954, 1991.
18. J. Sambrook et al., *Molecular Cloning A Laboratory Manual Second Edition*, Cold Spring Harbor Press, 1989.
19. M. Zijil et al., *Journal of Virology* 62, 2191–2195, 1988.
20. Mariatis et al., *Intervirology* 16, 201–217, 1981.
21. S. L. Mansour et al., *Proc. Natl. Acad. Sci. USA* 82, 1359–1363, 1985.
22. C. Thummel et al., *Cell* 33, 455–464, 1983.
23. D. Scolnick, *Cell* 24, 135–143, 1981.
24. C. Thummel et al., *Cell* 23, 825–836, 1981.
25 Y. Haj-Ahmed and F. L. Graham, *J. of Virology* 57, 267–274, 1986.
26. M. Mackett et al., *Proc. Natl. Acad. Sci. USA* 79, 7415–7419, 1982.
27. D. Panicali and E. Paoletti, *Proc. Natl. Acad. Sci. USA* 79, 4927–4931, 1982.
28. E. Paoletti et al., *Proc. Natl. acad. Sci. USA* 81, 193–197, 1984.
29. G. L. Smith et al., *Nature* 302, 490–495, 1983.
30. J. H. Gillespie et al., *J. Clin. Microbiology* 23, 283–288, 1986.
31. D. Panicali et al., *Proc. Natl. Acad. Sci. USA* 80, 5364–5368, 1983.
32. G. L. Smith et al., *Proc. Natl. Acad. Sci. USA* 80, 7155–7159, 1983.
33. G. L. Smith et al., *Science* 224, 397–399, 1984.
34. M. Mackett et al., *Science* 227, 433–435, 1985.
35. E. S. Moccarski et al., *Cell* 22, 243–255, 1980.
40. L. E. Post and B. Roizman, *Cell* 25, 227–232, 1981.
41. K. L. Poffenberger et al., *Proc. Natl. Acad. Sci. USA* 80, 2690–2694, 1981.
42. M. G. Gibson and P. G. Spear, *Journal of Virology* 48, 396–404, 1983.
43. G. T.-Y. Lee et al., *Proc. Natl. Acad. Sci. USA* 79, 6612–6616, 1982.
44. M.-F. Shih et al., *Proc. Natl. Acad. Sci. USA* 81, 5867–5870, 1984.
45. R. Desrosiers et al., *Ninth Annual Herpesvirus Meeting*, Seattle, Abstract #280, 1984.
46. M. Arsenakis and B. Roizman, in "The High Technology Route to Virus Vaccines", American Society for Microbiology, Washington D.C., 1985 (Proceedings of the First Annual Southwest Foundation for Biomedical Research International Symposium, Houston, Texas, 8–10 Nov. 1984).
47. L. E. Post et al., *Tenth International Herpesvirus Workshop*, Ann Arbor, Aug. 1985.
48. S. B. Mohanty and S. K. Dutta, *Veterinary Virology*, Lea and Febiger, pubs., Philadelphia, 1981.
49. A. M. Griffin, *Journal of General Virology* 72, 393–398, 1991.
50. D. R. Thomsen et al., *Gene* 16, 207–217, 1981.
51. Carpenter, D. E. and Misra, V. *Journal of General Virology* 72 3077–3084, 1991.
52. Kibenge, F. S., Jackwood, D. J., Mercado, C. C., *Journal of General Virology* 71 569–577, 1990.
53. Fukuchi et al., *Journal of Virology* 51 102–109, 1984.
54. Fukuchi et al., *Journal of Virology* 53 994–997, 1985.
55. Ross, N., et al., Virus *Genes* 7: 33–51, 1993.
56. Maotani, K. A., et al., journal of Virology 58: 657–659, 1986.
57. Ross, L. J. N., et al., *Journal of General Virology* 64:2785–2790, 1983.

What is claimed is:

1. A recombinant herpesvirus of turkeys comprising a foreign DNA inserted into a herpesvirus of turkeys genome, wherein the foreign DNA is inserted within a region which corresponds to an EcoR1 #9 fragment of the herpesvirus of turkeys genome, and is capable of being expressed in a host cell into which the virus is introduced.

2. The recombinant herpesvirus of turkeys of claim 1, wherein the foreign DNA is inserted within Open Reading Frame A (ORF A) of the EcoR1 #9 fragment.

3. The recombinant herpesvirus of turkeys of claim 1, wherein the foreign DNA is inserted within a XhoI site of the region which corresponds to the EcoR1 #9 fragment.

4. The recombinant herpesvirus of turkeys of claim 1, wherein the foreign DNA encodes a polypeptide.

5. The recombinant herpesvirus of turkeys of claim 1, wherein the foreign DNA encodes *E. coli* beta-galactosidase.

6. The recombinant herpesvirus of turkeys of claim 4, wherein the polypeptide is from Marek's Disease Virus, Newcastle Disease Virus, Infectious Laryngotracheitis Virus, Infectious Bronchitis Virus and Infectious Bursal Disease Virus.

7. The recombinant herpesvirus of turkeys of claim 6, wherein the polypeptide is Marek's Disease Virus glycoprotein A, Marek's Disease Virus glycoprotein B, or Marek's Disease Virus glycoprotein D.

8. The recombinant herpesvirus of turkeys of claim 6, wherein the polypeptide is Newcastle Disease virus fusion protein or Newcastle Disease virus hemagglutinin-neuraminidase.

9. The recombinant herpesvirus of turkeys of claim 6, wherein the polypeptide is Infectious Laryngotracheitis Virus glycoprotein B, Infectious Laryngotracheitis Virus glycoprotein I, or Infectious Laryngotracheitis Virus glycoprotein D.

10. The recombinant herpesvirus of turkeys of claim 6, wherein the polypeptide is Infectious Bronchitis Virus spike protein or Infectious Bronchitis Virus matrix protein.

11. The recombinant herpesvirus of turkeys of claim 6, wherein the polypeptide is Infectious Bursal Disease Virus VP2, Infectious Bursal Disease Virus VP3 or Infectious Bursal Disease Virus VP4.

12. The recombinant herpesvirus of turkeys of claim 1, wherein the foreign DNA is under the control of a herpesvirus promoter.

13. The recombinant herpesvirus of turkeys of claim 1, wherein the foreign DNA is under the control of a heterologous promoter.

14. The recombinant herpesvirus of turkeys of claim 12, wherein the promoter is Pseudorabies Virus glycoprotein X promoter, Herpes Simplex Virus-1 alpha 4 promoter, Human Cytomegalovirus Immediate Early promoter, Marek's Disease Virus glycoprotein A promoter, Marek's Disease Virus glycoprotein B promoter, Marek's Disease Virus glycoprotein D promoter, Infectious Laryngotracheitis Virus glycoprotein B promoter, Bovine Herpesvirus 1.1 VP8 promoter, or Infectious Laryngotracheitis Virus glycoprotein D promoter.

15. The recombinant virus of claim 4, wherein the polypeptide obtained is from a group consisting of: avian encephalomyelitis virus, avian reovirus, avian paramyxovirus, avian influenza virus, avian adenovirus, fowl pox virus, avian coronavirus, avian rotavirus, chick anemia virus (agent), *Salmonella* spp. *E. coli, Pasteurella* spp., *Bordetella* spp., *Eimeria* spp., *Histomonas* spp., *Trichomonas* spp., Poultry nematodes, cestodes, trematodes, poultry mites/lice and poultry protozoa.

16. The recombinant herpesvirus of turkeys of claim 1, designated S-HVT-138.

17. A vaccine which comprises an effective immunizing amount of the recombinant herpesvirus of turkeys of claim 1 and a suitable carrier.

18. A method of immunizing a bird which comprises administering to the bird an effecting immunizing dose of the vaccine of claim 17.

19. The recombinant herpesvirus of turkeys of claim 1, further comprising an additional foreign DNA inserted into the region which corresponds to an EcoR1 #9 fragment.

20. The recombinant herpesvirus of turkeys of claim 19, wherein the additional foreign DNA is inserted within Open Reading Frame A (ORF A) of the EcoR1 #9 fragment.

21. The recombinant herpesvirus of turkeys of claim 19, wherein the additional foreign DNA is inserted within the XhoI site of the region which corresponds to the EcoR1 #9 fragment.

22. The recombinant herpesvirus of turkeys of claim 19, wherein the additional foreign DNA is Infectious Laryngotracheitis Virus glycoprotein B, and Infectious Laryngotracheitis Virus glycoprotein D.

23. The recombinant herpesvirus of turkeys of claim 19, wherein the additional foreign DNA is Newcastle Disease virus fusion protein and Newcastle Disease virus hemagglutinin-neuraminidase.

24. The recombinant herpesvirus of turkeys of claim 1, further comprising one or more foreign DNA inserted within the StuI site within the US2 gene of the Unique short region of the herpesvirus of turkeys genome.

25. The recombinant herpesvirus of turkeys of claim 24, wherein the foreign DNA is Marek's Disease Virus glycoprotein A, Marek's Disease Virus glycoprotein B, and Marek's Disease Virus glycoprotein D.

26. The recombinant herpesvirus of turkeys of claim 24, wherein the foreign DNA is Newcastle Disease virus fusion protein and Newcastle Disease virus hemagglutinin-neuraminidase.

27. The recombinant herpesvirus of turkeys of claim 24, wherein the foreign DNA is Marek's Disease Virus glycoprotein A, Marek's Disease Virus glycoprotein B, Marek's Disease Virus glycoprotein D, Newcastle Disease virus fusion protein and Newcastle Disease virus hemagglutinin-neuraminidase.

* * * * *